US009061060B2

(12) United States Patent
Seed et al.

(10) Patent No.: US 9,061,060 B2
(45) Date of Patent: Jun. 23, 2015

(54) DEUTERATED BENZYLBENZENE DERIVATIVES AND METHODS OF USE

(75) Inventors: Brian Seed, Boston, MA (US); Binhua Lv, Shanghai (CN); Jacques Y. Roberge, Shanghai (CN); Yuanwei Chen, North Haven, CT (US); Kun Peng, Shanghai (CN); Jiajia Dong, San Diego, CA (US); Baihua Xu, Shanghai (CN); Jiyan Du, Shanghai (CN); Lili Zhang, Shanghai (CN); Xinxing Tang, Shanghai (CN); Ge Xu, Shanghai (CN); Yan Feng, Ridgefield, NJ (US); Min Xu, Shanghai (CN)

(73) Assignee: Theracos Inc., Marlborough, MA (US)

( * ) Notice: Subject to any disclaimer, the term of this patent is extended or adjusted under 35 U.S.C. 154(b) by 1076 days.

(21) Appl. No.: 12/503,384

(22) Filed: Jul. 15, 2009

(65) Prior Publication Data

US 2010/0063141 A1 Mar. 11, 2010

Related U.S. Application Data

(60) Provisional application No. 61/134,968, filed on Jul. 15, 2008.

(51) Int. Cl.
*A01N 43/16* (2006.01)
*A61K 31/35* (2006.01)
*C07D 315/00* (2006.01)
*A61K 45/06* (2006.01)
*C07D 309/10* (2006.01)

(52) U.S. Cl.
CPC .............. *A61K 45/06* (2013.01); *A61K 31/35* (2013.01); *C07D 309/10* (2013.01)

(58) Field of Classification Search
CPC .................... A61K 31/351; C07D 309/10
USPC ........................................ 514/460; 549/417
See application file for complete search history.

(56) References Cited

U.S. PATENT DOCUMENTS

| 4,871,721 | A | 10/1989 | Biller |
|---|---|---|---|
| 4,924,024 | A | 5/1990 | Biller |
| 5,023,269 | A | 6/1991 | Robertson et al. |
| 5,143,938 | A | 9/1992 | Calvet et al. |
| 5,324,859 | A | 6/1994 | Pettersen et al. |
| 5,545,633 | A | 8/1996 | Bretting |
| 5,595,872 | A | 1/1997 | Wetterau, II et al. |
| 5,712,279 | A | 1/1998 | Biller et al. |
| 5,712,396 | A | 1/1998 | Magnin et al. |
| 5,739,135 | A | 4/1998 | Biller et al. |
| 5,760,246 | A | 6/1998 | Biller et al. |
| 5,827,875 | A | 10/1998 | Dickson, Jr. et al. |
| 5,885,983 | A | 3/1999 | Biller et al. |
| 5,895,660 | A | 4/1999 | Hoffmann et al. |
| 5,962,440 | A | 10/1999 | Sulsky |
| 6,011,155 | A | 1/2000 | Villhauer |
| 6,172,081 | B1 | 1/2001 | Damon |
| 6,197,798 | B1 | 3/2001 | Fink et al. |
| 6,221,335 | B1 * | 4/2001 | Foster .......................... 424/1.81 |
| 6,334,997 | B1 | 1/2002 | Foster et al. |
| 6,376,531 | B1 | 4/2002 | Bell |
| 6,414,126 | B1 | 7/2002 | Ellsworth et al. |
| 6,432,969 | B1 | 8/2002 | Villhauer |
| 6,548,529 | B1 | 4/2003 | Robl et al. |
| 6,605,593 | B1 | 8/2003 | Naicker et al. |
| 6,617,325 | B1 | 9/2003 | Lehmann-Lintz et al. |
| 6,649,622 | B2 | 11/2003 | Sulsky et al. |
| 6,670,380 | B2 | 12/2003 | Sulsky et al. |
| 6,710,040 | B1 | 3/2004 | Hulin et al. |
| 6,727,261 | B2 | 4/2004 | Gobbi et al. |
| 6,821,967 | B2 | 11/2004 | Lehmann-Lintz et al. |
| 6,869,947 | B2 | 3/2005 | Kanstrup et al. |
| 6,878,707 | B2 | 4/2005 | Ksander |
| 6,919,323 | B2 | 7/2005 | Sulsky et al. |
| 6,936,590 | B2 | 8/2005 | Washburn et al. |
| 6,939,878 | B2 | 9/2005 | Naicker et al. |
| 6,984,645 | B2 | 1/2006 | Magnin et al. |
| 7,084,145 | B2 | 8/2006 | Armour et al. |
| 7,138,527 | B2 | 11/2006 | Brown et al. |
| 7,164,015 | B2 | 1/2007 | Shen et al. |
| 7,589,193 | B2 | 9/2009 | Washburn et al. |
| 8,124,646 | B2 | 2/2012 | Liu |
| 2003/0064935 | A1 | 4/2003 | Gougoutas |
| 2005/0069276 | A1 | 3/2005 | Alken |
| 2005/0176814 | A1 | 8/2005 | Alken |

(Continued)

FOREIGN PATENT DOCUMENTS

| CN | 1247059 A | 3/2000 |
|---|---|---|
| EP | 1783110 | 5/2007 |
| JP | 2004-196788 | 7/2004 |
| JP | 2004-359630 | 12/2004 |
| JP | 2005-509646 A | 4/2005 |
| JP | 2005-511742 A | 4/2005 |
| JP | 2005-247834 | 9/2005 |
| JP | 2005-530825 A | 10/2005 |
| WO | WO 96/38144 | 12/1996 |
| WO | WO 97/12613 | 4/1997 |

(Continued)

OTHER PUBLICATIONS

Hall et. al., Antimicrobial Agents and Chemotherapy, 1998, American Society for Microbiology, vol. 42, No. 3, pp. 666-674.*

(Continued)

*Primary Examiner* — Sarah Pihonak
(74) *Attorney, Agent, or Firm* — Clark & Elbing LLP

(57) ABSTRACT

Provided are compounds having an inhibitory effect on sodium-dependent glucose cotransporter SGLT. The invention also provides pharmaceutical compositions, methods of preparing the compounds, synthetic intermediates, and methods of using the compounds, independently or in combination with other therapeutic agents, for treating diseases and conditions that are affected by SGLT inhibition.

33 Claims, 11 Drawing Sheets

(56) References Cited

U.S. PATENT DOCUMENTS

| | | |
|---|---|---|
| 2005/0209166 A1 | 9/2005 | Eckhardt et al. |
| 2005/0222160 A1 | 10/2005 | Eggenweiler et al. |
| 2007/0032555 A1 | 2/2007 | Tung |
| 2007/0049537 A1 | 3/2007 | Eckhardt et al. |
| 2007/0116643 A1 | 5/2007 | Tung |
| 2007/0191381 A1 | 8/2007 | Tung |
| 2007/0191432 A1 | 8/2007 | Tung |
| 2007/0275907 A1 | 11/2007 | Chen et al. |
| 2007/0276001 A1 | 11/2007 | Tung |
| 2008/0242596 A1 | 10/2008 | Chen et al. |
| 2008/0318874 A1 | 12/2008 | Matsuoka et al. |
| 2009/0156516 A1 | 6/2009 | Chen et al. |

FOREIGN PATENT DOCUMENTS

| | | |
|---|---|---|
| WO | WO 97/12615 | 4/1997 |
| WO | WO 01/27128 | 4/2001 |
| WO | WO 01/68660 | 9/2001 |
| WO | WO 01/74834 | 10/2001 |
| WO | WO 02/28872 | 4/2002 |
| WO | WO 02/44192 | 6/2002 |
| WO | WO 02/064606 | 8/2002 |
| WO | WO 02/083066 | 10/2002 |
| WO | WO 03/011880 | 2/2003 |
| WO | WO 03/080635 | 10/2003 |
| WO | WO 03099836 A1 * | 12/2003 |
| WO | WO 2004/014930 | 2/2004 |
| WO | WO 2004/063209 | 7/2004 |
| WO | WO 2005/063785 | 7/2005 |
| WO | WO 2005/092877 | 10/2005 |
| WO | WO 2005/095429 | 10/2005 |
| WO | WO 2006/002912 | 1/2006 |
| WO | WO 2006/008038 | 1/2006 |
| WO | WO 2006/011469 | 2/2006 |
| WO | WO 2006/034489 | 3/2006 |
| WO | WO 2006/037537 | 4/2006 |
| WO | WO 2006/087997 | 8/2006 |
| WO | WO 2006/089872 | 8/2006 |
| WO | WO 2006/108842 | 10/2006 |
| WO | WO 2006/117359 | 11/2006 |
| WO | WO 2006/117360 | 11/2006 |
| WO | WO 2006/120208 | 11/2006 |
| WO | WO 2007/000445 | 1/2007 |
| WO | WO 2007/005643 | 1/2007 |
| WO | WO 2007/005644 | 1/2007 |
| WO | WO 2007/014894 | 2/2007 |
| WO | WO 2007/025943 | 3/2007 |
| WO | WO 2007/041630 | 4/2007 |
| WO | WO-2007/093450 A2 | 8/2007 |
| WO | WO 2007/093610 | 8/2007 |
| WO | WO 2007/126117 | 11/2007 |
| WO | WO 2007/128480 | 11/2007 |
| WO | WO 2007/136116 | 11/2007 |
| WO | WO 2007/139923 | 12/2007 |
| WO | WO-2007/140189 A2 | 12/2007 |
| WO | WO-2007/143507 A2 | 12/2007 |
| WO | WO 2007/146124 | 12/2007 |
| WO | WO 2007/146890 | 12/2007 |
| WO | WO 2008/001864 | 1/2008 |
| WO | WO 2008/002824 | 1/2008 |
| WO | WO 2008/008442 | 1/2008 |
| WO | WO 2008/016132 | 2/2008 |
| WO | WO 2008/020011 | 2/2008 |
| WO | WO-2008/022285 A1 | 2/2008 |
| WO | WO 2008/034859 | 3/2008 |
| WO | WO 2008/042688 | 4/2008 |
| WO | WO-2008/049116 A2 | 4/2008 |
| WO | WO 2008/055870 | 5/2008 |
| WO | WO 2008/072726 | 6/2008 |
| WO | WO-2008/073863 A2 | 6/2008 |
| WO | WO 2008/101939 | 8/2008 |
| WO | WO 2008/109591 | 9/2008 |
| WO | WO 2008/116179 | 9/2008 |
| WO | WO 2008/144346 | 11/2008 |
| WO | WO 2008133949 A1 * | 11/2008 |
| WO | WO 2009/014970 | 1/2009 |
| WO | WO 2009/022007 | 2/2009 |
| WO | WO 2009/026537 | 2/2009 |
| WO | WO 2009/121939 | 10/2009 |
| WO | WO 2010/009197 | 1/2010 |
| WO | WO 2010/023594 | 3/2010 |
| WO | WO 2010/031820 | 3/2010 |
| WO | WO 2010/048358 | 4/2010 |
| WO | WO 2010/092123 | 8/2010 |
| WO | WO 2010/092124 | 8/2010 |
| WO | WO 2010/092125 | 8/2010 |
| WO | WO 2010/092126 | 8/2010 |

OTHER PUBLICATIONS

Vippagunta et. al., Advanced Drug Delivery Reviews, 2001, Elsevier, vol. 48, pp. 3-26.*
The American Diabetes Association, Diabetes Care, Jan. 2008, vol. 31, supplement 1, pp. S55-S60.*
Rader et. al., Journal of Clinical Investigation, 2003, American Society for Clinical Investigation, vol. 111, No. 12, pp. 1795-1803.*
Antel et al., "CB1 Cannabinoid Receptor Antagonists for Treatment of Obesity and Prevention of Comorbid Metabolic Disorders," *J. Med. Chem.* 49: 4008-4016, 2006.
Arakawa et al., "Improved Diabetic Syndrome in C57BL/KsJ-db/db Mice by Oral Administration of the Na+- Glucose Inhibitor T-1095," *British J. Pharmacol.* 132: 578-586, 2001.
Boughton, "Naming Hydrogen Isotopes," *Science* 79: 159-160, 1934.
Dourish et al. "Deuterium Substitution Enhances the Effects of β-Phenylethylamine on Spontaneous Motor Activity in the Rat," *Pharmacol. Biochem. Behav.* 19: 471-475, 1983.
Fürstner et al., "Total Syntheses of the Telomerase Inhibitors Dictyodendrin B, C, and E," *J. Am. Chem. Soc.* 128: 8087-8094, 2006.
Guengerich et al., "Rate-limiting Steps in Oxidations Catalyzed by Rabbit Cytochrome P450 1A2," *Biochemistry* 43: 10755-10788, 2004.
Handlon et al., "Melanin-concentrating Hormone-1 Receptor Antagonists for the Treatment of Obesity," *J. Med. Chem.* 49: 4017-4022, 2006.
Handy et al., "A Modular Synthesis of the Lamellarins: Total Synthesis of Lamellarin G Trimethyl Ether," *J. Org. Chem.* 69: 2362-2366, 2004.
Highlights of Prescribing Information: Cymbalta (Duloxetine Hydrochloride) Delayed-Release Capsules for Oral Use, pp. 1-25, Revised Dec. 13, 2007.
Isaji, "Sodium-glucose Cotransporter Inhibitors for Diabetes," *Curr. Opin. Investig. Drugs* 8: 285-292, 2007.
Kim et al., "Oxidative N-Benzylation of N-Benzyl-N-Substituted Benzylamines Catalyzed by Cytochrome P450," *Bull. Korean Chem. Soc.* 25: 249-252, 2004.
Kim et al., "Kinetic Deuterium Isotope Effects for 7-Alkoxycoumarin O-Dealkylation Reactions Catalyzed by Human Cytochromes P450 and in Liver Microsomes," *FEBS J.* 273: 2223-2231, 2006.
Krauser et al., "Cytochrome P450 3A4-catalyzed Testosterone 6β-Hydroxylation Stereochemistry, Kinetic Deuterium Isotope Effects, and Rate-limiting steps," *J. Biol. Chem.* 280: 19496-19506, 2005.
Lebeau et al., "Oxidation of Benzyl Alcohol by a Dioxo Complex of Ruthenium(VI)," *Inorg. Chem.* 38: 2174-2181, 1999.
Maggs et al., "Metabolism of Lamotrigine to a Reactive Arene Ozide Intermediate," *Chem. Res. Toxicol.* 13: 1075-1081, 2000.
Nargund et al., "Melanocortin-4 Receptor (MC4R) Agonists for the Treatment of Obesity," *J. Med. Chem.* 49: 4035-4043, 2006.
Nelson et al., "The Use of Deuterium Isotope Effects to Probe the Active Site Properties, Mechanism of Cytochrome P450-catalyzed Reactions and, Mechanism of Metabolically Dependent Toxicity," *Drug Metab. Dispos.* 31: 1481-1498, 2003.
Nilsson, "5-Hydroxytryptamine 2C (5-HT2C) Receptor Agonists as Potential Antiobesity Agents," *J. Med. Chem.* 49: 4023-4034, 2006.

(56) References Cited

OTHER PUBLICATIONS

Oku et al., "T-1095, an Inhibitor of Renal Na+-Glucose Cotransporters, May Provide a Novel Approach to Treating Diabetes," *Diabetes* 48: 1794-1800, 1999.

Pereira et al., "Clozapine Bioactivation Induces Dose-dependent Drug-specific Toxicity of Human bone Marrow Stromal Cells: A Potential in vitro System for the Study of Agranulocytosis," *Biochem. Pharmacol.* 72: 783-793, 2006.

Santer et al., "Molecular Analysis of the SGLT2 Gene in Patients with Renal Glucosuria," *J. Am. Soc. Nephrol.* 14: 2873-2882, 2003.

Sobrado et al., "Solvent and Primary Deuterium Isotope Effects Show that Lactate CH and OH Bond Cleavages Are Concerted in Y254F Flavocytochrome $b2$, Consistent with a Hydride Transfer Mechanism," *Biochemistry* 42: 15208-15214, 2003.

Vats et al., "Emerging Targets for Diabetes," *Curr. Sci.* 88: 241-249, 2005.

Zamojski et al., "Preparation and NMR-spectral Characteristics of Benzyl-$\alpha,\alpha$-$d_2$ Ethers of Monosaccharides," *Carbohydr. Res.* 142: 165-171, 1985.

International Preliminary Report on Patentability for PCT/US2009/050710, date of issuance: Jan. 18, 2011.

International Search Report for PCT/US2009/050710, date of mailing: Sep. 21, 2009.

Written Opinion of the International Searching Authority for PCT/US2009/050710, date of mailing: Sep. 21, 2009.

Blake et al., "Studies with Deuterated Drugs," *J. Pharm. Sci.* 64:367-91 (1975).

Fisher et al., "The Complexities Inherent in Attempts to Decrease Drug Clearance by Blocking Sites of CYP-Mediated Metabolism," *Curr. Opin. Drug Discov. Devel.* 9:101-09 (2006).

Foster, "Deuterium Isotope Effects in the Metabolism of Drugs and Xenobiotics: Implications for Drug Design," *Adv. Drug Res.* 14:1-40 (1985).

Kushner et al., "Pharmacological Uses and Perspectives of Heavy Water and Deuterated Compounds," *Can. J. Physiol. Pharmacol.* 77:79-88 (1999).

Matsumoto et al., "Cilostazol Improves Endothelium-Derived Hyperpolarizing Factor-Type Relaxation in Mesenteric Arteries from Diabetic Rats," *Am. J. Physiol. Heart Circ. Physiol.* 289:H1933-H1940 (2005).

New Zealand Examination Report for New Zealand Patent Application No. 591109, dated Jun. 13, 2011.

European Search Opinion from European Application No. EP 09797806, dated Jul. 27, 2012.

Office Action in Chinese Patent Application No. 200980135856.7, dated Apr. 9, 2014 (22 pages).

Office Action in Taiwanese Patent Application No. 098123938, dated Dec. 25, 2013 (15 pages).

\* cited by examiner

Legend:
1 = Ref. A
2 = Ref. E
3 = Ref. D

Legend: 1 = Compound (24c)   2 = Ref. E-d5   3 = Ref. D

Metabolic pathway for Compound (24c), Ref. A, and Ref. D

Legend: 1 = Ref. A  2 = Ref. E  3 = Ref. D

Metabolic pathway for Compound (24c), Ref. A, and Ref. D

Legend: 3 = Ref. D

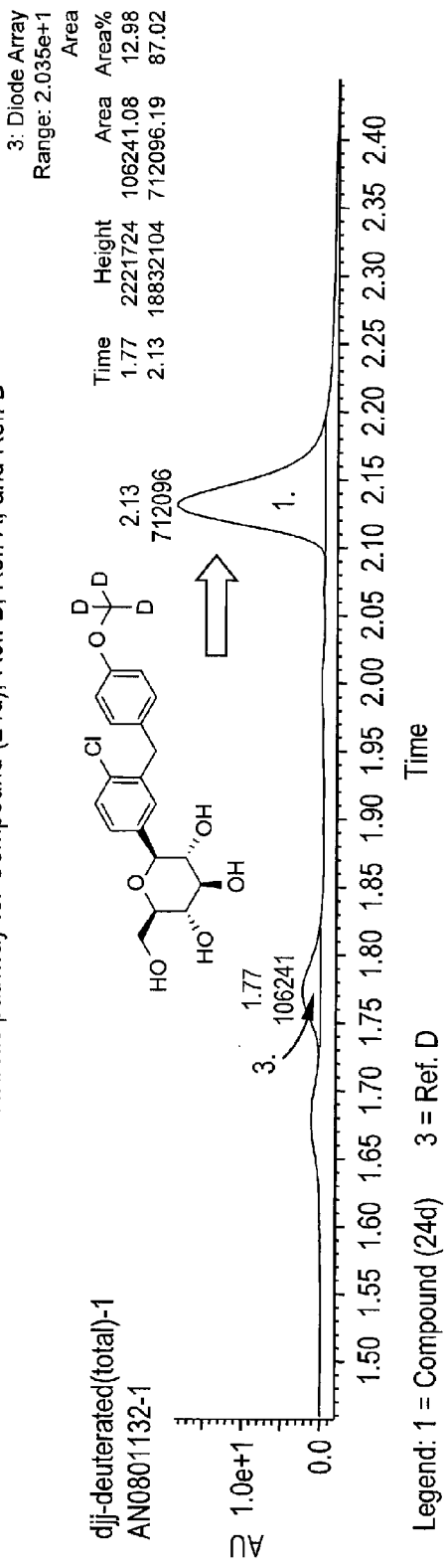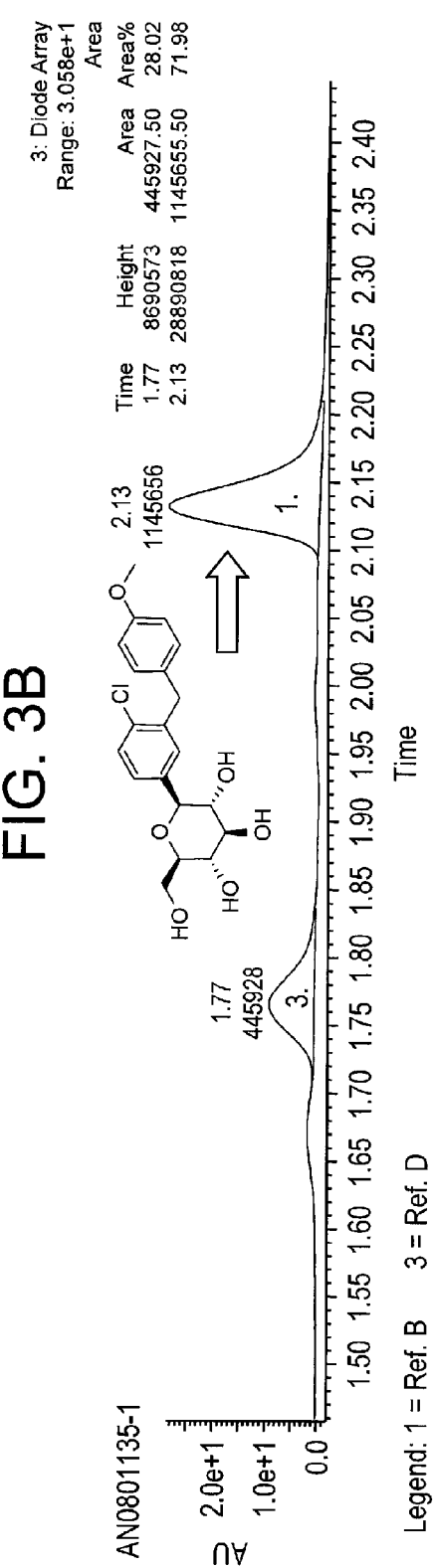

Metabolic pathway for Compound (24d), Ref. B, Ref. A, and Ref. D

FIG. 4A Metabolic pathway for Compound (9), Ref. A, and Ref. D

Metabolic pathway for Compound (9), Ref. B, Ref. A, and Ref. D

Legend: 3 = Ref. D

FIG. 6

Based on chromatographic peak area

|    | Ref A    | Cpd 16   | Ratio  |
|----|----------|----------|--------|
| M0 | 1.10E+06 | 1.30E+06 | 1 : 1.2 |
| M1 | 4.26E+05 | 2.33E+05 | 1.8 : 1 |
| M2 | 2.15E+06 | 3.38E+06 | 1 : 1.6 |
| M3 | 8.68E+05 | 4.43E+05 | 2 : 1 |
|    | Ref B    | Cpd 19   | Ratio  |
| M0 | 1.68E+06 | 1.67E+06 | 1 : 1 |
| M1 | 3.09E+05 | 2.85E+05 | 1.1 : 1 |
| M2 | 1.84E+06 | 1.06E+06 | 1.7 : 1 |
| M3 | 3.17E+05 | 3.10E+05 | 1 : 1 |
|    | Ref C    | Cpd 54   | Ratio  |
| M0 | 2.24E+05 | 2.64E+05 | 1 : 1.2 |
| M1 | 1.00E+06 | 1.26E+06 | 1 : 1.3 |
| M2 | 2.76E+06 | 1.18E+06 | 2.3 : 1 |
| M3 | 9.08E+05 | 4.54E+05 | 2 : 1 |

Based on mass response

|    | Ref A    | Cpd 16   | Ratio  |
|----|----------|----------|--------|
| M0 | 5.29E+05 | 7.42E+05 | 1 : 1.4 |
| M1 | 8.88E+05 | 3.88E+05 | 2.3 : 1 |
| M2 | 3.30E+05 | 2.14E+05 | 1.5 : 1 |
| M3 | 1.12E+05 | 3.81E+04 | 3.0 : 1 |
|    | Ref B    | Cpd 19   | Ratio  |
| M0 | 2.07E+06 | 2.06E+06 | 1 : 1 |
| M1 | 9.91E+05 | 3.70E+05 |  |
| M2 |          |          |  |
| M3 | 3.20E+04 | 1.94E+04 | 1.6 : 1 |
|    | Ref C    | Cpd 54   | Ratio  |
| M0 | 6.96E+04 | 1.08E+05 | 1 : 1.6 |
| M1 | 6.35E+05 | 7.13E+05 | 1 : 1.1 |
| M2 | 1.62E+05 | 7.50E+04 | 2.1 : 1 |
| M3 | 2.33E+04 | 1.27E+05 | 1 : 5.5 |

FIG. 7

LC/MS mass spectral data and the corresponding retention time for six compounds and their metabolites in rat urine

| Compound | M0 [M+Na]⁺ | M1 [M+NH₄]⁺ or [M+Na]⁺* | M2 [M-H₂O+H]⁺ | M3 [M-H2O+H]+ |
|---|---|---|---|---|
| Ref A | 431 (17.7 min) | 398 (13.9 min) | 407 (14.7 min) | 379 (10.8 min) |
| Cpd 16 | 438 (17.6 min) | 400 (13.5 min) | 413 (14.7 min) | 380 (10.7 min) |
| Ref B | 417 (16.3 min) | 398 (13.5 min) | 393 (13.4 min) | 379 (10.7 min) |
| Cpd 19 | 422 (16.3 min) | 400 (13.5 min) | 397 (13.4 min) | 380 (10.8 min) |
| Ref C | 427 (19.0 min) | 443 (14.7 min) | 403 (15.9 min) | 419 (12.3 min) |
| Cpd 54 | 429 (19.0 min) | 445 (14.6 min) | 404 (15.9 min) | 420 (12.1 min) |

* The base peak is [M+Na]+ for Ref C and Cpd 54

DEUTERATED BENZYLBENZENE DERIVATIVES AND METHODS OF USE

CROSS-REFERENCE TO RELATED APPLICATIONS

This application claims benefit of U.S. Provisional Application No. 61/134,968, filed Jul. 15, 2008, which is hereby incorporated by reference.

BACKGROUND OF THE INVENTION

The invention provides compositions including compounds having an inhibitory effect on sodium-dependent glucose cotransporter SGLT. The invention also provides pharmaceutical compositions and methods of using the compounds, independently or in combination with other therapeutic agents, for treating diseases and conditions that are affected by SGLT inhibition.

According to the World Health Organization, approximately 150 million people worldwide have diabetes mellitus. The two principal forms of diabetes are type 1 diabetes, in which the pancreas fails to produce insulin, and type 2 diabetes, in which the body fails to respond properly to the insulin produced (insulin resistance). Accounting for about 90% of all diabetes cases, type 2 diabetes is by far the most common. In both types of diabetes, the absence of insulin action or proper response to insulin results in elevated levels of serum glucose (hyperglycemia). Serious complications associated with diabetes include retinopathy (leading to visual impairment or blindness), cardiovascular disease, nephropathy, neuropathy, ulcers, and diabetic foot disease.

Individuals with type 1 diabetes currently require insulin therapy. While in many cases type 2 diabetes can be managed with diet and exercise, drug intervention is also frequently required. Besides insulin, which is needed by about one-third of patients with type 2 diabetes, current antidiabetic therapies include biguanides (which decrease glucose production in the liver and increase sensitivity to insulin), sulfonylureas and meglitinides (which stimulate insulin production), alpha-glucosidase inhibitors (which slow starch absorption and glucose production), and thiazolidinediones (which increase insulin sensitivity). These medicines are often used in combination, and even then may not provide adequate glycemic control or may produce undesired side effects. Such side effects include lactic acidosis (biguanides), hypoglycemia (sulfonylureas), and edema and weight gain (thiazolidinediones).

One promising target for therapeutic intervention in diabetes and related disorders is the glucose transport system of the kidneys. Cellular glucose transport is conducted by either facilitative ("passive") glucose transporters (GLUTs) or sodium-dependent ("active") glucose cotransporters (SGLTs). SGLT1 is found predominantly in the intestinal brush border, while SGLT2 is localized in the renal proximal tubule and is reportedly responsible for the majority of glucose reuptake by the kidneys. Recent studies suggest that inhibition of renal SGLT may be a useful approach to treating hyperglycemia by increasing the amount of glucose excreted in the urine (Arakawa et al., *Br J Pharmacol* 132:578-86, 2001; Oku et al., *Diabetes* 48:1794-1800, 1999). The potential of this therapeutic approach is further supported by recent findings that mutations in the SGLT2 gene occur in cases of familial renal glucosuria, an apparently benign syndrome characterized by urinary glucose excretion in the presence of normal serum glucose levels and the absence of general renal dysfunction or other disease (Santer et al., *J Am Soc Nephrol* 14:2873-82, 2003).

Therefore, compounds that inhibit SGLT, particularly SGLT2, are promising candidates for use as antidiabetic drugs and new antidiabetic agents providing improved glycemic control and lacking these adverse effects are highly desired.

SUMMARY OF THE INVENTION

The present invention provides compositions that include compounds having an inhibitory effect on sodium-dependent glucose cotransporter SGLT. The invention also provides pharmaceutical compositions and methods of using the compounds, independently or in combination with other therapeutic agents, for treating diseases and conditions which are affected by SGLT inhibition such as: type 1 diabetes mellitus, type 2 diabetes mellitus, hyperglycemia, diabetic complications, insulin resistance, metabolic syndrome (Syndrome X), hyperinsulinemia, hypertension, hyperuricemia, obesity, edema, dyslipidemia, chronic heart failure, and atherosclerosis.

In one aspect, the invention features compounds having the structure:

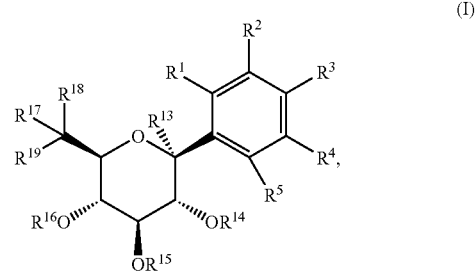

(I)

or any stereoisomer or tautomer thereof, or any pharmaceutically acceptable prodrug, salt, or solvate thereof, wherein
each $R^1$, $R^2$, $R^3$, $R^4$ and $R^5$ is, independently, —H, -D, a substituent that is optionally deuterated, or group Q:

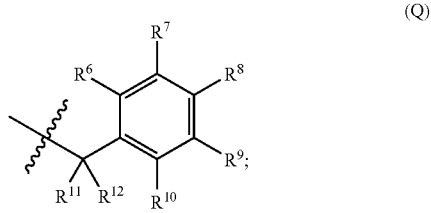

(Q)

each $R^6$, $R^7$, $R^8$, $R^9$, $R^{10}$, $R^{14}$, $R^{15}$, $R^{16}$, and $R^9$ is, independently, —H, -D, or a substituent that is optionally deuterated; and
each $R^{11}$, $R^{12}$, $R^{13}$, $R^{17}$ and $R^{18}$ is, independently, —H, -D, or halogen;
wherein
one of $R^1$, $R^2$, $R^3$, $R^4$ and $R^5$ is group Q;
at least one of $R^1$-$R^{19}$ is -D or comprises -D.
In certain embodiments of compounds of formula I:
one of $R^1$, $R^2$, $R^3$, $R^4$ and $R^5$ is group Q;
one of the remaining groups $R^1$, $R^2$, $R^3$, $R^4$ and $R^5$ represents hydrogen, deuterium, halo, cyano, nitro, amino, hydroxy, $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, $C_1$-$C_6$ alkoxy, $C_3$-$C_{10}$ cycloalkoxy, ($C_1$-$C_6$ alkoxy)$C_1$-$C_6$ alkoxy, $C_5$-$C_7$ cycloalkenyloxy, aryl, heteroaryl, aryloxy, heteroaryloxy, ($C_2$-$C_4$ alkenyl)$C_1$-$C_3$ alkoxy, ($C_2$-$C_4$ alkynyl)$C_1$-$C_3$ alkoxy, (aryl)$C_1$-$C_3$ alkoxy, (heteroaryl)$C_1$-$C_3$ alkoxy, ($C_3$-$C_{10}$ cycloalkyl)$C_1$-$C_3$ alkyl, ($C_3$-$C_{10}$ cycloalkyl)$C_1$-$C_3$ alkoxy, ($C_5$-$C_{10}$ cycloalkenyl)$C_1$-$C_3$ alkyl, ($C_5$-$C_{10}$ cycloalkenyl)$C_1$-$C_3$ alkoxy, ($C_1$-$C_4$ alkoxy)$C_1$-$C_3$ alkyl, ($C_3$-$C_7$ cycloalkoxy)$C_1$-$C_3$ alkyl, ($C_3$-$C_7$ cycloalkoxy)$C_2$-$C_4$ alkenyl, ($C_3$-$C_7$ cycloalkoxy)$C_2$-$C_4$ alkynyl, ($C_3$-$C_7$ cycloalkoxy)$C_1$-$C_3$ alkoxy, ($C_1$-$C_4$ alkylamino)$C_1$-$C_3$ alkyl, di-($C_1$-$C_3$ alkylamino)$C_1$-$C_3$ alkyl, tri-($C_1$-$C_4$ alkyl)silyl-$C_1$-$C_6$ alkyl, tri-($C_1$-$C_4$ alkyl)silyl-$C_2$-$C_6$ alkenyl, tri-($C_1$-$C_4$ alkyl)silyl-$C_2$-$C_6$ alkynyl, tri-($C_1$-$C_4$ alkyl)silyl-$C_1$-$C_6$ alkoxy, ($C_3$-$C_7$ cycloalkyl)$C_2$-$C_5$ alkenyl, ($C_3$-$C_7$ cycloalkyl)$C_3$-$C_5$ alkenyloxy, ($C_3$-$C_7$ cycloalkyl)$C_3$-$C_5$ alkynyloxy, ($C_5$-$C_8$ cycloalkenyl)$C_3$-$C_5$ alkenyloxy, ($C_5$-$C_8$ cycloalkenyl)$C_3$-$C_5$ alkynyloxy, $C_3$-$C_6$ cycloalkylidenmethyl, ($C_1$-$C_4$ alkyl)carbonyl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, ($C_1$-$C_4$ alkoxy)carbonyl, $C_1$-$C_4$ alkylamino, di-($C_1$-$C_3$ alkyl)amino, ($C_1$-$C_4$ alkyl)carbonylamino, arylcarbonylamino, heteroarylcarbonylamino, $C_1$-$C_4$ alkylsulfonylamino, arylsulfonylamino, $C_1$-$C_4$ alkylthio, $C_1$-$C_4$ alkylsulfinyl, $C_1$-$C_4$ alkylsulfonyl, $C_3$-$C_{10}$ cycloalkylthio, $C_3$-$C_{10}$ cycloalkylsulfinyl, $C_3$-$C_{10}$ cycloalkylsulfonyl, $C_5$-$C_{10}$ cycloalkenylthio, $C_5$-$C_{10}$ cycloalkenylsulfinyl, $C_5$-$C_{10}$ cycloalkenylsulfonyl, arylthio, arylsulfinyl or arylsulfonyl;

two of the remaining groups $R^1$, $R^2$, $R^3$, $R^4$ and $R^5$ each independently represent hydrogen, deuterium, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkoxy or $C_3$-$C_{10}$ cycloalkoxy; and one of the remaining groups $R^1$, $R^2$, $R^3$, $R^4$ and $R^5$ represents hydrogen or deuterium;

one of the groups $R^6$, $R^7$, $R^8$, $R^9$ and $R^{10}$ represents hydrogen, deuterium, halo, cyano, nitro, amino, hydroxy, $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, $C_1$-$C_6$ alkoxy, $C_3$-$C_{10}$ cycloalkoxy, ($C_1$-$C_6$ alkoxy)$C_1$-$C_6$ alkoxy, ($C_1$-$C_3$ alkoxy)$C_3$-$C_7$ cycloalkoxy, $C_5$-$C_7$ cycloalkenyloxy, aryl, heteroaryl, aryloxy, heteroaryloxy, ($C_2$-$C_4$ alkenyl)$C_1$-$C_3$ alkoxy, ($C_2$-$C_4$ alkynyl)$C_1$-$C_3$ alkoxy, (aryl)$C_1$-$C_3$ alkoxy, (heteroaryl)$C_1$-$C_3$ alkoxy, ($C_3$-$C_{10}$ cycloalkyl)$C_1$-$C_3$ alkyl, ($C_3$-$C_{10}$ cycloalkyl)$C_1$-$C_3$ alkoxy, ($C_5$-$C_{10}$ cycloalkenyl)$C_1$-$C_3$ alkyl, ($C_5$-$C_{10}$ cycloalkenyl)$C_1$-$C_3$ alkoxy, ($C_1$-$C_4$ alkoxy)$C_1$-$C_3$ alkyl, ($C_3$-$C_7$ cycloalkoxy)$C_1$-$C_3$ alkyl, ($C_3$-$C_7$ cycloalkoxy)$C_2$-$C_4$ alkenyl, ($C_3$-$C_7$ cycloalkoxy)$C_2$-$C_4$ alkynyl, ($C_3$-$C_7$ cycloalkoxy)$C_1$-$C_3$ alkoxy, ($C_1$-$C_4$ alkylamino)$C_1$-$C_3$ alkyl, di-($C_1$-$C_3$ alkylamino)$C_1$-$C_3$ alkyl, tri-($C_1$-$C_4$ alkyl)silyl-$C_1$-$C_6$ alkyl, tri-($C_1$-$C_4$ alkyl)silyl-$C_2$-$C_6$ alkenyl, tri-($C_1$-$C_4$ alkyl)silyl-$C_2$-$C_6$ alkynyl, tri-($C_1$-$C_4$ alkyl)silyl-$C_1$-$C_6$ alkoxy, ($C_3$-$C_7$ cycloalkyl)$C_2$-$C_5$ alkenyl, ($C_3$-$C_7$ cycloalkyl)$C_3$-$C_5$ alkenyloxy, ($C_3$-$C_7$ cycloalkyl)$C_3$-$C_5$ alkynyloxy, ($C_5$-$C_8$ cycloalkenyl)$C_3$-$C_5$ alkenyloxy, ($C_5$-$C_8$ cycloalkenyl)$C_3$-$C_5$ alkynyloxy, $C_3$-$C_6$ cycloalkylidenmethyl, ($C_1$-$C_4$ alkyl)carbonyl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, ($C_1$-$C_4$ alkoxy)carbonyl, $C_1$-$C_4$ alkylamino, di-($C_1$-$C_3$ alkyl)amino, ($C_1$-$C_4$ alkyl)carbonylamino, arylcarbonylamino, heteroarylcarbonylamino, $C_1$-$C_4$ alkylsulfonylamino, arylsulfonylamino, $C_1$-$C_4$ alkylthio, $C_1$-$C_4$ alkylsulfinyl, $C_1$-$C_4$ alkylsulfonyl, $C_3$-$C_{10}$ cycloalkylthio, $C_3$-$C_{10}$ cycloalkylsulfinyl, $C_3$-$C_{10}$ cycloalkylsulfonyl, $C_5$-$C_{10}$ cycloalkenylthio, $C_5$-$C_{10}$ cycloalkenylsulfinyl, $C_5$-$C_{10}$ cycloalkenylsulfonyl, arylthio, arylsulfinyl or arylsulfonyl;

two of the remaining groups $R^6$, $R^7$, $R^8$, $R^9$ and $R^{10}$ each independently represent hydrogen, deuterium, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkoxy or $C_3$-$C_{10}$ cycloalkoxy; and two of the remaining groups $R^6$, $R^7$, $R^8$, $R^9$ and $R^{10}$ each independently represent hydrogen or deuterium;

$R^{14}$, $R^{15}$ and $R^{16}$ each independently represent hydrogen, ($C_1$-$C_{18}$ alkyl)carbonyl, ($C_1$-$C_{18}$ alkyl)oxycarbonyl, arylcarbonyl, aryl-($C_1$-$C_3$ alkyl)carbonyl, ($C_3$-$C_{10}$ cycloalkyl)carbonyl, $C_1$-$C_6$ alkyl, $C_2$-$C_6$ alkenyl, $C_2$-$C_6$ alkynyl, ($C_5$-$C_7$ cycloalkenyl)$C_1$-$C_3$ alkyl, (aryl)$C_1$-$C_3$ alkyl, (heteroaryl)$C_1$-$C_3$ alkyl, $C_3$-$C_7$ cycloalkyl, $C_5$-$C_7$ cycloalkenyl, aryl, heteroaryl, ($C_3$-$C_7$ cycloalkyl)$C_1$-$C_3$ alkyl, ($C_5$-$C_7$ cycloalkenyl)$C_1$-$C_3$ alkyl, (aryl)$C_1$-$C_3$ alkyl, (heteroaryl)$C_1$-$C_3$ alkyl, $C_1$-$C_4$ alkylsulfonyl, arylsulfonyl, (aryl)$C_1$-$C_3$ alkylsulfonyl, trimethylsilyl or t-butyldimethylsilyl;

$R^{19}$ represents hydroxy, ($C_1$-$C_{18}$ alkyl)carbonyloxy, ($C_1$-$C_{18}$ alkyl)oxycarbonyloxy, arylcarbonyloxy, aryl-($C_1$-$C_3$ alkyl)carbonyloxy, ($C_3$-$C_{10}$ cycloalkyl)carbonyloxy, hydrogen, deuterium, halo, $C_1$-$C_6$ alkyl, $C_2$-$C_6$ alkenyl, $C_2$-$C_6$ alkynyl, ($C_3$-$C_{10}$ cycloalkyl)$C_1$-$C_3$ alkyl, ($C_5$-$C_7$ cycloalkenyl)$C_1$-$C_3$ alkyl, (aryl)$C_1$-$C_3$ alkyl, (heteroaryl)$C_1$-$C_3$ alkyl, $C_1$-$C_6$ alkoxy, $C_2$-$C_6$ alkenyloxy, $C_2$-$C_6$ alkynyloxy, $C_3$-$C_7$ cycloalkoxy, $C_5$-$C_7$ cycloalkenyloxy, aryloxy, heteroaryloxy, ($C_3$-$C_7$ cycloalkyl)$C_1$-$C_3$ alkoxy, ($C_5$-$C_7$ cycloalkenyl)$C_1$-$C_3$ alkoxy, (aryl)$C_1$-$C_3$ alkoxy, (heteroaryl)$C_1$-$C_3$ alkoxy, aminocarbonyl, hydroxycarbonyl, ($C_1$-$C_4$ alkyl)aminocarbonyl, di-($C_1$-$C_3$ alkyl)aminocarbonyl, ($C_1$-$C_4$ alkoxy)carbonyl, (aminocarbonyl)$C_1$-$C_3$ alkyl, ($C_1$-$C_4$ alkyl)aminocarbonyl-($C_1$-$C_3$)alkyl, di-($C_1$-$C_3$ alkyl)aminocarbonyl-($C_1$-$C_3$)alkyl, (hydroxycarbonyl)$C_1$-$C_3$ alkyl, ($C_1$-$C_4$ alkoxy)carbonyl-($C_1$-$C_3$)alkyl, ($C_3$-$C_7$ cycloalkoxy)$C_1$-$C_3$ alkyl, ($C_5$-$C_7$ cycloalkenyloxy)$C_1$-$C_3$ alkyl, (aryloxy)$C_1$-$C_3$ alkyl, (heteroaryloxy)$C_1$-$C_3$ alkyl, $C_1$-$C_4$ alkylsulfonyloxy, arylsulfonyloxy, (aryl)$C_1$-$C_3$ alkylsulfonyloxy, trimethylsilyloxy, t-butyldimethylsilyloxy, or cyano, wherein alkyl, alkenyl, alkynyl, cycloalkyl and cycloalkenyl groups or portions optionally may be partly or completely substituted with fluorine or deuterium and may be mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^a$, O, S, CO, SO or $SO_2$; $R^a$ independently represents hydrogen, $C_1$-$C_4$ alkyl or ($C_1$-$C_4$ alkyl)carbonyl, wherein alkyl groups or portions optionally may be partly or completely substituted with fluorine or deuterium.

In other embodiments, $R^{11}$ and $R^{12}$ may be both -D. $R^{13}$ is, for example, -D. One of $R^1$, $R^2$, $R^3$, or $R^5$ may be halogen, e.g., $R^3$ is —Cl. $R^4$ may be Q.

In various embodiments, each $R^1$, $R^2$, $R^3$, $R^4$ and $R^5$ is, independently, —H, -D, group Q, halogen, or an optionally deuterated substituent selected from hydroxyl, optionally substituted alkyl, haloalkyl, optionally substituted alkoxyalkyl, optionally substituted alkoxy, haloalkoxy, optionally substituted alkenyl, optionally substituted alkynyl, optionally substituted cycloalkyl, or optionally substituted alkcycloalkyl; each $R^6$, $R^7$, $R^8$, $R^9$, $R^{10}$, and $R^{10}$ is, independently, —H, -D, halogen, or an optionally deuterated substituent selected from hydroxyl, optionally substituted carbamoyl, optionally substituted alkyl, haloalkyl, optionally substituted alkoxyalkyl, optionally substituted alkoxy, haloalkoxy, optionally substituted alkenyl, optionally substituted alkynyl, optionally substituted cycloalkyl, or optionally substituted alkcycloalkyl; and each $R^{14}$, $R^{15}$, and $R^{16}$ is, independently, —H, -D, optionally substituted alkyl, haloalkyl, optionally substituted alkoxyalkyl, optionally substituted alkoxy, haloalkoxy, optionally substituted alkenyl, optionally substituted alkynyl, optionally substituted cycloalkyl, optionally substituted alkcycloalkyl, —C(O)$R^A$, —C(O)O$R^A$, or —C(O)N$R^A R^B$, wherein each $R^A$ and $R^B$ is, independently, hydrogen, deuterium, or an optionally deuterated substituent selected from optionally substituted alkyl, optionally substituted alkenyl, optionally substituted cycloalkyl, and optionally substituted aryl. For example, $R^4$ is Q and $R^8$ is -D, halogen, or an optionally deuterated substituent selected from hydroxyl, optionally substituted alkyl, haloalkyl, optionally substituted alkoxyalkyl, optionally substituted alkoxy, haloalkoxy, optionally substituted alkenyl, optionally substituted alkynyl, optionally substituted cycloalkyl, or optionally substituted alkcycloalkyl. In further embodiments, $R^2$ is H; $R^3$ is halogen, e.g., Cl; $R^5$, $R^6$, $R^7$, $R^9$, and $R^{10}$ are H; $R^8$ is a deuterated substituent; $R^{11}$ and $R^{12}$ are both -D; $R^{13}$ is -D; and/or $R^{14}$, $R^{15}$, and $R^{16}$ are, independently, selected from H, D, —C(O)$R^A$, —C(O)O$R^A$, or —C(O)N$R^A R^B$.

In some embodiments, $R^8$ is a deuterated substituent.

In some embodiments, the composition includes a compound selected from the group consisting of:

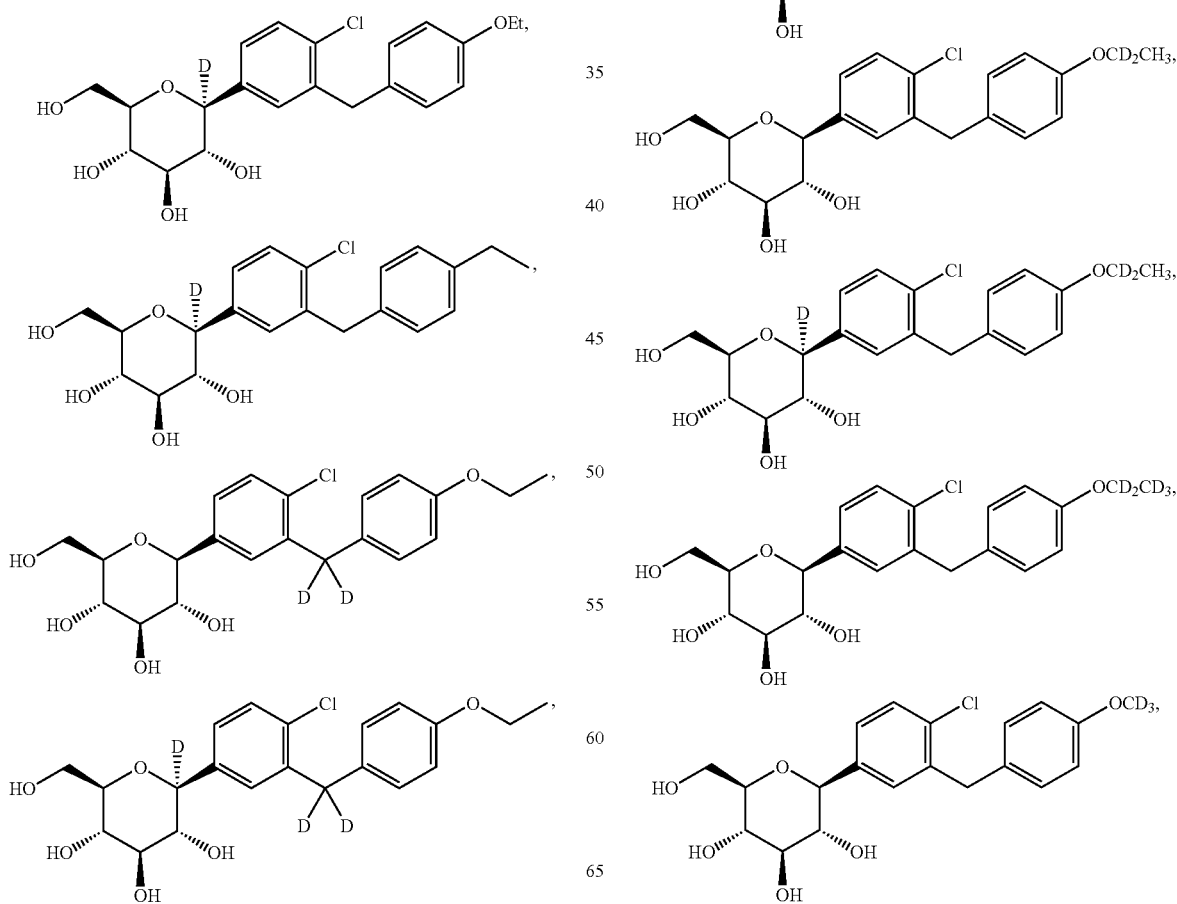

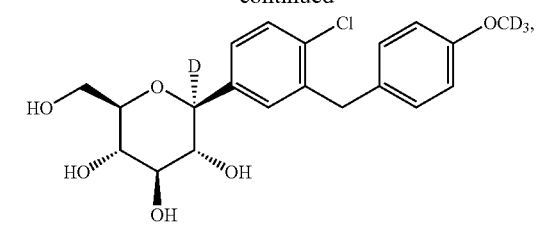
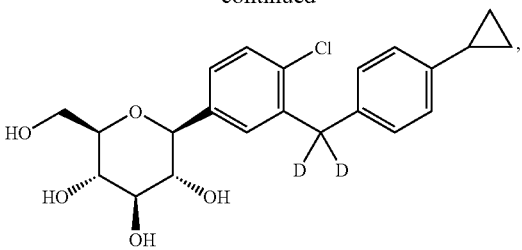
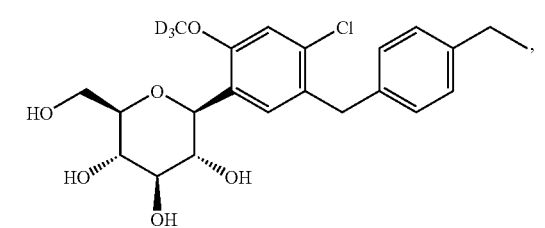
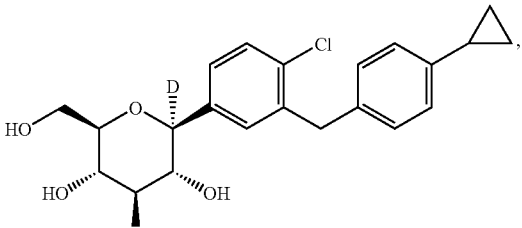
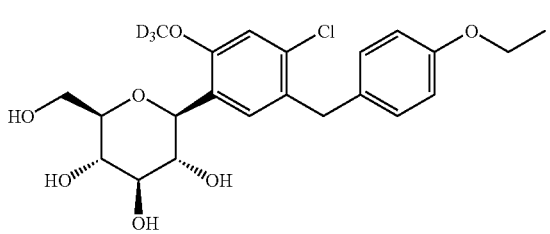
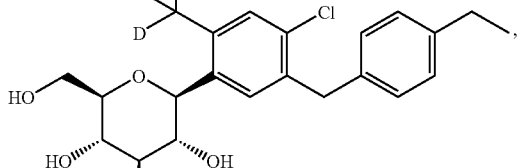
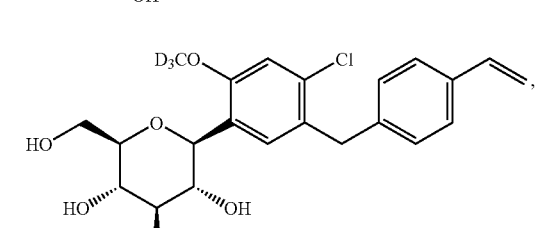
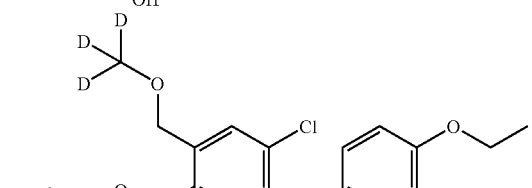
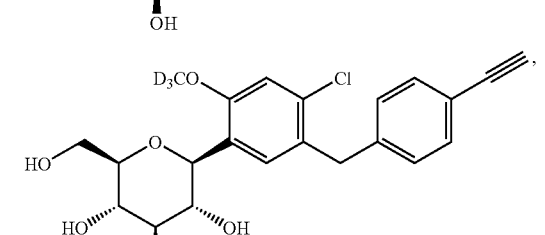
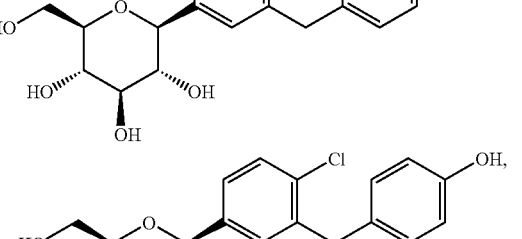
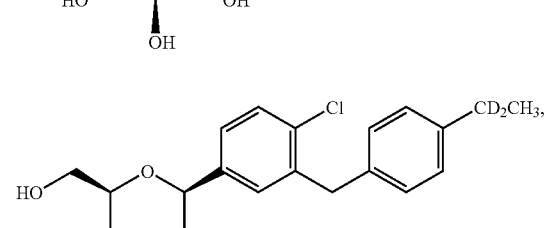
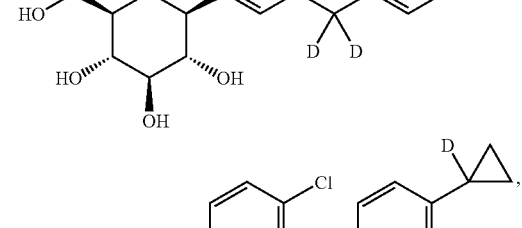
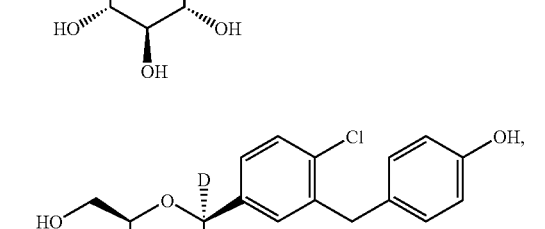
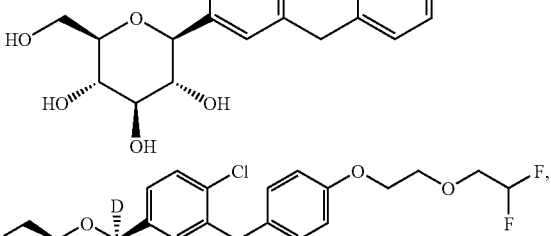

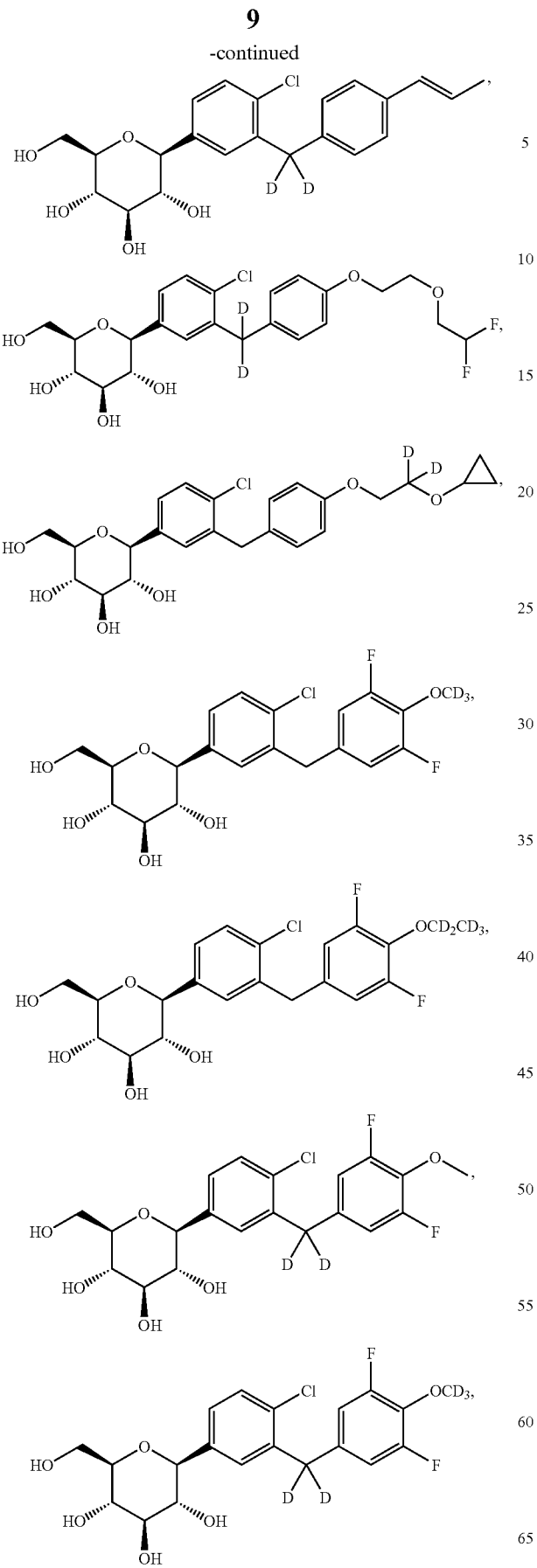

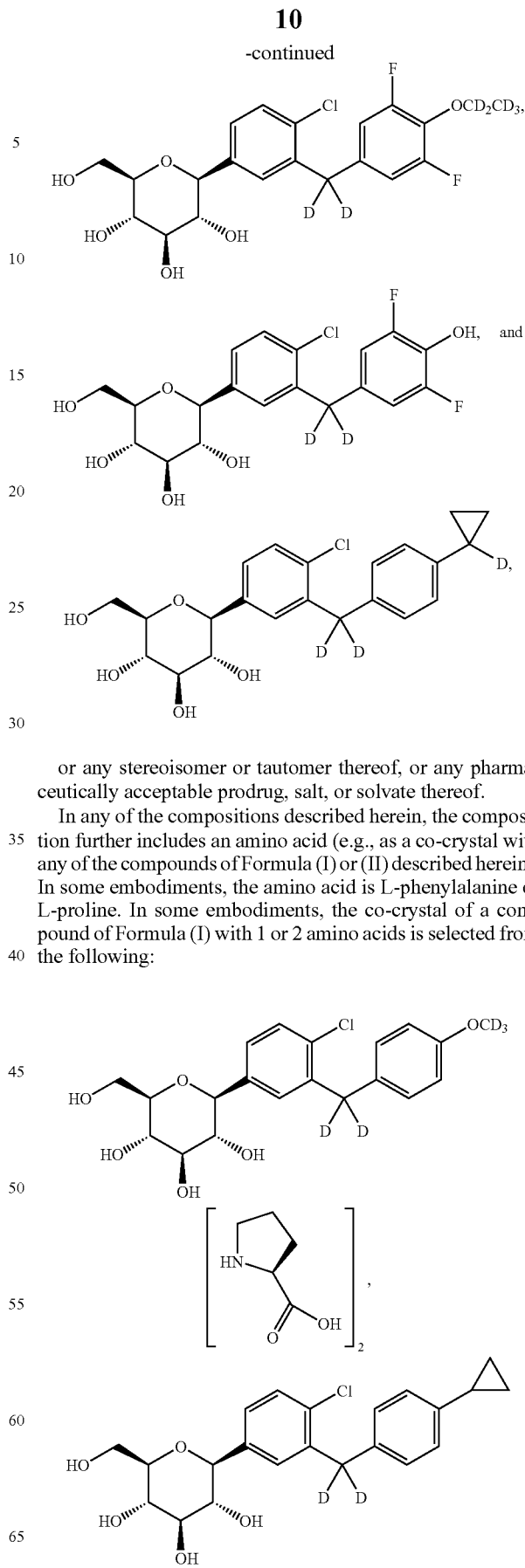

or any stereoisomer or tautomer thereof, or any pharmaceutically acceptable prodrug, salt, or solvate thereof.

In any of the compositions described herein, the composition further includes an amino acid (e.g., as a co-crystal with any of the compounds of Formula (I) or (II) described herein). In some embodiments, the amino acid is L-phenylalanine or L-proline. In some embodiments, the co-crystal of a compound of Formula (I) with 1 or 2 amino acids is selected from the following:

-continued

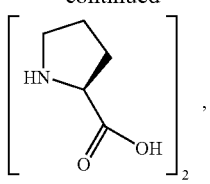,

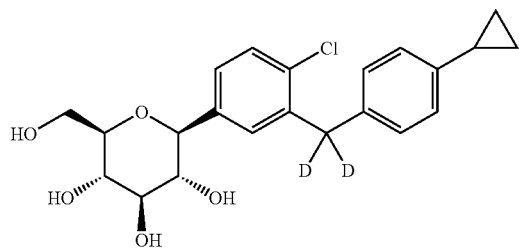

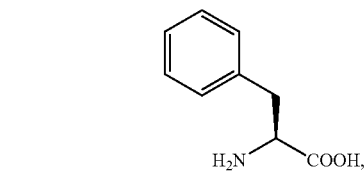

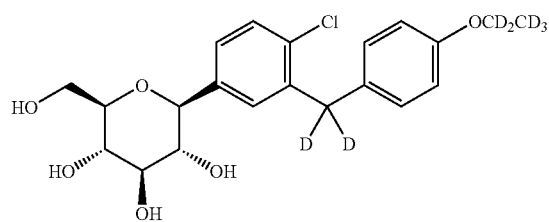

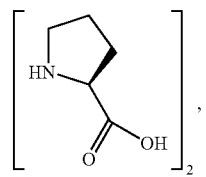,

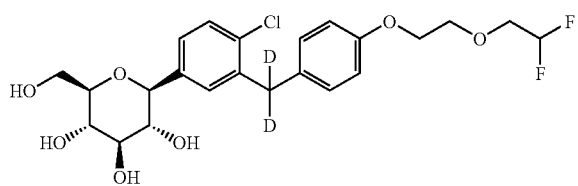

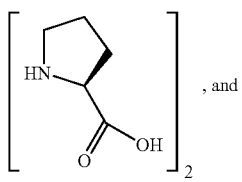, and

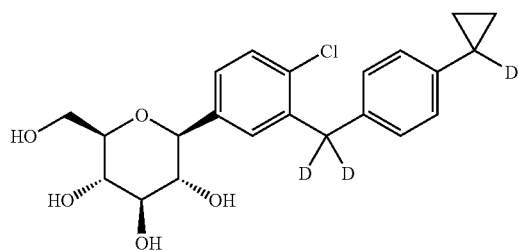

-continued

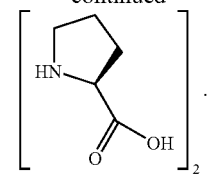.

In some embodiments, $R^1$-$R^{19}$ include 1, 2, 3, 4, or 5 deuterium atoms.

In further embodiments, the composition further includes a pharmaceutically acceptable carrier, and the compound of Formula (I) is present in an effective amount The invention also features compounds having the formula:

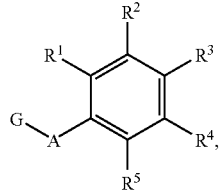

(II)

or any diastereomer, tautomer, or isomer thereof, or any pharmaceutically acceptable prodrug, salt, or solvate thereof, wherein
  each $R^1$, $R^2$, $R^3$, $R^4$ and $R^5$ is, independently, —H, -D, a substituent that is optionally deuterated, or group Q:

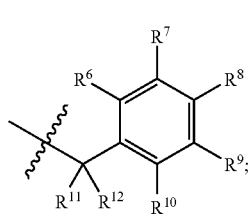

(Q)

A is selected from the group consisting of oxygen and a single bond;
G is selected from the group consisting of:

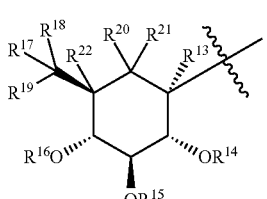

$G^1$

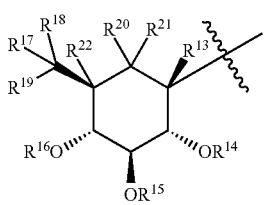

$G^2$

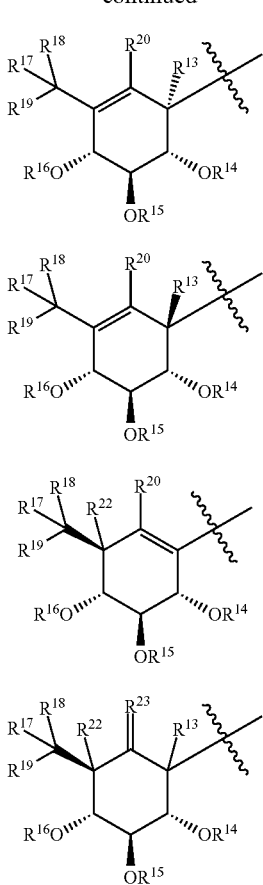

each $R^6$, $R^7$, $R^8$, $R^9$, $R^{10}$, $R^{14}$, $R^{15}$, $R^{16}$, $R^{19}$, and $R^{21}$, is, independently, —H, -D, or a substituent that is optionally deuterated; and each $R^{11}$, $R^{12}$, $R^{13}$, $R^{17}$, $R^{18}$, $R^{20}$, and $R^{22}$ is, independently, —H, -D, or halogen;

wherein one of $R^1$, $R^2$, $R^3$, $R^4$, and $R^5$ is group Q;

$R^{23}$ is $CH_2$, NH, O, or S; and at least one of $R^1$-$R^{23}$ is -D or includes -D. In certain embodiments, G is $G^6$. In further embodiments, $R^{21}$ is hydroxy.

In other embodiments of compounds of formula II:

one of $R^1$, $R^2 R^3$, $R^4$ and $R^5$ is group Q;

one of the remaining groups $R^1$, $R^2$, $R^3$, $R^4$ and $R^5$ represents hydrogen, deuterium, halo, cyano, nitro, amino, hydroxy, $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, $C_1$-$C_6$ alkoxy, $C_3$-$C_{10}$ cycloalkoxy, ($C_1$-$C_6$ alkoxy)$C_1$-$C_6$ alkoxy, $C_5$-$C_7$ cycloalkenyloxy, aryl, heteroaryl, aryloxy, heteroaryloxy, ($C_2$-$C_4$ alkenyl)$C_1$-$C_3$ alkoxy, ($C_2$-$C_4$ alkynyl)$C_1$-$C_3$ alkoxy, (aryl)$C_1$-$C_3$ alkoxy, (heteroaryl)$C_1$-$C_3$ alkoxy, ($C_3$-$C_{10}$ cycloalkyl)$C_1$-$C_3$ alkyl, ($C_3$-$C_{10}$ cycloalkyl)$C_1$-$C_3$ alkoxy, ($C_5$-$C_{10}$ cycloalkenyl)$C_1$-$C_3$ alkyl, ($C_5$-$C_{10}$ cycloalkenyl)$C_1$-$C_3$ alkoxy, ($C_1$-$C_4$ alkoxy)$C_1$-$C_3$ alkyl, ($C_3$-$C_7$ cycloalkoxy)$C_1$-$C_3$ alkyl, ($C_3$-$C_7$ cycloalkoxy)$C_2$-$C_4$ alkenyl, ($C_3$-$C_7$ cycloalkoxy)$C_2$-$C_4$ alkynyl, ($C_3$-$C_7$ cycloalkoxy)$C_1$-$C_3$ alkoxy, ($C_1$-$C_4$ alkylamino)$C_1$-$C_3$ alkyl, di-($C_1$-$C_3$ alkylamino)$C_1$-$C_3$ alkyl, tri-($C_1$-$C_4$ alkyl)silyl-$C_1$-$C_6$ alkyl, tri-($C_1$-$C_4$ alkyl)silyl-$C_2$-$C_6$ alkenyl, tri-($C_1$-$C_4$ alkyl)silyl-$C_2$-$C_6$ alkynyl, tri-($C_1$-$C_4$ alkyl)silyl-$C_1$-$C_6$ alkoxy, ($C_3$-$C_7$ cycloalkyl)$C_2$-$C_5$ alkenyl, ($C_3$-$C_7$ cycloalkyl)$C_3$-$C_5$ alkenyloxy, ($C_3$-$C_7$ cycloalkyl)$C_3$-$C_5$ alkynyloxy, ($C_5$-$C_8$ cycloalkenyl)$C_3$-$C_5$ alkenyloxy, ($C_5$-$C_8$ cycloalkenyl)$C_3$-$C_5$ alkynyloxy, $C_3$-$C_6$ cycloalkylidenmethyl, ($C_1$-$C_4$ alkyl)carbonyl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, ($C_1$-$C_4$ alkoxy)carbonyl, $C_1$-$C_4$ alkylamino, di-($C_1$-$C_3$ alkyl)amino, ($C_1$-$C_4$ alkyl)carbonylamino, arylcarbonylamino, heteroarylcarbonylamino, $C_1$-$C_4$ alkylsulfonylamino, arylsulfonylamino, $C_1$-$C_4$ alkylthio, $C_1$-$C_4$ alkylsulfinyl, $C_1$-$C_4$ alkylsulfonyl, $C_3$-$C_{10}$ cycloalkylthio, $C_3$-$C_{10}$ cycloalkylsulfinyl, $C_3$-$C_{10}$ cycloalkylsulfonyl, $C_5$-$C_{10}$ cycloalkenylthio, $C_5$-$C_{10}$ cycloalkenylsulfinyl, $C_5$-$C_{10}$ cycloalkenylsulfonyl, arylthio, arylsulfinyl or arylsulfonyl;

two of the remaining groups $R^1$, $R^2$, $R^3$, $R^4$ and $R^5$ each independently represent hydrogen, deuterium, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkoxy or $C_3$-$C_{10}$ cycloalkoxy, one of the remaining groups $R^1$, $R^2$, $R^3$, $R^4$ and $R^5$ represents hydrogen or deuterium;

one of the groups $R^6$, $R^7$, $R^8$, $R^9$ and $R^{10}$ represents hydrogen, deuterium, halo, cyano, nitro, amino, hydroxy, $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, $C_1$-$C_6$ alkoxy, $C_3$-$C_{10}$ cycloalkoxy, ($C_1$-$C_6$ alkoxy)$C_1$-$C_6$ alkoxy, $C_5$-$C_7$ cycloalkenyloxy, aryl, heteroaryl, aryloxy, heteroaryloxy, ($C_2$-$C_4$ alkenyl)$C_1$-$C_3$ alkoxy, ($C_2$-$C_4$ alkynyl)$C_1$-$C_3$ alkoxy, (aryl)$C_1$-$C_3$ alkoxy, (heteroaryl)$C_1$-$C_3$ alkoxy, ($C_3$-$C_{10}$ cycloalkyl)$C_1$-$C_3$ alkyl, ($C_3$-$C_{10}$ cycloalkyl)$C_1$-$C_3$ alkoxy, ($C_5$-$C_{10}$ cycloalkenyl)$C_1$-$C_3$ alkyl, ($C_5$-$C_{10}$ cycloalkenyl)$C_1$-$C_3$ alkoxy, ($C_1$-$C_4$ alkoxy)$C_1$-$C_3$ alkyl, ($C_3$-$C_7$ cycloalkoxy)$C_1$-$C_3$ alkyl, ($C_3$-$C_7$ cycloalkoxy)$C_2$-$C_4$ alkenyl, ($C_3$-$C_7$ cycloalkoxy)$C_2$-$C_4$ alkynyl, ($C_3$-$C_7$ cycloalkoxy)$C_1$-$C_3$ alkoxy, ($C_1$-$C_4$ alkylamino)$C_1$-$C_3$ alkyl, di-($C_1$-$C_3$ alkylamino)$C_1$-$C_3$ alkyl, tri-($C_1$-$C_4$ alkyl)silyl-$C_1$-$C_6$ alkyl, tri-($C_1$-$C_4$ alkyl)silyl-$C_2$-$C_6$ alkenyl, tri-($C_1$-$C_4$ alkyl)silyl-$C_2$-$C_6$ alkynyl, tri-($C_1$-$C_4$ alkyl)silyl-$C_1$-$C_6$ alkoxy, ($C_3$-$C_7$ cycloalkyl)$C_2$-$C_5$ alkenyl, ($C_3$-$C_7$ cycloalkyl)$C_3$-$C_5$ alkenyloxy, ($C_3$-$C_7$ cycloalkyl)$C_3$-$C_5$ alkynyloxy, ($C_5$-$C_8$ cycloalkenyl)$C_3$-$C_5$ alkenyloxy, ($C_5$-$C_8$ cycloalkenyl)$C_3$-$C_5$ alkynyloxy, $C_3$-$C_6$ cycloalkylidenmethyl, ($C_1$-$C_4$ alkyl)carbonyl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, ($C_1$-$C_4$ alkoxy)carbonyl, $C_1$-$C_4$ alkylamino, di-($C_1$-$C_3$ alkyl)amino, ($C_1$-$C_4$ alkyl)carbonylamino, arylcarbonylamino, heteroarylcarbonylamino, $C_1$-$C_4$ alkylsulfonylamino, arylsulfonylamino, $C_1$-$C_4$ alkylthio, $C_1$-$C_4$ alkylsulfinyl, $C_1$-$C_4$ alkylsulfonyl, $C_3$-$C_{10}$ cycloalkylthio, $C_3$-$C_{10}$ cycloalkylsulfinyl, $C_3$-$C_{10}$ cycloalkylsulfonyl, $C_5$-$C_{10}$ cycloalkenylthio, $C_5$-$C_{10}$ cycloalkenylsulfinyl, $C_5$-$C_{10}$ cycloalkenylsulfonyl, arylthio, arylsulfinyl or arylsulfonyl, two of the remaining groups $R^6$, $R^7$, $R^8$, $R^9$ and $R^{10}$ each independently represent hydrogen, deuterium, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkoxy or $C_3$-$C_{10}$ cycloalkoxy, two of the remaining groups $R^6$, $R^7$, $R^8 R^9$ and $R^{10}$ each independently represent hydrogen or deuterium;

$R^{14}$, $R^{15}$ and $R^{16}$ each independently represent hydrogen, ($C_1$-$C_{18}$ alkyl)carbonyl, ($C_1$-$C_{18}$ alkyl)oxycarbonyl, arylcarbonyl, aryl-($C_1$-$C_3$ alkyl)carbonyl, ($C_3$-$C_{10}$ cycloalkyl)carbonyl, $C_1$-$C_6$ alkyl, $C_2$-$C_6$ alkenyl, $C_2$-$C_6$ alkynyl, ($C_5$-$C_7$ cycloalkenyl)$C_1$-$C_3$ alkyl, (aryl)$C_1$-$C_3$ alkyl, (heteroaryl)$C_1$-$C_3$ alkyl, $C_3$-$C_7$ cycloalkyl, $C_5$-$C_7$ cycloalkenyl, aryl, heteroaryl, ($C_3$-$C_7$ cycloalkyl)$C_1$-$C_3$ alkyl, ($C_5$-$C_7$ cycloalkenyl)$C_1$-$C_3$ alkyl, (aryl)$C_1$-$C_3$ alkyl, (heteroaryl)$C_1$-$C_3$ alkyl, $C_1$-$C_4$ alkylsulfonyl, arylsulfonyl, (aryl)$C_1$-$C_3$ alkylsulfonyl, trimethylsilyl or t-butyldimethylsilyl, $R^{19}$ independently represents hydroxy, ($C_1$-$C_{18}$ alkyl)carbonyloxy, ($C_1$-$C_{18}$ alkyl)oxycarbonyloxy, arylcarbonyloxy, aryl-($C_1$-$C_3$ alkyl)carbonyloxy, ($C_3$-$C_{10}$ cycloalkyl)carbonyloxy, hydrogen, deuterium, halo, $C_1$-$C_6$ alkyl, $C_2$-$C_6$ alkenyl, $C_2$-$C_6$ alkynyl, ($C_3$-$C_{10}$ cycloalkyl)$C_1$-$C_3$ alkyl, ($C_5$-$C_7$ cycloalkenyl)$C_1$-$C_3$ alkyl, (aryl)$C_1$-$C_3$ alkyl, (heteroaryl)$C_1$-$C_3$ alkyl, $C_1$-$C_6$ alkoxy, $C_2$-$C_6$ alkenyloxy, $C_2$-$C_6$ alkynyloxy, $C_3$-$C_7$ cycloalkoxy, $C_5$-$C_7$ cycloalkenyloxy, aryloxy, heteroaryloxy, ($C_3$-$C_7$ cycloalkyl)$C_1$-$C_3$ alkoxy, ($C_5$-$C_7$ cycloalkenyl)$C_1$-$C_3$ alkoxy, (aryl)$C_1$-$C_3$ alkoxy, (heteroaryl) $C_1$-$C_3$ alkoxy, aminocarbonyl, hydroxycarbonyl, ($C_1$-$C_4$ alkyl)aminocarbonyl, di-($C_1$-$C_3$ alkyl)aminocarbonyl, ($C_1$-$C_4$ alkoxy)carbonyl, (aminocarbonyl)$C_1$-$C_3$ alkyl, ($C_1$-$C_4$ alkyl)aminocarbonyl-($C_1$-$C_3$)alkyl, di-($C_1$-$C_3$ alkyl)aminocarbonyl-($C_1$-$C_3$)alkyl, (hydroxycarbonyl)$C_1$-$C_3$ alkyl, ($C_1$-$C_4$ alkoxy)carbonyl-($C_1$-$C_3$)alkyl, ($C_3$-$C_7$ cycloalkoxy) $C_1$-$C_3$ alkyl, ($C_5$-$C_7$ cycloalkenyloxy)$C_1$-$C_3$ alkyl, (aryloxy) $C_1$-$C_3$ alkyl, (heteroaryloxy)$C_1$-$C_3$ alkyl, $C_1$-$C_4$ alkylsulfonyloxy, arylsulfonyloxy, (aryl)$C_1$-$C_3$ alkylsulfonyloxy, trimethylsilyloxy, t-butyldimethylsilyloxy, or cyano; and $R^{21}$ is H, D, or hydroxy;

wherein alkyl, alkenyl, alkynyl, cycloalkyl and cycloalkenyl groups or portions optionally may be partly or completely substituted with fluorine or deuterium and may be mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^a$, O, S, CO, SO or $SO_2$; $R^a$ independently represents hydrogen, $C_1$-$C_4$ alkyl or ($C_1$-$C_4$ alkyl)carbonyl, wherein alkyl groups or portions optionally may be partly or completely substituted with fluorine or deuterium.

In various embodiments, G is $G^1$, $R^{22}$ is -D, and/or $R^{11}$ and $R^{12}$ are both -D. In some embodiments, $G^1$ has the following structure:

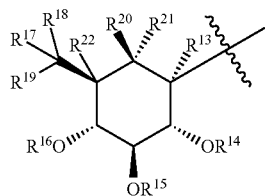

In other embodiments, each $R^1$, $R^2$, $R^3$, $R^4$ and $R^5$ is, independently, —H, -D, group Q, halogen, or an optionally deuterated substituent selected from hydroxyl, optionally substituted alkyl, haloalkyl, optionally substituted alkoxyalkyl, optionally substituted alkoxy, haloalkoxy, optionally substituted alkenyl, optionally substituted alkynyl, optionally substituted cycloalkyl, or optionally substituted alkcycloalkyl; each $R^6$, $R^7$, $R^8$, $R^9$, $R^{10}$, and $R^{10}$ is, independently, —H, -D, halogen, or an optionally deuterated substituent selected from hydroxyl, optionally substituted carbamoyl, optionally substituted alkyl, haloalkyl, optionally substituted alkoxyalkyl, optionally substituted alkoxy, haloalkoxy, optionally substituted alkenyl, optionally substituted alkynyl, optionally substituted cycloalkyl, or optionally substituted alkcycloalkyl; and each $R^{14}$, $R^{15}$, and $R^{16}$ is, independently, hydrogen, deuterium, optionally substituted alkyl, haloalkyl, optionally substituted alkoxyalkyl, optionally substituted alkoxy, haloalkoxy, optionally substituted alkenyl, optionally substituted alkynyl, optionally substituted cycloalkyl, optionally substituted alkcycloalkyl, —C(O)$R^A$, —C(O)O$R^A$, or —C(O)N$R^A R^B$, wherein each $R^A$ and $R^B$ is, independently, hydrogen, deuterium, or an optionally deuterated substituent selected from optionally substituted alkyl, optionally substituted alkenyl, optionally substituted cycloalkyl, and optionally substituted aryl. For example, $R^A$ is Q and $R^B$ is an optionally deuterated substituent selected from optionally substituted alkyl and optionally substituted alkoxy.

In some embodiments, the compound of Formula (II) is selected from the following group:

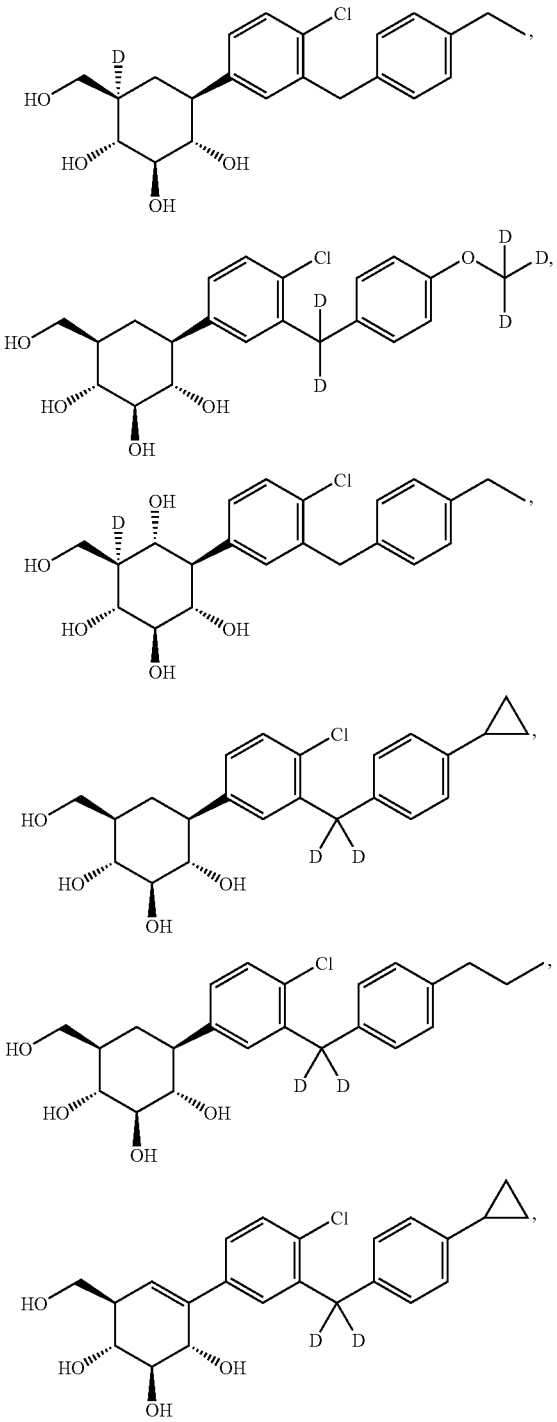

-continued

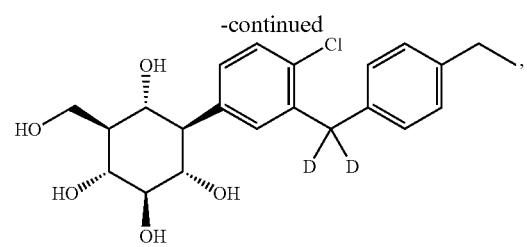
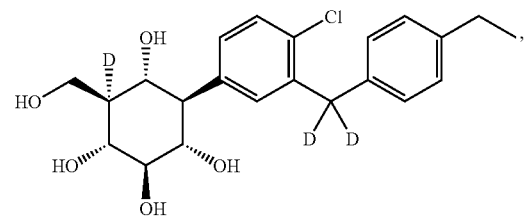
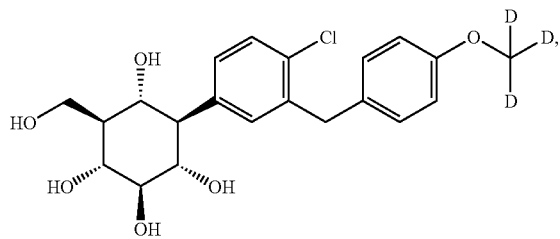
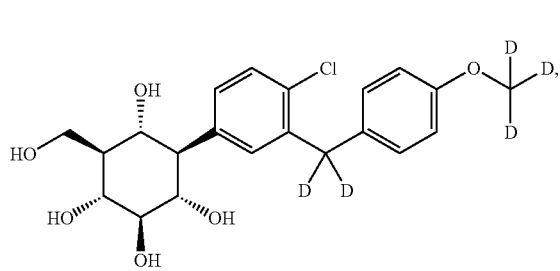
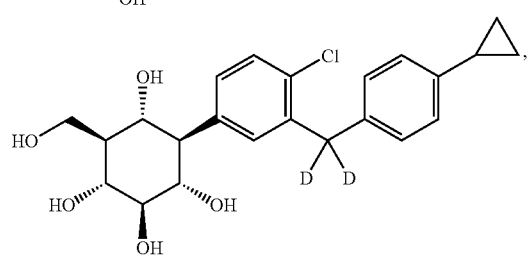
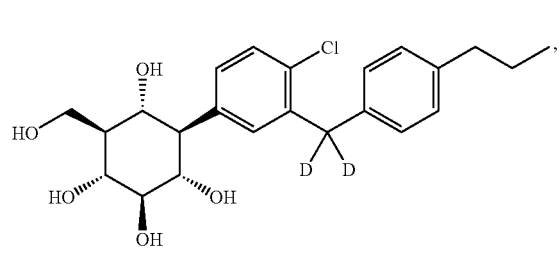
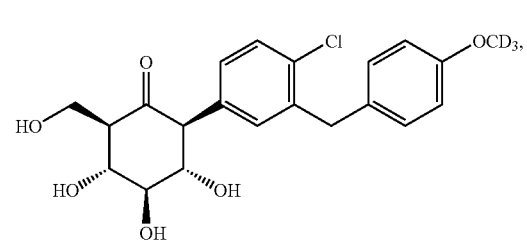

-continued

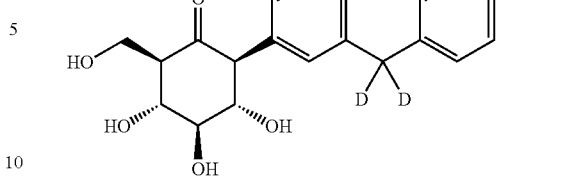
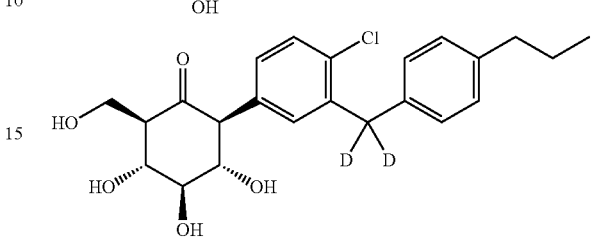
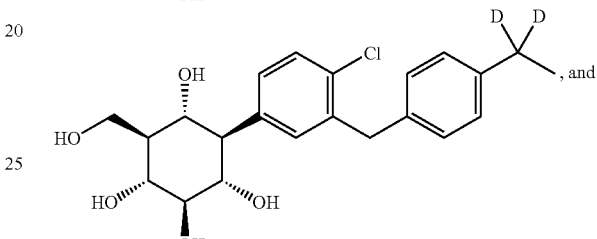
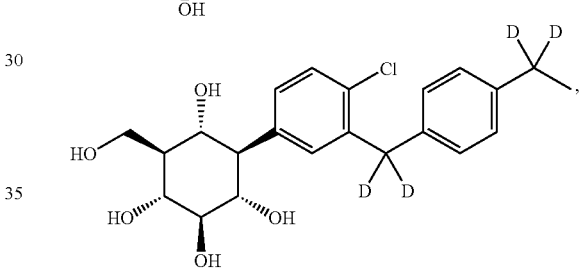

or any stereoisomer or tautomer thereof, or any pharmaceutically acceptable prodrug, salt, or solvate thereof.

In certain embodiments, the composition further includes a pharmaceutically acceptable carrier, and the compound of Formula (II) is present in an effective amount.

Where a group is described as having optional substituents (e.g., any of $R^1$-$R^{19}$ in Formula (I) or any of $R^1$-$R^{21}$ in Formula (II)), such substituents may be selected from the group consisting of halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl)$C_1$-$C_6$ alkoxy, ($C_3$-$C_8$ cycloalkoxy)$C_1$-$C_6$ alkoxy, $C_3$-$C_7$ heterocyclyl, ($C_3$-$C_7$ heterocyclyl)$C_1$-$C_6$ alkyl, ($C_3$-$C_7$ heterocyclyl)$C_2$-$C_6$ alkenyl, ($C_3$-$C_7$ heterocyclyl)$C_1$-$C_6$ alkoxy, ($C_1$-$C_6$ alkoxy)$C_1$-$C_6$ alkoxy, ($C_1$-$C_6$ haloalkoxy)$C_1$-$C_6$ alkoxy, hydroxy, carboxy, oxo, thio, $C_1$-$C_6$ alkylthio, aryl, heteroaryl, aryloxy, heteroaryloxy, aralkyl, aralkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl, or any substituent group as described herein. Such substituents may be undeuterated or deuterated. In a deuterated substituent, at least one hydrogen has been replaced with deuterium; e.g., 2, 3, 4, 5, or 6 hydrogens are replaced with deuterium. In some deuterated substituents, all hydrogens have been replaced with deuterium. In some embodiments, a substituent is not further substituted. Additional optional substituents for various groups are described herein. Compounds of the invention may include, for example, 1-5 deuterium atoms.

The invention further features compositions including any of the above compounds of formula I or II and having an isotopic enrichment factor for deuterium of at least 5, e.g., at least 500, 1000, or 3000. The invention also features pharmaceutical compositions including any of the above compounds of formula I or II and a pharmaceutically acceptable carrier and having an isotopic enrichment factor for deuterium of at least 5, e.g., at least 500, 1000, or 3000. A pharmaceutical composition is formulated, for example, for nonimmediate release, e.g., as an oral, parenteral, systemic, or buccal administration, or as a depot preparation.

Any of the compounds and compositions of the invention described herein may also be employed in methods for treating or preventing a disease affected by inhibition of the sodium-dependent glucose transporter (SGLT) such as type 1 diabetes mellitus, type 2 diabetes mellitus, hyperglycemia, diabetic complications, insulin resistance, metabolic syndrome (Syndrome X), hyperinsulinemia, hypertension, hyperuricemia, obesity, edema, dyslipidemia, chronic heart failure, or atherosclerosis. These methods may further include administering a second therapeutic agent, e.g., an antidiabetic agent, a lipid-lowering/lipid-modulating agent, an agent for treating diabetic complications, an anti-obesity agent, an antihypertensive agent, an antihyperuricemic agent, an agent for treating chronic heart failure, or an agent for treating atherosclerosis.

In another aspect, the invention features a method of enriching the deuterium content of a diarylmethylene compound, wherein said method includes (a) combining:
   (i) a diarylmethylene compound having a structure according to

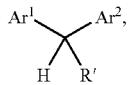

wherein R' is H or D, and each $Ar^1$ and $Ar^2$ is, independently, an optionally substituted aryl group; and
   (ii) a mixture that includes deuterium oxide and sodium hydride, e.g., dispersed in mineral oil; and
   (iii) a phase-transfer catalyst;
   wherein the combination of reagents (i), (ii), and (iii) results in the incorporation of deuterium at the methylene bridge of said diarylmethylene compound; and
(b) optionally combining the product obtained in step (a) one or more times with the reagents (ii) and (iii).

In some embodiments, the mixture of (ii) further includes mineral oil. In other embodiments, the mixture of step (a) stirs at 20-30° C. for at least 30 minutes (e.g., for 1-24 hours).

In some embodiments, the sodium hydride is dispersed in mineral oil as a 50%-75% (w/w) dispersion, e.g., a 60% dispersion.

In other embodiments, the phase-transfer catalyst is a tetraalkylammonium salt, e.g., tetrabutylammonium bisulfate.

In still other embodiments, R' and R" are each optionally substituted phenyl. In further embodiments, each R' and R" has the following structure:

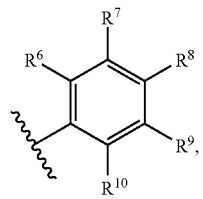

wherein each $R^6$, $R^7$, $R^8$, $R^9$, and $R^{10}$ is, independently, hydrogen, deuterium, halo, cyano, nitro, amino, hydroxy, $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, $C_1$-$C_6$ alkoxy, $C_3$-$C_{10}$ cycloalkoxy, ($C_1$-$C_6$ alkoxy)$C_1$-$C_6$ alkoxy, $C_5$-$C_7$ cycloalkenyloxy, aryl, heteroaryl, aryloxy, heteroaryloxy, ($C_2$-$C_4$ alkenyl)$C_1$-$C_3$ alkoxy, ($C_2$-$C_4$ alkynyl)$C_1$-$C_3$ alkoxy, (aryl)$C_1$-$C_3$ alkoxy, (heteroaryl)$C_1$-$C_3$ alkoxy, ($C_3$-$C_{10}$ cycloalkyl)$C_1$-$C_3$ alkyl, ($C_3$-$C_{10}$ cycloalkyl)$C_1$-$C_3$ alkoxy, ($C_5$-$C_{10}$ cycloalkenyl)$C_1$-$C_3$ alkyl, ($C_5$-$C_{10}$ cycloalkenyl)$C_1$-$C_3$ alkoxy, ($C_1$-$C_4$ alkoxy)$C_1$-$C_3$ alkyl, ($C_3$-$C_7$ cycloalkoxy)$C_1$-$C_3$ alkyl, ($C_3$-$C_7$ cycloalkoxy)$C_2$-$C_4$ alkenyl, ($C_3$-$C_7$ cycloalkoxy)$C_2$-$C_4$ alkynyl, ($C_3$-$C_7$ cycloalkoxy)$C_1$-$C_3$ alkoxy, ($C_1$-$C_4$ alkylamino)$C_1$-$C_3$ alkyl, di-($C_1$-$C_3$ alkylamino)$C_1$-$C_3$ alkyl, tri-($C_1$-$C_4$ alkyl)silyl-$C_1$-$C_6$ alkyl, tri-($C_1$-$C_4$ alkyl)silyl-$C_2$-$C_6$ alkenyl, tri-($C_1$-$C_4$ alkyl)silyl-$C_2$-$C_6$ alkynyl, tri-($C_1$-$C_4$ alkyl)silyl-$C_1$-$C_6$ alkoxy, ($C_3$-$C_7$ cycloalkyl)$C_2$-$C_5$ alkenyl, ($C_3$-$C_7$ cycloalkyl)$C_3$-$C_5$ alkenyloxy, ($C_3$-$C_7$ cycloalkyl)$C_3$-$C_5$ alkynyloxy, ($C_5$-$C_8$ cycloalkenyl)$C_3$-$C_5$ alkenyloxy, ($C_5$-$C_8$ cycloalkenyl)$C_3$-$C_5$ alkynyloxy, $C_3$-$C_6$ cycloalkylidenmethyl, ($C_1$-$C_4$ alkyl)carbonyl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, ($C_1$-$C_4$ alkoxy)carbonyl, $C_1$-$C_4$ alkylamino, di-($C_1$-$C_3$ alkyl)amino, ($C_1$-$C_4$ alkyl)carbonylamino, arylcarbonylamino, heteroarylcarbonylamino, $C_1$-$C_4$ alkylsulfonylamino, arylsulfonylamino, $C_1$-$C_4$ alkylthio, $C_1$-$C_4$ alkylsulfinyl, $C_1$-$C_4$ alkylsulfonyl, $C_3$-$C_{10}$ cycloalkylthio, $C_3$-$C_{10}$ cycloalkylsulfinyl, $C_3$-$C_{10}$ cycloalkylsulfonyl, $C_5$-$C_{10}$ cycloalkenylthio, $C_5$-$C_{10}$ cycloalkenylsulfinyl, $C_5$-$C_{10}$ cycloalkenylsulfonyl, arylthio, arylsulfinyl or arylsulfonyl, and wherein alkyl, alkenyl, alkynyl, cycloalkyl and cycloalkenyl groups or portions optionally may be partly or completely substituted with fluorine or deuterium and may be mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^a$, O, S, CO, SO or $SO_2$; $R^a$ independently represents hydrogen, $C_1$-$C_4$ alkyl or ($C_1$-$C_4$ alkyl)carbonyl, wherein alkyl groups or portions optionally may be partly or completely substituted with fluorine or deuterium.

Other features and advantages will be apparent from the following description and the claims.

DEFINITIONS

The terms "acyl" as used herein, represents an alkanoyl or aryloyl group as defined herein.

The term "alkanoyl," as used herein, represents an alkyl group, as defined herein, or hydrogen attached to the parent molecular group through a carbonyl group, as defined herein, and is exemplified by formyl, acetyl, propionyl, butanoyl and the like. Exemplary unsubstituted alkanoyl groups include from 2 to 7 carbons.

The term "$C_{x-y}$ alkaryl," as used herein, represents a chemical substituent of formula —RR', where R is an alkylene group of x to y carbons and R' is an aryl group as defined elsewhere herein. Similarly, by the term "$C_{x-y}$ alkheteroaryl" is meant a chemical substituent of formula —RR", where R is an alkylene group of x to y carbons and R" is a heteroaryl group as defined elsewhere herein. Other groups preceded by the prefix "alk-" are defined in the same manner. Exemplary unsubstituted alkaryl groups are of from 7 to 16 carbons.

The term "alkcycloalkyl" represents a cycloalkyl group attached to the parent molecular group through an alkylene group.

The term "alkenyl," as used herein, represents monovalent straight or branched chain groups of, unless otherwise specified, from 2 to 6 carbons containing one or more carbon-carbon double bonds. The radical may be a linear or branched chain, in the E or Z form, and where specified, optionally substituted with one to three substituents as defined herein. Illustrative examples of alkenyl groups include, but are not limited to, vinyl, 1-propenyl, 2-propenyl, isopropenyl, 1-butenyl, 2-butenyl, isobutenyl, 2-methyl-1-propenyl, 1-pentenyl, 2-pentenyl, 4-methyl-2-pentenyl, 1,3-pentadienyl, 2,4-pentadienyl, 1,3-butadienyl and the like. Preferred alkenyl groups include vinyl, 1-propenyl and 2-propenyl. Preferred optional substituents include deuterium, halo, methoxy, ethoxy, cyano, nitro, and amino. "Alkenyloxy" represents a chemical substituent of formula —OR, where R is an alkenyl group of 1 to 6 carbons.

The term "alkheterocyclyl" represents a heterocyclic group attached to the parent molecular group through an alkylene group. Exemplary unsubstituted alkheterocyclyl groups are of from 2 to 14 carbons.

The term "alkoxy" represents a chemical substituent of formula —OR, where R is an alkyl group of 1 to 6 carbons, unless otherwise specified. Illustrative examples of alkoxy groups include, but are not limited to, methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy, octoxy and the like. Preferred alkoxy groups include methoxy and ethoxy.

The term "alkoxyalkyl" represents an alkyl group that is substituted with an alkoxy group. Exemplary unsubstituted alkoxyalkyl groups include between 2 to 12 carbons.

The terms "alkyl" and the prefix "alk-," as used herein, are inclusive of both straight chain and branched chain saturated groups of from 1 to 6 carbons, unless otherwise specified. Alkyl groups are exemplified by methyl, ethyl, n- and isopropyl, n-, sec-, iso- and tert-butyl, n-pentyl, isopentyl (isoamyl), neopentyl, and n-hexyl. Preferred alkyl groups include methyl, ethyl, n-propyl and isopropyl. Alkyl groups may be optionally substituted with one, two, three or, in the case of alkyl groups of two carbons or more, four substituents independently selected from the group consisting of: (1) alkoxy of one to six carbon atoms; (2) alkylsulfinyl of one to six carbon atoms; (3) alkylsulfonyl of one to six carbon atoms; (4) amino; (5) aryl; (6) aralkoxy; (7) aryloyl; (8) azido; (9) carboxaldehyde; (10) cycloalkyl of three to eight carbon atoms; (11) halo; (12) heterocyclyl; (13) (heterocycle)oxy; (14) (heterocycle)oyl; (15) hydroxyl; (16) N-protected amino; (17) nitro; (18) oxo; (19) spirocyclyl of three to eight carbon atoms; (20) thioalkoxy of one to six carbon atoms; (21) thiol; (22) —$CO_2R^A$, where $R^A$ is selected from the group consisting of (a) alkyl, (b) aryl, (c) alkaryl, and (d) hydrogen, where the alkylene group is of one to six carbon atoms; (23) —$C(O)NR^BR^C$, where each of $R^B$ and $R^C$ is, independently, selected from the group consisting of (a) hydrogen, (b) alkyl, (c) aryl and (d) alkaryl, where the alkylene group is of one to six carbon atoms; (24) —$SO_2R^D$, where $R^D$ is selected from the group consisting of (a) alkyl, (b) aryl and (c) alkaryl, where the alkylene group is of one to six carbon atoms; (25) —$SO_2NR^ER^F$, where each of $R^E$ and $R^F$ is, independently, selected from the group consisting of (a) hydrogen, (b) alkyl, (c) aryl and (d) alkaryl, where the alkylene group is of one to six carbon atoms; and (26) —$NR^GR^H$, where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon, atoms, wherein in one embodiment no two groups are bound to the nitrogen atom through a carbonyl group or a sulfonyl group. Preferred optional substituents include deuterium, halo, methoxy, ethoxy, cyano, nitro and amino.

The term "alkylene," as used herein, represents a saturated divalent hydrocarbon group derived from a straight or branched chain saturated hydrocarbon by the removal of two hydrogen atoms, and is exemplified by methylene, ethylene, isopropylene, and the like.

The term "alkylsulfinyl," as used herein, represents an alkyl group attached to the parent molecular group through an —S(O)— group. Exemplary unsubstituted alkylsulfinyl groups are of from 1 to 6 carbons.

The term "alkylsulfonyl," as used herein, represents an alkyl group attached to the parent molecular group through an —$SO_2$— group. Exemplary unsubstituted alkylsulfonyl groups are of from 1 to 6 carbons.

The term "alkylsulfinylalkyl," as used herein, represents an alkyl group, as defined herein, substituted by an alkylsulfinyl group. Exemplary unsubstituted alkylsulfinylalkyl groups are of from 2 to 12 carbons.

The term "alkylsulfonylalkyl," as used herein, represents an alkyl group, as defined herein, substituted by an alkylsulfonyl group. Exemplary unsubstituted alkylsulfonylalkyl groups are of from 2 to 12 carbons.

The term "alkynyl," as used herein, represents monovalent straight or branched chain groups of from two to six carbon atoms containing a carbon-carbon triple bond. An alkynyl group may be a linear or branched chain and, where specified, optionally substituted with one to three substituents as herein. Illustrative examples of alkynyl groups include, but are not limited to, ethynyl, 1-propynyl, 2-propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like. Preferred alkynyl groups include ethynyl, 1-propynyl and 2-propynyl. Preferred optional substituents include deuterium, halo, methoxy, ethoxy, cyano, nitro and amino. "Alkynyloxy" represents a chemical substituent of formula —OR, where R is an alkynyl group of 1 to 6 carbons.

The term "amino," as used herein, represents —$NH_2$, —$NHR^{N1}$, or —$N(R^{N1})_2$, wherein each $R^{N1}$ is, independently, H, OH, $NO_2$, $NH_2$, $NR^{N2}_2$, $SO_2OR^{N2}$, $SO_2R^{N2}$, $SOR^{N2}$, optionally substituted $C_{1-6}$ alkyl, optionally substituted $C_{1-6}$ alkoxy, optionally substituted $C_{1-4}$ alkcycloalkyl, optionally substituted $C_{1-4}$ alkaryl, optionally substituted $C_{1-4}$ alkheterocyclyl, optionally substituted $C_{1-4}$ alkheteroaryl, optionally substituted $C_{3-8}$ cycloalkyl, optionally substituted $C_{2-9}$ heterocyclyl, or an N-protecting group, or two $R^{N1}$ combine to form an optionally substituted $C_{2-9}$ heterocyclyl, or an N-protecting group, and wherein each $R^{N2}$ is, independently, H, an optionally substituted alkyl group, or an optionally substituted aryl group. In a preferred embodiment, amino is —$NH_2$, or —$NHR^{N1}$, wherein each $R^{N1}$ is, independently, OH, $NO_2$, $NH_2$, $NR^{N2}{}_2$, $SO_2 OR^{N2}$, $SO_2R^{N2}$, $SOR^{N2}$, an optionally substituted alkyl group, or an optionally substituted aryl group, and each $R^{N2}$ can be H, an optionally substituted alkyl group, or an optionally substituted aryl group.

As used herein, "amino acid" refers to a compound comprising an amino functional group and a carboxylic functional group. Types of amino acids include "α-amino acids," wherein the amino and carboxylic groups are attached to the same carbon. In "β-amino acids," the carbon to which the amino group is attached is adjacent to the carbon to which the carboxylic group is attached, and in "γ-amino acids," there is an additional intervening carbon. Amino acids can have the L-configuration (for example, natural amino acids have the L-configuration) or the D-configuration. Amino acids include natural amino acids and unnatural amino acids. A "natural amino acid" refers to an amino acid that is naturally produced or found in a mammal. Natural amino acids can be encoded by the standard genetic code or may result from, for example, post-translational modifications. Natural amino acids include the twenty proteinogenic L-amino acids (Alanine (A), Cysteine (C), Serine (S), Threonine (T), Aspartic Acid (D), Glutamic Acid (E), Asparagine (N), Glutamine (Q), Histidine (H), Arginine (R), Lysine (K), Isoleucine (I), Leucine (L), Methionine (M), Valine (V), Phenylalanine (F), Tyrosine (Y), Tryptophan (W), Glycine (G), and Proline (P)). Preferred natural amino acids for use in any of the compositions and methods of the invention include L-phenylalanine and L-proline. An "unnatural amino acid" is an amino acid that is not naturally produced (e.g., encoded by the genetic code or resulting from a posttranslational modification) or naturally found in a mammal. Unnatural amino acids include amino acids that normally do not occur in proteins (e.g., an α-amino acid having the D-configuration, or a (D,L)-isomeric mixture thereof), homologues of naturally occurring amino acids, an α,α-disubstituted analogue of a naturally occurring amino acid, or an α-amino acid wherein the amino acid side chain has been shortened by one or two methylene groups or lengthened to up to 10 carbon atoms.

The term "aminoalkyl," as used herein, represents an alkyl group, as defined herein, substituted by an amino group.

As used herein, the term "aralkoxy" refers to an alkoxy radical of one to six carbons as described above substituted with an aryl group as described herein. Exemplary unsubstituted aralkoxy groups are of from 7 to 16 carbons.

The term "aryl," as used herein, represents a mono- or bicyclic carbocyclic ring system having six to ten carbon atoms form one or two aromatic rings and is exemplified by phenyl, naphthyl, 1,2-dihydronaphthyl, 1,2,3,4-tetrahydronaphthyl, fluorenyl, indanyl, indenyl, and the like, and may be optionally substituted with one, two, three, four, or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —$(CH_2)_q CO_2 R^A$, where q is an integer of from zero to four, and $R^A$ is selected from the group consisting of (a) alkyl, (b) aryl, (c) alkaryl, and (d) hydrogen, where the alkylene group is of one to six carbon atoms; (36) —$(CH_2)_q CONR^B R^C$, where q is an integer of from zero to four and where $R^B$ and $R^C$ are independently selected from the group consisting of (a) hydrogen, (b) alkyl, (c) aryl, and (d) alkaryl, where the alkylene group is of one to six carbon atoms; (37) —$(CH_2)_q SO_2 R^D$, where q is an integer of from zero to four and where $R^D$ is selected from the group consisting of (a) alkyl, (b) aryl, and (c) alkaryl, where the alkylene group is of one to six carbon atoms; (38) —$(CH_2)_q SO_2 NR^E R^F$, where q is an integer of from zero to four and where each of $R^E$ and $R^F$ is, independently, selected from the group consisting of (a) hydrogen, (b) alkyl, (c) aryl, and (d) alkaryl, where the alkylene group is of one to six carbon atoms; (39) —$(CH_2)_q NR^G R^H$, where q is an integer of from zero to four and where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, wherein in one embodiment no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; (46) aralkoxy; and (47) deuterium. Preferred aryl groups are phenyl and naphthyl, optionally mono- or disubstituted by identical or different substituents selected from deuterium, halo, cyano, $C_1$-$C_3$ alkyl, $C_3$-$C_6$ cycloalkyl, difluoromethyl, trifluoromethyl, $C_1$-$C_3$ alkoxy, difluoromethoxy and trifluoromethoxy.

The term "aryloxy" represents a chemical substituent of formula —OR', where R' is an aryl group of 6 to 18 carbons, unless otherwise specified.

The term "aryloyl" as used herein, represents an aryl group that is attached to the parent molecular group through a carbonyl group. Exemplary unsubstituted aryloyl groups are of 7 or 11 carbons.

The term "azido" represents an $N_3$ group, which can also be represented as N=N=N.

The term "azidoalkyl" represents an azido group attached to the parent molecular group through an alkyl group.

As used herein, the term "carbamoyl" refers to a monovalent radical of the form —$OC(O)N(R^1)(R^2)$, wherein each $R^1$ and $R^2$ is independently selected from hydrogen, deuterium, $C_1$-$C_6$ alkyl, $C_2$-$C_6$ alkenyl, $C_3$-$C_6$ cycloalkyl, or aryl as such terms are defined herein, and where the $C_1$-$C_6$ alkyl, $C_2$-$C_6$ alkenyl, $C_3$-$C_6$ cycloalkyl, or aryl is optionally deuterated.

As used herein, the term "carbonate ester" refers to a —OC(O)OR group, wherein R is hydrogen, deuterium, $C_1$-$C_6$ alkyl, $C_2$-$C_6$ alkenyl, $C_3$-$C_6$ cycloalkyl, or aryl as such terms are defined herein, and where the $C_1$-$C_6$ alkyl, $C_2$-$C_6$ alkenyl, $C_3$-$C_6$ cycloalkyl, or aryl is optionally deuterated.

The term "carbonyl," as used herein, represents a C(O) group, which can also be represented as C=O.

The term "carboxyaldehyde" represents a CHO group.

The term "carboxaldehydealkyl" represents a carboxyaldehyde group attached to the parent molecular group through an alkylene group.

As used herein, the term "cycloalkenyl" alone or in combination refers to a monovalent alicyclic hydrocarbon group having three or more carbons forming a carbocyclic ring and at least one carbon-carbon double bond and, where specified, optionally substituted with one to three substituents as defined herein. Illustrative examples of cycloalkenyl groups include, but are not limited to, cyclopentenyl, cyclohexenyl and the like. Preferred optional substituents include deuterium, halo, methyl, ethyl, methoxy, ethoxy, cyano, nitro and amino.

The term "cycloalkyl," as used herein represents a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1.]heptyl, cyclooctyl, cyclononyl and the like. The cycloalkyl groups of this invention can be optionally substituted with (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —$(CH_2)_qCO_2R^A$, where q is an integer of from zero to four, and $R^A$ is selected from the group consisting of (a) alkyl, (b) aryl, (c) alkaryl, and (d) hydrogen, where the alkylene group is of one to six carbon atoms; (36) —$(CH_2)_qCONR^BR^C$, where q is an integer of from zero to four and where $R^B$ and $R^C$ are independently selected from the group consisting of (a) hydrogen, (b) alkyl, (c) aryl, and (d) alkaryl, where the alkylene group is of one to six carbon atoms; (37) —$(CH_2)_qSO_2R^D$, where q is an integer of from zero to four and where $R^D$ is selected from the group consisting of (a) alkyl, (b) aryl, and (c) alkaryl, where the alkylene group is of one to six carbon atoms; (38) —$(CH_2)_qSO_2NR^ER^F$, where q is an integer of from zero to four and where each of $R^E$ and $R^F$ is, independently, selected from the group consisting of (a) hydrogen, (b) alkyl, (c) aryl, and (d) alkaryl, where the alkylene group is of one to six carbon atoms; (39) —$(CH_2)_qNR^GR^H$, where q is an integer of from zero to four and where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) aralkoxy; and (47) deuterium. Preferred optional substituents include deuterium, halo, methyl, ethyl, methoxy, ethoxy, cyano, nitro and amino.

The term "cycloalkoxy," as used herein, represent a cycloalkyl group, as defined herein, attached to the parent molecular group through an oxygen atom. Exemplary unsubstituted cycloalkoxy groups are of from 3 to 8 carbons.

As used herein, when a particular position in a compound of this invention is designated as being "deuterated" or "having deuterium" (the element deuterium is represented by the letter "D" in chemical structures and formulas and indicated with a lower case "d" in chemical names, according to the Boughton system), it is understood that the abundance of deuterium at that position is substantially greater than the natural abundance of deuterium, which is 0.015%. In certain embodiments, a composition of the invention has a minimum isotopic enrichment factor of at least 5 (0.075% deuterium incorporation), e.g., at least 10 (0.15% deuterium incorporation). In other embodiments, a composition has an isotopic enrichment factor of at least 50 (0.75% deuterium incorporation), at least 500 (7.5% deuterium incorporation), at least 2000 (30% deuterium incorporation), at least 3000 (45% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), or at least 6600 (99% deuterium incorporation). Any of the chemical groups, functional groups, or substituents described herein may be deuterated if the chemical group, functional group, or substituent has —H.

As used herein, the terms "di-($C_1$-$C_3$ alkyl)amino" and "di-($C_1$-$C_6$ alkyl)amino" refer to an amino group that is substituted with two groups independently selected from $C_1$-$C_3$ alkyl or $C_1$-$C_6$ alkyl, respectively.

The term an "effective amount" of an agent, as used herein, is that amount sufficient to effect beneficial or desired results, such as clinical results, and, as such, an "effective amount" depends upon the context in which it is being applied.

As used herein, the term "esterified hydroxyl" refers to a hydroxyl in which the hydrogen has been replaced with —C(O)R group, where R is hydrogen, deuterium, $C_1$-$C_6$ alkyl, $C_2$-$C_6$ alkenyl, $C_3$-$C_6$ cycloalkyl, or aryl as such terms are defined herein, and where the $C_1$-$C_6$ alkyl, $C_2$-$C_6$ alkenyl, $C_3$-$C_6$ cycloalkyl, or aryl is optionally deuterated. Exemplary, non-limiting esterified hydroxyls include —OC(O)CH$_3$, —OC(O)CH$_2$CH$_3$, and —OC(O)Ph.

The term "halogen," as used herein, represent bromine ("bromo" or "—Br"), chlorine ("chloro" or "—Cl"), iodine ("iodo" or "—I"), or fluorine ("fluoro" or "—F"). Preferred halogen groups are fluoro, chloro, and bromo.

As used herein, the term "haloalkoxy" refers to an alkoxy radical as described above substituted with one or more halogens. Illustrative examples of haloalkoxy groups include, but are not limited to, trifluoromethoxy, difluoromethoxy and the like.

As used herein, unless otherwise indicated, the term "haloalkyl" refers to an alkyl radical as described above substituted with one or more halogens. Illustrative examples of haloalkyl groups include, but are not limited to, chloromethyl, dichloromethyl, fluoromethyl, difluoromethyl, trifluoromethyl, 2,2,2-trichloroethyl and the like.

As used herein, the term "heteroaralkoxy" refers to an alkoxy radical of one to six carbons as described above substituted with a heteroaryl group as described above.

The term "heteroaryl," as used herein, represents that subset of heterocycles, as defined herein, which are aromatic: i.e., they contain 4n+2 pi electrons within the mono- or multicyclic ring system. Illustrative examples of heteroaryl groups include, but are not limited to, pyridyl, pyridazinyl, pyrazinyl, pyrimidinyl, triazinyl, quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridines, benzothiaxolyl, benzofuranyl, benzothienyl, indolyl, isothiazolyl, pyrazolyl, indazolyl, imidazolyl, triazolyl, tetrazolyl, oxazolyl, isoxazolyl, oxadiazolyl, thiadiazolyl, pyrrolyl, thiazolyl, furyl, thienyl and the like. Five- or six-membered monocyclic heteroaryl rings include: pyridyl, pyridazinyl, pyrazinyl, pyrimidinyl, triazinyl, isothiazolyl, pyrazolyl, imidazolyl, triazolyl, tetrazolyl, oxazolyl, isoxazolyl, oxadiazolyl, thiadiazolyl, pyrrolyl, thiazolyl, furyl, thienyl and the like. Eight- to ten-membered bicyclic heteroaryl rings having one to four heteroatoms include: quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridinyl, benzothiaxolyl, benzofuranyl, benzothienyl, indolyl, indazolyl, and the like. Preferred optional substituents include one, two, three, four, or five identical or different substituents selected from deuterium, halo, cyano, $C_1$-$C_3$ alkyl, $C_3$-$C_6$ cycloalkyl, difluoromethyl, trifluoromethyl, $C_1$-$C_3$ alkoxy, difluoromethoxy and trifluoromethoxy.

The terms "heterocyclyl" or "heterocycle," as used herein, represents a 5-, 6- or 7-membered ring, unless otherwise specified, containing one, two, three, or four heteroatoms independently selected from the group consisting of nitrogen, oxygen, and sulfur. The 5-membered ring has zero to two double bonds and the 6- and 7-membered rings have zero to three double bonds. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocycle" includes bicyclic, tricyclic and tetracyclic groups in which any of the above heterocyclic rings is fused to one, two, or three rings, e.g., an aryl ring, a cyclohexane ring, a cyclohexene ring, a cyclopentane ring, a cyclopentene ring and another monocyclic heterocyclic ring, such as indolyl, quinolyl, isoquinolyl, tetrahydroquinolyl, benzofuryl, benzothienyl and the like. Examples of fused heterocycles include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Heterocyclic groups also include groups of the formula

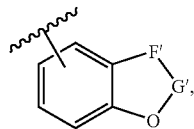

where
F' is selected from the group consisting of —CH$_2$—, —CH$_2$O— and —O—, and G' is selected from the group consisting of —C(O)— and —(C(R')(R''))$_v$—, where each of R' and R'' is, independently, selected from the group consisting of hydrogen or alkyl of one to four carbon atoms, and v is one to three and includes groups, such as 1,3-benzodioxolyl, 1,4-benzodioxanyl, and the like. Any of the heterocycle groups mentioned herein may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —(CH$_2$)$_q$CO$_2$R$^A$, where q is an integer of from zero to four, and R$^A$ is selected from the group consisting of (a) alkyl, (b) aryl, (c) alkaryl, and (d) hydrogen where the alkylene group is of one to six carbon atoms; (36) —(CH$_2$)$_q$CONR$^B$R$^C$, where q is an integer of from zero to four and where R$^B$ and R$^C$ are independently selected from the group consisting of (a) hydrogen, (b) alkyl, (c) aryl, and (d) alkaryl, where the alkylene group is of one to six carbon atoms; (37) —(CH$_2$)$_q$SO$_2$R$^D$, where q is an integer of from zero to four and where R$^D$ is selected from the group consisting of (a) alkyl, (b) aryl, and (c) alkaryl, where the alkylene group is of one to six carbon atoms; (38) —(CH$_2$)$_q$SO$_2$NR$^E$R$^F$, where q is an integer of from zero to four and where each of R$^E$ and R$^F$ is, independently, selected from the group consisting of (a) hydrogen, (b) alkyl, (c) aryl, and (d) alkaryl, where the alkylene group is of one to six carbon atoms; (39) —(CH$_2$)$_q$NR$^G$R$^H$, where q is an integer of from zero to four and where each of R$^G$ and R$^H$ is, independently, selected from the group consisting of (a) hydrogen; (b) an N-protecting group; (c)

alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, wherein in one embodiment no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; (46) aralkoxy; and (47) deuterium.

The term "heterocyclyloxy," as used herein, represents a heterocycle group, as defined herein, attached to the parent molecular group through an oxygen atom.

The terms "heterocyclyloyl," as used herein, represent a heterocycle group, as defined herein, attached to the parent molecular group through a carbonyl group.

The term "hydroxyl," as used herein, represents an —OH group.

The term "hydroxyalkyl," as used herein, represents an alkyl group, as defined herein, substituted by one to three hydroxyl groups, with the proviso that no more than one hydroxyl group may be attached to a single carbon atom of the alkyl group and is exemplified by hydroxymethyl, dihydroxypropyl, and the like.

As used herein, the term "isotopic enrichment factor" refers to the ratio of the isotopic abundance of a composition to the natural abundance of the specified isotope. For example, deuterium has a natural abundance of 0.015%. A compound with, for example, 45% deuterium incorporation at a specified position, has an isotopic enrichment factor of 3000 at that site relative to the natural abundance of deuterium.

The term "nitro," as used herein, represents an —NO$_2$ group.

The term "nonimmediate release" is defined in *Remington: The Science and Practice of Pharmacy*, 21$^{st}$ Ed., Gennaro, Ed., Lippencott Williams & Wilkins (2005). As discussed therein, immediate and nonimmediate release can be defined kinetically by reference to the following equation:

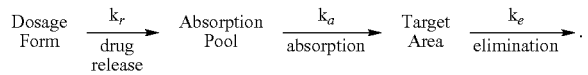

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For nonimmediate release formulations, the opposite is true, i.e., $k_r \ll k_a$, such that the rate of release of drug from the dosage form is the rate-limiting step in the delivery of the drug to the target area.

The term "nonimmediate release" refers to a drug formulation that provides for gradual release of a drug over an extended period of time, for example, 12 hours or more, and that preferably, although not necessarily, results in substantially constant blood levels of a drug over an extended time period. As used herein, the term "delayed release" refers to a pharmaceutical preparation that passes through the stomach intact and dissolves in the small intestine.

The term "oxo" as used herein, represents =O.

The term "perfluoroalkyl," as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "perfluoroalkoxy," as used herein, represents an alkoxy group, as defined herein, where each hydrogen radical bound to the alkoxy group has been replaced by a fluoride radical.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M Berge et al. describe pharmaceutically acceptable salts in detail in *J Pharmaceutical Sciences* 66:1-19, 1977. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "Ph" as used herein means phenyl.

The term "solvate" as used herein means a compound of the invention wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

The term "spirocycle," as used herein, represents an alkylene diradical, both ends of which are bonded to the same carbon atom of the parent group to form a spirocyclic group and also heteroalkylene diradical, both ends of which are bonded to the same atom.

The term "sulfonyl," as used herein, represents an —S(O)$_2$— group.

The term "thioalkheterocyclyl," as used herein, represents a thioalkoxy group substituted with a heterocyclyl group.

The term "thioalkoxy," as used herein, represents an alkyl group attached to the parent molecular group through a sulfur atom. Exemplary unsubstituted alkylthio groups are of from 1 to 6 carbons.

The term "thiol" represents an —SH group.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also refer to delaying the onset of, retarding or reversing the progress of, or alleviating or preventing either the disease or condition to which the term applies, or one or more symptoms of such disease or condition.

Other features and advantages will be apparent from the following detailed description and the claims.

BRIEF DESCRIPTION OF THE DRAWINGS

FIGS. 3A-3D show the HPLC data corresponding to the metabolic pathways for (A) Compound (24d), (B) Compound (62) Ref. B, (C) Ref. A, and (D) Ref. D.

FIGS. 4A-4C show the HPLC data corresponding to the metabolic pathways for (A) Compound (9), (B) Ref. A, and (C) Ref. D.

FIG. 6 illustrates the use of mass spectrometry to identify metabolites formed from the compounds of the invention.

FIG. 7 illustrates LC/MS mass spectral data and corresponding retention times for Compounds 16, 19, and 54 and Reference Compounds A, B, and C, and their metabolites.

DETAILED DESCRIPTION OF THE INVENTION

Figure 1:
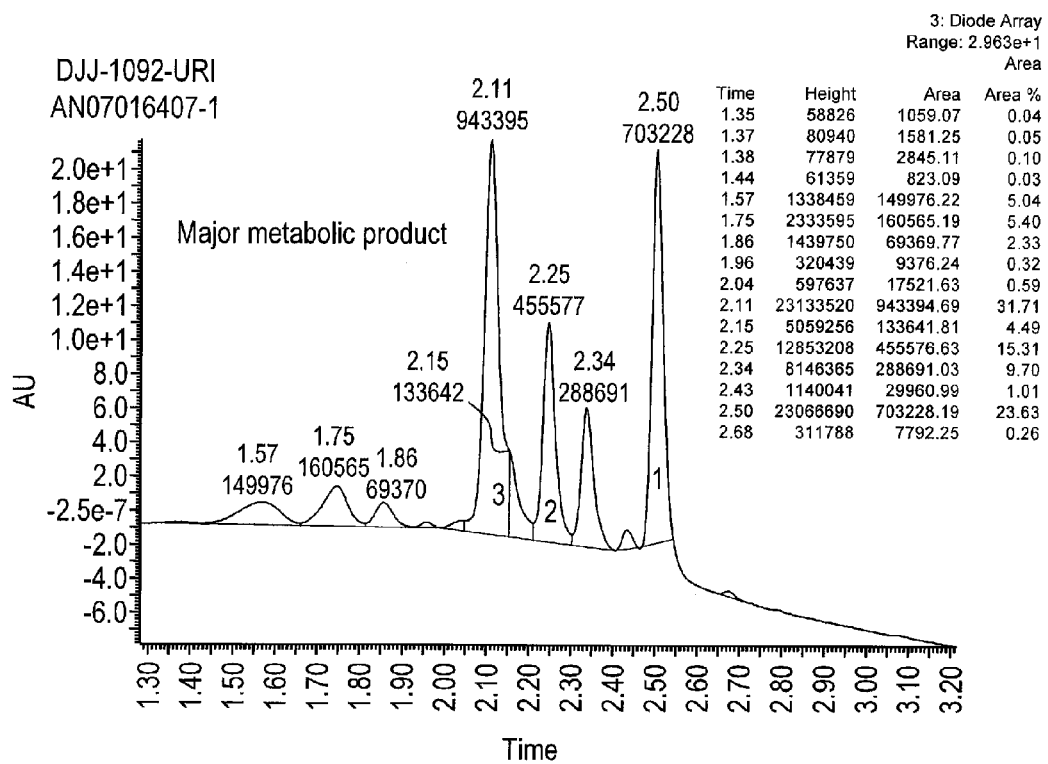
FIG. 1 shows the HPLC data corresponding to the metabolic pathway for Reference Compound A.
Figure 1:
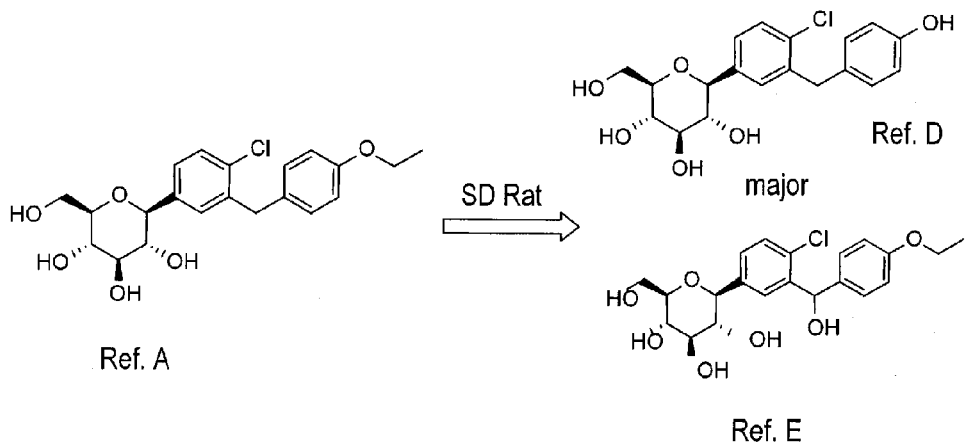
Figure 2A:
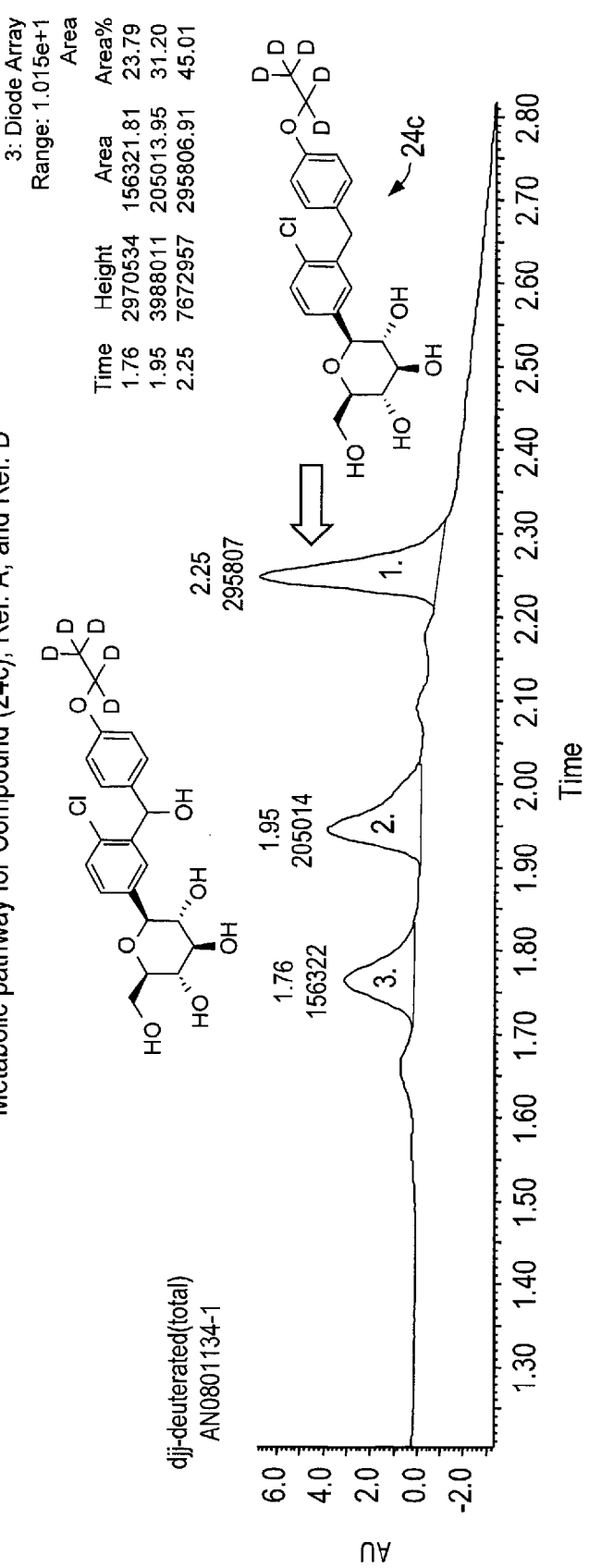
FIGS. 2A-2C show the HPLC data corresponding to metabolic pathways for (A) Compound (24c), (B) Ref. A, and (C) Ref. D.
Figure 2B:
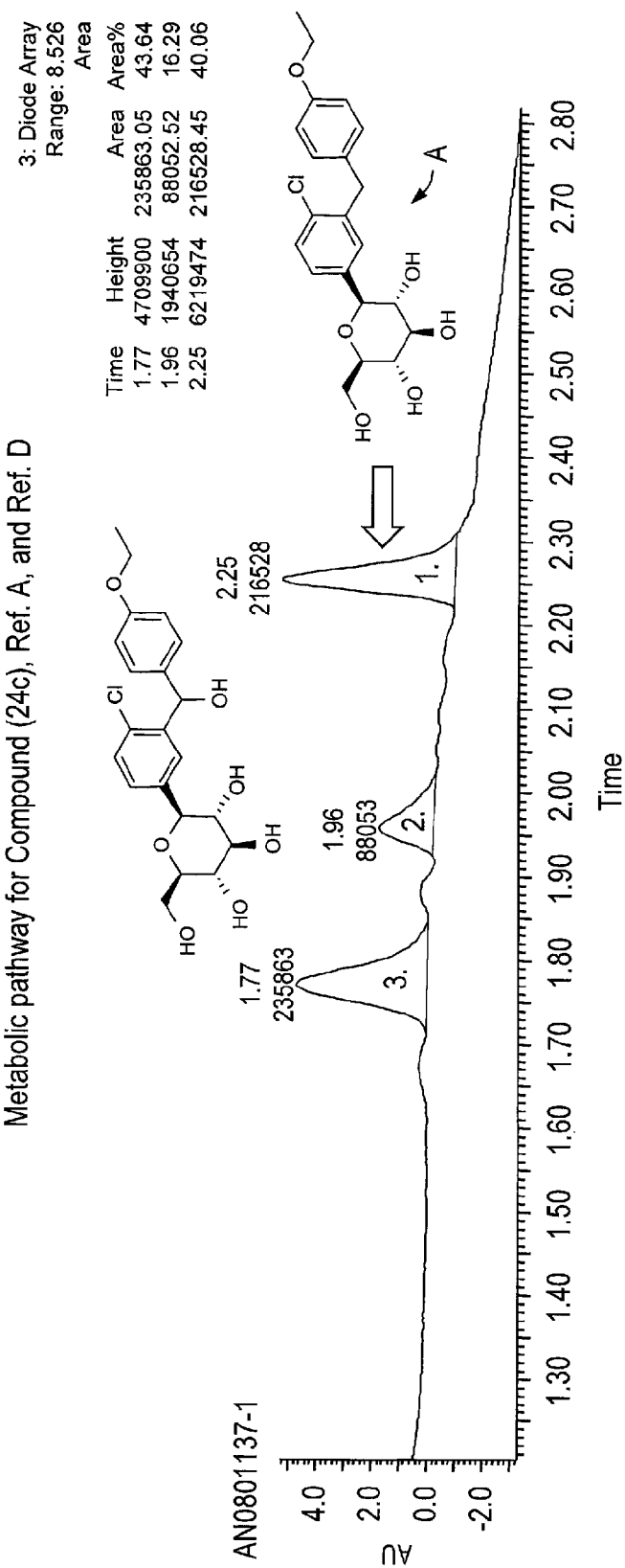
Figure 2C:
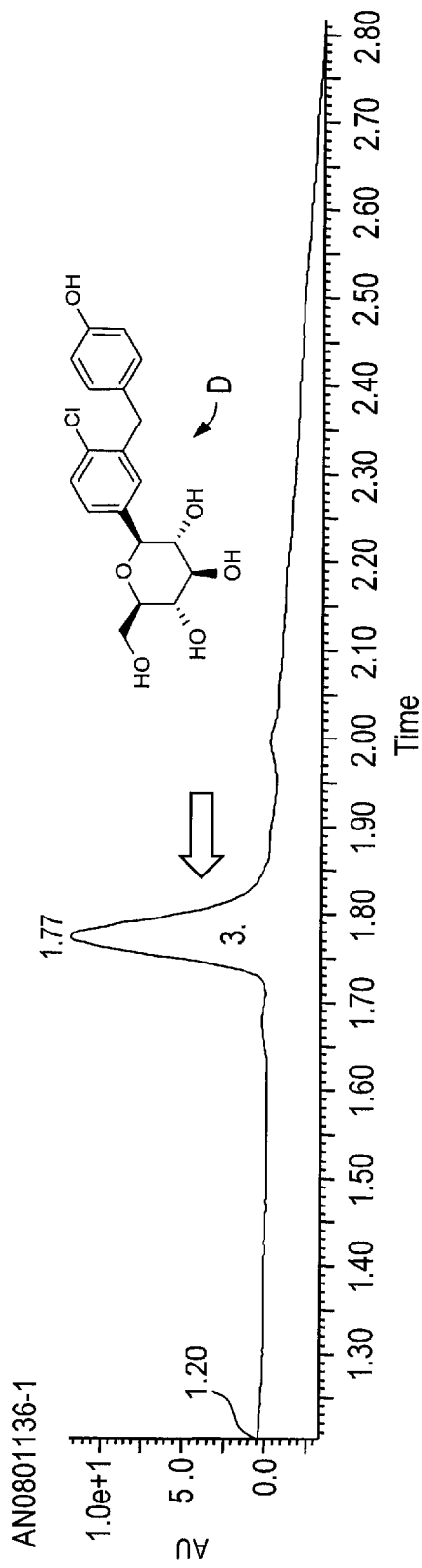
Figure 3C:
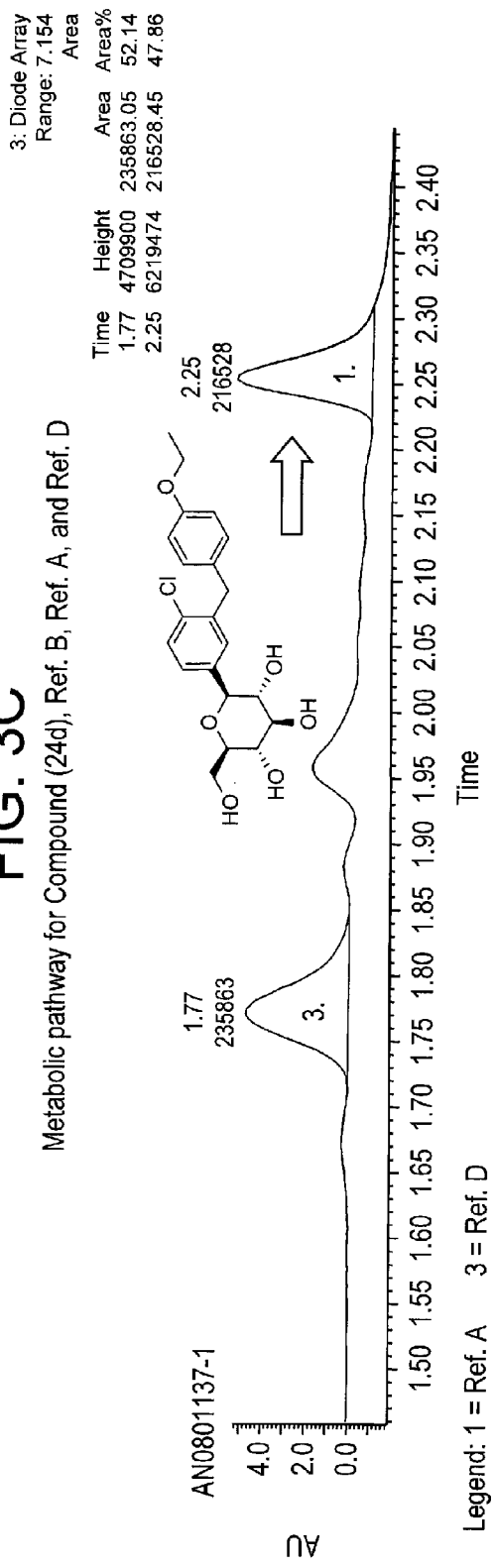
Figure 3D:
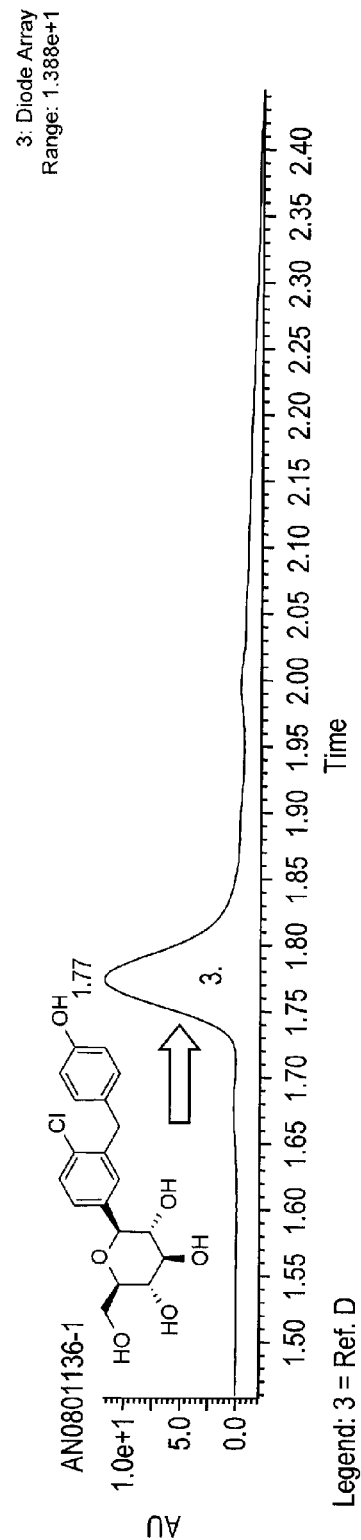
Figure 4B:
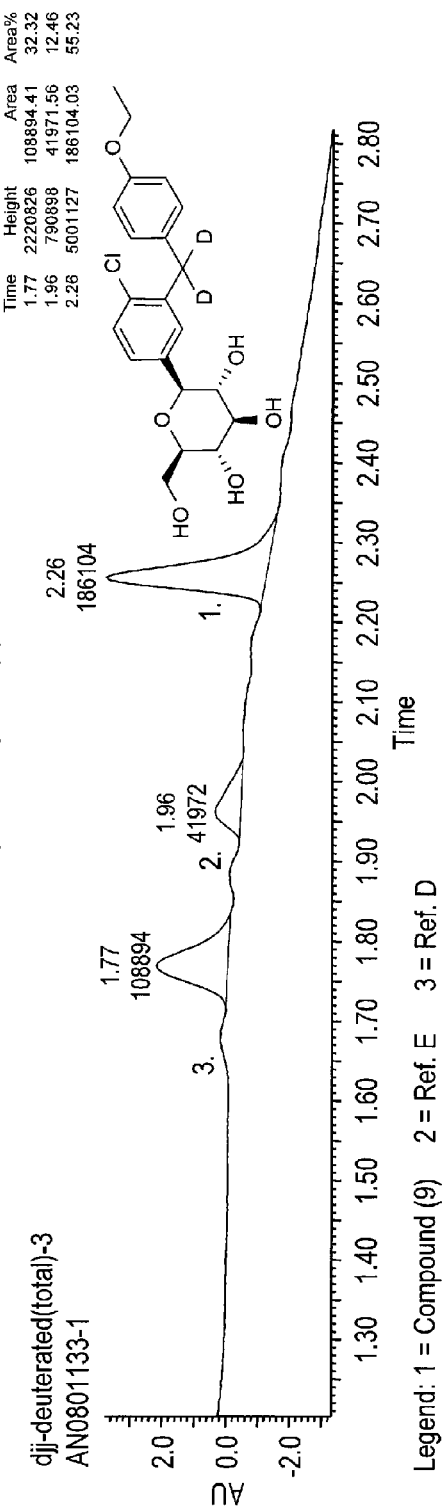
Figure 4B:
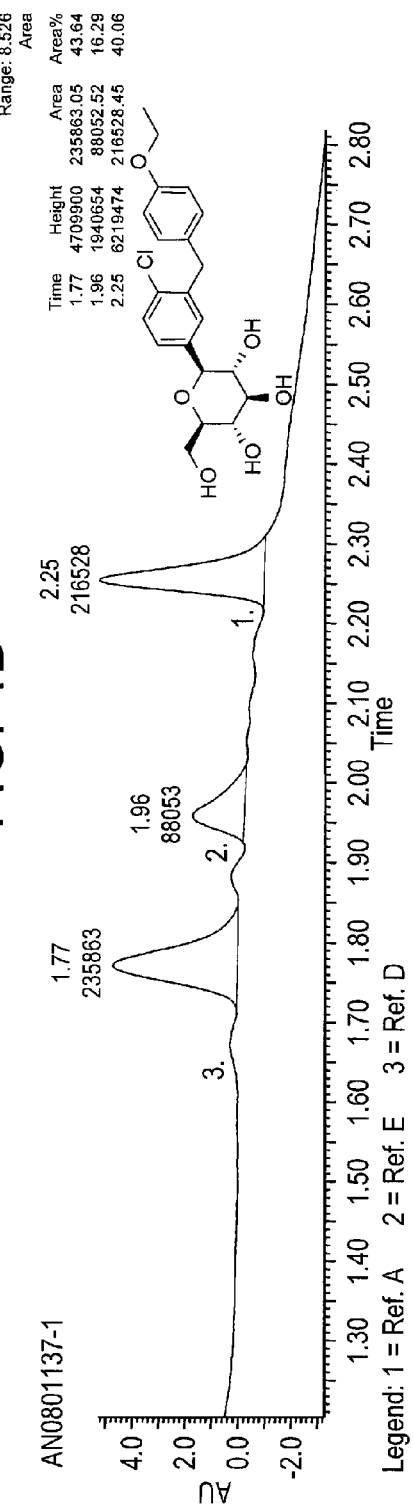
Figure 4C:
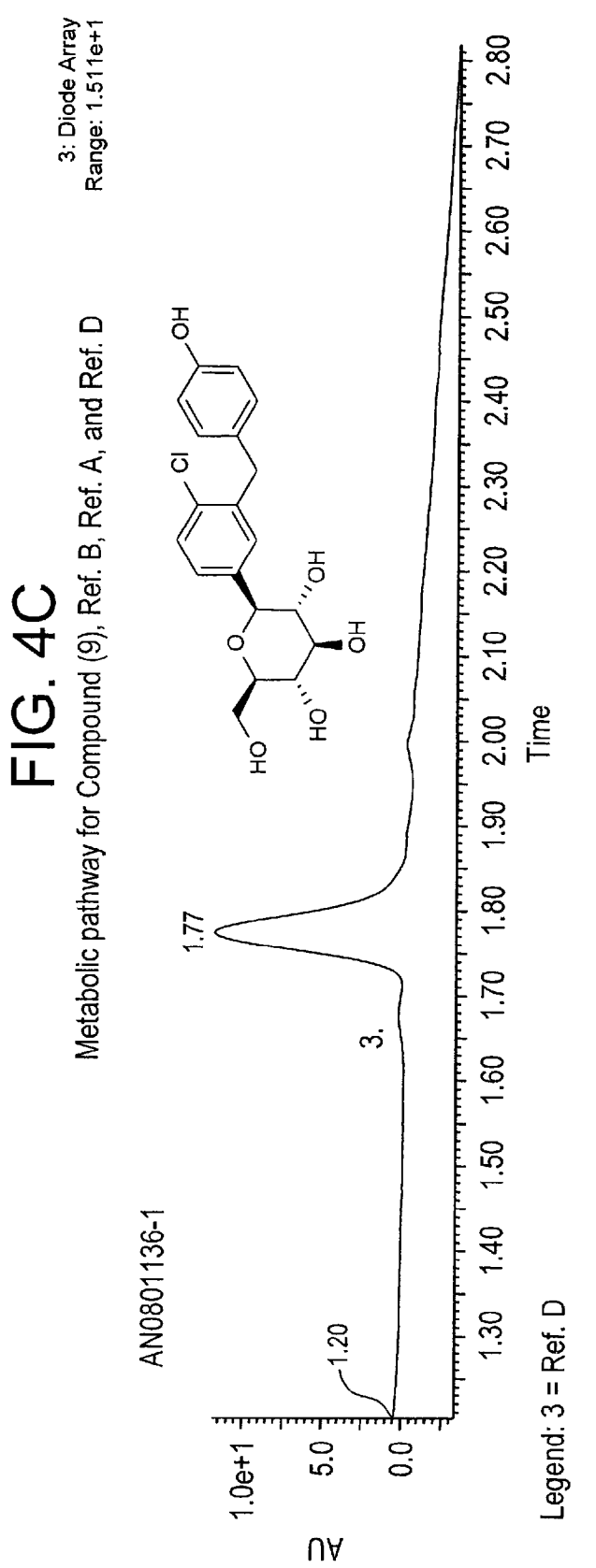

The present invention provides compounds having an inhibitory effect on sodium-dependent glucose cotransporter SGLT (e.g., SGLT2). Some compounds according to the present invention also have an inhibitory effect on sodium-dependent glucose cotransporter SGLT1. Owing to their ability to inhibit SGLT, the compounds of the present invention are suitable for the treatment and/or prevention of any and all conditions and diseases that are affected by inhibition of SGLT activity. Therefore, the compounds of the present invention are suitable for the prevention and treatment of diseases and conditions, particularly metabolic disorders, including but not limited to type 1 and type 2 diabetes mellitus, hyperglycemia, diabetic complications (such as retinopathy, nephropathy [e.g., progressive renal disease], neuropathy, ulcers, micro- and macroangiopathies, and diabetic foot disease), insulin resistance, metabolic syndrome (Syndrome X), hyperinsulinemia, hypertension, hyperuricemia, obesity, edema, dyslipidemia, chronic heart failure, atherosclerosis, and related diseases.

The present invention also provides pharmaceutically acceptable salts and prodrugs of compounds according to the present invention.

The present invention further provides pharmaceutical compositions comprising an effective amount of a compound or mixture of compounds according to the present invention, or a pharmaceutically acceptable salt or prodrug thereof, in a pharmaceutically acceptable carrier.

The present invention further provides synthetic intermediates and processes for preparing the compounds of the present invention.

The present invention also provides methods of using the compounds according to the present invention, independently, or in combination with other therapeutic agents, for treating diseases and conditions that may be affected by SGLT inhibition.

The present invention also provides methods of using the compounds according to the present invention for the preparation of a medicament for treating diseases and conditions that may be affected by SGLT inhibition.

Compounds and Preparative Methods

The present invention provides for compounds having the following formula:

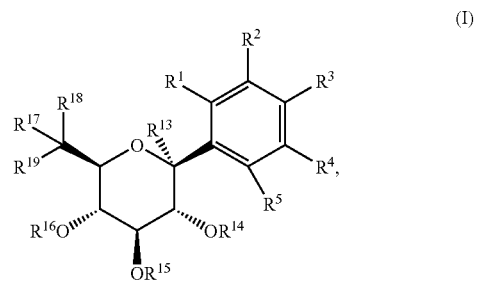

(I)

or any diastereomer, tautomer, or isomer thereof, or any pharmaceutically acceptable prodrug, salt, or solvate thereof, wherein each $R^1$, $R^2$, $R^3$, $R^4$ and $R^5$ is, independently, —H, -D, a substituent that is optionally deuterated, or group Q:

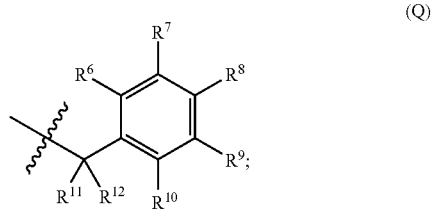

(Q)

each $R^6$, $R^7$, $R^8$, $R^9$, $R^{10}$, $R^{14}$, $R^{15}$, $R^{16}$, and $R^{10}$ is, independently, —H, -D, or a substituent that is optionally deuterated; and each $R^{11}$, $R^{12}$, $R^{13}$, $R^{17}$ and $R^{18}$ is, independently, —H, -D, or halogen;

wherein one of $R^1$, $R^2$, $R^3$, $R^4$ and $R^5$ is group Q;

at least one of $R^1$-$R^{19}$ is -D or includes -D.

The compounds are preferably present in a composition having an isotopic enrichment factor of at least 5.

Substituents for $R^1$, $R^2$, $R^3$, $R^4$, $R^5$, $R^6$, $R^7$, $R^8$, $R^9$, $R^{10}$, $R^{14}$, $R^{15}$, $R^{16}$, and $R^{10}$ include H, halogen, cyano, nitro, optionally substituted $C_{1-6}$ alkyl, optionally substituted $C_2$-$C_6$ alkenyl, optionally substituted $C_2$-$C_6$ alkynyl, optionally substituted $C_3$-$C_{10}$ cycloalkyl, optionally substituted $C_{6-10}$ aryl, optionally substituted $C_{1-6}$ alkaryl, optionally substituted $C_{2-9}$ heterocyclyl, hydroxy, optionally substituted $C_{1-6}$ alkoxy, optionally substituted $C_3$-$C_{10}$ cycloalkoxy, optionally substituted $C_{1-6}$ thioalkoxy, amino, and optionally substituted $C_{1-4}$ alkheterocyclyl. Additional substituents for $R^6$, $R^7$, $R^8$, $R^9$, $R^{10}$, $R^{14}$, $R^{15}$, $R^{16}$, and $R^{10}$ include (aryl)$C_1$-$C_3$ alkyl, (aryl) $C_1$-$C_3$ alkoxy, (aryl)$C_1$-$C_3$ alkylsulfonyl, (aryl)$C_1$-$C_3$ alkylsulfonyloxy, ($C_1$-$C_{12}$ alkyl)carbonyl, ($C_1$-$C_{12}$ alkoxy)carbonyl, ($C_1$-$C_4$ alkyl)aminocarbonyl, ($C_1$-$C_4$ alkyl)

carbonylamino, ($C_1$-$C_4$ alkylamino)$C_1$-$C_3$ alkyl, ($C_1$-$C_6$ alkoxy)$C_1$-$C_6$ alkyl, ($C_1$-$C_6$ alkoxy)$C_1$-$C_6$ alkoxy, ($C_2$-$C_4$ alkenyl)$C_1$-$C_3$ alkoxy, ($C_2$-$C_4$ alkenyloxy)$C_1$-$C_3$ alkoxy, ($C_2$-$C_4$ alkynyl)$C_1$-$C_3$ alkoxy, ($C_2$-$C_4$ alkynyloxy)$C_1$-$C_3$ alkoxy, ($C_3$-$C_{10}$ cycloalkyl)$C_1$-$C_3$ alkyl, ($C_3$-$C_{10}$ cycloalkyl)$C_1$-$C_3$ alkoxy, ($C_3$-$C_{10}$ cycloalkyl)carbonyl, ($C_3$-$C_7$ cycloalkyl)$C_2$-$C_8$ alkenyl, ($C_3$-$C_7$ cycloalkyl)$C_3$-$C_8$ alkenyloxy, ($C_3$-$C_7$ cycloalkyl)$C_3$-$C_8$ alkynyloxy, ($C_3$-$C_7$ cycloalkoxy)$C_1$-$C_3$ alkyl, ($C_3$-$C_7$ cycloalkoxy)$C_1$-$C_3$ alkoxy, ($C_3$-$C_7$ cycloalkoxy)$C_2$-$C_4$ alkenyl, ($C_3$-$C_7$ cycloalkoxy)$C_2$-$C_4$ alkynyl, ($C_5$-$C_{10}$ cycloalkenyl)$C_1$-$C_3$ alkyl, ($C_5$-$C_{10}$ cycloalkenyl)$C_1$-$C_3$ alkoxy, ($C_5$-$C_8$ cycloalkenyl)$C_3$-$C_8$ alkenyloxy, ($C_5$-$C_8$ cycloalkenyl)$C_3$-$C_8$ alkynyloxy, (heteroaryl)$C_1$-$C_3$ alkyl, (heteroaryl)$C_1$-$C_3$ alkoxy, amino, aminocarbonyl, aryl-($C_1$-$C_3$ alkyl)carbonyl, aryl-($C_1$-$C_3$ alkyl)carbonyloxy, aryl, arylcarbonyl, arylcarbonylamino, arylcarbonyloxy, aryloxy, arylthio, arylsulfinyl, arylsulfonyl, arylsulfonylamino, arylsulfonyloxy, $C_1$-$C_4$ alkylamino, $C_1$-$C_4$ alkylthio, $C_1$-$C_4$ alkylsulfinyl, $C_1$-$C_4$ alkylsulfonyl, $C_1$-$C_4$ alkylsulfonylamino, $C_1$-$C_4$ alkylsulfonyloxy, $C_1$-$C_6$ alkyl, $C_1$-$C_6$ alkoxy, $C_2$-$C_6$ alkenyl, $C_2$-$C_6$ alkenyloxy, $C_2$-$C_6$ alkynyl, $C_2$-$C_6$ alkynyloxy, $C_3$-$C_{10}$ cycloalkyl, $C_3$-$C_{10}$ cycloalkoxy, $C_3$-$C_{10}$ cycloalkylthio, $C_3$-$C_{10}$ cycloalkylsulfinyl, $C_3$-$C_{10}$ cycloalkylsulfonyl, $C_3$-$C_6$ cycloalkylidenmethyl, $C_5$-$C_{10}$ cycloalkenyl, $C_5$-$C_{10}$ cycloalkenyloxy, $C_5$-$C_{10}$ cycloalkenylthio, $C_5$-$C_{10}$ cycloalkenylsulfinyl, $C_5$-$C_{10}$ cycloalkenylsulfonyl, cyano, deuterium, di-($C_1$-$C_3$ alkyl)amino, di-($C_1$-$C_3$ alkyl)aminocarbonyl, di-($C_1$-$C_3$ alkylamino)$C_1$-$C_3$ alkyl, halo, heteroaryl, heteroarylcarbonyl, heteroarylcarbonylamino, heteroaryloxy, hydrogen, hydroxy, hydroxycarbonyl, nitro, t-butyldimethylsilyl, t-butyldimethylsilyloxy, tri-($C_1$-$C_4$ alkyl)silyl-$C_1$-$C_6$ alkyl, tri-($C_1$-$C_4$ alkyl)silyl-$C_1$-$C_6$ alkoxy, tri-($C_1$-$C_4$ alkyl)silyl-$C_2$-$C_6$ alkenyl, tri-($C_1$-$C_4$ alkyl)silyl-$C_2$-$C_6$ alkynyl, trimethylsilyl, and trimethylsilyloxy. Those substituents including hydrogen atoms may be further substituted with deuterium.

In preferred embodiments of Formula I, $R^4$ is group Q; three of the groups $R^1$, $R^2$, $R^3$, and $R^5$ each independently represent hydrogen, deuterium, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkoxy, or $C_3$-$C_{10}$ cycloalkoxy; and one of the remaining groups $R^1$, $R^2$, $R^3$, and $R^5$ independently represents hydrogen or deuterium. In particularly preferred embodiments of Formula I, $R^4$ is group Q; $R^3$ independently represents hydrogen, deuterium, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkoxy, or $C_3$-$C_{10}$ cycloalkoxy; and $R^1$, $R^2$, and $R^5$ each independently represent hydrogen or deuterium. In more particularly preferred embodiments of Formula I, $R^4$ is group Q; $R^3$ independently represents hydrogen, deuterium, halogen, or $C_1$-$C_6$ alkyl; and $R^1$, $R^2$, and $R^5$ each independently represent hydrogen or deuterium.

In certain preferred embodiments of Formula I, $R^8$ independently represents hydroxy, cyano, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkoxy, $C_3$-$C_{10}$ cycloalkoxy, ($C_3$-$C_{10}$ cycloalkyl)$C_1$-$C_3$ alkoxy, or ($C_3$-$C_8$ cycloalkoxy)$C_1$-$C_6$ alkoxy, ($C_3$-$C_7$ cycloalkyl)$C_3$-$C_5$ alkenyloxy, ($C_3$-$C_7$ cycloalkyl)$C_3$-$C_5$ alkynyloxy, or ($C_1$-$C_6$ haloalkoxy)$C_1$-$C_6$ alkoxy; two of the groups $R^6$, $R^7$, $R^9$ and $R^{10}$ each independently represent hydrogen, deuterium, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkoxy, or $C_3$-$C_{10}$ cycloalkoxy; and two of the remaining groups $R^6$, $R^7$, $R^9$, and $R^{10}$ each independently represent hydrogen or deuterium.

In other preferred embodiments of Formula I, $R^8$ independently represents ($C_3$-$C_8$ cycloalkoxy)$C_1$-$C_6$ alkoxy, ($C_3$-$C_7$ cycloalkyl)$C_3$-$C_5$ alkenyloxy, ($C_3$-$C_7$ cycloalkyl)$C_3$-$C_5$ alkynyloxy, or ($C_1$-$C_6$ haloalkoxy)$C_1$-$C_6$ alkoxy; two of the groups $R^6$, $R^7$, $R^9$ and $R^{10}$ each independently represent hydrogen, deuterium, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkoxy, or $C_3$-$C_{10}$ cycloalkoxy; and two of the remaining groups $R^6$, $R^7$, $R^9$, and $R^{10}$ each independently represent hydrogen or deuterium.

In certain particularly preferred embodiments of Formula I, $R^8$ independently represents hydroxy, cyano, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkoxy, $C_3$-$C_{10}$ cycloalkoxy, or ($C_3$-$C_{10}$ cycloalkyl)$C_1$-$C_3$ alkoxy, ($C_3$-$C_7$ cycloalkyl)$C_3$-$C_5$ alkenyloxy, or ($C_3$-$C_7$ cycloalkyl)$C_3$-$C_5$ alkynyloxy; two of the groups $R^6$, $R^7$, $R^9$, and $R^{10}$ each independently represent hydrogen, deuterium, halo, or $C_1$-$C_6$ alkyl; and two of the remaining groups $R^6$, $R^7$, $R^9$, and $R^{10}$ each independently represent hydrogen or deuterium. In other particularly preferred embodiments of Formula I, $R^8$ independently represents ($C_3$-$C_8$ cycloalkoxy)$C_1$-$C_6$ alkoxy, ($C_3$-$C_7$ cycloalkyl)$C_3$-$C_5$ alkenyloxy, ($C_3$-$C_7$ cycloalkyl)$C_3$-$C_5$ alkynyloxy, or ($C_1$-$C_6$ haloalkoxy)$C_1$-$C_6$ alkoxy; two of the groups $R^6$, $R^7$, $R^9$, and $R^{10}$ each independently represent hydrogen, deuterium, halo, or $C_1$-$C_6$ alkyl; and two of the remaining groups $R^6$, $R^7$, $R^9$, and $R^{10}$ each independently represent hydrogen or deuterium.

In certain more particularly preferred embodiments of Formula I, $R^8$ independently represents hydroxy, cyano, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkoxy, $C_3$-$C_{10}$ cycloalkoxy, or ($C_3$-$C_{10}$ cycloalkyl)$C_1$-$C_3$ alkoxy, ($C_3$-$C_7$ cycloalkyl)$C_3$-$C_5$ alkenyloxy, or ($C_3$-$C_7$ cycloalkyl)$C_3$-$C_5$ alkynyloxy; and $R^6$, $R^7$, $R^9$, and $R^{10}$ each independently represent hydrogen or deuterium. In other more particularly preferred embodiments of Formula I, $R^8$ independently represents ($C_3$-$C_8$ cycloalkoxy)$C_1$-$C_6$ alkoxy, ($C_3$-$C_7$ cycloalkyl)$C_3$-$C_5$ alkenyloxy, ($C_3$-$C_7$ cycloalkyl)$C_3$-$C_5$ alkynyloxy, or ($C_1$-$C_6$ haloalkoxy)$C_1$-$C_6$ alkoxy; and $R^6$, $R^7$, $R^9$, and $R^{10}$ each independently represent hydrogen or deuterium.

In preferred embodiments of Formula I, $R^{11}$, $R^{12}$, $R^{13}$, $R^{17}$, and $R^{18}$ each independently represent hydrogen or deuterium.

In preferred embodiments of Formula I, $R^{14}$, $R^{15}$, and $R^{16}$ each independently represent hydrogen, ($C_1$-$C_{18}$ alkyl)carbonyl, arylcarbonyl, ($C_3$-$C_{10}$ cycloalkyl)carbonyl, $C_1$-$C_6$ alkyl, $C_3$-$C_7$ cycloalkyl, aryl, heteroaryl, ($C_3$-$C_7$ cycloalkyl)$C_1$-$C_3$ alkyl, (aryl)$C_1$-$C_3$ alkyl, or trimethylsilyl. In particularly preferred embodiments of Formula I, $R^{14}$, $R^{15}$, and $R^{16}$ each independently represent hydrogen, $C_1$-$C_6$ alkyl, $C_3$-$C_7$ cycloalkyl, aryl, ($C_3$-$C_7$ cycloalkyl)$C_1$-$C_3$ alkyl, or trimethylsilyl. In more particularly preferred embodiments of Formula I, $R^{14}$, $R^{15}$, and $R^{16}$ each independently represent hydrogen.

In preferred embodiments of Formula I, $R^{19}$ independently represents hydroxy, ($C_1$-$C_{18}$ alkyl)carbonyloxy, arylcarbonyloxy, ($C_3$-$C_{10}$ cycloalkyl)carbonyloxy, hydrogen, deuterium, halo, $C_1$-$C_6$ alkyl, $C_1$-$C_6$ alkoxy, $C_3$-$C_7$ cycloalkoxy, aryloxy, heteroaryloxy, ($C_3$-$C_7$ cycloalkyl)$C_1$-$C_3$ alkoxy, (aryl)$C_1$-$C_3$ alkoxy or trimethylsilyloxy. In particularly preferred embodiments of Formula I, $R^{19}$ independently represents hydroxy, hydrogen, deuterium, halo, $C_1$-$C_6$ alkyl, $C_1$-$C_6$ alkoxy, $C_3$-$C_7$ cycloalkoxy, aryloxy, ($C_3$-$C_7$ cycloalkyl)$C_1$-$C_3$ alkoxy, or trimethylsilyloxy. In more particularly preferred embodiments of Formula I, $R^{19}$ independently represents hydroxy.

In the foregoing preferred embodiments, alkyl, alkenyl, alkynyl, and cycloalkyl and cycloalkenyl groups or portions may be partly or completely substituted with fluorine or deuterium and may be mono- or disubstituted by identical or different substituents selected from chlorine, hydroxy, $C_1$-$C_3$ alkoxy and $C_1$-$C_3$ alkyl; and in cycloalkyl and cycloalkenyl groups or portions, one or two methylene groups are optionally replaced independently by N, $NR^a$ (defined herein), O, S, CO, SO or $SO_2$.

Formula IA represents still other preferred embodiments of Formula I:

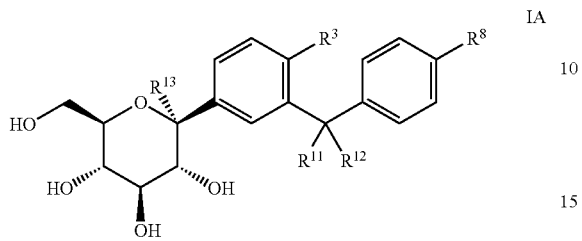

(IA)

wherein $R^3$ independently represents hydrogen, deuterium, halogen, or $C_1$-$C_6$ alkyl; $R^8$ independently represents hydroxy, cyano, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkoxy, $C_3$-$C_{10}$ cycloalkoxy, or ($C_3$-$C_{10}$ cycloalkyl)$C_1$-$C_3$ alkoxy, ($C_3$-$C_7$ cycloalkyl)$C_3$-$C_5$ alkenyloxy, or ($C_3$-$C_7$ cycloalkyl)$C_3$-$C_5$ alkynyloxy; and $R^{11}$, $R^{12}$ and $R^{13}$ each independently represent hydrogen or deuterium;

wherein at least (i) one of $R^{11}$, $R^{12}$ and $R^{13}$ is deuterium, or (ii) $R^8$ is selected from $C_1$-$C_6$ alkyl, $C_2$-$C_6$ alkenyl, $C_2$-$C_6$ alkynyl, $C_3$-$C_{10}$ cycloalkyl, $C_1$-$C_6$ alkoxy, $C_3$-$C_{10}$ cycloalkoxy, and ($C_3$-$C_{10}$ cycloalkyl)$C_1$-$C_3$ alkoxy, ($C_3$-$C_7$ cycloalkyl)$C_3$-$C_5$ alkenyloxy and ($C_3$-$C_7$ cycloalkyl)$C_3$-$C_5$ alkynyloxy, wherein the alkyl, alkenyl, alkynyl, or cycloalkyl, or cycloalkenyl group or portion is partly or completely substituted with deuterium.

The invention further provides compounds having the following formula:

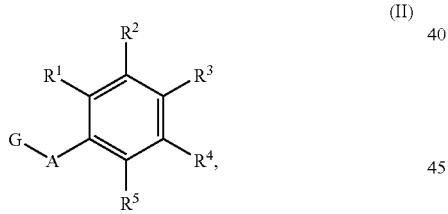

(II)

or any diastereomer, tautomer, or isomer thereof, or any pharmaceutically acceptable prodrug, salt, or solvate thereof, wherein each $R^1$, $R^2$, $R^3$, $R^4$ and $R^5$ is, independently, —H, -D, a substituent that is optionally deuterated, or group Q:

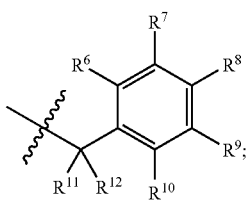

(Q)

A is selected from the group consisting of oxygen and a single bond;

G is selected from the group consisting of:

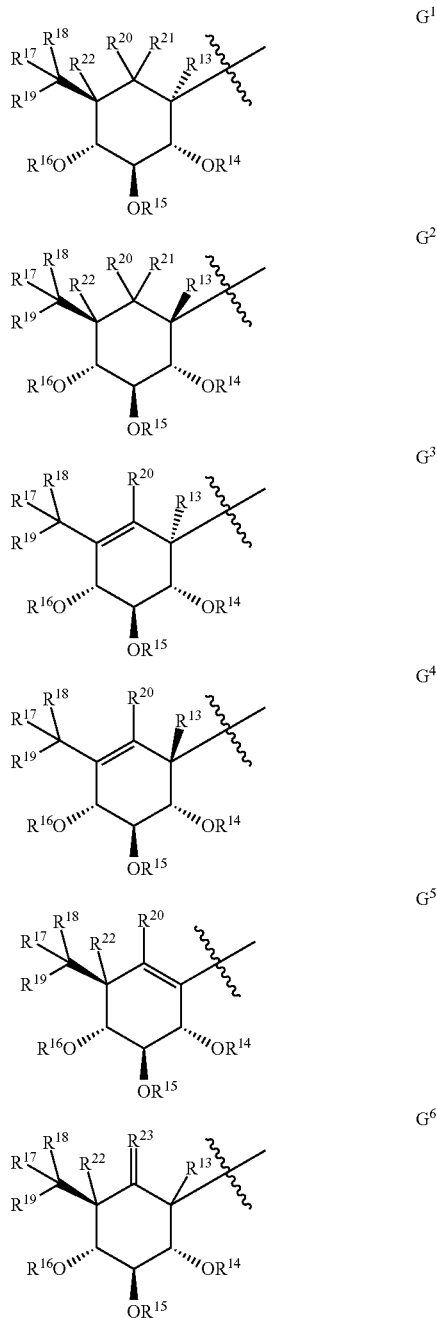

$G^1$ $G^2$ $G^3$ $G^4$ $G^5$ $G^6$ each $R^6$, $R^7$, $R^8$, $R^9$, $R^{10}$, $R^{14}$, $R^{15}$, $R^{16}$, $R^{19}$, and $R^{21}$, is, independently, —H, -D, or a substituent that is optionally deuterated; and
each $R^{11}$, $R^{12}$, $R^{13}$, $R^{17}$, $R^{18}$, $R^{20}$, and $R^{22}$ is, independently, —H, -D, or halogen;
wherein
one of $R^1$, $R^2$, $R^3$, $R^4$ and $R^5$ is group Q;
$R^{23}$ is $CH_2$, NH, O, or S; and
at least one of $R^1$-$R^{23}$ is -D or includes -D.

The compounds are preferably present in a composition having an isotopic enrichment factor of at least 5.

Substituents for $R^1$, $R^2$, $R^3$, $R^4$, $R^5$, $R^6$, $R^7$, $R^8$, $R^9$, $R^{10}$, $R^{14}$, $R^{15}$, $R^{16}$, $R^{19}$, and $R^{21}$ include H, halogen, cyano, nitro, optionally substituted $C_{1-6}$ alkyl, optionally substituted $C_2$-$C_6$ alkenyl, optionally substituted $C_2$-$C_6$ alkynyl, optionally substituted $C_3$-$C_{10}$ cycloalkyl, optionally substituted $C_{6-10}$ aryl, optionally substituted $C_{1-6}$ alkaryl, optionally substituted $C_{2-9}$ heterocyclyl, hydroxy, optionally substituted $C_{1-6}$ alkoxy, optionally substituted $C_3$-$C_{10}$ cycloalkoxy, optionally substituted $C_{1-6}$ thioalkoxy, amino, and optionally substituted $C_{1-4}$ alkheterocyclyl. Additional substituents for $R^6$, $R^7$, $R^8$, $R^9$, $R^{10}$, $R^{14}$, $R^{15}$, $R^{16}$, and $R^{10}$ include (aryl)$C_1$-$C_3$ alkyl, (aryl)$C_1$-$C_3$ alkoxy, (aryl)$C_1$-$C_3$ alkylsulfonyl, (aryl)$C_1$-$C_3$ alkylsulfonyloxy, ($C_1$-$C_{12}$ alkyl)carbonyl, ($C_1$-$C_{12}$ alkoxy)carbonyl, ($C_1$-$C_4$ alkyl)aminocarbonyl, ($C_1$-$C_4$ alkyl)carbonylamino, ($C_1$-$C_4$ alkylamino)$C_1$-$C_3$ alkyl, ($C_1$-$C_6$ alkoxy)$C_1$-$C_6$ alkyl, ($C_1$-$C_6$ alkoxy)$C_1$-$C_6$ alkoxy, ($C_2$-$C_4$ alkenyl)$C_1$-$C_3$ alkoxy, ($C_2$-$C_4$ alkenyloxy)$C_1$-$C_3$ alkoxy, ($C_2$-$C_4$ alkynyl)$C_1$-$C_3$ alkoxy, ($C_2$-$C_4$ alkynyloxy)$C_1$-$C_3$ alkoxy, ($C_3$-$C_{10}$ cycloalkyl)$C_1$-$C_3$ alkyl, ($C_3$-$C_{10}$ cycloalkyl)$C_1$-$C_3$ alkoxy, ($C_3$-$C_{10}$ cycloalkyl)carbonyl, ($C_3$-$C_7$ cycloalkyl)$C_2$-$C_5$ alkenyl, ($C_3$-$C_7$ cycloalkyl)$C_3$-$C_8$ alkenyloxy, ($C_3$-$C_7$ cycloalkyl)$C_3$-$C_8$ alkynyloxy, ($C_3$-$C_7$ cycloalkoxy)$C_1$-$C_3$ alkyl, ($C_3$-$C_7$ cycloalkoxy)$C_1$-$C_3$ alkoxy, ($C_3$-$C_7$ cycloalkoxy)$C_2$-$C_4$ alkenyl, ($C_3$-$C_7$ cycloalkoxy)$C_2$-$C_4$ alkynyl, ($C_5$-$C_{10}$ cycloalkenyl)$C_1$-$C_3$ alkyl, ($C_5$-$C_{10}$ cycloalkenyl)$C_1$-$C_3$ alkoxy, ($C_5$-$C_8$ cycloalkenyl)$C_3$-$C_5$ alkenyloxy, ($C_5$-$C_8$ cycloalkenyl)$C_3$-$C_8$ alkynyloxy, (heteroaryl)$C_1$-$C_3$ alkyl, (heteroaryl)$C_1$-$C_3$ alkoxy, amino, aminocarbonyl, aryl-($C_1$-$C_3$ alkyl)carbonyl, aryl-($C_1$-$C_3$ alkyl)carbonyloxy, aryl, arylcarbonyl, arylcarbonylamino, arylcarbonyloxy, aryloxy, arylthio, arylsulfinyl, arylsulfonyl, arylsulfonylamino, arylsulfonyloxy, $C_1$-$C_4$ alkylamino, $C_1$-$C_4$ alkylthio, $C_1$-$C_4$ alkylsulfinyl, $C_1$-$C_4$ alkylsulfonyl, $C_1$-$C_4$ alkylsulfonylamino, $C_1$-$C_4$ alkylsulfonyloxy, $C_1$-$C_6$ alkyl, $C_1$-$C_6$ alkoxy, $C_2$-$C_6$ alkenyl, $C_2$-$C_6$ alkenyloxy, $C_2$-$C_6$ alkynyl, $C_2$-$C_6$ alkynyloxy, $C_3$-$C_{10}$ cycloalkyl, $C_3$-$C_{10}$ cycloalkoxy, $C_3$-$C_{10}$ cycloalkylthio, $C_3$-$C_{10}$ cycloalkylsulfinyl, $C_3$-$C_{10}$ cycloalkylsulfonyl, $C_3$-$C_6$ cycloalkylidenmethyl, $C_5$-$C_{10}$ cycloalkenyl, $C_5$-$C_{10}$ cycloalkenyloxy, $C_5$-$C_{10}$ cycloalkenylthio, $C_5$-$C_{10}$ cycloalkenylsulfinyl, $C_5$-$C_{10}$ cycloalkenylsulfonyl, cyano, deuterium, di-($C_1$-$C_3$ alkyl)amino, di-($C_1$-$C_3$ alkyl)aminocarbonyl, di-($C_1$-$C_3$ alkylamino)$C_1$-$C_3$ alkyl, halo, heteroaryl, heteroarylcarbonyl, heteroarylcarbonylamino, heteroaryloxy, hydrogen, hydroxy, hydroxycarbonyl, nitro, t-butyldimethylsilyl, t-butyldimethylsilyloxy, tri-($C_1$-$C_4$ alkyl)silyl-$C_1$-$C_6$ alkyl, tri-($C_1$-$C_4$ alkyl)silyl-$C_1$-$C_6$ alkoxy, tri-($C_1$-$C_4$ alkyl)silyl-$C_2$-$C_6$ alkenyl, tri-($C_1$-$C_4$ alkyl)silyl-$C_2$-$C_6$ alkynyl, trimethylsilyl, and trimethylsilyloxy. Those substituents including hydrogen atoms may be further substituted with deuterium.

In preferred embodiments of Formula II, $R^4$ is group Q; three of the groups $R^1$, $R^2$, $R^3$ and $R^5$ each independently represent hydrogen, deuterium, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkoxy or $C_3$-$C_{10}$ cycloalkoxy; and one of the remaining groups $R^1$, $R^2$, $R^3$ and $R^5$ independently represents hydrogen or deuterium. In particularly preferred embodiments of Formula II, $R^4$ is group Q; $R^3$ independently represents hydrogen, deuterium, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkoxy or $C_3$-$C_{10}$ cycloalkoxy; and $R^1$, $R^2$ and $R^5$ each independently represent hydrogen or deuterium. In more particularly preferred embodiments of Formula II, $R^4$ is group Q; $R^3$ independently represents hydrogen, deuterium, halogen, or $C_1$-$C_6$ alkyl; and $R^1$, $R^2$ and $R^5$ each independently represent hydrogen or deuterium.

In preferred embodiments of Formula II, $R^8$ independently represents hydroxy, cyano, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkoxy, $C_3$-$C_{10}$ cycloalkoxy, ($C_3$-$C_{10}$ cycloalkyl)$C_1$-$C_3$ alkoxy, ($C_3$-$C_7$ cycloalkyl)$C_3$-$C_5$ alkenyloxy, or ($C_3$-$C_7$ cycloalkyl)$C_3$-$C_5$ alkynyloxy; two of the groups $R^6$, $R^7$, $R^9$ and $R^{10}$ each independently represent hydrogen, deuterium, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkoxy or $C_3$-$C_{10}$ cycloalkoxy; and two of the remaining groups $R^6$, $R^7$, $R^9$ and $R^{10}$ each independently represent hydrogen or deuterium. In particularly preferred embodiments of Formula II, $R^8$ independently represents hydroxy, cyano, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkoxy, $C_3$-$C_{10}$ cycloalkoxy, ($C_3$-$C_{10}$ cycloalkyl)$C_1$-$C_3$ alkoxy, ($C_3$-$C_7$ cycloalkyl)$C_3$-$C_5$ alkenyloxy, or ($C_3$-$C_7$ cycloalkyl)$C_3$-$C_5$ alkynyloxy; two of the groups $R^6$, $R^7$, $R^9$ and $R^{10}$ each independently represent hydrogen, deuterium, halo, or $C_1$-$C_6$ alkyl; and two of the remaining groups $R^6$, $R^7$, $R^9$ and $R^{10}$ each independently represent hydrogen or deuterium. In particularly preferred embodiments of Formula II, $R^8$ independently represents hydroxy, cyano, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkoxy, $C_3$-$C_{10}$ cycloalkoxy, ($C_3$-$C_{10}$ cycloalkyl)$C_1$-$C_3$ alkoxy, ($C_3$-$C_7$ cycloalkyl)$C_3$-$C_5$ alkenyloxy, or ($C_3$-$C_7$ cycloalkyl)$C_3$-$C_5$ alkynyloxy; and $R^6$, $R^7$, $R^9$ and $R^{10}$ each independently represent hydrogen or deuterium.

In preferred embodiments of Formula II, $R^{11}$, $R^{12}$, $R^{13}$, $R^{17}$, $R^{18}$, $R^{20}$, and $R^{22}$ each independently represent hydrogen or deuterium.

In preferred embodiments of Formula II, $R^{14}$, $R^{15}$ and $R^{16}$ each independently represent hydrogen, ($C_1$-$C_{18}$ alkyl)carbonyl, arylcarbonyl, ($C_3$-$C_{10}$ cycloalkyl)carbonyl, $C_1$-$C_6$ alkyl, $C_3$-$C_7$ cycloalkyl, aryl, heteroaryl, ($C_3$-$C_7$ cycloalkyl)$C_1$-$C_3$ alkyl, (aryl)$C_1$-$C_3$ alkyl, or trimethylsilyl. In particularly preferred embodiments of Formula II, $R^{14}$, $R^{15}$ and $R^{16}$ each independently represent hydrogen, $C_1$-$C_6$ alkyl, $C_3$-$C_7$ cycloalkyl, aryl, ($C_3$-$C_7$ cycloalkyl)$C_1$-$C_3$ alkyl, or trimethylsilyl. In more particularly preferred embodiments of Formula II, $R^{14}$, $R^{15}$ and $R^{16}$ each independently represent hydrogen.

In preferred embodiments of Formula II, $R^{19}$ independently represents hydroxy, ($C_1$-$C_{18}$ alkyl)carbonyloxy, arylcarbonyloxy, ($C_3$-$C_{10}$ cycloalkyl)carbonyloxy, hydrogen, deuterium, halo, $C_1$-$C_6$ alkyl, $C_1$-$C_6$ alkoxy, $C_3$-$C_7$ cycloalkoxy, aryloxy, heteroaryloxy, ($C_3$-$C_7$ cycloalkyl)$C_1$-$C_3$ alkoxy, (aryl)$C_1$-$C_3$ alkoxy, or trimethylsilyloxy. In particularly preferred embodiments of Formula II, $R^{19}$ independently represents hydroxy, hydrogen, deuterium, halo, $C_1$-$C_6$ alkyl, $C_1$-$C_6$ alkoxy, $C_3$-$C_7$ cycloalkoxy, aryloxy, ($C_3$-$C_7$ cycloalkyl)$C_1$-$C_3$ alkoxy, or trimethylsilyloxy. In other embodiments of Formula II, $R^{19}$ is hydroxy.

In preferred embodiments of Formula II, $R^{21}$ is hydroxy, hydrogen, or deuterium.

In preferred embodiments of Formula II, $R^{23}$ is oxygen.

In the foregoing preferred embodiments, alkyl, alkenyl, alkynyl, cycloalkyl and cycloalkenyl groups or portions optionally may be partly or completely substituted with fluorine or deuterium and may be mono- or disubstituted by identical or different substituents selected from chlorine, hydroxy, $C_1$-$C_3$ alkoxy, and $C_1$-$C_3$ alkyl; and in cycloalkyl and cycloalkenyl groups or portions one or two methylene groups are optionally replaced independently of one another by N, NR$^a$, O, S, CO, SO or SO$_2$, where R$^a$ is selected from hydrogen, deuterium, ($C_1$-$C_{18}$ alkyl)carbonyl, arylcarbonyl, ($C_3$-$C_{10}$ cycloalkyl)carbonyl, $C_1$-$C_6$ alkyl, $C_3$-$C_7$ cycloalkyl, aryl, heteroaryl, ($C_3$-$C_7$ cycloalkyl)$C_1$-$C_3$ alkyl, (aryl)$C_1$-$C_3$ alkyl, or trimethylsilyl.

Formula IIA represents still other preferred embodiments of Formula II:

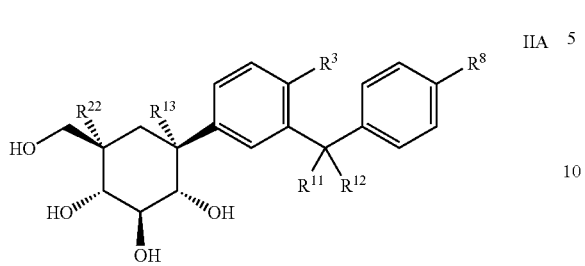

wherein R³ independently represents hydrogen, deuterium, halogen, or C₁-C₆ alkyl; R⁸ independently represents hydroxy, cyano, C₁-C₆ alkyl, C₂-C₆ alkenyl, C₂-C₆ alkynyl, C₃-C₁₀ cycloalkyl, C₁-C₆ alkoxy, C₃-C₁₀ cycloalkoxy, (C₃-C₁₀ cycloalkyl)C₁-C₃ alkoxy, (C₃-C₇ cycloalkyl)C₃-C₅ alkenyloxy, or (C₃-C₇ cycloalkyl)C₃-C₅ alkynyloxy; and R¹¹, R¹² and R¹³ each independently represent hydrogen or deuterium;

wherein at least (i) one of R¹¹, R¹², R¹³ and R²² is deuterium, or (ii) R⁸ is selected from C₁-C₆ alkyl, C₂-C₆ alkenyl, C₂-C₆ alkynyl, C₃-C₁₀ cycloalkyl, C₁-C₆ alkoxy, C₃-C₁₀ cycloalkoxy, (C₃-C₁₀ cycloalkyl)C₁-C₃ alkoxy, (C₃-C₇ cycloalkyl)C₃-C₅ alkenyloxy and (C₃-C₇ cycloalkyl)C₃-C₅ alkynyloxy, wherein the alkyl, alkenyl, alkynyl, cycloalkyl or cycloalkenyl group or portion is partly or completely substituted with deuterium.

Formula IIB represents still other preferred embodiments of Formula II:

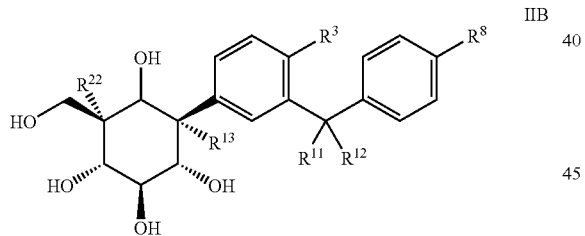

wherein R³ independently represents hydrogen, deuterium, halogen, or C₁-C₆ alkyl; R⁸ independently represents hydroxy, cyano, C₁-C₆ alkyl, C₂-C₆ alkenyl, C₂-C₆ alkynyl, C₃-C₁₀ cycloalkyl, C₁-C₆ alkoxy, C₃-C₁₀ cycloalkoxy, (C₃-C₁₀ cycloalkyl)C₁-C₃ alkoxy, (C₃-C₇ cycloalkyl)C₃-C₅ alkenyloxy, or (C₃-C₇ cycloalkyl)C₃-C₅ alkynyloxy; and R¹¹, R¹² and R¹³ each independently represent hydrogen or deuterium;

wherein at least (i) one of R¹¹, R¹², R¹³ and R²² is deuterium, or (ii) R⁸ is selected from C₁-C₆ alkyl, C₂-C₆ alkenyl, C₂-C₆ alkynyl, C₃-C₁₀ cycloalkyl, C₁-C₆ alkoxy, C₃-C₁₀ cycloalkoxy, (C₃-C₁₀ cycloalkyl)C₁-C₃ alkoxy, (C₃-C₇ cycloalkyl)C₃-C₅ alkenyloxy and (C₃-C₇ cycloalkyl)C₃-C₅ alkynyloxy, wherein the alkyl, alkenyl, alkynyl, cycloalkyl or cycloalkenyl group or portion is partly or completely substituted with deuterium.

Exemplary compounds of the invention include:

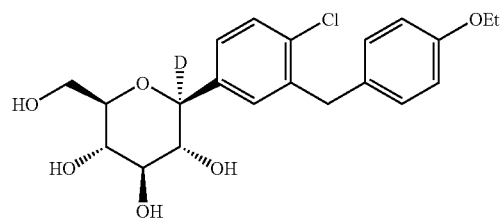 [SMILES: [2H][C@@]1(c2ccc(Cl)c(Cc3ccc(OCC)cc3)c2)O[C@H](CO)[C@@H](O)[C@H](O)[C@H]1O]

(2S,3R,4R,5S,6R)-2-(4-chloro-3-(4-ethoxybenzyl)phenyl)-6-(hydroxymethyl)tetrahydro-2H-pyran-2-d-3,4,5-triol;

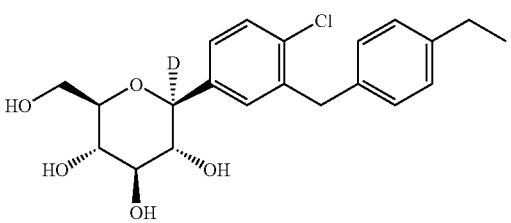 [SMILES: [2H][C@@]1(c2ccc(Cl)c(Cc3ccc(CC)cc3)c2)O[C@H](CO)[C@@H](O)[C@H](O)[C@H]1O]

(2S,3R,4R,5S,6R)-2-(4-chloro-3-((4-ethylbenzyl)phenyl)-6-(hydroxymethyl)tetrahydro-2H-pyran-2-d-3,4,5-triol;

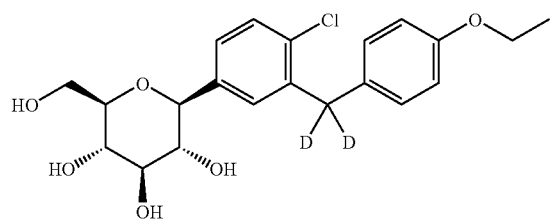

(2S,3R,4R,5S,6R)-2-(4-chloro-3-((4-ethoxyphenyl)methyl-d₂)phenyl)-6-(hydroxymethyl)tetrahydro-2H-pyran-3,4,5-triol;

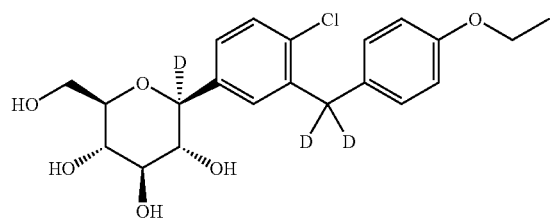 [SMILES: [2H]C([2H])(c1ccc(OCC)cc1)c1cc([C@]2([2H])O[C@H](CO)[C@@H](O)[C@H](O)[C@H]2O)ccc1Cl]

(2S,3R,4R,5S,6R)-2-(4-chloro-3-((4-ethoxyphenyl)methyl-d₂)phenyl)-6-(hydroxymethyl)tetrahydro-2H-pyran-2-d-3,4,5-triol;

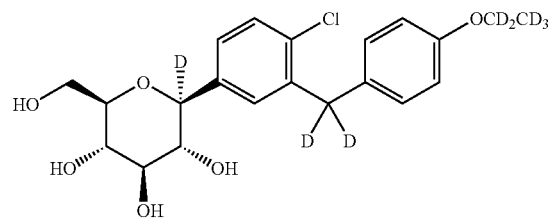

(2S,3R,4R,5S,6R)-2-(4-chloro-3-((4-(ethoxy-d₅)phenyl)methyl-d₂)phenyl)-6-(hydroxymethyl)tetrahydro-2H-pyran-2-d-3,4,5-triol;

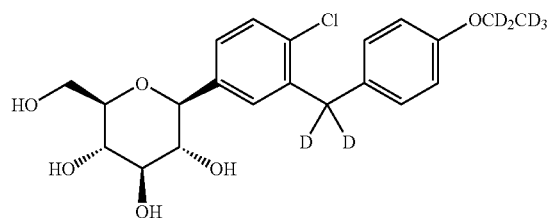

(2S,3R,4R,5S,6R)-2-(4-chloro-3-((4-(ethoxy-d$_5$)phenyl)methyl-d$_2$)phenyl)-6-(hydroxymethyl)tetrahydro-2H-pyran-3,4,5-triol;

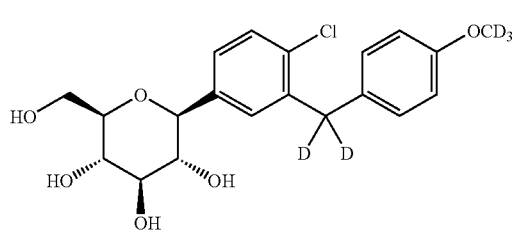

(2S,3R,4R,5S,6R)-2-(4-chloro-3-((4-(methoxy-d$_3$)phenyl)methyl-d$_2$)phenyl)-6-(hydroxymethyl)tetrahydro-2H-pyran-3,4,5-triol;

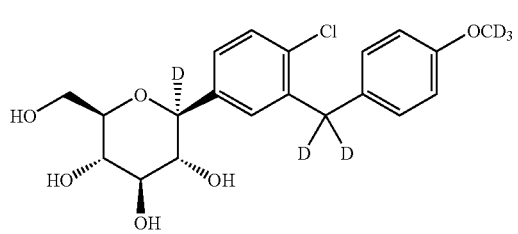

(2S,3R,4R,5S,6R)-2-(4-chloro-3-((4-(methoxy-d$_3$)phenyl)methyl-d$_2$)phenyl)-6-(hydroxymethyl)tetrahydro-2H-pyran-2-d-3,4,5-triol;

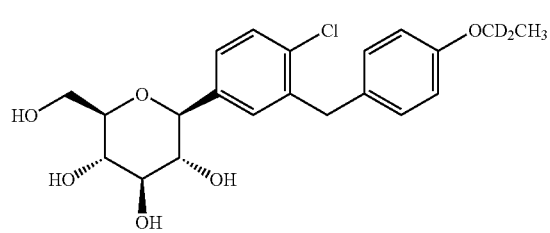

(2S,3R,4R,5S,6R)-2-(4-chloro-3-(4-(ethoxy-1,1-d$_2$)benzyl)phenyl)-6-(hydroxymethyl)tetrahydro-2H-pyran-3,4,5-triol;

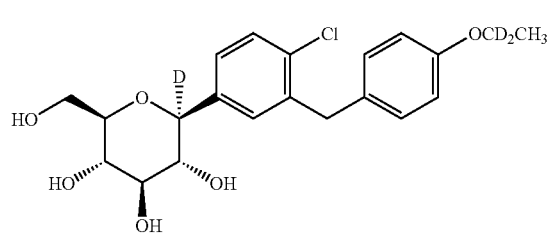

(2S,3R,4R,5S,6R)-2-(4-chloro-3-(4-(ethoxy-1,1-d$_2$)benzyl)phenyl)-6-(hydroxymethyl)tetrahydro-2H-pyran-2-d-3,4,5-triol;

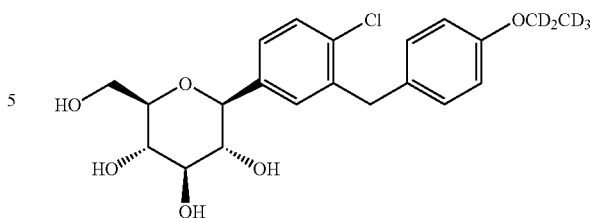

(2S,3R,4R,5S,6R)-2-(4-chloro-3-(4-(ethoxy-d$_5$)benzyl)phenyl)-6-(hydroxymethyl)tetrahydro-2H-pyran-3,4,5-triol;

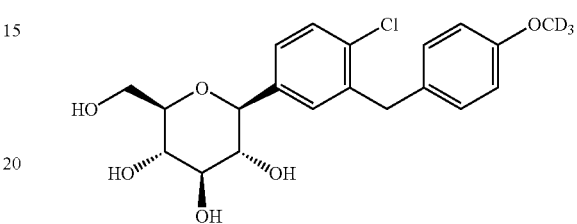

(2S,3R,4R,5S,6R)-2-(4-chloro-3-(4-(methoxy-d$_3$)benzyl)phenyl)-6-(hydroxymethyl)tetrahydro-2H-pyran-3,4,5-triol;

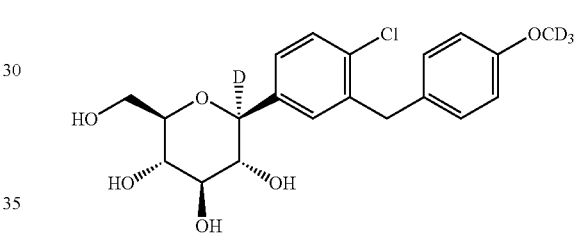

(2S,3R,4R,5S,6R)-2-(4-chloro-3-(4-(methoxy-d$_3$)benzyl)phenyl)-6-(hydroxymethyl)tetrahydro-2H-pyran-2-d-3,4,5-triol;

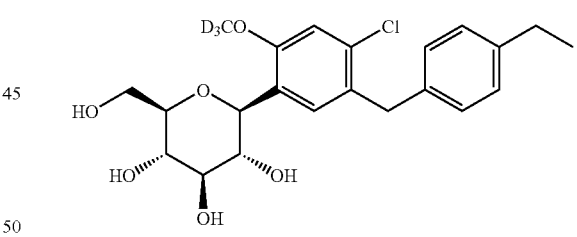

(2S,3R,4R,5S,6R)-2-(4-chloro-5-(4-ethylbenzyl)-2-(methoxy-d$_3$)phenyl)-6-(hydroxymethyl)tetrahydro-2H-pyran-3,4,5-triol;

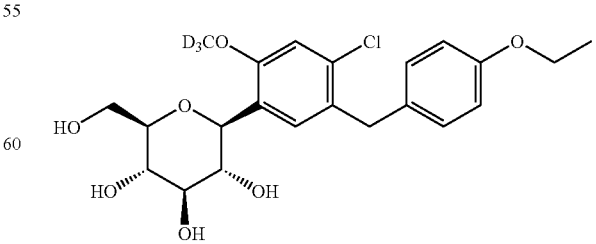

(2S,3R,4R,5S,6R)-2-(4-chloro-5-(4-ethoxybenzyl)-2-(methoxy-d$_3$)phenyl)-6-(hydroxymethyl)tetrahydro-2H-pyran-3,4,5-triol;

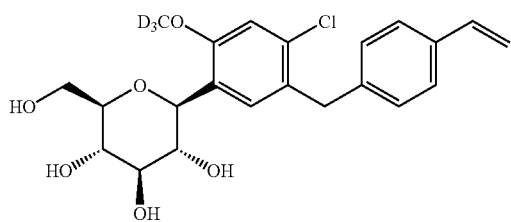

(2S,3R,4R,5S,6R)-2-(4-chloro-5-(4-vinylbenzyl)-2-(methoxy-d$_3$)phenyl)-6-(hydroxymethyl)tetrahydro-2H-pyran-3,4,5-triol;

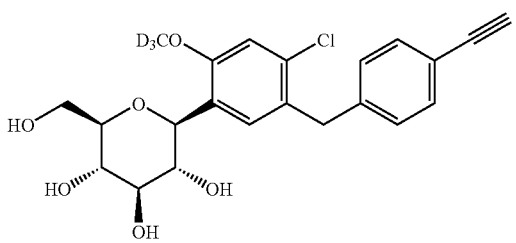

(2S,3R,4R,5S,6R)-2-(4-chloro-5-(4-ethynylbenzyl)-2-(methoxy-d$_3$)phenyl)-6-(hydroxymethyl)tetrahydro-2H-pyran-3,4,5-triol;

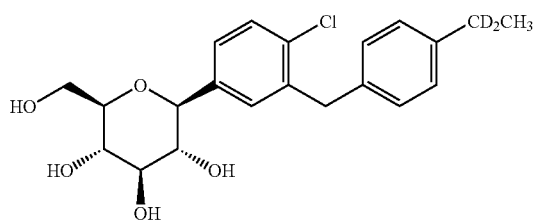

(2S,3R,4R,5S,6R)-2-(4-chloro-3-(4-(ethyl-1,1-d$_2$)benzyl)phenyl)-6-(hydroxymethyl)tetrahydro-2H-pyran-3,4,5-triol;

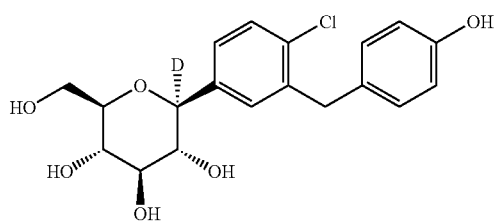 [SMILES: [2H][C@@]1(c2ccc(Cl)c(Cc3ccc(O)cc3)c2)O[C@H](CO)[C@@H](O)[C@H](O)[C@H]1O]

(2S,3R,4R,5S,6R)-2-(4-chloro-3-(4-hydroxybenzyl)phenyl)-6-(hydroxymethyl)tetrahydro-2H-pyran-2-d-3,4,5-triol;

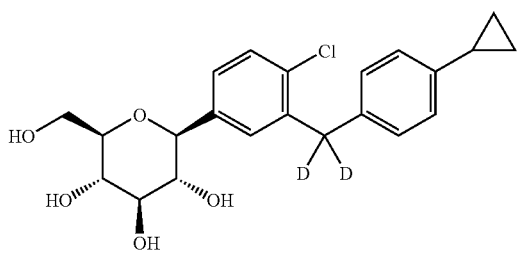 [SMILES: [2H]C([2H])(c1ccc(C2CC2)cc1)c1cc([C@@H]2O[C@H](CO)[C@@H](O)[C@H](O)[C@H]2O)ccc1Cl]

(2S,3R,4R,5S,6R)-2-(4-chloro-3-((4-cyclopropylphenyl)methyl-d$_2$)phenyl)-6-(hydroxymethyl)tetrahydro-2H-pyran-3,4,5-triol; and

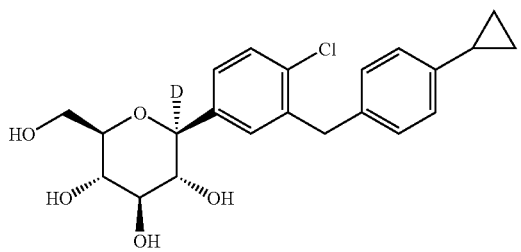

(2S,3R,4R,5S,6R)-2-(4-chloro-3-(4-cyclopropylbenzyl)phenyl)-6-(hydroxymethyl)tetrahydro-2H-pyran-2-d-3,4,5-triol;

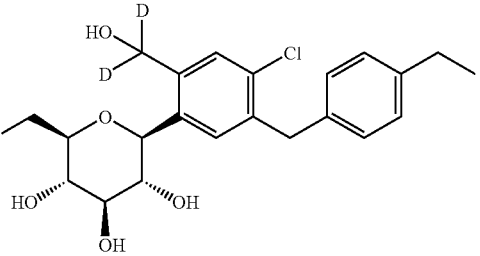

(2S,3R,4R,5S,6R)-2-(4-chloro-5-(4-ethylbenzyl)-2-(hydroxy(methyl-d$_2$))phenyl)-6-(hydroxymethyl)tetrahydro-2H-pyran-3,4,5-triol;

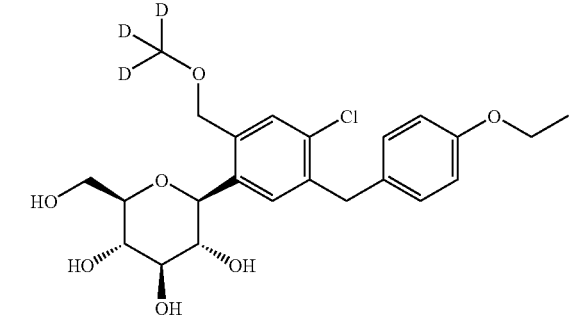 [SMILES: [2H]C([2H])([2H])OCc1cc(Cl)c(Cc2ccc(OCC)cc2)cc1[C@@H]1O[C@H](CO)[C@@H](O)[C@H](O)[C@H]1O]

(2S,3R,4R,5S,6R)-2-(4-chloro-5-(4-ethoxybenzyl)-2-((methoxy-d$_3$)methyl)phenyl)-6-(hydroxymethyl)tetrahydro-2H-pyran-3,4,5-triol;

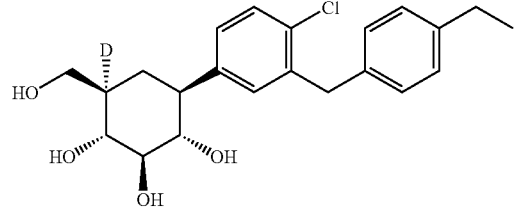 [SMILES: [2H][C@]1(CO)C[C@@H](c2ccc(Cl)c(Cc3ccc(CC)cc3)c2)[C@H](O)[C@@H](O)[C@@H]1O]

(1R,2R,3S,4S,6R)-4-(4-chloro-3-(4-ethylbenzyl)phenyl)-6-(hydroxymethyl)cyclohexane-6-d-1,2,3-triol;

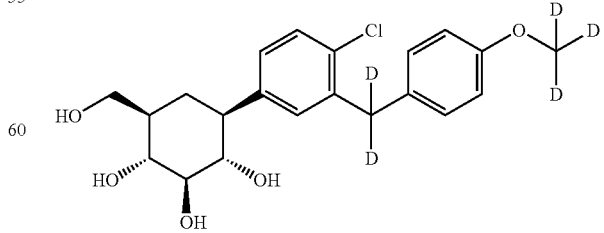

(1R,2R,3S,4S,6R)-4-(4-chloro-3-((4-(methoxy-d$_3$)phenyl)methyl-d$_2$)phenyl)-6-(hydroxymethyl)cyclohexane-1,2,3-triol;

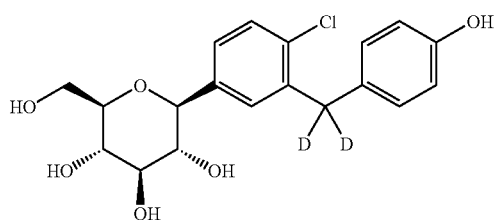 [SMILES: [2H]C([2H])(c1ccc(O)cc1)c1cc([C@@H]2O[C@H](CO)[C@@H](O)[C@H](O)[C@H]2O)ccc1Cl]

(2S,3R,4R,5S,6R)-2-(4-chloro-3-((4-hydroxyphenyl)methyl-d₂)phenyl)-6-(hydroxymethyl)tetrahydro-2H-pyran-3,4,5-triol;

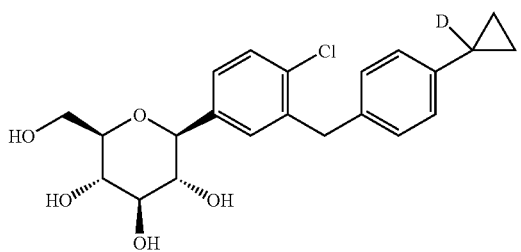 [SMILES: [2H]C1(c2ccc(Cc3cc([C@@H]4O[C@H](CO)[C@@H](O)[C@H](O)[C@H]4O)ccc3Cl)cc2)CC1]

(2S,3R,4R,5S,6R)-2-(4-chloro-3-(4-(cyclopropyl-1-d)benzyl)phenyl)-6-(hydroxymethyl)tetrahydro-2H-pyran-3,4,5-triol;

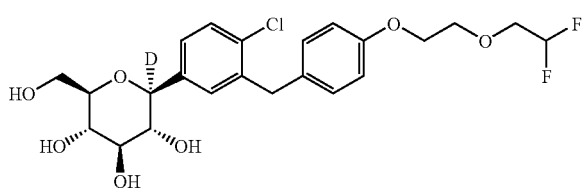 [SMILES: [2H][C@@]1(c2ccc(Cl)c(Cc3ccc(OCCOCC(F)F)cc3)c2)O[C@H](CO)[C@@H](O)[C@H](O)[C@H]1O]

(2S,3R,4R,5S,6R)-2-(4-chloro-3-(4-(2-(2,2-difluoroethoxy)ethoxy)benzyl)phenyl)-6-(hydroxymethyl)tetrahydro-2H-pyran-2-d-3,4,5-triol;

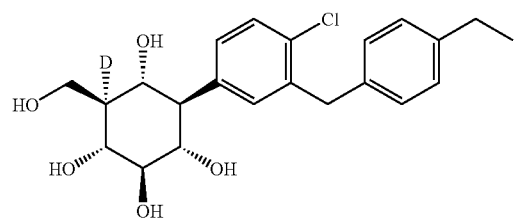 [SMILES: [2H][C@]1(CO)[C@H](O)[C@@H](c2ccc(Cl)c(Cc3ccc(CC)cc3)c2)[C@H](O)[C@@H](O)[C@@H]1O]

(1R,2R,3S,4R,5R,6S)-4-(4-chloro-3-(4-ethylbenzyl)phenyl)-6-(hydroxymethyl)cyclohexane-6-d-1,2,3,5-tetraol;

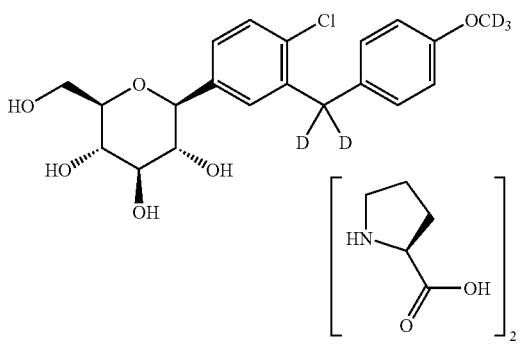

(2S,3R,4R,5S,6R)-2-(4-chloro-3-((4-(methoxy-d₃)phenyl)methyl-d₂)phenyl)-6-(hydroxymethyl)tetrahydro-2H-pyran-3,4,5-triol, bis(L-proline) complex;

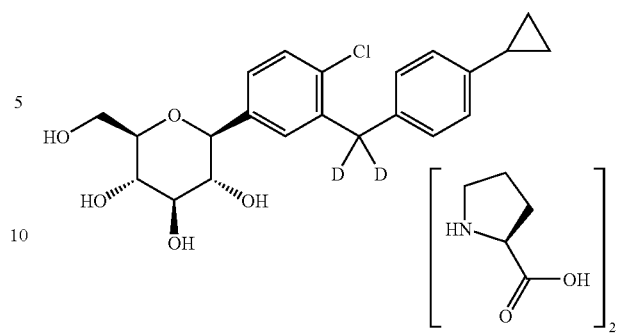

(2S,3R,4R,5S,6R)-2-(4-chloro-3-((4-cyclopropylphenyl)methyl-d₂)phenyl)-6-(hydroxymethyl)tetrahydro-2H-pyran-3,4,5-triol, bis(L-proline) complex;

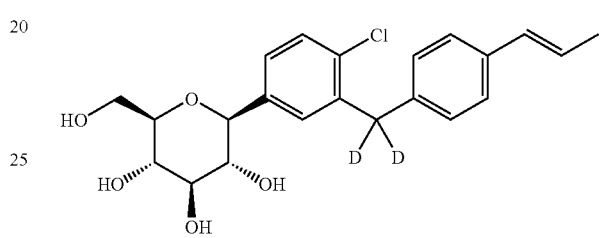

(2S,3R,4R,5S,6R)-2-(4-chloro-3-((4-((E)-prop-1-enyl)phenyl)methyl-d₂)phenyl)-6-(hydroxymethyl)tetrahydro-2H-pyran-3,4,5-triol

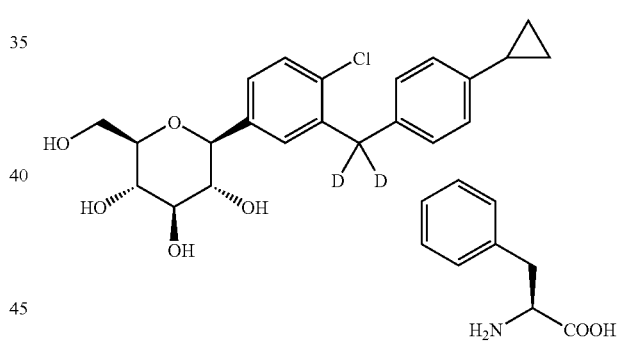

(2S,3R,4R,5S,6R)-2-(4-chloro-3-((4-cyclopropylphenyl)methyl-d₂)phenyl)-6-(hydroxymethyl)tetrahydro-2H-pyran-3,4,5-triol, L-phenylalanine complex (1:1)

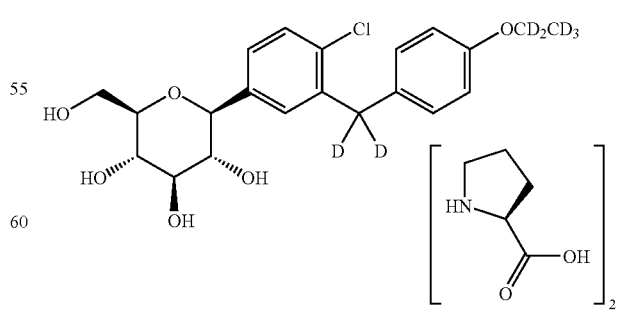

(2S,3R,4R,5S,6R)-2-(4-chloro-3-((4-(ethoxy-d₅)phenyl)methyl-d₂)phenyl)-6-(hydroxymethyl)tetrahydro-2H-pyran-3,4,5-triol, bis(L-proline) complex

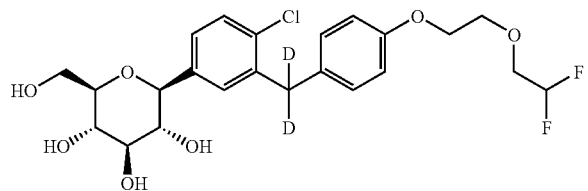 [SMILES: [2H]C([2H])(c1ccc(OCCOCC(F)F)cc1)c1cc([C@@H]2O[C@H](CO)[C@@H](O)[C@H](O)[C@H]2O)ccc1Cl]

(2S,3R,4R,5S,6R)-2-(4-chloro-3-((4-(2-(2,2-difluoroethoxy)ethoxy)phenyl)methyl-d₂)phenyl)-6-(hydroxymethyl)-tetrahydro-2H-pyran-3,4,5-triol;

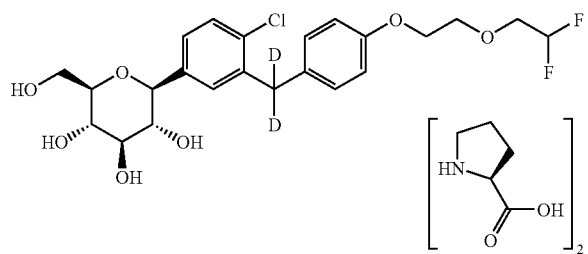

(2S,3R,4R,5S,6R)-2-(4-chloro-3-((4-(2-(2,2-difluoroethoxy)ethoxy)phenyl)methyl-d₂)phenyl)-6-(hydroxymethyl)-tetrahydro-2H-pyran-3,4,5-triol, bis(L-proline) complex;

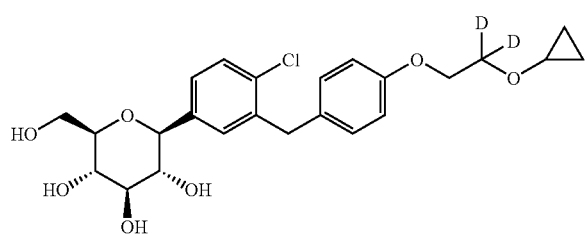 [SMILES: [2H]C([2H])(COc1ccc(Cc2cc([C@@H]3O[C@H](CO)[C@@H](O)[C@H](O)[C@H]3O)ccc2Cl)cc1)OC1CC1]

(2S,3R,4R,5S,6R)-2-(4-chloro-3-(4-(2-cyclopropoxy(ethoxy-2,2-d₂))benzyl)phenyl)-6-(hydroxymethyl)tetrahydro-2H-pyran-3,4,5-triol;

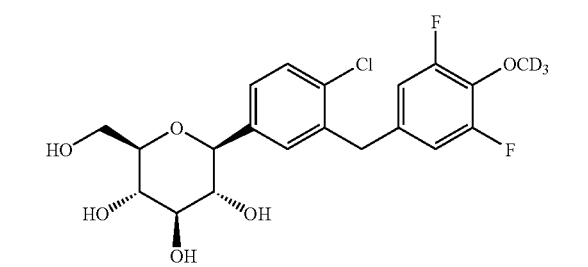

(2S,3R,4R,5S,6R)-2-(4-chloro-3-(3,5-difluoro-4-(methoxy-d₃)benzyl)phenyl)-6-(hydroxymethyl)tetrahydro-2H-pyran-3,4,5-triol;

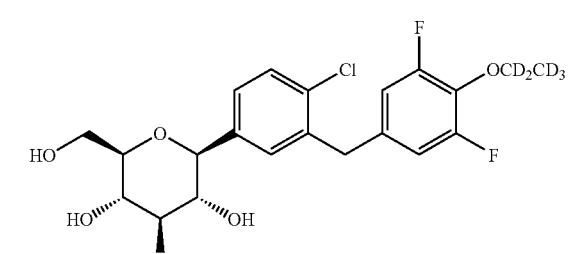

(2S,3R,4R,5S,6R)-2-(4-chloro-3-(3,5-difluoro-4-(ethoxy-d₅)benzyl)phenyl)-6-(hydroxymethyl)tetrahydro-2H-pyran-3,4,5-triol;

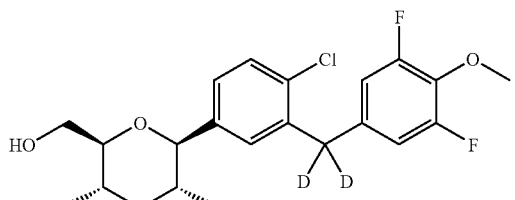

(2S,3R,4R,5S,6R)-2-(4-chloro-3-((3,5-difluoro-4-methoxyphenyl)methyl-d₂)phenyl)-6-(hydroxymethyl)tetrahydro-2H-pyran-3,4,5-triol;

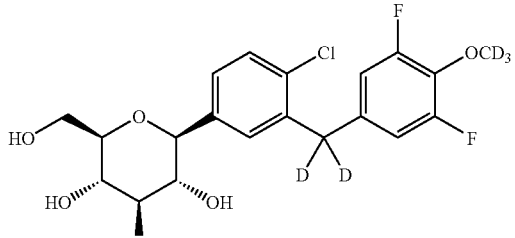

(2S,3R,4R,5S,6R)-2-(4-chloro-3-((3,5-difluoro-4-(methoxy-d₃)phenyl)methyl-d₂)phenyl)-6-(hydroxymethyl)tetrahydro-2H-pyran-3,4,5-triol;

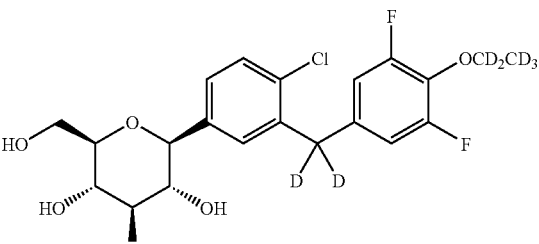

(2S,3R,4R,5S,6R)-2-(4-chloro-3-((3,5-difluoro-4-(ethoxy-d₅)phenyl)methyl-d₂)phenyl)-6-(hydroxymethyl)tetrahydro-2H-pyran-3,4,5-triol;

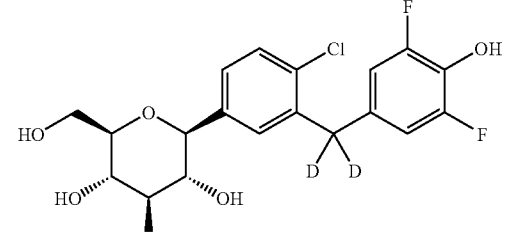

(2S,3R,4R,5S,6R)-2-(4-chloro-3-((3,5-difluoro-4-hydroxyphenyl)methyl-d₂)phenyl)-6-(hydroxymethyl)tetrahydro-2H-pyran-3,4,5-triol;

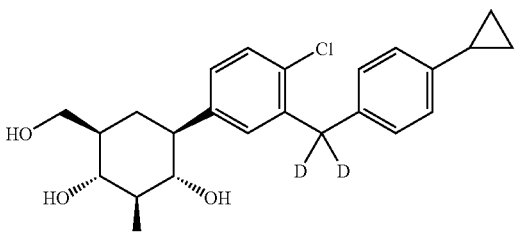

(1R,2R,3S,4S,6R)-4-(4-chloro-3-((4-cyclopropylphenyl)methyl-d₂)phenyl)-6-(hydroxymethyl)cyclohexane-1,2,3-triol;

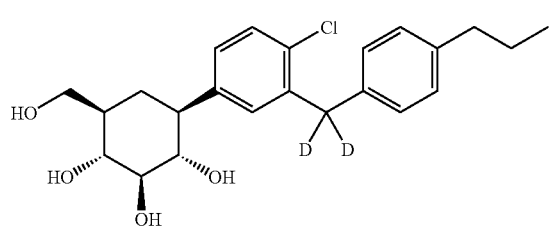

(1R,2R,3S,4S,6R)-4-(4-chloro-3-((4-propylphenyl)methyl-d₂)phenyl)-6-(hydroxymethyl)cyclohexane-1,2,3-triol;

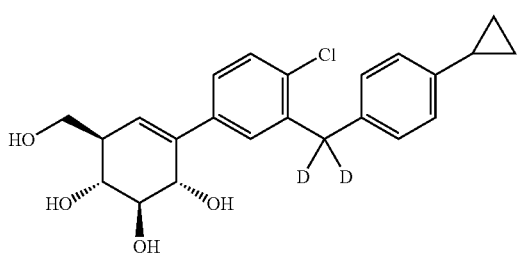 [SMILES: [2H]C([2H])(c1ccc(C2CC2)cc1)c1cc(C2=C[C@H](CO)[C@@H](O)[C@H](O)[C@H]2O)ccc1Cl]

(1R,2S,3S,6R)-4-(4-chloro-3-((4-cyclopropylphenyl)methyl-d₂)phenyl)-6-(hydroxymethyl)cyclohex-4-ene-1,2,3-triol;

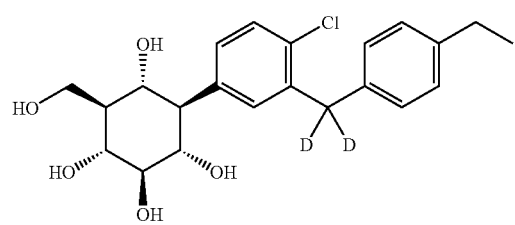 [SMILES: [2H]C([2H])(c1ccc(CC)cc1)c1cc([C@H]2[C@H](O)[C@@H](O)[C@H](O)[C@@H](CO)[C@@H]2O)ccc1Cl]

(1R,2R,3S,4R,5R,6S)-4-(4-chloro-3-((4-ethylphenyl)methyl-d₂)phenyl)-6-(hydroxymethyl)cyclohexane-1,2,3,5-tetraol;

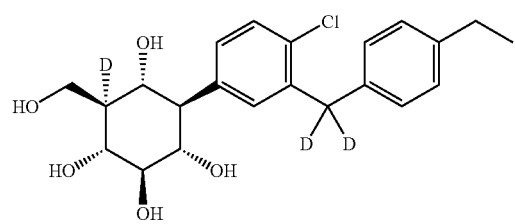

(1R,2R,3S,4R,5R,6S)-4-(4-chloro-3-((4-ethylphenyl)methyl-d₂)phenyl)-6-(hydroxymethyl)cyclohexane-6-d-1,2,3,5-tetraol;

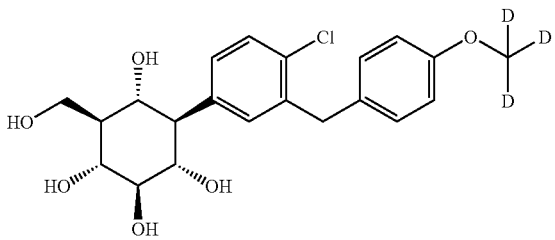 [SMILES: [2H]C([2H])([2H])Oc1ccc(Cc2cc([C@H]3[C@H](O)[C@@H](O)[C@H](O)[C@@H](CO)[C@@H]3O)ccc2Cl)cc1]

(1R,2R,3S,4R,5R,6S)-4-(4-chloro-3-(4-(methoxy-d₃)benzyl)phenyl)-6-(hydroxymethyl)cyclohexane-1,2,3,5-tetraol;

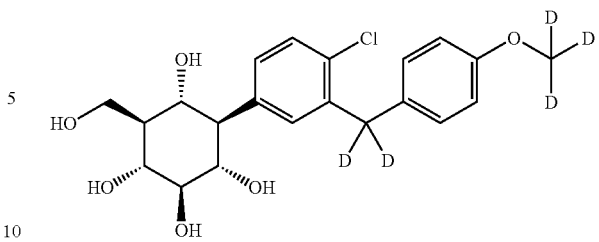

(1R,2R,3S,4R,5R,6S)-4-(4-chloro-3-((4-(methoxy-d₃)phenyl)methyl-d₂)phenyl)-6-(hydroxymethyl)cyclohexane-1,2,3,5-tetraol;

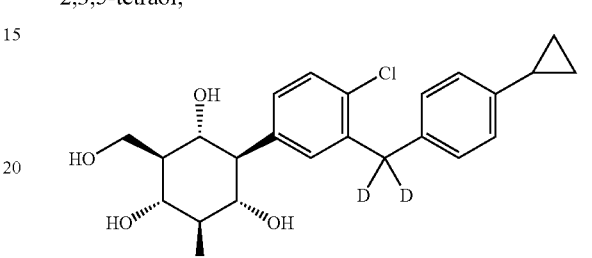

(1R,2R,3S,4R,5R,6S)-4-(4-chloro-3-((4-cyclopropylphenyl)methyl-d₂)phenyl)-6-(hydroxymethyl)cyclohexane-1,2,3,5-tetraol;

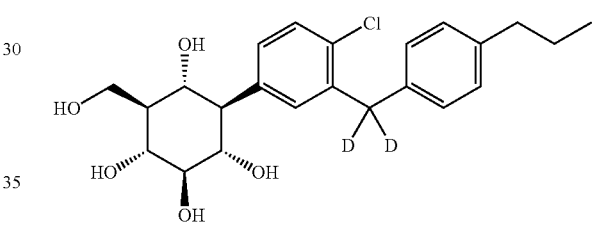

(1R,2R,3S,4R,5R,6S)-4-(4-chloro-3-((4-propylphenyl)methyl-d₂)phenyl)-6-(hydroxymethyl)cyclohexane-1,2,3,5-tetraol;

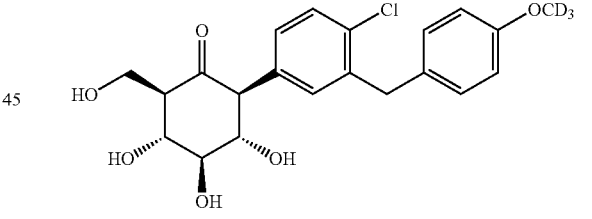

(2S,3S,4R,5R,6R)-2-(4-chloro-3-(4-(methoxy-d₃)benzyl)phenyl)-3,4,5-trihydroxy-6-(hydroxymethyl)cyclohexanone

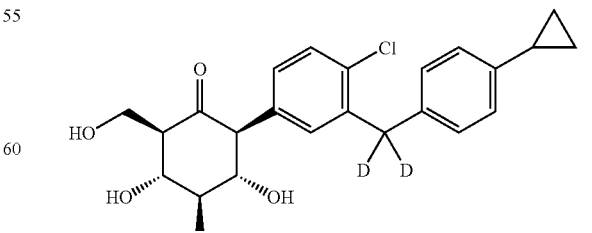

(2S,3S,4R,5R,6R)-2-(4-chloro-3-((4-cyclopropylphenyl)methyl-d₂)phenyl)-6-(hydroxymethyl)cyclohexanone

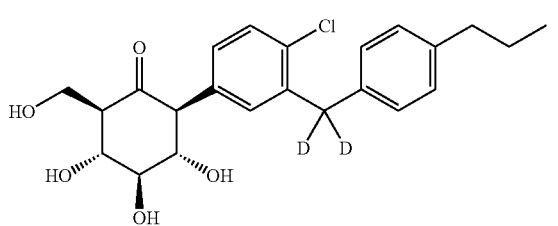 [SMILES: [2H]C([2H])(c1ccc(CCC)cc1)c1cc([C@@H]2C(=O)[C@H](CO)[C@@H](O)[C@H](O)[C@H]2O)ccc1Cl]

(2S,3S,4R,5R,6R)-2-(4-chloro-3-((4-propylphenyl)methyl-d$_2$)phenyl)-6-(hydroxymethyl)cyclohexanone

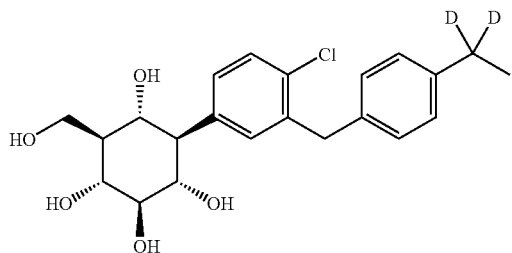 [SMILES: [2H]C([2H])(C)c1ccc(Cc2cc([C@H]3[C@H](O)[C@@H](O)[C@H](O)[C@@H](CO)[C@@H]3O)ccc2Cl)cc1]

(1R,2R,3S,4R,5R,6S)-4-(4-chloro-3-(4-(ethyl-1,1-d$_2$)benzyl)phenyl)-6-(hydroxymethyl)cyclohexane-1,2,3,5-tetraol;

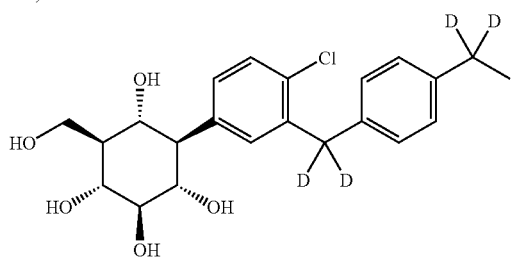

(1R,2R,3S,4R,5R,6S)-4-(4-chloro-3-((4-(ethyl-1,1-d$_2$)phenyl)methyl-d$_2$)phenyl)-6-(hydroxymethyl)cyclohexane-1,2,3,5-tetraol;

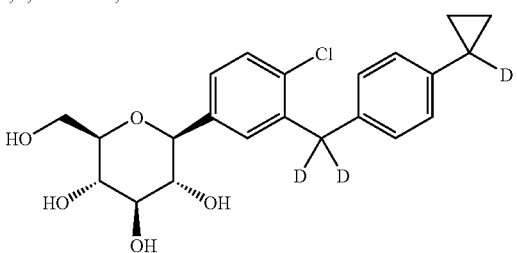

(2S,3R,4R,5S,6R)-2-(4-chloro-3-((4-(cyclopropyl-1-d)phenyl)methyl-d$_2$)phenyl)-6-(hydroxymethyl)tetrahydro-2H-pyran-3,4,5-triol; and

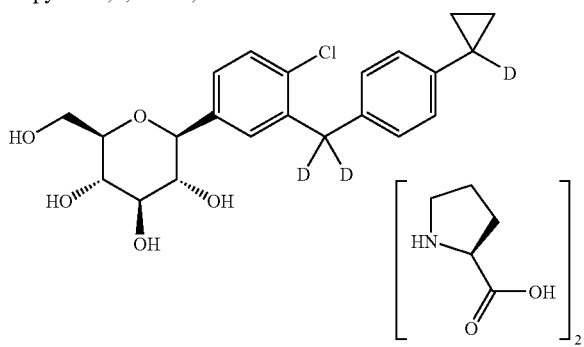

(2S,3R,4R,5S,6R)-2-(4-chloro-3-((4-(cyclopropyl-1-d)phenyl)methyl-d$_2$)phenyl)-6-(hydroxymethyl)tetrahydro-2H-pyran-3,4,5-triol, bis(L-proline) complex.

The present invention includes all tautomers and stereoisomers of compounds of Formulas I and II, either in admixture or in pure or substantially pure form. The compounds of the present invention can have asymmetric centers at the carbon atoms, and therefore the compounds of Formulas I and II can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

The present invention also provides for the prodrugs of compounds of Formulas I and II. Prodrugs of compounds of the invention include, but are not limited to, carboxylate esters, carbonate esters, hemi-esters, phosphorus esters, nitro esters, sulfate esters, sulfoxides, amides, carbamates, azo compounds, phosphamides, glycosides, ethers, acetals, and ketals. Prodrug esters and carbonates may be formed, for example, by reacting one or more hydroxyl groups of compounds of Formulas I and II with alkyl, alkoxy or aryl substituted acylating reagents using methods known to those of skill in the art to produce methyl carbonates, acetates, benzoates, pivalates and the like. Illustrative examples of prodrug esters of the compounds of the present invention include, but are not limited to, compounds of Formulas I and II having a carboxyl moiety wherein the free hydrogen is replaced by $C_1$-$C_4$ alkyl, $C_1$-$C_7$ alkanoyloxymethyl, 1-(($C_1$-$C_5$)alkanoyloxy)ethyl, 1-methyl-1-(($C_1$-$C_5$)alkanoyloxy)-ethyl, $C_1$-$C_5$ alkoxycarbonyloxymethyl, 1-(($C_1$-$C_5$)alkoxycarbonyloxy)ethyl, 1-methyl-1-(($C_1$-$C_5$)alkoxycarbonyloxy)ethyl, N—(($C_1$-$C_5$)alkoxycarbonyl)aminomethyl, 1-(N—(($C_1$-$C_5$)alkoxycarbonyl)amino)ethyl, 3-phthalidyl, 4-crotonolactonyl, gamma-butyrolacton-4-yl, di-N,N—($C_1$-$C_2$)alkylamino ($C_2$-$C_3$)alkyl (e.g., beta-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl. Oligopeptide modifications and biodegradable polymer derivatives (as described, for example, in Int. J. Pharm. 115, 61-67, 1995) are within the scope of the invention. Methods for selecting and preparing suitable prodrugs are provided, for example, in the following: T. Higuchi and V. Stella, "Prodrugs as Novel Delivery Systems," Vol. 14, ACS Symposium Series, 1975; H. Bundgaard, "Design of Prodrugs," Elsevier, 1985; and "Bioreversible Carriers in Drug Design," ed. Edward Roche, American Pharmaceutical Association and Pergamon Press, 1987.

The present invention also provides for the pharmaceutically acceptable salts of compounds of Formulas I and II and prodrugs thereof. The acids that can be used as reagents to prepare the pharmaceutically acceptable acid addition salts of the basic compounds of this invention are those which form non-toxic acid addition salts, i.e., salts containing pharmacologically acceptable anions (such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (1,1'-methylene-bis-2-hydroxy-3-naphthoate) salts). The bases that can be used as reagents to prepare the pharmaceutically acceptable base salts of the acidic compounds of the present invention are those that form non-toxic base salts with such compounds, including, but not limited to, those derived from pharmacologically acceptable cations such as alkali metal cations (e.g., potassium, lithium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines (e.g., methylamine, ethylamine, propylamine, dimethylamine, triethanolamine, diethylamine, t-butylamine, t-octylamine, trimethylamine, triethylamine, ethylenediamine, hydroxyethylamine, morpholine, piperazine, dehydroabietylamine, lysine and guanidine).

The present invention also includes isotopically-labeled compounds of Formulas I and II, wherein one or more atoms (other than hydrogen) are isotopically labeled, i.e., present in a composition at an abundance greater than that naturally occurring. Examples of isotopes that can be incorporated into compounds of the invention include, but are not limited to, tritium and isotopes of carbon, nitrogen, oxygen, fluorine, sulfur, and chlorine (such as $^3H$, $^{13}C$, $^{14}C$, $^{15}N$, $^{18}O$, $^{17}O$, $^{18}F$, $^{35}S$ and $^{36}Cl$). Isotopically-labeled compounds of Formulas I and II and prodrugs thereof, as well as isotopically-labeled, pharmaceutically acceptable salts of compounds of Formulas I and II and prodrugs thereof, are within the scope of the present invention. Isotopically-labeled compounds of the present invention are useful in assays of the tissue distribution of the compounds and their prodrugs and metabolites; preferred isotopes for such assays include $^3H$ and $^{14}C$. Isotopically-labeled compounds of this invention and prodrugs thereof can generally be prepared according to the methods described herein by substituting an isotopically-labeled reagent for a non-isotopically labeled reagent.

In another aspect, the present invention includes the compounds of Formulas I and II, and pharmaceutically acceptable salts, prodrugs and/or isotopically labeled compounds thereof, wherein alkyl, alkenyl, alkynyl, cycloalkyl, cycloalkenyl, aryl and heteroaryl groups or portions are optionally substituted with one to three substituents as defined above.

General Synthetic Methods

In other aspects, the present invention provides intermediates and processes useful for preparing the intermediates below as well as the compounds of Formulas I and II, and pharmaceutically acceptable salts and prodrugs thereof. Such processes are outlined in the following general preparative methods, with more detailed particular examples being presented below in the experimental section describing the working examples. By following the general preparative methods discussed below, or employing variations or alternative methods, the compounds of the invention can be readily prepared by the use of chemical reactions and procedures known to those of skill in the art. Unless otherwise specified, the variables (e.g., R groups) denoting groups in the general methods described below have the meanings as hereinbefore defined.

Those of skill in the art will recognize that compounds of the invention with each described functional group are generally prepared using slight variations of the below-listed general methods. Within the scope of each method, functional groups that are suitable to the reaction conditions are used. Functional groups that might interfere with certain reactions are presented in protected forms where necessary, and the removal of such protective groups is completed at appropriate stages by methods well known to those skilled in the art.

In certain cases compounds of the invention can be prepared from other compounds of the invention by elaboration, transformation, exchange and the like of the functional groups present. Such elaboration includes, but is not limited to, hydrolysis, reduction, oxidation, alkylation, acylation, esterification, amidation and dehydration. Such transformations can in some instances require the use of protecting groups by the methods disclosed in T. W. Greene and P. G. M. Wuts, *Protective Groups in Organic Synthesis;* $4^{th}$ Edition, Wiley: New York, (2007) or P. J. Kocienski. *Protecting Groups*. 3rd Edition. Georg Thieme Verlag, Stuttgart, (2005), and incorporated herein by reference. Such methods would be initiated after synthesis of the desired compound or at another place in the synthetic route that would be readily apparent to one skilled in the art.

When the following abbreviations and acronyms are used throughout the disclosure, they have the following meanings: $Ac_2O$, acetic anhydride; AcOEt, ethyl acetate; AcOH, acetic acid; $AlCl_3$, aluminum chloride; $BF_3.Et_2O$, boron trifluoride etherate; n-BuLi, n-butyllithium; calc., calculated; $CD_3OD$, methanol-$d_4$; $CDCl_3$, chloroform-d; $CH_2Cl_2$, methylene chloride; $CH_3CN$, acetonitrile; $(COCl)_2$, oxalyl chloride; DAST, (diethylamino)sulfur trifluoride; DCM, dichloromethane; DIAD, diisopropyl azodicarboxylate; DMEM, Dulbecco's Modified Eagle Medium; DMF, N,N-dimethylformamide; DMSO, dimethylsulfoxide; EA, ethyl acetate; eq, equivalents; ESI, electrospray ionization; Et, ethyl; $Et_3SiH$, triethylsilane; EtOAc, ethyl acetate; EtOH, ethanol; FBS, fetal bovine serum; h, hour; $H_2$, hydrogen gas; Hepes, 4-(2-hydroxyethyl)-1-piperazineethanesulfonic acid; $^1H$-NMR, proton nuclear magnetic resonance; HPLC, high performance liquid chromatography; LC-MS, liquid chromatography—mass spectroscopy; Lg, leaving group; $LiOH.H_2O$, lithium hydroxide monohydrate; Me, methyl; MeCN, acetonitrile; MeOH, methanol; $MeSO_3H$, methanesulfonic acid; Mg, magnesium; min, minute; MS, mass spectroscopy; MsOH, methanesulfonic acid; Pd/C, palladium on carbon; PE, petroleum ether; Ph, phenyl; RT, room temperature; TFA, trifluoroacetic acid; THF, tetrahydrofuran; TLC, thin layer chromatography; TMS, trimethylsilyl; $TsOH.H_2O$, 4-methylbenzenesulfonic acid hydrate; Ts or Tos, 4-methylbenzenesulfonyl, Tris, trishydroxymethylaminomethane (or 2-amino-2-(hydroxymethyl)propane-1,3-diol).

Methods of Deuteration

Phase Transfer Catalysis Methods

Preferred methods of deuteration employ phase transfer catalysts (e.g., tetraalkylammonium salts such as $NBu_4HSO_4$ as employed in Examples 30-31, 34-35, and 57). The use of phase transfer catalysis to exchange the methylene protons of diphenylmethane compounds resulted in a higher deuterium incorporation than reduction with deuterated silanes (e.g., triethyldeuteriosilane) in the presence of acid (e.g., methanesulfonic acid) or with sodium borodeuteride with a Lewis acid such as aluminum trichloride. Phase transfer catalysts are employed with deuterated water and in situ generated sodium hydroxide. An advantage of these methods is that the deuterated water and catalyst mixture can be reused to pre-enrich additional diphenylmethane compounds. The level of deuterium incorporation can be increased further by repeating the treatment with fresh reagent, which is not possible with the deuterated silanes or the sodium borodeuteride methods. The use of mineral oil also provided improved reaction yields and increased the percentage of deuterium incorporation.

Other phase transfer catalysts include: tributylmethylammonium chloride; tricaprylmethylammonium chloride; benzyl trimethylammonium chloride or bromide (TMBA); benzyltriethylammonium chloride or bromide (TEBA); tetra-n-butylammonium chloride, bromide, chlorate, or hydroxide; cetyl trimethylammonium chloride or bromide; tetra n-pentyl ammonium chloride or bromide; tetra n-hexyl ammonium chloride or bromide; trioctyl propyl ammonium chloride or bromide; benzyltribuytylammonium chloride, benzyltriphenyl phosphonium iodide, crown ethers, and cryptates.

General Synthetic Methods for Compounds of Formula I

Compounds of Formula I can be prepared using the methods summarized in Scheme 1 by those skilled in the art.

Scheme 1

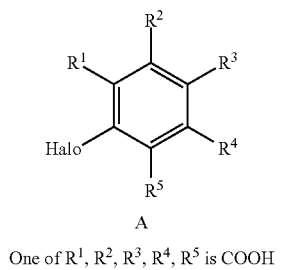

A

One of $R^1$, $R^2$, $R^3$, $R^4$, $R^5$ is COOH 1. activation
2. Catalyst or reagent

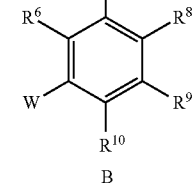

B

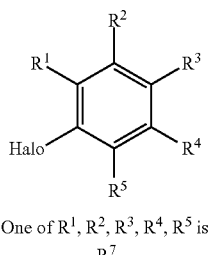

Reduction

One of $R^1$, $R^2$, $R^3$, $R^4$, $R^5$ is

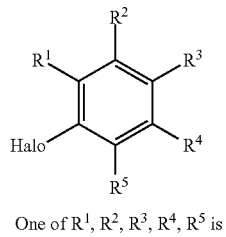

One of $R^1$, $R^2$, $R^3$, $R^4$, $R^5$ is

1. Activation
2. Deprotection
3. Protection

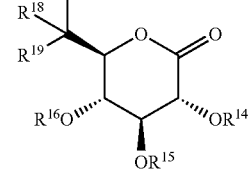

E

-continued

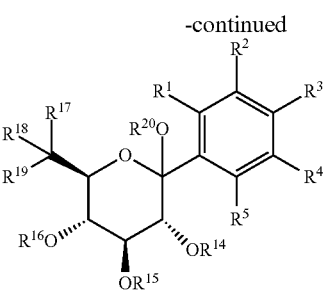

F

One of $R^1$, $R^2$, $R^3$, $R^4$, $R^5$ is

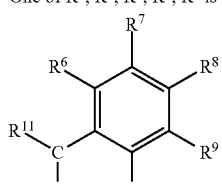

$R^{11}$ and $R^{12}$ = H or D

Reduction

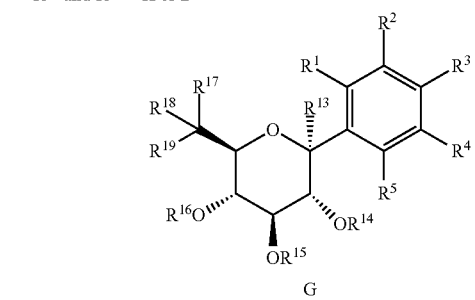

G

One of $R^1$, $R^2$, $R^3$, $R^4$, $R^5$ is

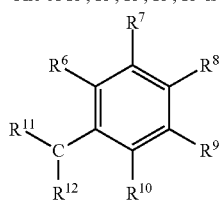

$R^{11}$ and $R^{12}$ = H or D
$R^{13}$ = H or D

As shown in Scheme 1, a compound of type A that has a carboxylic acid can be activated using an acid halide, carbonate, trifluoroacetate or triflate like thionyl chloride (SOCl$_2$), phosphoryl oxychloride (POCl$_3$), oxalyl chloride ((COCl)$_2$), oxalyl bromide ((COBr)$_2$), no activation or other acyl activators and coupled with an appropriately substituted aryl of type B (W═H) to give a benzophenone of type C in the presence of an appropriate catalyst like aluminum trichloride, tin tetrachloride, titanium tetrabromide, ferric chloride, zinc chloride, iron or others. Alternatively, the acid may be converted to an ester or an alkoxyalkylamide (Weinreb's amide) and reacted with an aryl metal of type B (W═Li, Mg, Na, K, or others) to give a benzophenone. The benzophenone carbonyl can be reduced using a metal borohydride like lithium, sodium, or zinc borohydride and an acid like trifluoroacetic acid, acetic acid, trichloroacetic acid or a Lewis acid like boron trifluoride etherate, aluminum trichloride (the acids and the reducing agents maybe deuterated) or using Clemmensen-type reduction with a metal like zinc; cadmium, in an acid like acetic acid, hydrochloric acid (the acids maybe deuterated) or using a homogeneous or heterogeneous catalyst and an atmosphere of hydrogen (or deuterium) or using various in situ source of hydride (or deuteride) like ammonium formate, cyclohexene to give products of type D. The halogen group of the products of type D can be activated by various organometallics (Li, Na, K, Mg, Zn, Sn or others) or boron derivatives and coupled with appropriately substituted lactones of type E. The protecting groups may or may not be removed with catalytic amount of acids (hydrochloric, hydrobromic, sulfuric, trifluoromethane sulfonic, methanesulfonic or others) in alcohols (methanol, ethanol, propanol or others) to give products of type F ($R^{20}$ is hydrogen, alkyl, alkylsilyl, arylalkylsilyl, or arylsilyl). The products of type F may be reduced with a source of hydride (or deuteride) like alkyl silane (triethyl silane, phenyl silane, pentafluorophenol and others), metal hydrides (deuterated or not) (sodium cyanoborohydride, sodium borohydride, dichloroalane, diisobutylaluminum hydride, lithium aluminum hydride), low oxidation metal (samarium diiodide) or borane (borane-dimethylsulfide) and an acid (trifluoroacetic acid, methanesulfonic acid, Nafion resin and others) or Lewis acid (trialkyltin chloride, zirconium tetrachloride, aluminum trichloride, TMS triflate, titanium tetrachloride, diethyl aluminum fluoride, tin tetrachloride) or other catalysts (Wilkinson's catalyst).

As shown in Scheme 2, compounds of type D where $R^{23}$ is an alkyl (Me, Et, Pr, Bn or other alkyls and aryl alkyl), a silyl ether (t-butyldimethyl silyl, triethylsilyl, triphenylsilyl, TMS, triisopropylsilyl or others) or other compatible oxygen protecting groups, can be reacted with a suitable reagent like Lewis acids: boron bromide, dimethylboron bromide, boron trifluoride etherate with or without additives, strong acids (sulfuric acid, TFA or others), salts in hot polar aprotic solvents (lithium, sodium, potassium or cesium halides/DMSO or others), fluoride sources (tetrabutylammonium fluoride, hydrofluoric acid, amine bases and hydrogen fluoride complexes and others), catalyst and hydride or hydrogen sources to give the free phenol where $R^{23}$ is H. This product may be coupled with a suitably an alkyl deuterated with one or more deuterium using Mitsunobu-type couplings (trialkylphosphine, dialkylazodicarboxylate or other dehydrating activating agent and a deuterated alcohol) or using base and a deuterated alkyl with a suitable leaving group in a suitable solvent using heat or not to give compounds of type H where $R^{23}$ is a deuterated (partially or fully or a combination of deuterium or fluoride) alkyl. Compound of type I can be prepared from compound of type H using similar condition as those described in Scheme 1 using the steps D+E→F→G but to give compounds of type I as the final product.

Scheme 2

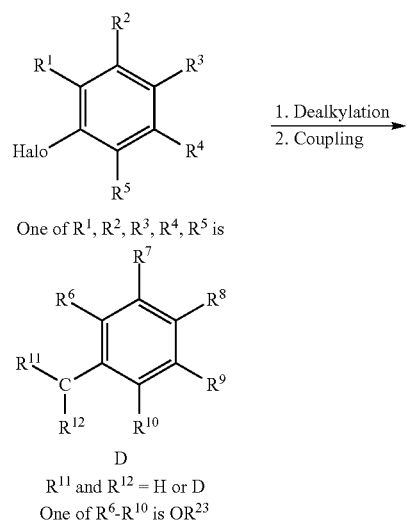

One of $R^1$, $R^2$, $R^3$, $R^4$, $R^5$ is

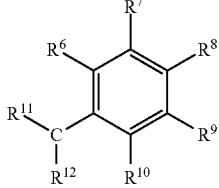

$R^{11}$ and $R^{12}$ = H or D
One of $R^6$-$R^{10}$ is $OR^{23}$

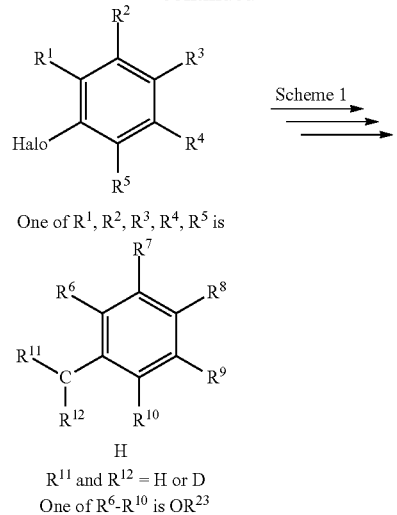

One of $R^1$, $R^2$, $R^3$, $R^4$, $R^5$ is

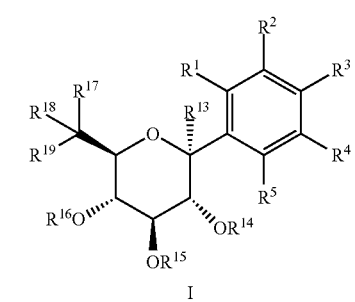

$R^{11}$ and $R^{12}$ = H or D
One of $R^6$-$R^{10}$ is $OR^{23}$

As shown in Scheme 3, compounds of type G where $R^1$ to $R^5$ is a nucleophile or a modified nucleophile can be prepared from compound of type J where one of $R^1$ to $R^5$ is an amine, one of $R^1$ to $R^5$ is a fluoride and one of the remaining $R^1$ to $R^5$ is a carboxylic acid or other carbonyl equivalent by treatment with a source of electrophilic halogen (Br+ or I+) like N-halosuccinimide (Br, I), or equivalent, bromine, iodine, iodine monobromide, with or without a catalyst in a suitable solvent to give compounds of type K. Conversion of the amine group of compounds of type K to a suitable leaving group (like a diazonium) followed by substitution with a halogen like chloride or other groups (Sandmeyer reaction) in the presence of a suitable catalyst like copper chloride or copper cyanide to give compounds of type L. The carboxylic acid of this type of compound can be activated using an acid halide, carbonate, trifluoroacetate or triflate like thionyl chloride (SOCl$_2$), phosphoryl oxychloride (POCl$_3$), oxalyl chloride ((COCl)$_2$), oxalyl bromide ((COBr)$_2$), no activation or other acyl activators and coupled with an appropriately substituted aryls of type M (W═H) to give benzophenones of type C in the presence of an appropriate catalyst like aluminum trichloride, tin tetrachloride, titanium tetrabromide, ferric chloride, zinc chloride, iron or others. Alternatively, the acid may be converted to an ester or an alkoxyalkylamide (Weinreb's amide) and reacted with an aryl metal of type M (W=Li, Mg, Na, K, or others) to give a benzophenone of type N. The fluoride of N could be displaced with nucleophiles like ROH (where R is alkyl deuterated or not) or other groups. The nucleophile of N could be further modified and the benzophenone carbonyl can be reduced using a metal borohydride like lithium, sodium, or zinc borohydride and an acid like trifluoroacetic acid, acetic acid, trichloroacetic acid or a Lewis acid like boron trifluoride etherate, aluminum trichloride (the acids and the reducing agents maybe deuterated) or using Clemmensen-type reduction with a metal like zinc, cadmium, in an acid like acetic acid, hydrochloric acid (the acids maybe deuterated) or using a homogeneous or heterogeneous catalyst and an atmosphere of hydrogen (or deuterium) or using various in situ source of hydride (or deuteride) like ammonium formate, cyclohexene to give products of type O. Compound of type G can be prepared from compound of type O using similar condition as those described in FIG. 1 using the steps D+E→F→G.

Scheme 3

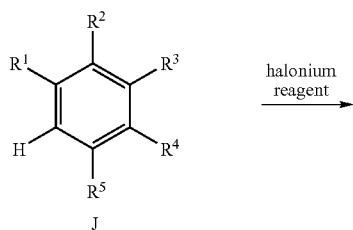

J

One of R1, R2, R3, R4, R5 is COOH
and one of R1, R2, R3, R4, R5 is F
and one of R1, R2, R3, R4, R5 is NH$_2$

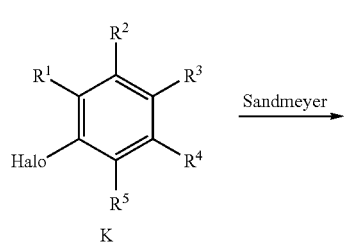

K

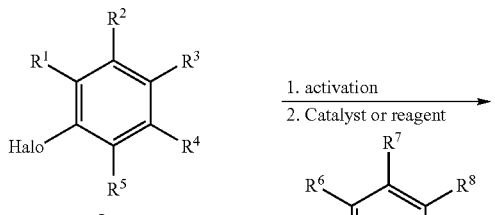

L

One of R1, R2, R3, R4, R5 is COOH
and one of R1, R2, R3, R4, R5 is F
and another one of R1, R2, R3,
R4, R5 is halogen

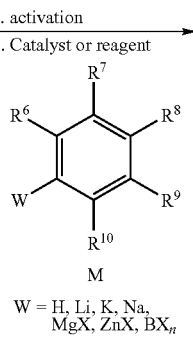

M

W = H, Li, K, Na,
MgX, ZnX, BX$_n$

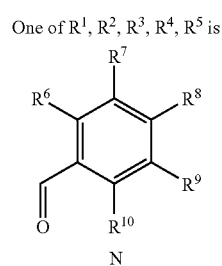

One of R$^1$, R$^2$, R$^3$, R$^4$, R$^5$ is

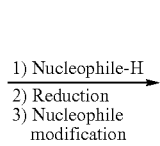

N and one of R1, R2, R3, R4, R5 is F
and another one of R1, R2, R3,
R4, R5 is halogen

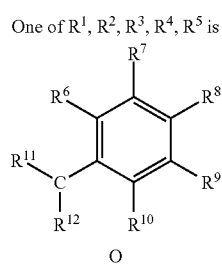

One of R$^1$, R$^2$, R$^3$, R$^4$, R$^5$ is

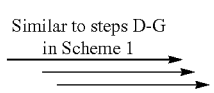

O

R$^{11}$ and R$^{12}$ = H or D
and one of R1, R2, R3, R4,
R5 is Nucleophile
and one of R1, R2, R3,R4,
R5 is halogen

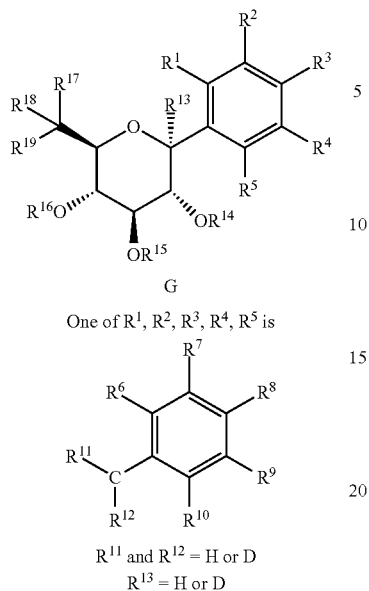

One of $R^1, R^2, R^3, R^4, R^5$ is $R^{11}$ and $R^{12}$ = H or D
$R^{13}$ = H or D

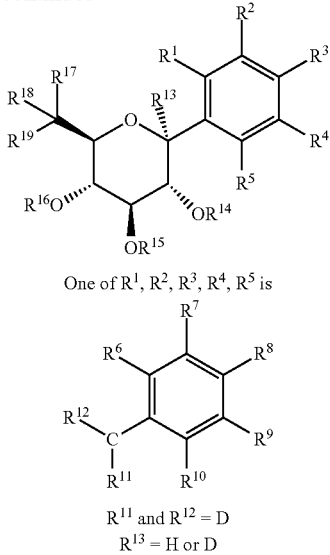

One of $R^1, R^2, R^3, R^4, R^5$ is $R^{11}$ and $R^{12}$ = D
$R^{13}$ = H or D

Compounds of Formula (I) can also be prepared according to the following synthetic schemes. For example, compounds can be prepared according to Scheme 4, as exemplified in Examples 31-33, 35, 39-42, and 57.

Scheme 4

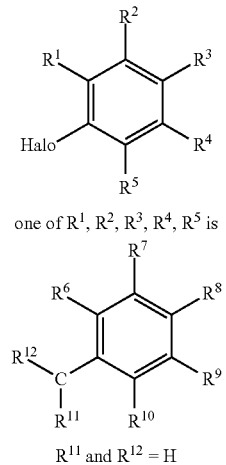

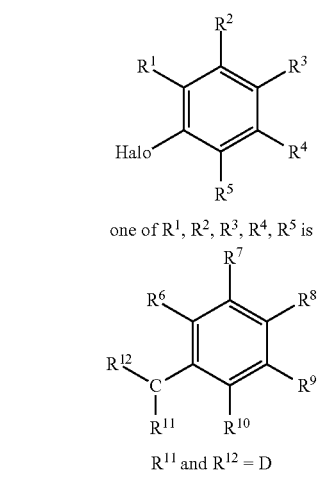

Compounds of Formula (I) can also be prepared according to Scheme 5 (see, for example, Example 30):

Scheme 5

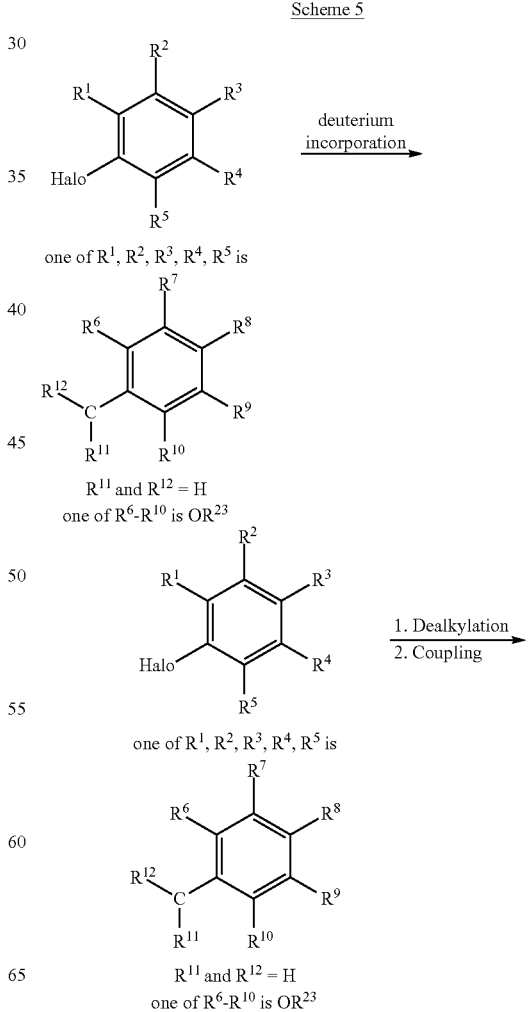

-continued

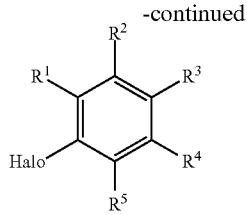

one of $R^1, R^2, R^3, R^4, R^5$ is

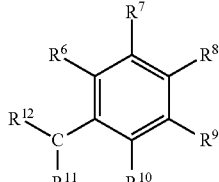

$R^{11}$ and $R^{12}$ = D
one of $R^6$-$R^{10}$ is $OR^{23}$

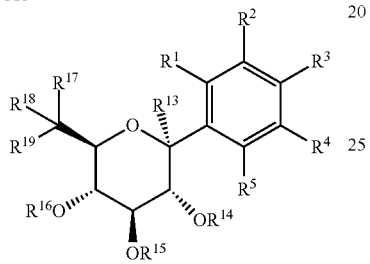

One of $R^1, R^2, R^3, R^4, R^5$ is

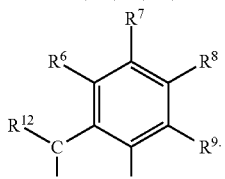

$R^{11}$ and $R^{12}$ = D
one of $R^6$-$R^{10}$ is $OR^{23}$
$R^{13}$ = H or D

Scheme 6 provides another generalized method for the synthesis of compounds of Formula (I) and is exemplified in Example 34.

Scheme 6

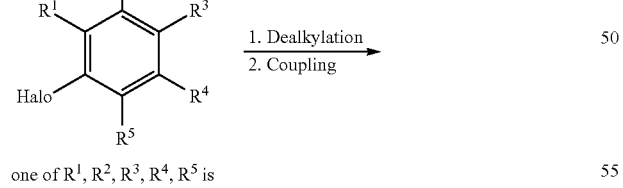

one of $R^1, R^2, R^3, R^4, R^5$ is

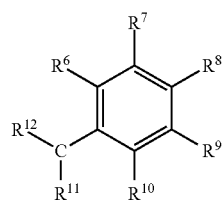

$R^{11}$ and $R^{12}$ = H
one of $R^6$-$R^{10}$ is $OR^{23}$

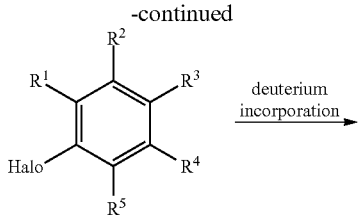

one of $R^1, R^2, R^3, R^4, R^5$ is

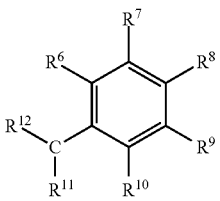

$R^{11}$ and $R^{12}$ = H
one of $R^6$-$R^{10}$ is $OR^{23}$

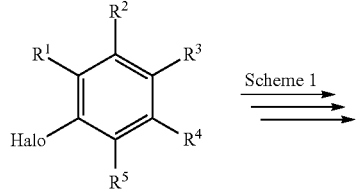

one of $R^1, R^2, R^3, R^4, R^5$ is

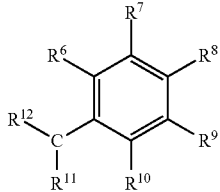

$R^{11}$ and $R^{12}$ = D
one of $R^6$-$R^{10}$ is $OR^{23}$

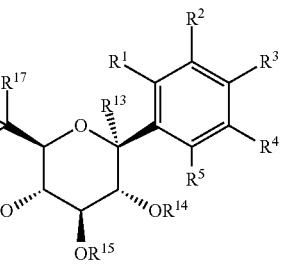

one of $R^1, R^2, R^3, R^4, R^5$ is

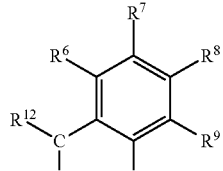

$R^{11}$ and $R^{12}$ = D
one of $R^6$-$R^{10}$ is $OR^{23}$
$R^{13}$ = H or D

General Synthetic Methods for Compounds of Formula II

Compounds of Formula II can be prepared using the methods summarized in Schemes 7 and 8. In Schemes 7 and 8, deuterium is incorporated into the compounds of the invention by replacing: protic acids with deuterated acids, undeuterated reducing agents with deuterated reducing agents, hydrogen ($H_2$) with $D_2$, hydride reagents with deuteride reagents, or in situ hydride reagents with in situ deuteride reagents.

As shown in Scheme 7, compounds of type D or O, prepared as described in Schemes 1-3, were treated with an activating agent such as n-BuLi, s-BuLi, or t-BuLi, or Mg at appropriate temperature in a solvent such as THF, followed by addition to intermediate A5, to produce intermediate A6. Intermediate A7 is obtained by treatment of A6 with a reducing agent such as $Et_3SiH$ or $Et_3SiD$ in the presence of a Lewis acid such as $BF_3.Et_2O$ or TFA. Then A7 is oxidized to form intermediate A8, which is deprotected to provide compound A10. This step can be applied to any protecting group present on functional groups in the molecule (e.g., in $R^1$, $R^2$, $R^3$ and the like). Alternatively, A7 maybe reduced with hydrogen (or deuterium) gas and catalyst or other reducing agents to give compounds of type A9 after deprotection. Compounds of type A11 can also be prepared by oxidation of intermediate A8 and deprotection.

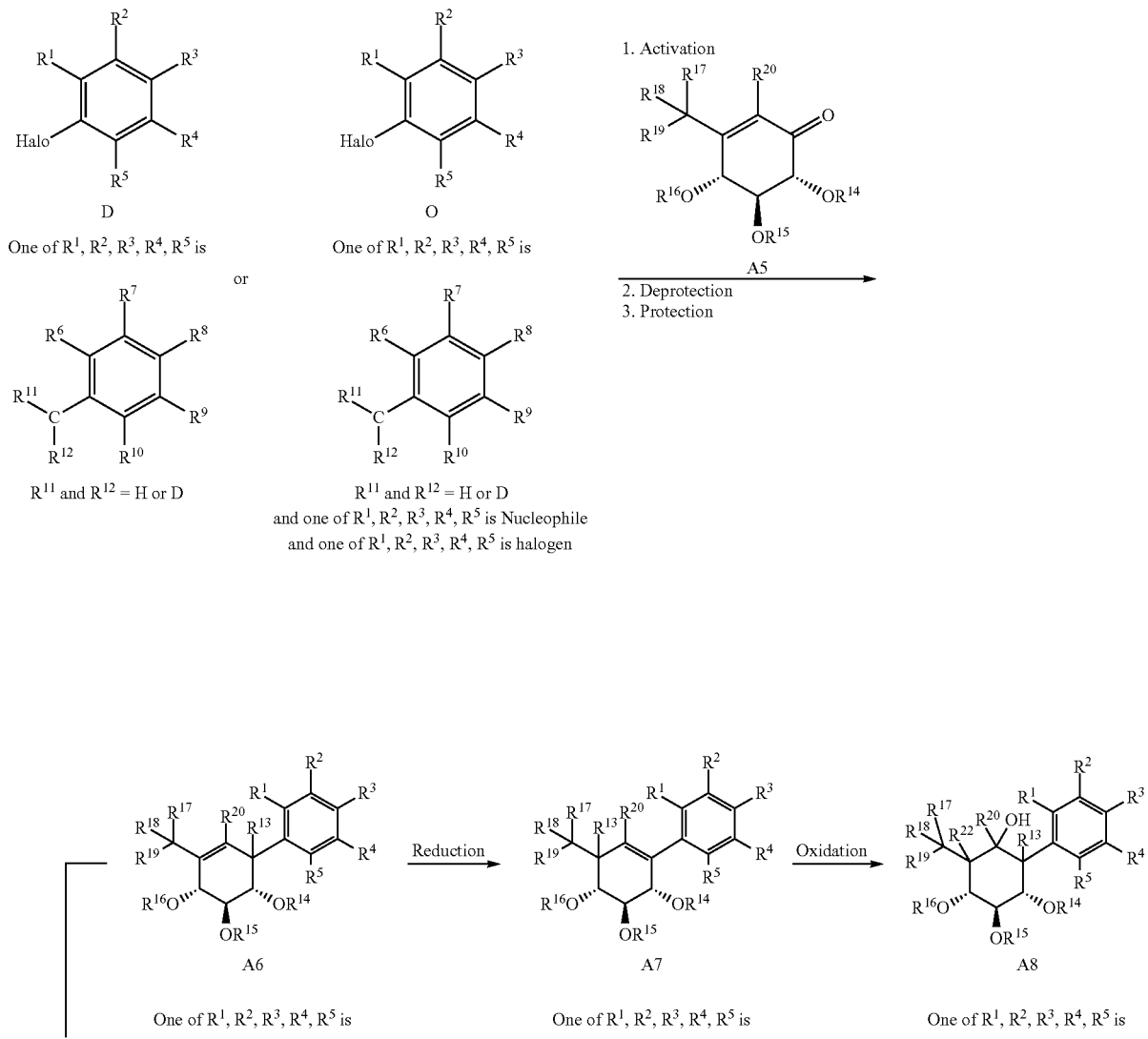

-continued

A9

R¹¹ and R¹² = H or D
R¹³ = OR
or
R¹¹ and R¹² = H or D
R¹³ = OR
and one of R¹, R², R³, R⁴, R⁵ is Nucleophile
and one of R¹, R², R³, R⁴, R⁵ is halogen

A11

R¹¹ and R¹² = H or D
R¹³ = H or D
or
R¹¹ and R¹² = H or D
R¹³ = H or D
and one of R¹, R², R³, R⁴, R⁵ is Nucleophile
and one of R¹, R², R³, R⁴, R⁵ is halogen

A10

R¹¹ and R¹² = H or D
R¹³ = H or D; R²² = H or D
or
R¹¹ and R¹² = H or D
R¹³ = H or D; R²² = H or D
and one of R¹, R², R³, R⁴, R⁵ is Nucleophile
and one of R¹, R², R³, R⁴, R⁵ is halogen 1) Reduction  2) Deprotection Reduction Deprotection → A9

Oxidation Deprotection → A11

Deprotection → A10

One of R¹, R², R³, R⁴, R⁵ is

R¹¹ and R¹² = H or D
R¹³ = H or D
R²¹ and R²² = H or D
or
R¹¹ and R¹² = H or D
R¹³, R²², and R²¹ = H or D;
and one of R¹, R², R³, R⁴, R⁵ is Nucleophile
and one of R¹, R², R³, R⁴, R⁵ is halogen One of R¹, R², R³, R⁴, R⁵ is R¹¹ and R¹² = H or D
R¹³ = H or D
R²⁰, R²² = H or D
or
R¹¹ and R¹² = H or D
R¹³ = H or D; R²² = H or D
and one of R¹, R², R³, R⁴, R⁵ is Nucleophile
and one of R¹, R², R³, R⁴, R⁵ is halogen One of R¹, R², R³, R⁴, R⁵ is R¹¹ and R¹² = H or D
R¹³ = H or D; R²² = H or D
or
R¹¹ and R¹² = H or D
R¹³ = H or D; R²² = H or D
and one of R¹, R², R³, R⁴, R⁵ is Nucleophile
and one of R¹, R², R³, R⁴, R⁵ is halogen Compounds of Formula II can also be prepared according to the methods summarized in Scheme 8. As shown in Scheme 8, compounds of the type A12, with PX being a protected form of a phenol group or a functional group than can be converted into a hydroxyl (halo [F, Cl, Br, I] via direct displacement with a suitable nucleophilic hydroxyl equivalent or an alkylsilyl or equivalent oxidizable group) either commercially available or prepared according to standard literature methods, is activated as described above in Scheme 1 and coupled with a suitable substrate of type A13 to give A14. The ketone group of intermediate A14 is selectively reduced to methylene with a reducing agent as described above in Scheme 1 followed by hydroxylation and deprotection or deprotection to give the phenol intermediate A15. Coupling of A15 with A16 provides intermediate A17. Oxidation and deprotection of A17 produces compounds of the type A18.

Scheme 8

A12

One of R¹, R², R³, R⁴, R⁵ is COOH
W = H, Li, K, Na, MgX, ZnX, BX₂

1. activation
2. Catalyst or reagent

A13

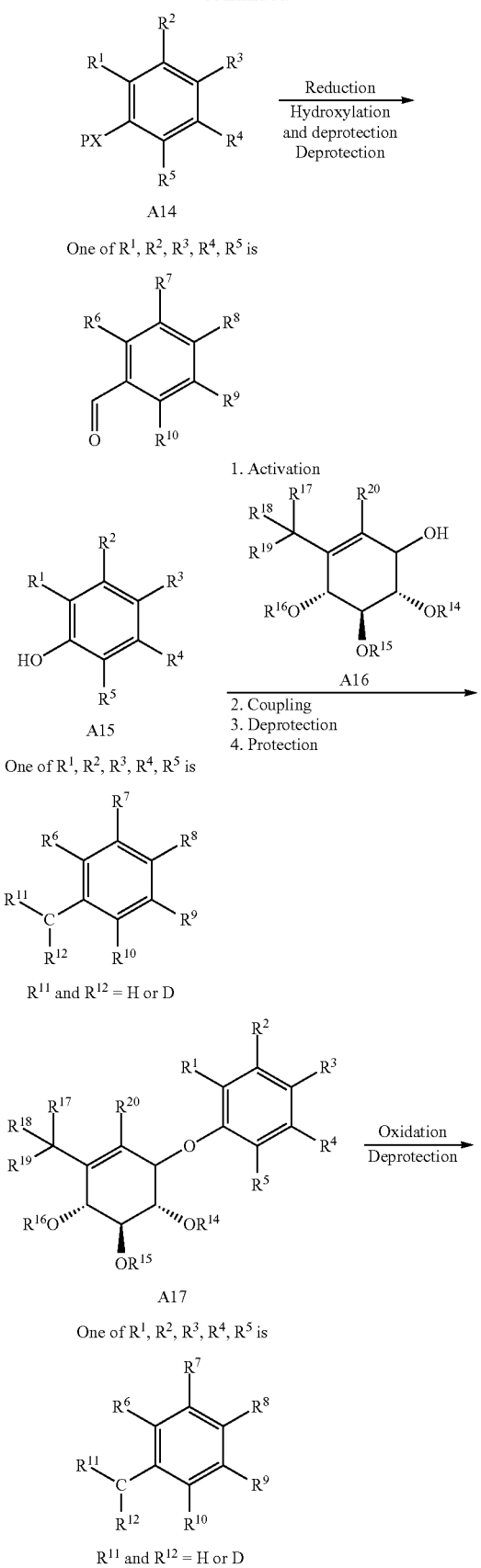

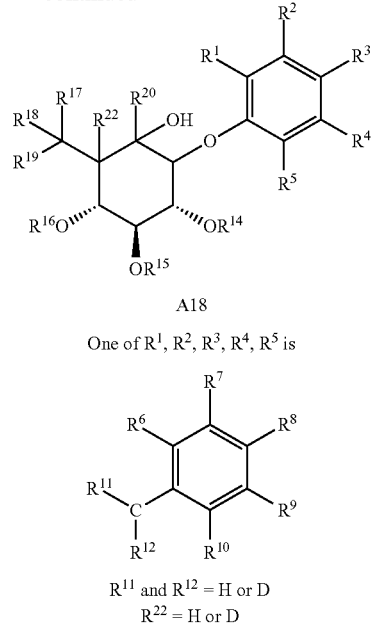

Pharmaceutical Compositions and Methods of Use

The present invention further provides a pharmaceutical composition comprising an effective amount of a compound or mixture of compounds of Formulas I or II, or a pharmaceutically acceptable salt or prodrug thereof, in a pharmaceutically acceptable carrier.

A compound of this invention can be incorporated into a variety of formulations for therapeutic administration. More particularly, a compound of the present invention can be formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of a compound of the present invention can be achieved in various ways, including oral, buccal, parenteral, intravenous, intradermal (e.g., subcutaneous, intramuscular), transdermal, etc., administration. Moreover, the compound can be administered in a local rather than systemic manner, for example, in a depot or nonimmediate release formulation.

Suitable formulations for use in the present invention are found in Remington. *The Science and Practice of Pharmacy*, 21$^{st}$ Ed., Gennaro, Ed., Lippencott Williams & Wilkins (2003), which is hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

Administration of the compositions of the invention includes oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, and the like.

The compositions of the present invention can be prepared for delivery in a nonimmediate formulation, for example, in semipermeable matrices of solid hydrophobic polymers containing the therapeutic agent. Various types of nonimmediate-release materials have been established and are well known by those skilled in the art. Current nonimmediate-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Nonimmediate-release delivery systems can, depending on their design, release the compounds over the course of hours or days, for instance, over 4, 6, 8, 10, 12, 16, 20, 24 hours or more. Usually, nonimmediate release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The nonimmediate release formulations can also be prepared using natural ingredients, such as minerals, including titanium dioxide, silicon dioxide, zinc oxide, and clay (see, U.S. Pat. No. 6,638,521, herein incorporated by reference). Exemplified nonimmediate release formulations that can be used in delivering a compound of the present invention include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080; and 6,524,621, each of which is hereby incorporated herein by reference. Nonimmediate release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817; and 5,296,483, each of which is hereby incorporated herein by reference. Those skilled in the art will readily recognize other applicable sustained release formulations.

For oral administration, a compound of the present invention can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compounds can be formulated for parenteral administration by injection, e.g., by bolus injection or continuous infusion. For injection, the compound can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, a compound of the invention can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. For topical administration, the agents are formulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use in the present invention include those described in U.S. Pat. Nos. 6,589,549; 6,544,548; 6,517,864; 6,512,010; 6,465,006; 6,379,696; 6,312,717; and 6,310,177, each of which are hereby incorporated herein by reference.

For buccal administration, the compositions can take the form of tablets or lozenges formulated in conventional manner.

In addition to the formulations described previously, a compound of the present invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The present invention also contemplates pharmaceutical compositions comprising the compounds of Formula I or II in admixture with an effective amount of other therapeutic agents as combination partners, particularly those used for treating diseases and conditions which can be affected by SGLT inhibition, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. An effective amount of the compound and/or combination partner will, of course, be dependent on the subject being treated, the severity of the affliction and the manner of administration. Determination of an effective amount is well within the capability of those skilled in the art, especially in light of the detailed disclosure provided herein. Generally, an effective amount of a compound is determined by first administering a low dose or small amount, and then incrementally increasing the administered dose or dosages until a desired therapeutic effect is observed in the treated subject, with minimal or no toxic side effects. Applicable methods for determining an appropriate dose and dosing schedule for administration of the present invention are described, for example, in *Goodman and Gilman's The Pharmacological Basis of Therapeutics*, 11$^{th}$ Ed., Brunton, Lazo and Parker, Eds., McGraw-Hill (2006), and in *Remington: The Science and Practice of Pharmacy*, 21$^{st}$ Ed., Gennaro, Ed., Lippencott Williams & Wilkins (2003), both of which are hereby incorporated herein by reference.

The present invention further provides methods of using the compounds of Formulas I and II for the prevention and treatment of disease. In one embodiment the invention provides a method of treating type 1 and type 2 diabetes mellitus, hyperglycemia, diabetic complications (such as retinopathy, nephropathy, neuropathy, ulcers, micro- and macroangiopathies, gout and diabetic foot disease), insulin resistance, metabolic syndrome (Syndrome X), hyperinsulinemia, hypertension, hyperuricemia, obesity, edema, dyslipidemia, chronic heart failure, atherosclerosis and related diseases, which comprises administering an effective amount of a compound or mixture of compounds of Formulas I and II, or a pharmaceutically acceptable salt or prodrug thereof, to a subject in need thereof. In another embodiment the invention provides a method of using a compound or mixture of compounds of Formulas I and II, or a pharmaceutically acceptable salt or prodrug thereof, for the preparation of a medicament for treating type 1 and type 2 diabetes mellitus, hyperglycemia, diabetic complications, insulin resistance, metabolic syndrome, hyperinsulinemia, hypertension, hyperuricemia, obesity, edema, dyslipidemia, chronic heart failure, atherosclerosis and related diseases.

The present invention also contemplates the use of the compounds of Formulas I and II, or pharmaceutically acceptable salts or prodrugs thereof, in combination with other therapeutic agents, particularly those used for treating the above-mentioned diseases and conditions, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. Those skilled in the art will appreciate that other therapeutic agents discussed below can have multiple therapeutic uses and the listing of an agent in one particular category should not be construed to limit in any way its usefulness in combination therapy with compounds of the present invention.

Examples of antidiabetic agents suitable for use in combination with compounds of the present invention include insulin and insulin mimetics, sulfonylureas (such as acetohexamide, carbutamide, chlorpropamide, glibenclamide, glibomuride, gliclazide, glimepiride, glipizide, gliquidone, glisoxepide, glyburide, glyclopyramide, tolazamide, tolcyclamide, tolbutamide and the like), insulin secretion enhancers (such as JTT-608, glybuzole and the like), biguanides (such as metformin, buformin, phenformin and the like), sulfonylurea/biguanide combinations (such as glyburide/metformin and the like), meglitinides (such as repaglinide, nateglinide, mitiglinide and the like), thiazolidinediones (such as rosiglitazone, pioglitazone, isaglitazone, netoglitazone, rivoglitazone, balaglitazone, darglitazone, CLX-0921 and the like), thiazolidinedione/biguanide combinations (such as pioglitazone/metformin and the like), oxadiazolidinediones (such as YM440 and the like), peroxisome proliferator-activated receptor (PPAR)-gamma agonists (such as farglitazar, metaglidasen, MBX-2044, GI 262570, GW1929, GW7845 and the like), PPAR-alpha/gamma dual agonists (such as muraglitazar, naveglitazar, tesaglitazar, peliglitazar, JTT-501, GW-409544, GW-501516 and the like), PPAR-alpha/gamma/delta pan agonists (such as PLX204, GlaxoSmithKline 625019, GlaxoSmithKline 677954 and the like), retinoid X receptor agonists (such as ALRT-268, AGN-4204, MX-6054, AGN-194204, LG-100754, bexarotene and the like), alpha-glucosidase inhibitors (such as acarbose, miglitol and the like), stimulants of insulin receptor tyrosine kinase (such as TER-17411, L-783281, KRX-613 and the like), tripeptidyl peptidase II inhibitors (such as UCL-1397 and the like), dipeptidyl peptidase IV inhibitors (such as sitagliptin, vildagliptin, denagliptin, saxagliptin, NVP-DPP728, P93/01, P32/98, FE 99901, TS-021, TSL-225, GRC8200, compounds described in U.S. Pat. Nos. 6,869,947; 6,727,261; 6,710,040; 6,432,969; 6,172,081; 6,011,155 and the like), protein tyrosine phosphatase-IB inhibitors (such as KR61639, IDD-3, PTP-3848, PTP-112, OC-86839, PNU-177496, compounds described in Vats, R. K., et al., *Current Science, Vol.* 88, No. 2, 25 Jan. 2005, pp. 241-249, and the like), glycogen phosphorylase inhibitors (such as N,N-4201, CP-368296 and the like), glucose-6-phosphatase inhibitors, fructose 1,6-bis-phosphatase inhibitors (such as CS-917, MB05032 and the like), pyruvate dehydrogenase inhibitors (such as AZD-7545 and the like), imidazoline derivatives (such as BL11282 and the like), hepatic gluconeogenesis inhibitors (such as FR-225659 and the like), D-chiroinositol, glycogen synthase kinase-3 inhibitors (such as compounds described in Vats, R. K., et al., *Current Science*, Vol. 88, No. 2, 25 Jan. 2005, pp. 241-249, and the like), incretin mimetics (such as exenatide and the like), glucagon receptor antagonists (such as BAY-27-9955, N,N-2501, NNC-92-1687 and the like), glucagon-like peptide-1 (GLP-1), GLP-1 analogs (such as liraglutide, CJC-1131, AVE-0100 and the like), GLP-1 receptor agonists (such as AZM-134, LY-315902, GlaxoSmithKline 716155 and the like), amylin, amylin analogs and agonists (such as pramlintide and the like), fatty acid binding protein (aP2) inhibitors (such as compounds described in U.S. Pat. Nos. 6,984,645; 6,919,323; 6,670,380; 6,649,622; 6,548,529 and the like), beta-3 adrenergic receptor agonists (such as solabegron, CL-316243, L-771047, FR-149175 and the like), and other insulin sensitivity enhancers (such as reglixane, ONO-5816, MBX-102, CRE-1625, FK-614, CLX-0901, CRE-1633, N,N-2344, BM-13125, BM-501050, HQL-975, CLX-0900, MBX-668, MBX-675, S-15261, GW-544, AZ-242, LY-510929, AR-H049020, GW-501516 and the like).

Examples of agents for treating diabetic complications suitable for use in combination with compounds of the present invention include aldose reductase inhibitors (such as epalrestat, imirestat, tolrestat, minalrestat, ponalrestat, zopolrestat, fidarestat, ascorbyl gamolenate, ADN-138, BAL-ARI8, ZD-5522, ADN-311, GP-1447, IDD-598, risarestat, zenarestat, methosorbinil, AL-1567, M-16209, TAT, AD-5467, AS-3201, NZ-314, SG-210, JTT-811, lindolrestat, sorbinil and the like), inhibitors of advanced glycation end-products (AGE) formation (such as pyridoxamine, OPB-9195, ALT-946, ALT-711, pimagedine and the like), AGE breakers (such as ALT-711 and the like), sulodexide, 5-hydroxy-1-methylhydantoin, insulin-like growth factor-I, platelet-derived growth factor, platelet-derived growth factor analogs, epidermal growth factor, nerve growth factor, uridine, protein kinase C inhibitors (such as ruboxistaurin, midostaurin and the like), sodium channel antagonists (such as mexiletine, oxcarbazepine and the like), nuclear factor-kappaB (NF-kappaB) inhibitors (such as dexlipotam and the like), lipid peroxidase inhibitors (such as tirilazad mesylate and the like), N-acetylated-alpha-linked-acid-dipeptidase inhibitors (such as GPI-5232, GPI-5693 and the like), and carnitine derivatives (such as carnitine, levacecamine, levocamitine, ST-261 and the like).

Examples of antihyperuricemic agents suitable for use in combination with compounds of the present invention include uric acid synthesis inhibitors (such as allopurinol, oxypurinol and the like), uricosuric agents (such as probenecid, sulfinpyrazone, benzbromarone and the like) and urinary alkalinizers (such as sodium hydrogen carbonate, potassium citrate, sodium citrate and the like).

Examples of lipid-lowering/lipid-modulating agents suitable for use in combination with compounds of the present invention include hydroxymethylglutaryl coenzyme A reductase inhibitors (such as acitemate, atorvastatin, bervastatin, carvastatin, cerivastatin, colestolone, crilvastatin, dalvastatin, fluvastatin, glenvastatin, lovastatin, mevastatin, nisvastatin, pitavastatin, pravastatin, ritonavir, rosuvastatin, saquinavir, simvastatin, visastatin, SC-45355, SQ-33600, CP-83101, BB-476, L-669262, S-2468, DMP-565, U-20685, BMS-180431, BMY-21950, compounds described in U.S. Pat. Nos. 5,753,675; 5,691,322; 5,506,219; 4,686,237; 4,647,576; 4,613,610; 4,499,289 and the like), fibric acid derivatives (such as gemfibrozil, fenofibrate, bezafibrate, beclobrate, binifibrate, ciprofibrate, clinofibrate, clofibrate, etofibrate, nicofibrate, pirifibrate, ronifibrate, simfibrate, theofibrate, AHL-157 and the like), PPAR-alpha agonists (such as GlaxoSmithKline 590735 and the like), PPAR-delta agonists (such as GlaxoSmithKline 501516 and the like), acyl-coenzyme A:cholesterol acyltransferase inhibitors (such as avasimibe, eflucimibe, eldacimibe, lecimibide, NTE-122, MCC-147, PD-132301-2, C1-1011, DUP-129, U-73482, U-76807, TS-962, RP-70676, P-06139, CP-113818, RP-73163, FR-129169, FY-038, EAB-309, KY-455, LS-3115, FR-145237, T-2591, J-104127, R-755, FCE-27677, FCE-28654, YIC-C8-434, CI-976, RP-64477, F-1394, CS-505, CL-283546, YM-17E, 447C88, YM-750, E-5324, KW-3033, HL-004, and the like), probucol, thyroid hormone receptor agonists (such as liothyronine, levothyroxine, KB-2611, GC-1, and the like), cholesterol absorption inhibitors (such as ezetimibe, SCH48461, and the like), lipoprotein-associated phospholipase A2 inhibitors (such as rilapladib, darapladib, and the like), microsomal triglyceride transfer protein inhibitors (such as CP-346086, BMS-201038, compounds described in U.S. Pat. Nos. 5,595,872; 5,739,135; 5,712,279; 5,760,246; 5,827,875; 5,885,983; 5,962,440; 6,197,798; 6,617,325; 6,821,967; 6,878,707, and the like), low density lipoprotein receptor activators (such as LY295427, MD-700 and the like), lipoxygenase inhibitors (such as compounds described in WO 97/12615, WO 97/12613, WO 96/38144, and the like), carnitine palmitoyl-transferase inhibitors (such as etomoxir and the like), squalene synthase inhibitors (such as YM-53601, TAK-475, SDZ-268-198, BMS-188494, A-87049, RPR-101821, ZD-9720, RPR-107393, ER-27856, compounds described in U.S. Pat. Nos. 5,712,396; 4,924,024; 4,871,721, and the like), nicotinic acid derivatives (such as acipimox, nicotinic acid, ricotinamide, nicomol, niceritrol, nicorandil, and the like), bile acid sequestrants (such as colestipol, cholestyramine, colestilan, colesevelam, GT-102-279, and the like), sodium/bile acid cotransporter inhibitors (such as 264W94, S-8921, SD-5613, and the like), and cholesterol ester transfer protein inhibitors (such as torcetrapib, JTT-705, PNU-107368E, SC-795, CP-529414, and the like).

Examples of anti-obesity agents suitable for use in combination with compounds of the present invention include serotonin-norepinephrine reuptake inhibitors (such as sibutramine, milnacipran, mirtazapine, venlafaxine, duloxetine, desvenlafaxine and the like), norepinephrine-dopamine reuptake inhibitors (such as radafaxine, bupropion, amineptine and the like), selective serotonin reuptake inhibitors (such as citalopram, escitalopram, fluoxetine, fluvoxamine, paroxetine, sertraline and the like), selective norepinephrine reuptake inhibitors (such as reboxetine, atomoxetine and the like), norepinephrine releasing stimulants (such as rolipram, YM-992 and the like), anorexiants (such as amphetamine, methamphetamine, dextroamphetamine, phentermine, benzphetamine, phendimetrazine, phenmetrazine, diethylpropion, mazindol, fenfluramine, dexfenfluramine, phenylpropanolamine and the like), dopamine agonists (such as ER-230, doprexin, bromocriptine mesylate and the like), $H_3$-histamine antagonists (such as impentamine, thioperamide, ciproxifan, clobenpropit, GT-2331, GT-2394, A-331440, and the like), 5-HT2c receptor agonists (such as 1-(m-chlorophenyl)piperazine (m-CPP), mirtazapine, APD-356 (lorcaserin), SCA-136 (vabicaserin), ORG-12962, ORG-37684, ORG-36262, ORG-8484, Ro-60-175, Ro-60-0332, VER-3323, VER-5593, VER-5384, VER-8775, LY-448100, WAY-161503, WAY-470, WAY-163909, BVT.933, YM-348, IL-639, IK-264, ATH-88651, ATHX-105 and the like (see, e.g., Nilsson B M, J. Med. Chem. 2006, 49:4023-4034)), beta-3 adrenergic receptor agonists (such as L-796568, CGP 12177, BRL-28410, SR-58611A, 1CI-198157, ZD-2079, BMS-194449, BRL-37344, CP-331679, CP-331648, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696 and the like), cholecystokinin agonists (such as SR-146131, SSR-125180, BP-3.200, A-71623, FPL-15849, GI-248573, GW-7178, GI-181771, GW-7854, A-71378 and the like), antidepressant/acetylcholinesterase inhibitor combinations (such as venlafaxine/rivastigmine, sertraline/galanthamine and the like), lipase inhibitors (such as orlistat, ATL-962 and the like), anti-epileptic agents (such as topiramate, zonisamide and the like), leptin, leptin analogs and leptin receptor agonists (such as LY-355101 and the like), neuropeptide Y (NPY) receptor antagonists and modulators (such as SR-120819-A, PD-160170, NGD-95-1, BIBP-3226, 1229-U-91, CGP-71683, BIBO-3304, CP-671906-01, J-115814 and the like), ciliary neurotrophic factor (such as Axokine and the like), thyroid hormone receptor-beta agonists (such as KB-141, GC-1, GC-24, GB98/284425 and the like), cannabinoid CB1 receptor antagonists (such as rimonabant, SR147778, SLV 319 and the like (see, e.g., Antel J et al., *J. Med. Chem.* 2006, 49:4008-4016)), melanin-concentrating hormone receptor antagonists (including GlaxoSmithKline 803430X, GlaxoSmithKline 856464, SNAP-7941, T-226296 and the like (see, e.g., Handlon A L and Zhou H, *J. Med. Chem.* 2006, 49:4017-4022)), melanocortin-4 receptor agonists (including PT-15, Ro27-3225, THIQ, NBI 55886, NBI 56297, NBI 56453, NBI 58702, NBI 58704, MB243 and the like (see, e.g., Nargund R P et al., *J. Med. Chem.* 2006, 49:4035-4043)), selective muscarinic receptor $M_1$ antagonists (such as telenzepine, pirenzepine and the like), opioid receptor antagonists (such as naltrexone, methylnaltrexone, nalmefene, naloxone, alvimopan, norbinaltorphimine, nalorphine and the like), orexin receptor antagonists (such as almorexant and the like), and combinations thereof.

Examples of antihypertensive agents and agents for treating chronic heart failure, atherosclerosis or related diseases suitable for use in combination with compounds of the present invention include bimoclomol, angiotensin-converting enzyme inhibitors (such as captopril, enalapril, fosinopril, lisinopril, perindopril, quinapril, ramipril and the like), neutral endopeptidase inhibitors (such as thiorphan, omapatrilat, MDL-100240, fasidotril, sampatrilat, GW-660511, mixanpril, SA-7060, E-4030, SLV-306, ecadotril and the like), angiotensin II receptor antagonists (such as candesartan cilexetil, eprosartan, irbesartan, losartan, olmesartan medoxomil, telmisartan, valsartan, tasosartan, enoltasosartan and the like), endothelin-converting enzyme inhibitors (such as CGS 35066, CGS 26303, CGS-31447, SM-19712 and the like), endothelin receptor antagonists (such as tracleer, sitaxsentan, ambrisentan, L-749805, TBC-3214, BMS-182874, BQ-610, TA-0201, SB-215355, PD-180988, BMS-193884, darusentan, TBC-3711, bosentan, tezosentan, J-104132, YM-598, S-0139, SB-234551, RPR-118031A, ATZ-1993, RO-61-1790, ABT-546, enlasentan, BMS-207940 and the like), diuretic agents (such as hydrochlorothiazide, bendroflumethiazide, trichlormethiazide, indapamide, metolazone, furosemide, bumetanide, torsemide, chlorthalidone, metolazone, cyclopenthiazide, hydroflumethiazide, tripamide, mefruside, benzylhydrochlorothiazide, penflutizide, methyclothiazide, azosemide, etacrynic acid, torasemide, piretanide, meticrane, potassium canrenoate, spironolactone, triamterene, aminophylline, cicletanine, LLU-alpha, PNU-80873A, isosorbide, D-mannitol, D-sorbitol, fructose, glycerin, acetazolamide, methazolamide, FR-179544, OPC-31260, lixivaptan, conivaptan and the like), calcium channel antagonists (such as amlodipine, bepridil, diltiazem, felodipine, isradipine, nicardipen, nimodipine, verapamil, S-verapamil, aranidipine, efonidipine, barnidipine, benidipine, manidipine, cilnidipine, nisoldipine, nitrendipine, nifedipine, nilvadipine, felodipine, pranidipine, lercanidipine, isradipine, elgodipine, azelnidipine, lacidipine, vatanidipine, lemildipine, diltiazem, clentiazem, fasudil, bepridil, gallopamil and the like), vasodilating antihypertensive agents (such as indapamide, todralazine, hydralazine, cadralazine, budralazine and the like), beta blockers (such as acebutolol, bisoprolol, esmolol, propanolol, atenolol, labetalol, carvedilol, metoprolol and the like), sympathetic blocking agents (such as amosulalol, terazosin, bunazosin, prazosin, doxazosin, propranolol, atenolol, metoprolol, carvedilol, nipradilol, celiprolol, nebivolol, betaxolol, pindolol, tertatolol, bevantolol, timolol, carteolol, bisoprolol, bopindolol, nipradilol, penbutolol, acebutolol, tilisolol, nadolol, urapidil, indoramin and the like), alpha-2-adrenoceptor agonists (such as clonidine, methyldopa, CHF-1035, guanabenz acetate, guanfacine, moxonidine, lofexidine, talipexole and the like), centrally acting antihypertensive agents (such as reserpine and the like), thrombocyte aggregation inhibitors (such as warfarin, dicumarol, phenprocoumon, acenocoumarol, anisindione, phenindione, ximelagatran and the like), and antiplatelets agents (such as aspirin, clopidogrel, ticlopidine, dipyridamole, cilostazol, ethyl icosapentate, sarpogrelate, dilazep, trapidil, beraprost and the like).

Furthermore, in another aspect, the invention provides for a pharmaceutical composition comprising effective amounts of a compound or mixture of compounds of Formulas I and II, or a pharmaceutically acceptable salt or prodrug thereof, and at least one member selected from the group of therapeutic agents listed above as combination partners, in a pharmaceutically acceptable carrier.

The treatment of the present invention can be administered prophylactically to prevent or delay the onset or progression of a disease or condition (such as hyperglycemia), or therapeutically to achieve a desired effect (such as a desired level of serum glucose) for a sustained period of time.

The compounds of the present invention can be administered to a subject, e.g., a human patient, a domestic animal such as a cat or a dog, or livestock such as cows, pigs, or sheep, independently or together with a combination partner, in the form of their pharmaceutically acceptable salts or prodrugs, or in the form of a pharmaceutical composition where the compounds and/or combination partners are mixed with suitable carriers or excipient(s) in a therapeutically effective amount. Consequently, a compound or mixture of compounds of Formulas I and II, or a pharmaceutically acceptable salt or prodrug thereof, and an additional active agent to be combined therewith, can be present in a single formulation, for example a capsule or tablet, or in two separate formulations, which can be the same or different, for example, in the form of a kit comprising selected numbers of doses of each agent.

The appropriate dosage of compound will vary according to the chosen route of administration and formulation of the composition, among other factors, such as patient response. The dosage can be increased or decreased over time, as required by an individual patient. A patient initially may be given a low dose, which is then increased to an efficacious dosage tolerable to the patient. Typically, a useful dosage for adults may be from 1 to 2000 mg, preferably 1 to 200 mg, when administered by oral route, and from 0.1 to 100 mg, preferably 1 to 30 mg, when administered by intravenous route, in each case administered from 1 to 4 times per day. When a compound of the invention is administered in combination with another therapeutic agent, a useful dosage of the combination partner may be from 20% to 100% of the normally recommended dose.

Dosage amount and interval can be adjusted individually to provide plasma levels of the active compounds, which are sufficient to maintain therapeutic effect. Preferably, therapeutically effective serum levels will be achieved by administering single daily doses, but efficacious multiple daily dose schedules are included in the invention. In cases of local administration or selective uptake, the effective local concentration of the drug may not be related to plasma concentration. One having skill in the art will be able to optimize therapeutically effective local dosages without undue experimentation.

EXAMPLES

The following examples are offered for illustrative purposes, and are not intended to limit the invention in any manner. Those of skill in the art will readily recognize a variety of noncritical parameters, which can be changed or modified to yield essentially the same results.

The names of compounds shown in the following examples were derived from the structures shown using the Cambridge-Soft Struct=Name algorithm as implemented in ChemDraw Ultra version 10.0, with general application of the Boughton nomenclature system for deuterium modified compounds (Boughton W A, Science 79:159-60, 1934). Unless otherwise indicated, the structures of compounds synthesized in the examples below were confirmed using the following procedures:

(1) Gas chromatography—mass spectra with electrospray ionization (MS ESI) were obtained with an Agilent 5973N mass spectrometer equipped with an Agilent 6890 gas chromatograph with an HP-5 MS column (0.25 µm coating; 30 m×0.25 mm). The ion source was maintained at 230° C. and spectra were scanned from 25-500 amu at 3.09 sec per scan.

(2) High pressure liquid chromatography mass spectra (LC-MS) were obtained using Finnigan Surveyor HPLC equipped with a quaternary pump, a variable wavelength detector set at 254 nm, an XB-C18 column (4.6×50 mm, 5 µm), and a Finnigan LCQ ion trap mass spectrometer with electrospray ionization. Spectra were scanned from 80-2000 amu using a variable ion time according to the number of ions in the source. The eluents were B: acetonitrile and D: water. Gradient elution from 10% B to 90% in 8 min at a flow rate of 1.0 mL/min is used with a final hold at 90% B of 7 min. Total run time is 15 min. The following LC-MS methods were used in characterization of the compounds:

a. Method 1: Waters 2695 Separations Module equipped with a Waters 2996 Photodiode Array Detector and a Waters Micromass ZQ Detector; Waters XTerra C18 3.5 µm, 20 mm×2.1 mm column, 1.0 mL/min, detection at 190~400 nm; 1.7 min gradient 10-50% A, followed by 1.8 min gradient 50-95% A, hold 1 min at 95% A; solvent A: 0.045% formic acid in acetonitrile, solvent B: 0.1% formic acid in Milli-Q water. Gradient time table:

| Time (minute) | A (%) | B (%) | Curve |
| --- | --- | --- | --- |
| 0 | 10 | 90 | 1 |
| 1.70 | 50 | 50 | 6 |
| 3.50 | 95.0 | 5 | 6 |
| 4.50 | 95.0 | 5 | 6 | b. Method 2: Waters 2695 Separations Module equipped with a Waters 2996 Photodiode Array Detector and a Waters Micromass ZQ Detector; Waters XTerra C18 5 µm, 50 mm×2.1 mm column; 1.0 mL/min, detection at 190~400 nm; 6 min gradient 10-95% A, hold 8 min at 95% A; solvent A: 0.045% formic acid in acetonitrile, solvent B: 0.1% formic acid in Milli-Q water. Gradient time table:

| Time (minute) | A (%) | B (%) | Curve |
| --- | --- | --- | --- |
| 0 | 10 | 90 | 1 |
| 6 | 95 | 5 | 6 |
| 8 | 95 | 5 | 6 | c. Method 3: Waters 2695 Separations Module equipped with a Waters 2996 Photodiode Array Detector and a Waters Micromass ZQ Detector; Sepax GP C18 5 um, 250 mm×4.6 mm ID column, 1.0 ml/min, detection PDA, 190~400 nm, solvent A: 0.045% formic acid in acetonitrile; solvent B: 0.1% formic acid in Milli-Q water. Gradient time table:

| Time (minute) | A (%) | B (%) | Curve |
| --- | --- | --- | --- |
| 0 | 25 | 75 | 1 |
| 25 | 95 | 5 | 6 |
| 30 | 95 | 5 | 6 |

Routine one-dimensional NMR spectroscopy was performed on 400 MHz or 300 MHz Varian Mercury-Plus spectrometers. The samples were dissolved in deuterated solvents obtained from Qingdao Tenglong Weibo Technology Co., Ltd., and transferred to 5 mm ID NMR tubes. The spectra were acquired at 293 K. The chemical shifts were recorded on the ppm scale and were referenced to the appropriate solvent signals, such as 2.49 ppm for DMSO-$d_6$, 1.93 ppm for $CD_3CN$, 3.30 ppm for $CD_3OD$, 5.32 ppm for $CD_2Cl_2$ and 7.26 ppm for $CDCl_3$ for $^1H$ spectra.

Example 1

This example illustrates the preparation of compound 5 according to the approach provided in Scheme 9. The general method is applicable to other compounds of the present invention.

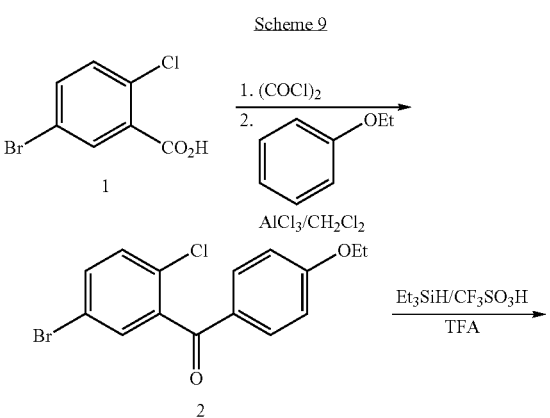

Scheme 9

-continued

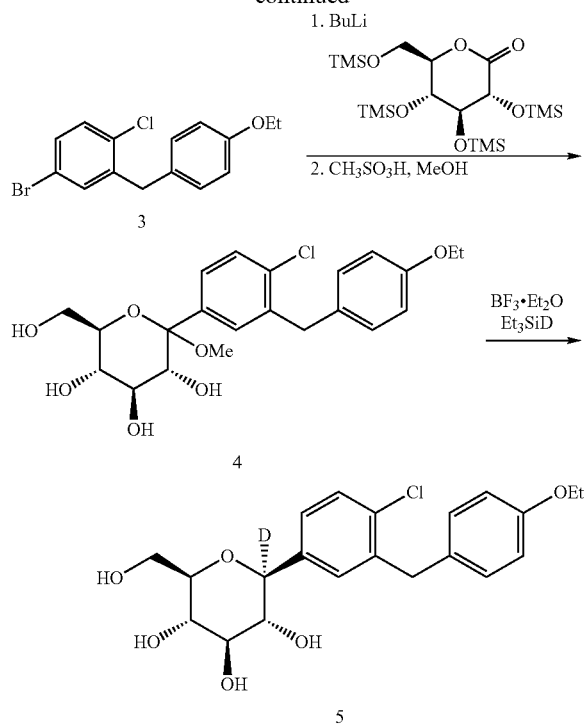

Preparation of (5-bromo-2-chlorophenyl)(4-ethoxyphenyl)methanone (2)

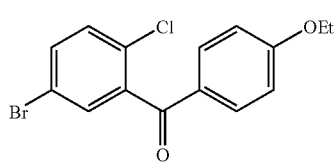 [SMILES: CCOc1ccc(C(=O)c2cc(Br)ccc2Cl)cc1]

To 5-bromo-2-chlorobenzoic acid (1500 g, 6.41 mol) and oxalyl chloride (975 g, 7.69 mol) in DCM (2.8 L) was added DMF (9 mL). Once the vigorous evolution of gas ceased, the reaction was stirred for 10 hours at RT. The solution was concentrated under vacuum to give a yellow residue. The residue was dissolved in DCM (1.2 L), then the stirred mixture was cooled to −3° C., and phenetole (799 g, 6.54 mol) was added. After the addition was complete, aluminum (III) chloride (973 g, 6.54 mol) was added over 1 hour while maintaining the reaction temperature below 4° C. The mixture was poured over 10 kg ice and stirred at 4° C. for 1 hour. The suspension was diluted with water (3 L) and extracted with DCM (10 L×2). The combined organic layers were washed with 1 N HCl (7.5 L×2), water (10 L), 1N sodium hydroxide (7.5 L×2), and brine (10 L×2), and dried over sodium sulfate (1000 g). After removal of the volatiles, the residues were recrystallized from absolute ethanol (3.5 L) to give compound 2 as a white solid (1450 g, 67% yield, HPLC purity>99%).

Preparation of 4-bromo-1-chloro-2-(4-ethoxybenzyl)benzene (3)

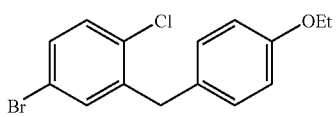 [SMILES: CCOc1ccc(Cc2cc(Br)ccc2Cl)cc1]

To (5-bromo-2-chlorophenyl)(4-ethoxyphenyl)methanone (1440 g, 4.26 mol) and triethylsilane (1.37 L, 8.6 mol) in trifluoroacetic acid (820 mL) was slowly added trifluoromethanesulfonic acid (1.9 mL). After refluxing for 6 hours, additional triethylsilane (400 mL, 2.47 mol) was added. After refluxing for another 8 hours, the mixture was evaporated under reduced pressure. The residue was dissolved in dichloromethane (20 L), washed with water (10 L), aqueous sodium carbonate (10 L), and brine (10 L), and concentrated to give crude product. The crude product was distilled to remove $(Et_3Si)_2O$ under vacuum. The residue was recrystallized from absolute ethanol (5 L) and dried under vacuum to give compound 3 (1310 g, 94% yield, HPLC purity>99%).

Preparation of (3R,4S,5S,6R)-2-(4-chloro-3-(4-ethoxybenzyl)phenyl)-6-(hydroxymethyl)-2-methoxytetrahydro-2H-pyran-3,4,5-triol (4)

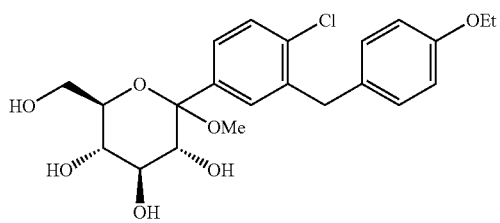 [SMILES: CCOc1ccc(Cc2cc(C3(OC)O[C@H](CO)[C@@H](O)[C@H](O)[C@H]3O)ccc2Cl)cc1]

To 4-bromo-1-chloro-2-(4-ethoxybenzyl)benzene (10 g, 0.031 mol) in anhydrous toluene/THF (78 mL, v/v=2:1) was added dropwise n-BuLi (2.5 M in hexane, 13.5 mL) at −65° C. and stirred for 30 minutes at −65° C. The mixture was transferred to a solution of (3R,4S,5R,6R)-3,4,5-tris(trimethylsilyloxy)-6-((trimethylsilyloxy)methyl)tetrahydro-2H-pyran-2-one (15.7 g, 0.034 mol) in toluene (78 mL) at −65° C. The mixture was stirred at −65° C. for 2 hours until starting material was consumed. The reaction was quenched with methanesulfonic acid (4.18 mL, 0.065 mol) in methanol (70 mL), and the mixture was allowed to warm to RT and stirred overnight. The reaction was quenched with saturated sodium bicarbonate, the organic phase was separated, and the aqueous phase was extracted with ethyl acetate. The combined organic phases were washed with saturated bicarbonate, then with water, then with brine, and were dried over sodium sulfate. After removal of the volatiles, the residue was slurried in toluene/hexane (120 mL, 1:5), filtered, and dried under vacuum to give compound 4 as a white solid (12.5 g). The crude product was used in the next step without further purification.

Preparation of (2S,3R,4R,5S,6R)-2-(4-chloro-3-(4-ethoxybenzyl)phenyl)-6-(hydroxymethyl)tetrahydro-2H-pyran-2-d-3,4,5-triol (5)

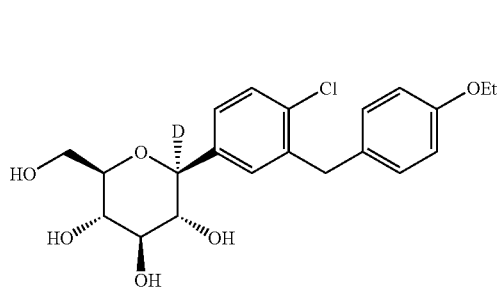 [SMILES: [2H][C@@]1(c2ccc(Cl)c(Cc3ccc(OCC)cc3)c2)O[C@H](CO)[C@@H](O)[C@H](O)[C@H]1O]

To a cold (−15° C.) solution of (3R,4S,5S,6R)-2-(4-chloro-3-(4-ethoxybenzyl)phenyl)-6-(hydroxymethyl)-2-methoxytetrahydro-2H-pyran-3,4,5-triol (0.2 g, 0.456 mmol) in anhydrous acetonitrile/dichloromethane (2 mL, 1:1) was added triethylsilane-d (0.107 g, 0.912 mmol, 97 atom % D), then $BF_3 \cdot Et_2O$ (0.09 mL, 0.684 mmol) was added dropwise and the mixture was stirred for 4 hours at −10° C. The reaction was quenched with saturated aqueous bicarbonate. The volatiles were removed under reduced pressure, and the residue was extracted with ethyl acetate, washed with water and then with brine, dried over sodium sulfate, and concentrated to give a solid. The solid was purified by preparative HPLC-MS to obtain compound 5 as a white solid (70 mg). $^1$H-NMR (CD$_3$OD, 400 MHz): δ 7.34~7.25 (m, 3H), 7.08 (d, J=8.8 Hz, 2H), 6.78 (d, J=8.8 Hz, 2H), 4.06~3.95 (m, 4H), 3.88~3.85 (m, 1H), 3.69~3.65 (m, 1H), 3.47~3.37 (m, 3H), 3.27 (m, 1H), 1.35 (t, J=7.2 Hz, 3H); MS ESI (m/z): 410 [M+H]$^+$, calc. 409.

Example 2

Preparation of (2S,3R,4R,5S,6R)-2-(4-chloro-3-(4-ethylbenzyl)phenyl)-6-(hydroxymethyl)tetrahydro-2H-pyran-2-d-3,4,5-triol (6)

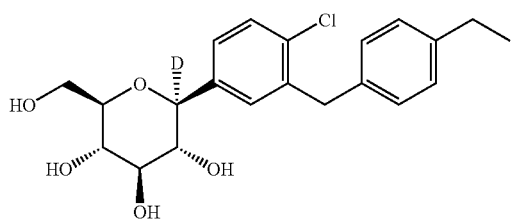 [SMILES: [2H][C@@]1(c2ccc(Cl)c(Cc3ccc(CC)cc3)c2)O[C@H](CO)[C@@H](O)[C@H](O)[C@H]1O]

Compound 6 was prepared using methods analogous to those described in Example 1 above by using ethylbenzene instead of phenetole as starting material. $^1$H-NMR (CD$_3$OD, 400 MHz): δ 7.36~7.25 (m, 3H), 7.08 (s, 4H), 4.11~3.99 (dd, J=20.4 and 12 Hz, 2H), 3.89~3.84 (dd, J=11.7 and 1.8 Hz, 1H), 3.70~3.65 (m, 1H), 3.45~3.37 (m, 3H), 3.27 (m, 1H), 2.65~2.55 (q, J=15 and 7.5 Hz, 2H), 1.21~1.16 (t, J=7.5 Hz, 3H); MS ESI (m/z): 394 [M+H]$^+$, calc. 393.

Example 3

This example illustrates the preparation of compound 9 according to the approach provided in Scheme 10. The general method is applicable to other compounds of the present invention.

Scheme 10

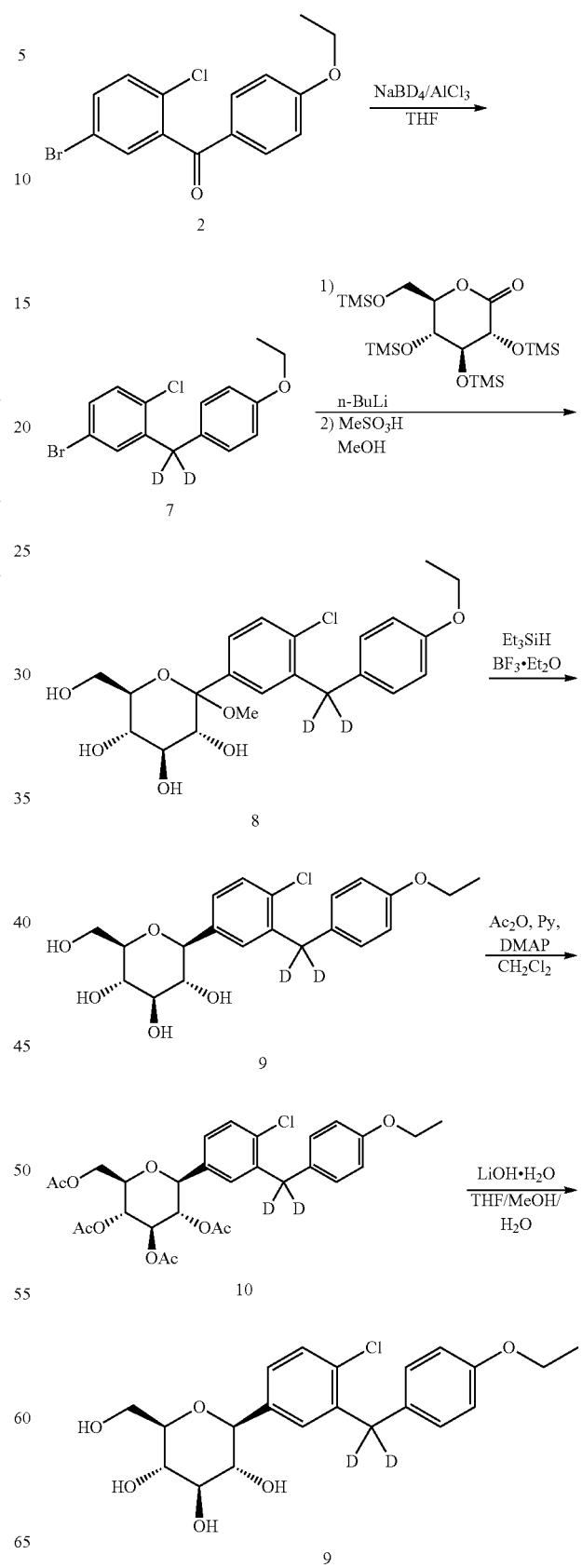

Preparation of 4-bromo-1-chloro-2-((4-ethoxyphenyl)methyl-d₂)benzene (7)

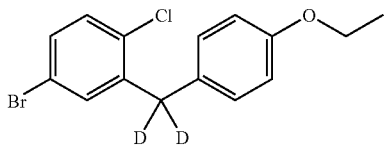 [SMILES: [2H]C([2H])(c1ccc(OCC)cc1)c1cc(Br)ccc1Cl]

To a solution of (5-bromo-2-chlorophenyl)(4-ethoxyphenyl)methanone (2) (7.0 g, 0.021 mol) in anhydrous THF (60 mL) at 5° C. was added sodium borodeuteride (0.95 g, 0.023 mol, 99 atom % D) followed by aluminum trichloride (5.50 g, 0.041 mol) in one portion at 5° C. After stirring the reaction for 15 minutes, the mixture was heated at 70° C. overnight. The reaction was cooled between 0~5° C., slowly quenched with ice-water (10 mL), and then extracted with ethyl acetate. The combined organic layers were washed with saturated bicarbonate, then with brine and then with water, and then dried over anhydrous sodium sulfate, and concentrated. The residue was purified by column chromatography to afford compound 7 as a white solid (6.7 g). $^1$H NMR (CDCl$_3$, 400 MHz): δ 7.31~7.24 (m, 3H), 7.13~7.11 (m, 2H), 6.88~6.85 (m, 2H), 4.07~4.01 (q, J=14 and 7.2 Hz, 2H), 1.45~1.42 (t, J=7.2 Hz, 3H).

Preparation of (3R,4S,5S,6R)-2-(4-chloro-3-((4-ethoxyphenyl)methyl-d₂)phenyl)-6-(hydroxymethyl)-2-methoxytetrahydro-2H-pyran-3,4,5-triol (8)

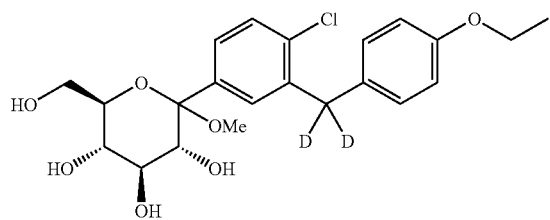 [SMILES: [2H]C([2H])(c1ccc(OCC)cc1)c1cc(C2(OC)O[C@H](CO)[C@@H](O)[C@H](O)[C@H]2O)ccc1Cl]

To a solution of 4-bromo-1-chloro-2-((4-ethoxyphenyl)methyl-d₂)benzene (6.7 g, 0.021 mol) in anhydrous toluene/tetrahydrofuran (60 mL, v/v=2:1) was added dropwise n-BuLi (2.5 M in hexane, 9.84 mL), and the reaction mixture was stirred for another 30 minutes at −65° C. The mixture was transferred to a solution of (3R,4S,5R,6R)-3,4,5-tris(trimethylsilyloxy)-6-((trimethylsilyloxy)methyl)tetrahydro-2H-pyran-2-one (10.51 g, 0.023 mol) in 60 mL of toluene at −65° C. The mixture was stirred at −65° C. for 2 hours until starting material was consumed. The reaction was quenched with methanesulfonic acid (3.19 mL, 0.049 mol) in methanol (50 mL), and the mixture was allowed to warm to RT overnight. The reaction was quenched with saturated bicarbonate, and the organic phase was separated. The aqueous phase was extracted with ethyl acetate, and the combined organic phases were washed with saturated bicarbonate, then with water, and then with brine, and then dried over sodium sulfate. After removal of the volatiles, the residue was slurried in 100 mL of 1:5 toluene/hexane, then filtered, and dried under vacuum to give compound 8 as a crude glassy product (8.1 g), which was used in the next step without further purification.

Preparation of crude (2S,3R,4R,5S,6R)-2-(4-chloro-3-((4-ethoxyphenyl)methyl-d₂)phenyl)-6-(hydroxymethyl)tetrahydro-2H-pyran-3,4,5-triol (9)

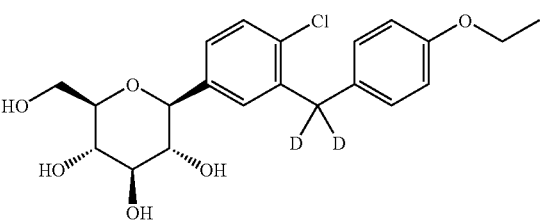 [SMILES: [2H]C([2H])(c1ccc(OCC)cc1)c1cc([C@@H]2O[C@H](CO)[C@@H](O)[C@H](O)[C@H]2O)ccc1Cl]

To a solution of the crude (3R,4S,5S,6R)-2-(4-chloro-3-((4-ethoxyphenyl)methyl-d₂)phenyl)-6-(hydroxymethyl)-2-methoxytetrahydro-2H-pyran-3,4,5-triol (8.1 g, 0.018 mol) in anhydrous acetonitrile/dichloromethane (80 mL, 1:1) at −20° C. was added triethylsilane (5.54 mL, 0.037 mol) followed by dropwise addition of BF$_3$.Et$_2$O (3.5 mL, 0.028 mol). The mixture was stirred for 4 hours at −15° C., and the reaction was quenched with saturated aqueous bicarbonate. The volatiles were removed under reduced pressure, and the residue was extracted with ethyl acetate, washed with water and then with brine, and then dried over sodium sulfate The sample was concentrated and used in the next step without further purification.

Preparation of (2R,3R,4R,5S,6S)-2-(acetoxymethyl)-6-(4-chloro-3-((4-ethoxyphenyl)methyl-d₂)phenyl)tetrahydro-2H-pyran-3,4,5-triyl triacetate (10)

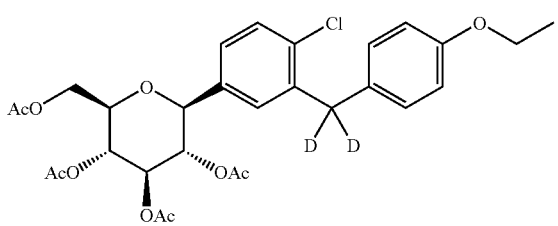 [SMILES: [2H]C([2H])(c1ccc(OCC)cc1)c1cc([C@@H]2O[C@H](COC(C)=O)[C@@H](OC(C)=O)[C@H](OC(C)=O)[C@H]2OC(C)=O)ccc1Cl]

To a solution of the crude (2S,3R,4R,5S,6R)-2-(4-chloro-3-((4-ethoxyphenyl)methyl-d₂)phenyl)-6-(hydroxymethyl)tetrahydro-2H-pyran-3,4,5-triol (4.0 g, 0.01 mol) in dichloromethane (30 mL) was added pyridine (7.88 mL, 0.098 mol) and DMAP (60 mg, 0.491 mmol), and then acetic anhydride (9.21 mL, 0.098 mol) was added, and the mixture was stirred for 2.5 hours at RT. The reaction was quenched by addition of water (50 mL), and the mixture was extracted with dichloromethane (2×150 mL). The combined organic layers were washed with 3 N HCl (2×100 mL), water (100 mL), and brine (100 mL), and then dried over sodium sulfate and concentrated. The residue was recrystallized from absolute ethanol (50 mL) to yield compound 10 as a white solid (3.36 g).

Preparation of (2S,3R,4R,5S,6R)-2-(4-chloro-3-((4-ethoxyphenyl)methyl-d₂)phenyl)-6-(hydroxymethyl)tetrahydro-2H-pyran-3,4,5-triol (9)

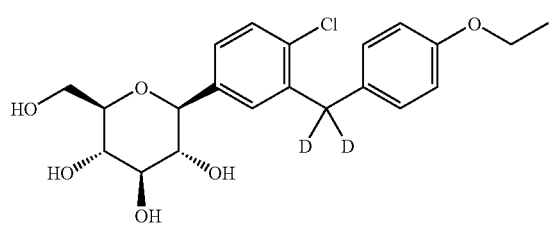 [SMILES: [2H]C([2H])(c1ccc(OCC)cc1)c1cc([C@@H]2O[C@H](CO)[C@@H](O)[C@H](O)[C@H]2O)ccc1Cl]

To a solution of (2R,3R,4R,5S,6S)-2-(acetoxymethyl)-6-(4-chloro-3-((4-ethoxyphenyl)methyl-d₂)phenyl)tetrahydro-2H-pyran-3,4,5-triyl triacetate (10) (3.36 g, 5.59 mmol) in THF/MeOH/H₂O (60 mL, 2:3:1) at 20° C. was added lithium hydroxide monohydrate (0.35 g, 8.39 mol), and the mixture was stirred for 4 hours. The volatiles were removed under reduced pressure, and the residue was partitioned between ethyl acetate and water. The organic layer was washed with brine, then with 5% aqueous potassium hydrogen sulfate, and then with water, and then dried over sodium sulfate. The solvent was removed under reduced pressure to yield compound 9 as a glassy off-white solid (2.50 g). $^1$H-NMR (CD₃OD, 400 MHz): δ 7.34~7.25 (m, 3H), 7.08 (d, J=8.8 Hz, 2H), 6.78 (d, J=8.8 Hz, 2H), 4.08 (d, J=9.2 Hz, 1H), 3.98 (q, J=14 and 7.2 Hz, 2H), 3.86 (m, 1H), 3.68 (m, 1H), 3.47~3.37 (m, 3H), 3.26 (m, 1H), 1.35 (t, J=6.8 Hz, 3H); MS ESI (m/z): 411 [M+H]⁺, calc. 410.

Example 4

Preparation of (2S,3R,4R,5S,6R)-2-(4-chloro-3-((4-ethoxyphenyl)methyl-d₂)phenyl)-6-(hydroxymethyl)tetrahydro-2H-pyran-2-d-3,4,5-triol (11)

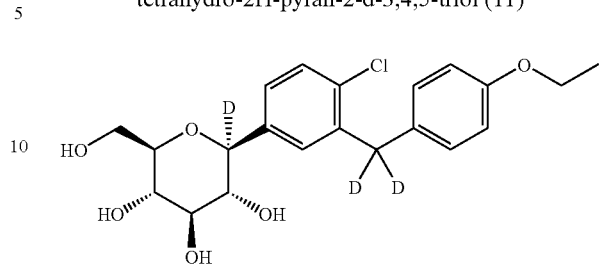

To a solution of (3R,4S,5S,6R)-2-(4-chloro-3-((4-ethoxyphenyl)methyl-d₂)phenyl)-6-(hydroxymethyl)-2-methoxytetrahydro-2H-pyran-3,4,5-triol (8) (0.5 g, 1.14 mmol) in anhydrous acetonitrile/dichloromethane (6 mL, 1:1) at −15° C. was added triethylsilane-d (0.267 g, 2.27 mmol, 97 atom % D) followed by the dropwise addition of BF₃.Et₂O (0.22 mL, 1.70 mmol), and then the mixture was stirred for 4 hours at −10° C. The reaction was quenched with saturated aqueous bicarbonate, and the volatiles were removed under reduced pressure. The residue was extracted with ethyl acetate, washed with water and then with brine, and then dried over sodium sulfate and concentrated. The resulting solid was purified by preparative HPLC-MS to give compound 11 as a white solid (175 mg). $^1$H-NMR (CD₃OD, 400 MHz): δ 7.37~7.34 (m, 3H), 7.11 (d, J=8.8 Hz, 2H), 6.81 (d, J=8.8 Hz, 2H), 3.99 (q, J=14 and 7.2 Hz, 2H), 3.89 (m, 1H), 3.71 (m, 1H), 3.48~3.41 (m, 3H), 3.30 (m, 1H), 1.37 (t, J=6.8 Hz, 3H); MS ESI (m/z): 412 [M+H]⁺, calc. 411.

Example 5

This example illustrates the preparation of compound 15 according to the approach provided in Scheme 11. The general method is applicable to other compounds of the present invention.

Scheme 11

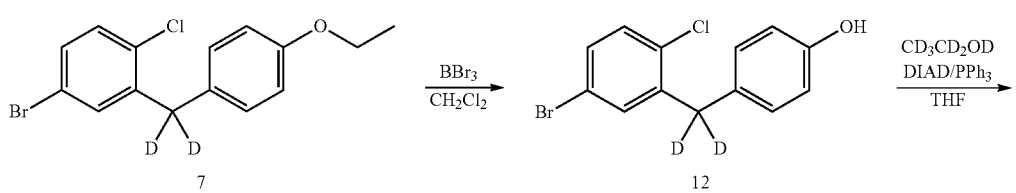

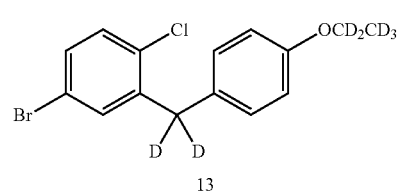

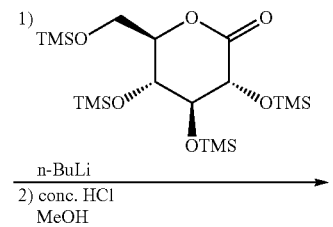

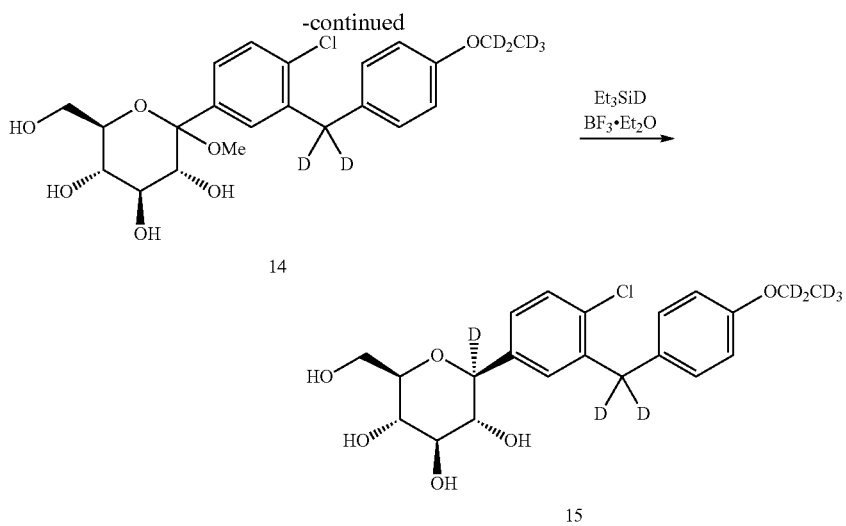

14

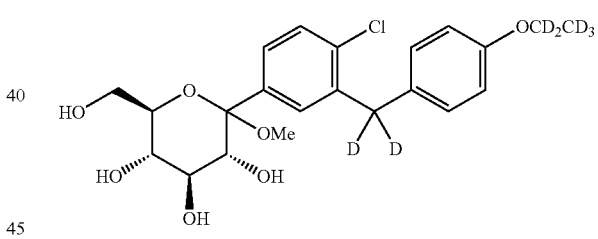

15

Preparation of 4-((5-bromo-2-chlorophenyl)methyl-d₂)phenol (12)

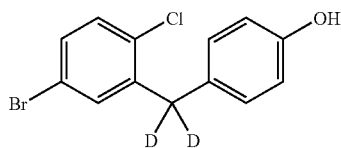 [SMILES: [2H]C([2H])(c1ccc(O)cc1)c1cc(Br)ccc1Cl]

To a solution of 4-bromo-1-chloro-2-((4-ethoxyphenyl)methyl-d₂)benzene (7) (6.7 g, 0.02 mol) in dichloromethane (70 mL) at −20° C. was added boron tribromide (2.16 mL, 0.022 mol) over 10 minutes at a rate that maintained the reaction temperature below −10° C. After addition, the mixture was slowly warmed to 0° C. and stirred for 2 hours. The reaction mixture was poured into 100 mL of ice water and extracted with dichloromethane (100 mL×2). The combined organic layers were washed with saturated bicarbonate (80 mL), water (80 mL), and brine (80 mL), and then dried over sodium sulfate. The sample was concentrated and purified by column chromatography to give compound 12a white solid (5.8 g).

Preparation of 4-bromo-1-chloro-2-((4-(ethoxy-d₅)phenyl)methyl-d₂)benzene (13)

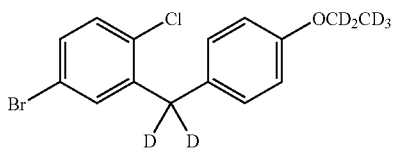

To a stirred suspension of 4-((5-bromo-2-chlorophenyl)methyl-d₂)phenol (3.80 g, 0.013 mol) and triphenylphosphine (6.70 g, 0.026 mol) in THF (45 mL) was added DIAD (1.1 mL, 0.026 mol), and the mixture was stirred for 30 minutes at 30° C. Ethanol-d₆ (1 g, 0.019 mol, 99.5 atom % D) was added and the mixture was stirred overnight at 30° C. The solvents were removed under reduced pressure, the mixture was triturated with petroleum ether, and the solid was filtered and washed with petroleum ether. The filtrate was concentrated under reduced pressure, and the residue was purified by column chromatography to give compound 13 as a white solid (2.25 g). ¹H NMR (CDCl₃, 400 MHz): δ 7.31~7.24 (m, 3H), 7.13~7.11 (m, 2H), 6.88~6.85 (m, 2H).

Preparation of (3R,4S,5S,6R)-2-(4-chloro-3-((4-(ethoxy-d₅)phenyl)methyl-d₂)phenyl)-6-(hydroxymethyl)-2-methoxytetrahydro-2H-pyran-3,4,5-triol (14)

To a solution of 4-bromo-1-chloro-2-((4-(ethoxy-d₅)phenyl)methyl-d₂)benzene (1.250 g, 3.95 mmol) in dry tetrahydrofuran:toluene (9 mL, 1:2) at −78° C. was added dropwise a solution of n-BuLi (1.74 mL, 2.5 M in hexane) at −78° C. under argon at such a rate as to keep the internal temperature below −70° C., and the mixture was stirred for 50 min. The reaction mixture was transferred via cannula to a solution of (3R,4S,5R,6R)-3,4,5-tris(trimethylsilyloxy)-6-((trimethylsilyloxy)methyl)tetrahydro-2H-pyran-2-one (2.024 g, 4.34 mmol) in toluene (9 mL) at −78° C. at a rate that maintained the reaction temperature below −70° C. The mixture was stirred for 2.5 hours at −78° C., and concentrated HCl (1 mL, 36.5%) in methanol (9 mL) below −75° C. was added. After addition, the reaction solution was gradually warmed to RT and stirred overnight. The reaction was quenched with saturated aqueous bicarbonate, and the aqueous layer was extracted twice with ethyl acetate. The combined organic portions were washed with brine, dried over sodium sulfate, and then concentrated to afford compound 14 as a glassy residue (1.863 g), which was used in the next step without further purification.

Preparation of (2S,3R,4R,5S,6R)-2-(4-chloro-3-((4-(ethoxy-d5)phenyl)methyl-d2)phenyl)-6-(hydroxymethyl)tetrahydro-2H-pyran-2-d-3,4,5-triol (15)

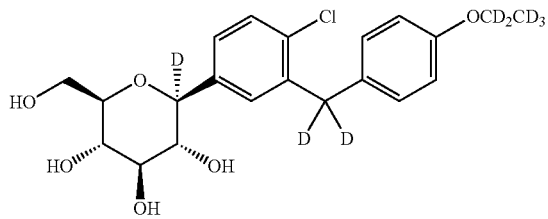

To a −15° C. solution of (3R,4S,5S,6R)-2-(4-chloro-3-((4-(ethoxy-d5)phenyl)methyl-d2)phenyl)-6-(hydroxymethyl)-2-methoxytetrahydro-2H-pyran-3,4,5-triol (0.3 g, 0.67 mmol) in anhydrous acetonitrile/dichloromethane (3 mL, 1:1) was added triethylsilane-d (0.22 mL, 1.35 mmol, 97 atom % D). BF3.Et2O (0.13 mL, 1.01 mmol) was added dropwise, and then the mixture was stirred for 3 hours at −15° C. The reaction was quenched with saturated aqueous bicarbonate and the volatiles were removed under reduced pressure. The residues were extracted with ethyl acetate, washed with water, then with brine, dried over sodium sulfate, concentrated and then purified by preparative HPLC-MS to obtain compound 15 as a white solid (120 mg). $^1$H-NMR (CD$_3$OD, 400 MHz): δ 7.37~7.28 (m, 3H), 7.13 (d, J=8.4 Hz, 2H), 6.81 (d, J=8.4 Hz, 2H), 3.89 (m, 1H), 3.73~3.68 (m, 1H), 3.49~3.40 (m, 3H), 3.30 (m, 1H); MS ESI (m/z): 417 [M+H]$^+$, calc. 416.

Example 6

Preparation of (2S,3R,4R,5S,6R)-2-(4-chloro-3-((4-(ethoxy-d5)phenyl)methyl-d2)phenyl)-6-(hydroxymethyl)tetrahydro-2H-pyran-3,4,5-triol (16)

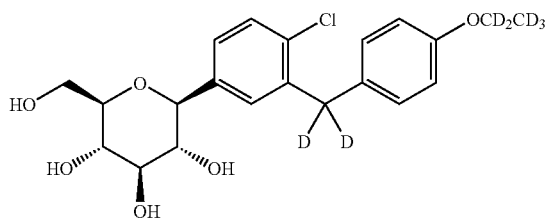

To a solution of crude (3R,4S,5S,6R)-2-(4-chloro-3-((4-(ethoxy-d5)phenyl)methyl-d2)phenyl)-6-(hydroxymethyl)-2-methoxytetrahydro-2H-pyran-3,4,5-triol (14) (from Example 5) (1.2 g, 2.69 mmol) in anhydrous acetonitrile/dichloromethane (12 mL, 1:1) at −15° C. was added triethylsilane (1.70 mL, 10.78 mmol). BF3.Et2O (1.02 mL, 8.08 mmol) was added dropwise, then the mixture was stirred for 2 hours at −15° C. The reaction was quenched with saturated aqueous bicarbonate, and the volatiles were removed under reduced pressure. The residues were extracted with ethyl acetate, washed with water, then with brine, and dried over sodium sulfate. The sample was concentrated and purified by preparative HPLC-MS to give compound 16 as a white solid (560 mg). $^1$H-NMR (CD$_3$OD, 400 MHz): δ 7.37~7.28 (m, 3H), 7.13 (d, J=8.8 Hz, 2H), 6.81 (d, J=8.8 Hz, 2H), 4.10 (d, J=9.2 Hz, 1H), 3.90~3.88 (m, 1H), 3.73~3.68 (m, 1H), 3.49~3.40 (m, 3H), 3.30~3.28 (m, 1H); MS ESI (m/z): 416 [M+H]$^+$, calc. 415.

Example 7

This example illustrates the preparation of compound 19 according to the approach provided in Scheme 12. The general method is applicable to other compounds of the present invention.

Scheme 12

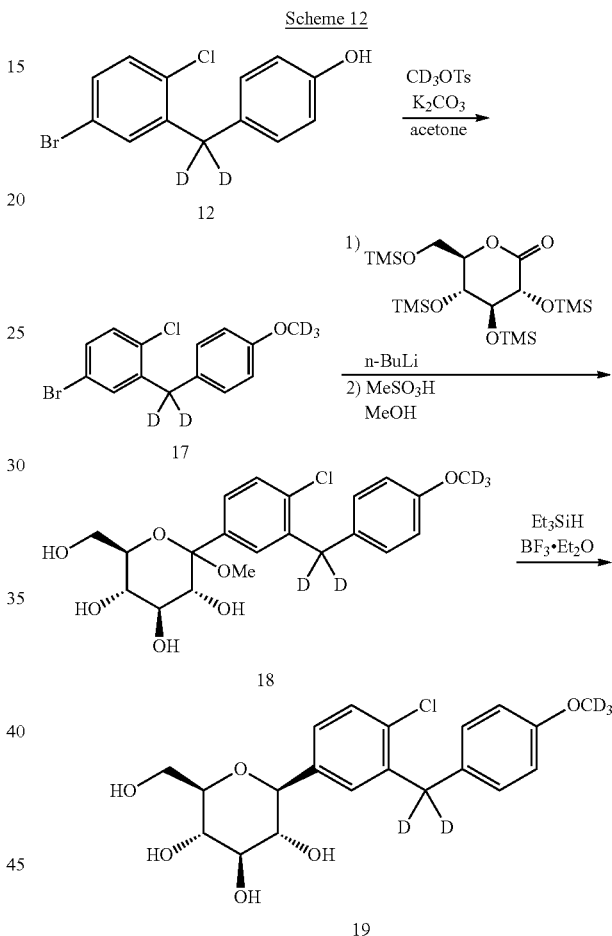

Preparation of 4-bromo-1-chloro-2-((4-(methoxy-d3)phenyl)methyl-d2)benzene (17)

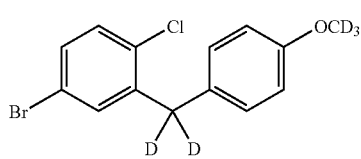

To a stirred solution of 4-((5-bromo-2-chlorophenyl)methyl-d2)phenol (12) (1.2 g, 0.004 mol) in acetone (4 mL) was added potassium carbonate (1.7 g, 0.012 mol) and methyl-d3 4-methylbenzenesulfonate (1.2 g, 0.005 mol, 99.8 atom % D) at RT. The mixture was heated to 75° C. and stirred for 5 hours. The reaction mixture was cooled to RT, quenched with water and extracted with ethyl acetate. The combined organic layers were washed with water, then with brine, dried over sodium sulfate, and concentrated. The residue was purified by column chromatography (ethyl acetate/petroleum ether, 1:200) to give compound 17 as a white solid (1.05 g).

Preparation of (3R,4S,5S,6R)-2-(4-chloro-3-((4-(methoxy-d₃)phenyl)methyl-d₂)phenyl)-6-(hydroxymethyl)-2-methoxytetrahydro-2H-pyran-3,4,5-triol (18)

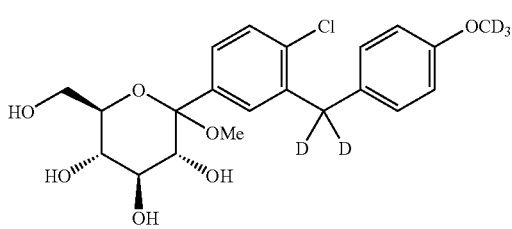

To a solution of 4-bromo-1-chloro-2-((4-(methoxy-d₃)phenyl)methyl-d₂)benzene (1.05 g, 3.32 mmol) in dry THF:toluene (9 mL, 1:2) at −78° C. was added dropwise a solution of n-BuLi (1.46 mL, 2.5 M in hexane, 3.65 mmol) at −78° C. at a rate that maintained the reaction temperature below −70° C., and the mixture was stirred for 40 min. The reaction mixture was transferred by cannula to a stirred solution of (3R,4S,5R,6R)-3,4,5-tris(trimethylsilyloxy)-6-((trimethylsilyloxy)methyl)tetrahydro-2H-pyran-2-one (1.70 g, 3.65 mmol) in toluene (8 mL) at −78° C. at a rate that maintained the reaction temperature below −70° C. The mixture was stirred for 5 hours at −78° C., and methanesulfonic acid (0.45 mL, 6.97 mmol) in methanol (8 mL) was slowly added. The reaction mixture was gradually warmed to RT and stirred overnight. Saturated aqueous bicarbonate was added, and the aqueous layer was extracted twice with ethyl acetate. The combined organic portions were washed with brine, dried over sodium sulfate, and concentrated to give compound 18 as a glassy residue (118 g), which was used in the next step without further purification.

Preparation of (2S,3R,4R,5S,6R)-2-(4-chloro-3-((4-(methoxy-d₃)phenyl)methyl-d₂)phenyl)-6-(hydroxymethyl)tetrahydro-2H-pyran-3,4,5-triol (19)

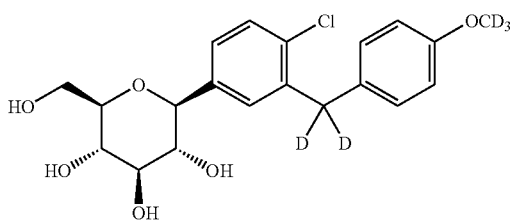

To a solution of the crude (3R,4S,5S,6R)-2-(4-chloro-3-((4-(methoxy-d₃)phenyl)methyl-d₂)phenyl)-6-(hydroxymethyl)-2-methoxytetrahydro-2H-pyran-3,4,5-triol (0.6 g, 1.40 mmol) in anhydrous acetonitrile/dichloromethane (6 mL, 1:1) at −15° C. was added triethylsilane (0.45 mL, 2.79 mmol). BF₃·Et₂O (0.22 mL, 1.71 mmol) was added dropwise, and the mixture was stirred for 2.5 hours at −15° C. The reaction was quenched with saturated aqueous bicarbonate, and the volatiles were removed under reduced pressure. The residue was extracted with ethyl acetate, washed with water, then with brine, and dried over sodium sulfate. The sample was concentrated and purified by preparative HPLC-MS to give compound 19 as a white solid (220 mg). ¹H-NMR (CD₃OD, 400 MHz): δ 7.37~7.28 (m, 3H), 7.12 (d, J=8.8 Hz, 2H), 6.81 (d, J=8.8 Hz, 2H), 4.11 (d, J=9.2 Hz, 1H), 3.91~3.88 (m, 1H), 3.73~3.69 (m, 1H), 3.50~3.41 (m, 3H), 3.33~3.29 (m, 1H); MS ESI (m/z): 400 [M+H]⁺, calc. 399.

Example 8

Preparation of (2S,3R,4R,5S,6R)-2-(4-chloro-3-((4-(methoxy-d₃)phenyl)methyl-d₂)phenyl)-6-(hydroxymethyl)tetrahydro-2H-pyran-2-d-3,4,5-triol (20)

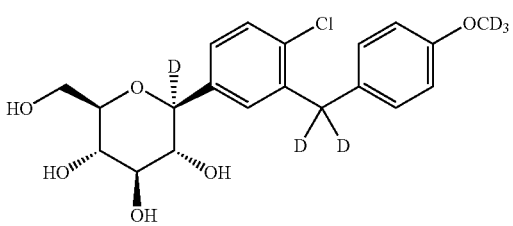

To a solution of the crude (3R,4S,5S,6R)-2-(4-chloro-3-((4-(methoxy-d₃)phenyl)methyl-d₂)phenyl)-6-(hydroxymethyl)-2-methoxytetrahydro-2H-pyran-3,4,5-triol (18) (from Example 7) (0.6 g, 1.40 mmol) in anhydrous acetonitrile/dichloromethane (6 mL, 1:1) at −15° C. was added triethylsilane-d (0.33 g, 2.79 mmol, 97 atom % D). BF₃·Et₂O (0.22 mL, 1.71 mmol) was added, and the mixture was stirred for 2.5 hours at −15° C. The reaction was quenched with saturated aqueous bicarbonate, and the volatiles were removed under reduced pressure. The residue was extracted with ethyl acetate, washed with water, then with brine, and dried over sodium sulfate. The sample was concentrated and purified by preparative HPLC-MS to give compound 20 as a white solid (200 mg). ¹H-NMR (CD₃OD, 400 MHz): δ 7.37~7.28 (m, 3H), 7.12 (d, J=8.4 Hz, 2H), 6.82 (d, J=8.4 Hz, 2H), 3.91~3.88 (m, 1H), 3.73~3.68 (m, 1H), 3.50~3.40 (m, 3H), 3.33~3.30 (m, 1H); MS ESI (m/z): 401 [M+H]⁺, calc. 400.

Example 9

This example illustrates the preparation of compound 24a according to the approach provided in Scheme 13. In this example, Rˣ is —OCD₂CH₃, and Rʸ is H. The general method is applicable to other compounds of the present invention.

Scheme 13

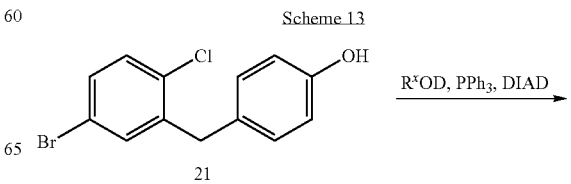

21

-continued

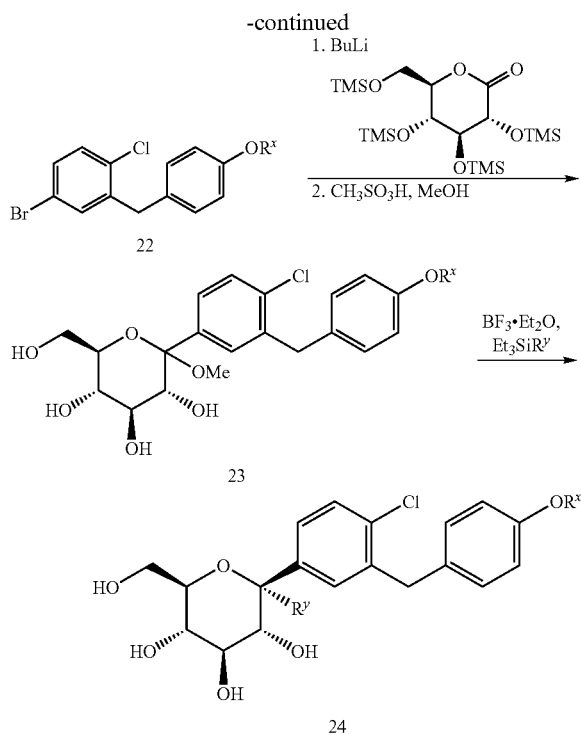

Preparation of 4-bromo-1-chloro-2-(4-(ethoxy-1,1-d₂)benzyl)benzene (22a)

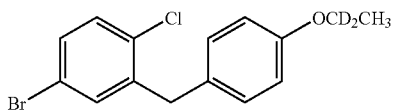

To a stirred suspension of 4-(5-bromo-2-chlorobenzyl)phenol (4.1 g, 13.8 mmol) in tetrahydrofuran (50 mL) and triphenylphosphine (7.72 g, 27.6 mmol) was added 1,2-diisopropyldiazodicarboxylate (5.5 mL, 27.6 mmol). The mixture was stirred for 30 minutes at 30° C. Ethyl-1,1-d₂ alcohol (1.6 mL, 20.7 mmol, 98 atom % D) was added, and the mixture was stirred overnight at 30° C. The volatiles were removed under reduced pressure, and petroleum ether was added. The solid was filtered and washed with petroleum ether, and the combined filtrate was concentrated under reduced pressure. The residue was purified by column chromatography to give compound 22a as a white solid (2.6 g, 63% yield). $^1$H-NMR (CDCl₃, 400 MHz): δ 7.21-7.28 (m, 3H), 7.01-7.09 (d, J=8.0 Hz, 2H), 6.82-6.84 (d, J=8.0 Hz, 2H), 3.99 (s, 2H), 1.38 (s, 3H).

Preparation of (3R,4S,5S,6R)-2-(4-chloro-3-(4-(ethoxy-1,1-d₂)benzyl)phenyl)-6-(hydroxymethyl)-2-methoxytetrahydro-2H-pyran-3,4,5-triol (23a)

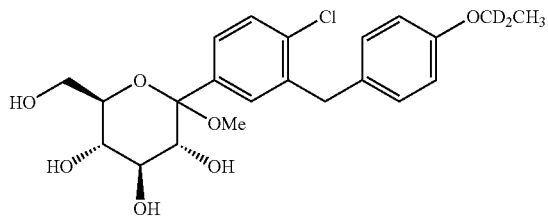

To a solution of 4-bromo-1-chloro-2-((4-ethoxy-1,1-d₂)benzyl)benzene) (2.6 g, 7.9 mmol) in anhydrous toluene/tetrahydrofuran (42 mL v/v=2:1) at −65° C. was added dropwise n-butyllithium (2.5 M in hexane, 8.1 mL), and the pale yellow mixture was stirred for 30 minutes at −65° C. The mixture was transferred to a solution of (3R,4S,5R,6R)-3,4,5-tris(trimethylsilyloxy)-6-((trimethylsilyloxy)methyl)tetrahydro-2H-pyran-2-one (4.8 g, 9.48 mmol) in toluene (21 mL) at −65° C. The mixture was stirred at −65° C. for 2 hours until starting material was consumed. The reaction was quenched with methanesulfonic acid (1.1 mL, 16.6 mmol) in methanol (19 mL), and the mixture was allowed to warm to 20° C. and stirred overnight. The reaction was quenched with saturated sodium bicarbonate. The organic phase was separated, and the aqueous phase was extracted with ethyl acetate. The organic phases were combined, washed with saturated sodium bicarbonate, then with water and then with brine, and dried over anhydrous sodium sulfate. After removal of volatiles, crude compound 23a was obtained as a solid product (3.6 g), which was used in the next step without further purification.

Preparation of (2S,3R,4R,5S,6R)-2-(4-chloro-3-(4-(ethoxy-1,1'-d)benzyl)phenyl)-6-(hydroxymethyl)tetrahydro-2H-pyran-3,4,5-triol (24a)

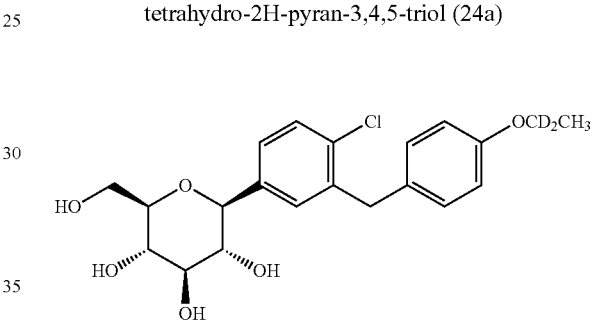

To a solution of the crude (3R,4S,5S,6R)-2-(4-chloro-3-(4-(ethoxy-1,1-d₂)benzyl)phenyl)-6-(hydroxymethyl)-2-methoxytetrahydro-2H-pyran-3,4,5-triol (3.6 g, 7.9 mmol) in anhydrous acetonitrile/dichloromethane (25 mL, 1:1) at −15° C., was added triethylsilane (1.5 mL, 9.3 mmol). Boron trifluoride diethyl etherate (0.09 mL, 6.84 mmol) was added dropwise, and then the mixture was stirred for 4 hours at −10° C. The reaction was quenched with saturated aqueous sodium bicarbonate. The volatiles were removed under reduced pressure, and the residue was extracted with ethyl acetate, washed with water and then with brine, and dried over anhydrous sodium sulfate. The residue was filtered, concentrated to a solid, and purified by preparative HPLC-MS to obtain compound 24a (204 mg, HPLC purity=95%). HPLC retention time: 2.25 min; Waters 2695 Separations Module equipped with a Waters 2996 Photodiode Array Detector and a Waters Micromass ZQ Detector; Waters XTerra C18 3.5 μm, 20 mm×2.1 mm column, 1.0 mL/min, detection at 190~400 nm; 1.7 min gradient 10-50% A, followed by 1.8 min gradient 50-95% A, hold 1 min at 95% A; solvent A: 100% acetonitrile+0.045% formic acid; solvent B: Milli-Q water+0.1% formic acid. $^1$H-NMR (CD₃OD, 400 MHz): δ 7.24-7.34 (m, 3H), 7.06-7.09 (m, 2H), 6.76-6.80 (m, 2H), 4.06-4.08 (d, J=9.6 Hz, 1H), 4.02-4.06 (d, J=15.2 Hz, 1H), 3.96-4.00 (d, J=15.2 Hz, 1H), 3.84-3.87 (m, 1H), 3.65-3.69 (m, 1H), 3.36-3.46 (m, 3H), 3.25-3.27 (m, 1H), 1.32 (s, 3H); MS ESI (m/z): 455 (M+45)⁻.

Example 10

This example illustrates the preparation of compound 24b according to the approach provided in Scheme 13. In this example, $R^X$ is —OCD$_2$CH$_3$, and $R^Y$ is deuterium.

Preparation of (2S,3R,4R,5S,6R)-2-(4-chloro-3-(4-(ethoxy-1,1-d$_2$)benzyl)phenyl)-6-(hydroxymethyl)tetrahydro-2H-pyran-2-d-3,4,5-triol (24b)

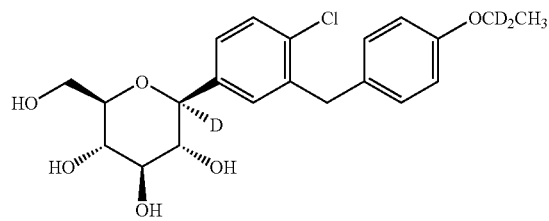

To a solution of the crude (3R,4S,5S,6R)-2-(4-chloro-3-(4-(ethoxy-1,1-d$_2$)benzyl)phenyl)-6-(hydroxymethyl)-2-methoxytetrahydro-2H-pyran-3,4,5-triol (23a) (from Example 9) (0.5 g, 1 mmol) in acetonitrile/dichloromethane (10 mL, v/v 1:1) at −15° C. was added triethylsilane-d (0.25 g, 2 mmol, 97 atom % D). Boron trifluoride diethyl etherate (0.22 mL, 1.5 mmol) was added while the temperature was maintained between −5° C. -1~−10° C. The stirred solution was allowed to warm to 0° C. over 5 hours. The reaction was quenched with saturated aqueous sodium bicarbonate, and the volatiles were removed under reduced pressure. The residue was extracted with ethyl acetate, washed with water and then with brine, and dried over sodium sulfate. The sample was filtered, concentrated to give a white foam, and purified by preparative HPLC-MS to obtain compound 24b (95.6 mg, HPLC purity=95%). HPLC retention time: 2.24 min; Waters 2695 Separations Module equipped with a Waters 2996 Photodiode Array Detector and a Waters Micromass ZQ Detector; Waters XTerra C18 3.5 µm, 20 mm×2.1 mm column, 1.0 mL/min, detection at 190~400 nm; 1.7 min gradient 10-50% A, followed by 1.8 min gradient 50-95% A, hold 1 min at 95% A; solvent A: 100% acetonitrile+0.045% formic acid; solvent B: Milli-Q water+0.1% formic acid. $^1$H-NMR (CD$_3$OD, 400 MHz): δ 7.24-7.34 (m, 3H), 7.06-7.09 (m, 2H), 6.76-6.80 (m, 2H), 4.02-4.06 (d, J=15.2 Hz, 1H), 3.96-4.00 (d, J=15.2 Hz, 1H), 3.84-3.87 (m, 1H), 3.65-3.69 (m, 1H), 3.36-3.46 (m, 3H), 3.25-3.27 (m, 1H), 1.32 (s, 3H); MS ESI (m/z): 456 (M+45)$^-$.

Example 11

This example illustrates the preparation of compound 24c according to the approach provided in Scheme 13. In this example, $R^X$ is —OCD$_2$CH$_3$, and $R^Y$ is hydrogen.

Preparation of 4-bromo-1-chloro-2-(4-(ethoxy-d$_5$)benzyl)benzene (22c)

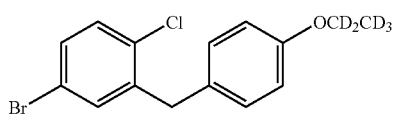

To a stirred suspension of 4-(5-bromo-2-chlorobenzyl)phenol (2.8 g, 9.4 mmol) in tetrahydrofuran (30 mL) and triphenylphosphine (4.9 g, 18.8 mmol) was added 1,2-diisopropyldiazodicarboxylate (3.7 mL, 18.8 mmol). The mixture was stirred for 30 minutes at 30° C., and ethanol-d$_6$ (1 g, 18.8 mmol, 99.5 atom % D) was added and stirred overnight at 30° C. The volatiles were removed under reduced pressure, and petroleum ether was added. The solid was filtered and washed with petroleum ether, and the combined filtrate was concentrated under reduced pressure. The residue was purified by column chromatography to give compound 22c as a white solid (2.8 g, 90% yield). $^1$H-NMR (CDCl$_3$, 400 MHz): δ 7.21-7.28 (m, 3H), 7.01-7.09 (d, J=8.0 Hz, 2H), 6.82-6.84 (d, J=8.0 Hz, 2H), 3.99 (s, 2H).

Preparation of (3R,4S,5S,6R)-2-(4-chloro-3-(4-(ethoxy-d$_5$)benzyl)phenyl)-6-(hydroxymethyl)-2-methoxytetrahydro-2H-pyran-3,4,5-triol (23c)

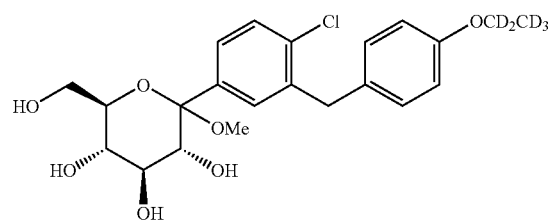

To a solution of 4-bromo-1-chloro-2-(4-(ethoxy-d$_5$)benzyl)benzene (2.8 g, 8.1 mmol) in anhydrous toluene/tetrahydrofuran (21 mL, v/v=2:1) at −65° C. was added dropwise n-butyllithium (2.5 M in hexane, 3.7 mL, 8.9 mmol), and the pale yellow solution was stirred for 30 minutes at −65° C. The mixture was transferred to a solution of (3R,4S,5R,6R)-3,4,5-tris(trimethylsilyloxy)-6-((trimethylsilyloxy)methyl)tetrahydro-2H-pyran-2-one (5.1 g, 10.5 mmol) in toluene (14 mL) at −65° C. The mixture was stirred at −65° C. for 2 hours until starting material was consumed. The reaction was quenched with methanesulfonic acid (1.1 mL, 17.0 mmol) in methanol (19 mL), and the mixture was allowed to warm to 20° C. and stirred overnight. The reaction was quenched with saturated sodium bicarbonate. The organic phase was separated, and the aqueous phase was extracted with ethyl acetate. The organic phases were combined, washed with saturated sodium bicarbonate, then with water and then with brine, and dried over sodium sulfate. After removal of volatiles, crude compound 23c was obtained as a solid product (3.8 g), which was used in the next step without further purification.

Preparation of (2S,3R,4R,5S,6R)-2-(4-chloro-3-(4-(ethoxy-d$_5$)benzyl)phenyl)-6-(hydroxymethyl)tetrahydro-2H-pyran-3,4,5-triol (24c)

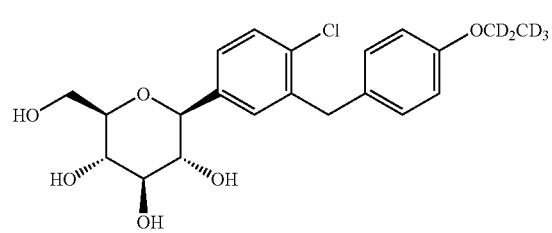

To a solution of crude (3R,4S,5S,6R)-2-(4-chloro-3-(4-(ethoxy-d$_5$)benzyl)phenyl)-6-(hydroxymethyl)-2-methoxytetrahydro-2H-pyran-3,4,5-triol (3.8 g, 8.5 mmol) in anhydrous acetonitrile/dichloromethane (30 mL, v/v=1:1) at −15° C., was added triethylsilane (2.7 mL, 17.0 mmol). Then boron trifluoride diethyl etherate (1.6 mL, 12.7 mmol) was added dropwise, and the mixture was stirred for 4 hours at −10° C. The reaction was quenched with saturated aqueous sodium bicarbonate. The volatiles were removed under reduced pressure, and the residue was extracted with ethyl acetate, washed with water and then with brine, and dried over sodium sulfate. The sample was filtered and concentrated to give a white foam, which was purified by preparative HPLC-MS to obtain compound 24c (1.9 g, HPLC purity=95%). HPLC retention time: 2.85 min; Waters XTerra C18, 5 μm pore size, 2.1×50 mm column; 1.0 mL/min, 8 min gradient; mobile phase: solvent A: 0.045% formic acid in acetonitrile, solvent B: 0.1% formic acid in Milli-Q water. $^1$H-NMR (CD$_3$OD, 400 MHz): δ 7.24-7.34 (m, 3H), 7.06-7.09 (m, 2H), 6.76-6.80 (m, 2H), 4.06-4.08 (d, J=9.6 Hz, 1H), 4.02-4.06 (d, J=15.2 Hz, 1H), 3.96-4.00 (d, J=15.2 Hz, 1H), 3.84-3.87 (m, 1H), 3.65-3.69 (m, 1H), 3.36-3.46 (m, 3H), 3.25-3.27 (m, 1H); MS ESI (m/z): 458 (M+45)$^-$.

Example 12

This example illustrates the preparation of compound 24d according to the approach provided in Scheme 14. The general method is applicable to other compounds of the present invention.

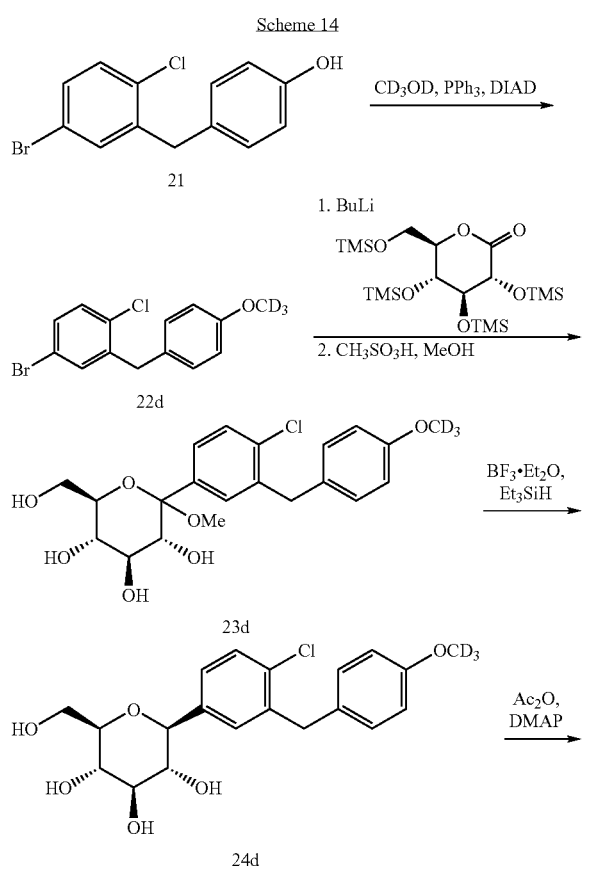

Scheme 14

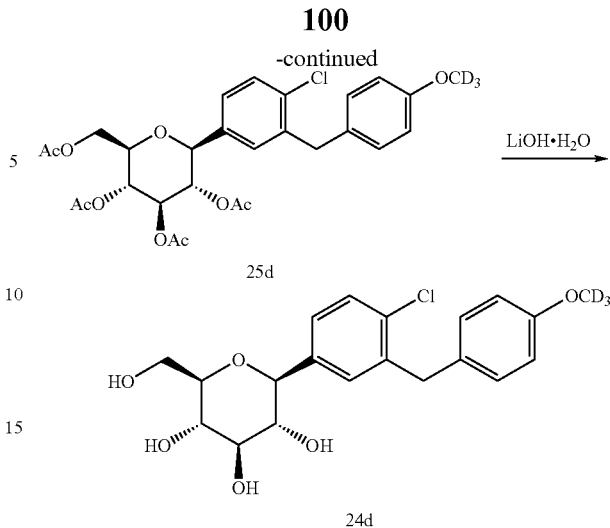

Preparation of 4-bromo-1-chloro-2-(4-(methoxy-d$_3$)benzyl)benzene (22d)

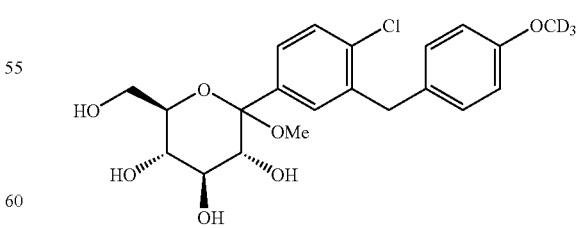

To a stirred suspension of 4-(5-bromo-2-chlorobenzyl)phenol (5 g, 16.9 mmol) in tetrahydrofuran (100 mL) and triphenylphosphine (8.86 g, 33.8 mmol) was added 1,2-diisopropyldiazodicarboxylate (6.7 mL, 33.8 mmol). The mixture was stirred for 30 minutes at 30° C., and methanol-d$_4$ (1.6 mL, 33.8 mmol, 99.8 atom % D) was added and stirred overnight at 30° C. The volatiles were removed under reduced pressure, and petroleum ether was added. The solid was filtered and washed with petroleum ether, and the combined filtrate was concentrated under reduced pressure. The residue was purified by column chromatography to give compound 22d as a white solid (5.3 g, 99% yield). $^1$H-NMR (CDCl$_3$, 400 MHz): δ 7.21-7.28 (m, 3H), 7.01-7.09 (d, J=8.0 Hz, 2H), 6.82-6.84 (d, J=8.0 Hz, 2H), 3.99 (s, 2H).

Preparation of (3R,4S,5S,6R)-2-(4-chloro-3-(4-(methoxy-d$_3$)benzyl)phenyl)-6-(hydroxymethyl)-2-methoxytetrahydro-2H-pyran-3,4,5-triol (23d)

To a solution of 4-bromo-1-chloro-2-(4-(methoxy-d$_3$)benzyl)benzene (5.8 g, 18 mmol) in anhydrous toluene/tetrahydrofuran (42 mL, v/v=2:1) at −65° C. was added dropwise n-butyllithium (2.5 M in hexane, 8.1 mL, 23.4 mmol), and the pale yellow solution was stirred for 30 minutes at −65° C.

Then the mixture was transferred to a solution of (3R,4S,5R,6R)-3,4,5-tris(trimethylsilyloxy)-6-((trimethylsilyloxy)methyl)tetrahydro-2H-pyran-2-one (11.8 g, 23.4 mmol) in toluene (21 mL) at −65° C. The mixture was stirred at −65° C. for 2 hours until starting material was consumed. The reaction was quenched with methanesulfonic acid (2.1 mL, 37.8 mmol) in methanol (42 mL), and the mixture was allowed to warm to 20° C. and stirred overnight. The reaction was quenched with saturated sodium bicarbonate. The organic phase was separated, and the aqueous phase was extracted with ethyl acetate. The organic phases were combined, washed with saturated sodium bicarbonate, then with water, and then with brine, and then dried over anhydrous sodium sulfate. After removal of volatiles, crude compound 23d was obtained as a solid product (7.3 g), which was used in the next step without further purification.

Preparation of crude (2S,3R,4R,5S,6R)-2-(4-chloro-3-(4-(methoxy-d₃)benzyl)phenyl)-6-(hydroxymethyl)tetrahydro-2H-pyran-3,4,5-triol (24d)

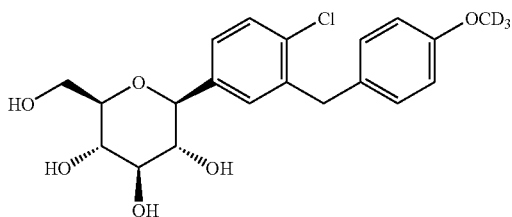

To a solution of the crude (3R,4S,5S,6R)-2-(4-chloro-3-(4-(methoxy-d₃)benzyl)phenyl)-6-(hydroxymethyl)-2-methoxytetrahydro-2H-pyran-3,4,5-triol (7.3 g, ~17 mmol) in anhydrous acetonitrile/dichloromethane (50 mL, v/v=1:1) at −15° C., was added triethylsilane (5.5 mL, 34 mmol), boron trifluoride diethyl etherate (3.25 mL, 25.5 mmol) was added dropwise, and the mixture was stirred for 4 hours at −10° C. The reaction was quenched with saturated aqueous sodium bicarbonate. Volatiles were removed under reduced pressure, and the residue was extracted with ethyl acetate, washed with water, then with brine, and dried over sodium sulfate. The sample was filtered and concentrated to give crude compound 24d as a white, foamy solid (6.2 g), which was used in the next step without further purification.

Preparation of (2R,3R,4R,5S,6S)-2-(acetoxymethyl)-6-(4-chloro-3-(4-(methoxy-d₃)benzyl)phenyl)tetrahydro-2H-pyran-3,4,5-triyl triacetate (25d)

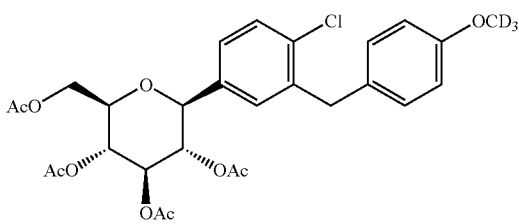

To a solution of the crude (2S,3R,4R,5S,6R)-2-(4-chloro-3-(4-(methoxy-d₃)benzyl)phenyl)-6-(hydroxymethyl)tetrahydro-2H-pyran-3,4,5-triol (3.7 g, ~9 mmol) in dichloromethane (20 mL) was added pyridine (7.6 mL, 81 mmol) and 4-dimethylamino-pyridine (60 mg, 0.491 mmol). Then acetic anhydride (8 mL, 81.9 mmol) was added, and the mixture was stirred for 2.5 hours at RT. The reaction was quenched by addition of water (50 mL) once HPLC analysis indicated the reaction was complete. The mixture was extracted with dichloromethane (2×150 mL). The combined organic layers were washed with hydrochloric acid (3N, 2×100 mL), then with water (100 mL), then with brine (100 mL), and then dried over sodium sulfate. After removal of volatiles, the residue was recrystallized from 30 mL of absolute ethanol to yield compound 25d as a white solid (3 g).

Preparation of (2S,3R,4R,5S,6R)-2-(4-chloro-3-(4-(methoxy-d₃)benzyl)phenyl)-6-(hydroxymethyl)tetrahydro-2H-pyran-3,4,5-triol (24d)

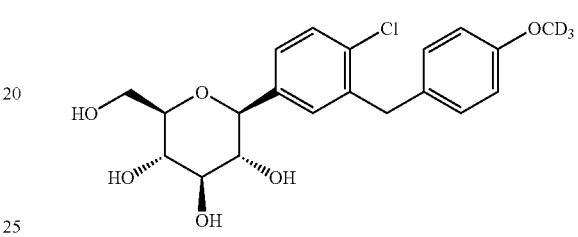

To a stirred solution of (2R,3R,4R,5S,6S)-2-(acetoxymethyl)-6-(4-chloro-3-(4-(methoxy-d₃)benzyl)phenyl)tetrahydro-2H-pyran-3,4,5-triyl triacetate (3 g, ~5.3 mmol) in tetrahydrofuran/methanol/water (60 mL, v/v/v=2:3:1) at 20° C. was added LiOH.H₂O (0.47 g, 11.1 mmol). After stirring for 4 hours, volatiles were removed using a rotary evaporator. The residue was partitioned in ethyl acetate and water. The organic layer was washed with brine, then with 5% aqueous potassium bicarbonate sulfate, and then with water, and then dried over sodium sulfate. The solvent was removed and the resultant oil foamed under vacuum and purified by preparative HPLC-MS to yield compound 24d as a glassy off-white solid (2.4 g, HPLC purity=95%). HPLC retention time: 2.61 min; Waters XTerra C18, 5 μm pore size, 2.1×50 mm column; 1.0 mL/min, 8 min gradient; mobile phase: solvent A: 0.045% formic acid in acetonitrile, solvent B: 0.1% formic acid in Milli-Q water. ¹H-NMR (CD₃OD, 400 MHz): δ 7.24-7.34 (m, 3H), 7.06-7.09 (m, 2H), 6.76-6.80 (m, 2H), 4.0-4.08 (d, J=15.2 Hz, 1H), 4.02-4.06 (d, J=15.2 Hz, 1H), 3.96-4.00 (m, 1H), 3.84-3.87 (m, 1H), 3.65-3.69 (m, 3H), 3.36-3.46 (m, 3H), 3.25-3.27 (1H, m); MS ESI (m/z): 442 (M+45)⁻.

Example 13

This example illustrates the preparation of compound 24e according to the approach provided in Scheme 2. In this example, R⁸ is —OCD₃ and R¹¹ and R² are deuterium.

Preparation of (2S,3R,4R,5S,6R)-2-(4-chloro-3-(4-(methoxy-d₃)benzyl)phenyl)-6-(hydroxymethyl)tetrahydro-2H-pyran-2-d-3,4,5-triol (24e)

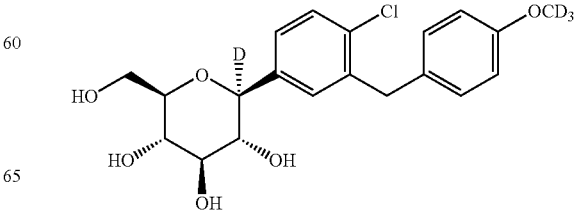

To a solution of the crude (3R,4S,5S,6R)-2-(4-chloro-3-(4-(methoxy-d₃)benzyl)phenyl)-6-(hydroxymethyl)-2-methoxytetrahydro-2H-pyran-3,4,5-triol (23d) (from Example 12) (0.5 g, ~1 mmol) in acetonitrile/dichloromethane (10 mL, v/v 1:1) at −15° C. was added triethylsilane-d (0.25 g, 2 mmol, 97 atom % D), and boron trifluoride diethyl etherate (0.22 mL, 1.5 mmol) was added while the reaction temperature was maintained between −5° C.~−10° C. The stirred solution was allowed to warm to 0° C. over 5 hours, and then the reaction was quenched with saturated aqueous sodium bicarbonate. Volatiles were removed under reduced pressure, and the residue was extracted with ethyl acetate, washed with water and then with brine, and dried over sodium sulfate. The sample was filtered and concentrated to a white foam and purified by preparative HPLC-MS to obtain compound 24e (100 mg, HPLC purity=95%). HPLC retention time: 2.60 min; Waters XTerra C18, 5 μm pore size, 2.1×50 mm column; 1.0 mL/min, 8 minutes gradient; mobile phase: solvent A: 0.045% formic acid in acetonitrile, solvent B: 0.1% formic acid in Milli-Q water. ¹H-NMR (CD₃OD, 400 MHz): δ 7.24-7.34 (m, 3H), 7.06-7.09 (m, 2H), 6.76-6.80 (m, 2H), 4.02-4.06 (d, J=15.2 Hz, 1H), 3.96-4.00 (d, J=15.2 Hz, 1H), 3.84-3.87 (m, 1H), 3.65-3.69 (m, 1H), 3.36-3.46 (m, 3H), 3.25-3.27 (m, 1H); MS ESI (m/z): 443 (M+45)⁻

Example 14

This example illustrates the preparation of compound 35a according to the approach provided in Scheme 15. In this example, R is ethyl. The general method is applicable to other compounds of the present invention.

Scheme 15

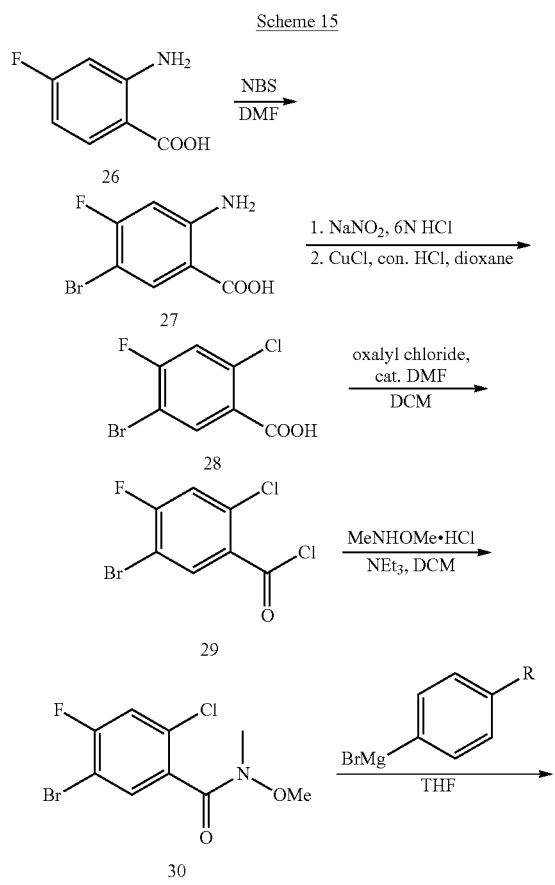

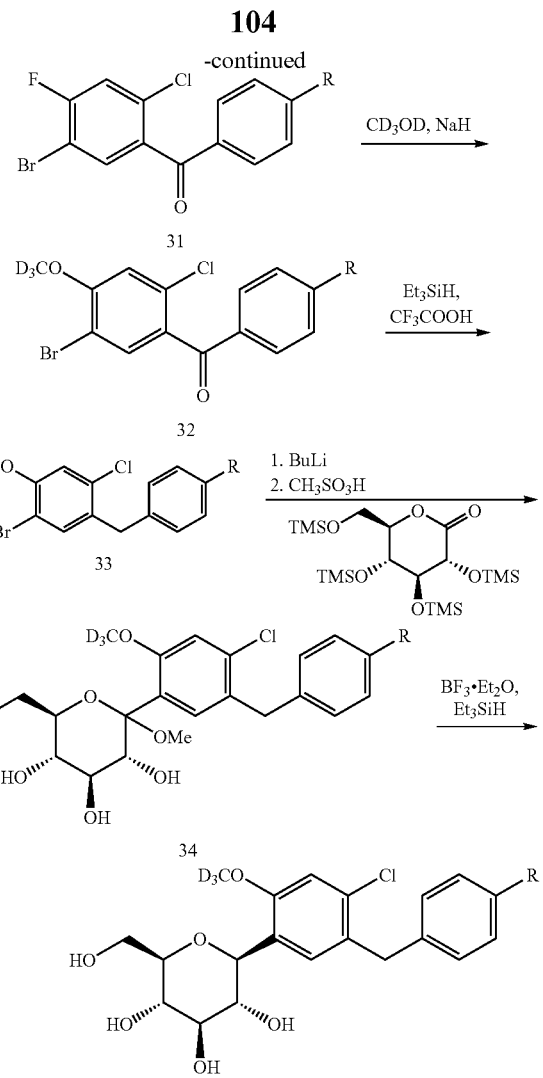

Preparation of 2-amino-5-bromo-4-fluorobenzoic acid (27)

To a solution of 2-amino-4-fluorobenzoic acid (10 g, 64.5 mmol) in N,N-dimethylformamide (100 mL) at −10° C., was added dropwise a solution of N-bromosuccinimide (11.2 g, 62.9 mmol) in N,N-dimethylformamide (50 mL) over 1 hour. After the addition was complete, the mixture was stirred at −10° C. for 1 hour. The reaction was quenched with aqueous sodium bisulfate and partitioned between ethyl acetate and water. The organic layer was separated, and the aqueous layer was extracted twice with ethyl acetate. The combined organic layers were washed with water and then with brine, and then dried over sodium sulfate. The sample was concentrated to give the crude product 27 (14.5 g, yield: 96.5%), which was used for the next step without further purification.

Preparation of 5-bromo-2-chloro-4-fluorobenzoic acid (28)

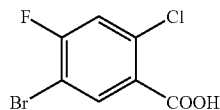

To a solution of 2-amino-5-bromo-4-fluorobenzoic acid (14.5 g, 62.2 mmol) in concentrated hydrochloric acid (30 mL) at 0° C. was added dropwise a solution of sodium nitrate (4.72 g, 68.4 mmol) in water (15 mL). The mixture was stirred at 0° C. for 2 hours, then diluted with 1,4-dioxane (40 mL) and added dropwise to a solution of copper chloride (7.4 g, 74.4 mmol) in concentrated hydrochloric acid (25 mL) under mechanical stirring while the reaction temperature was kept below 7° C. (ice-salt bath). After the addition was complete, the mixture was stirred at 0° C. for another 1 hour. Water was added, and the precipitate was filtered. The filter cake was washed with water and dissolved in ethyl acetate. The filtrate was extracted with ethyl acetate once and washed with water and then with brine. The combined organic layers were dried over sodium sulfate and concentrated to give the crude product 28 (14.5 g, 92%), which was used for the next step without further purification. MS ESI (m/z): 251 (M−H)⁻.

Preparation of 5-bromo-2-chloro-4-fluoro-N-methoxy-N-methylbenzamide (30)

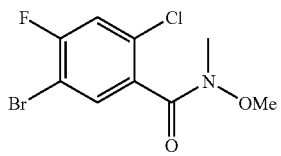

To a solution of 5-bromo-2-chloro-4-fluorobenzoic acid (14.7 g, ~57.5 mmol) in dichloromethane (100 mL) was added oxalyl chloride (7.42 mL, 86.3 mmol). Then N,N-dimethylformamide (1 mL) at 20° C. was added, and the reaction mixture was stirred for 2 hours to produce 29. The mixture was concentrated, dissolved in dichloromethane (120 mL), and O,N-dimethylhydroxylamine hydrochloride (11.1 g, 115 mmol) was added. Then triethylamine (26.5 mL, 190 mmol) was added dropwise, and the mixture was stirred at 25° C. overnight. The reaction mixture was diluted with dichloromethane, washed with water, then with 2 M hydrochloric acid, and then with brine, and dried over sodium sulfate. The crude product was recrystallized from dichloromethane/petroleum ether to give the pure product 30 (11.1 g, 65% yield).

Preparation of (5-bromo-2-chloro-4-fluorophenyl)(4-ethylphenyl)methanone (31a)

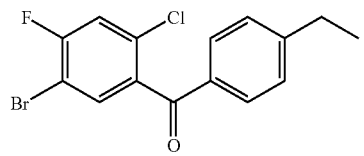 [SMILES: CCc1ccc(C(=O)c2cc(Br)c(F)cc2Cl)cc1]

To a solution of 5-bromo-2-chloro-4-fluoro-N-methoxy-N-methylbenzamide (936 mg, 3.17 mmol) in tetrahydrofuran (15 mL) was added (4-ethylphenyl)magnesium bromide (9.5 mmol, 9.5 mL, 1 M in tetrahydrofuran) at 0° C. The mixture was stirred at 25° C. for 1 hour, then the reaction was quenched with saturated ammonium chloride, and most of the tetrahydrofuran was evaporated under reduced pressure. The residue was partitioned between ethyl acetate and water; the organic layer was separated, washed with water, then with brine, and dried over sodium sulfate. The sample was concentrated and then purified by preparative thin layer chromatography (petroleum ether:ethyl acetate, 4:1) to provide pure product 31a as a white solid (995 mg, 88% yield). ¹H-NMR (CDCl₃, 400 MHz): δ 7.71 (d, J=8.4 Hz, 2H), 7.58 (d, J=6.8 Hz, 1H), 7.31 (d, J=8.4 Hz, 2H), 7.26 (d, J=6.8 Hz, 1H), 2.73 (q, J=8 Hz, 2H), 1.27 (t, J=8 Hz, 2H).

Preparation of (5-bromo-2-chloro-4-(methoxy-d₃)phenyl)(4-ethylphenyl)methanone (32a)

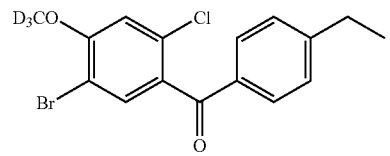

To a solution of methanol-d₄ (0.6 mL, 99.8% D) in tetrahydrofuran (30 mL) at 0° C. was added sodium hydride (0.776 g, 32 mmol), and the mixture was stirred at 0° C. for 30 min. (5-bromo-2-chloro-4-fluorophenyl)(4-ethylphenyl)methanone (1 g, 3 mmol) in tetrahydrofuran (10 mL) was added dropwise, and the mixture was stirred for 3 hours. Ethyl acetate and water were added, and the organic layer was separated, washed with water, then with brine, and dried over sodium sulfate. The sample was concentrated to give the crude product 32a (1 g), which was used in the next step without further purification.

Preparation of 1-bromo-4-chloro-5-(4-ethylbenzyl)-2-(methoxy-d₃)benzene (33a)

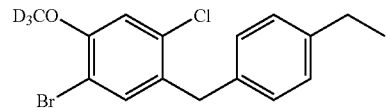

To a solution of the crude (5-bromo-2-chloro-4-(methoxy-d₃)phenyl)(4-ethylphenyl)methanone (1.03 g, 2.9 mmol) in trifluoroacetic acid (10 mL) at 0° C. was added dropwise triethylsilane (0.93 mL, 5.8 mmol). Then trifluoromethanesulfonic acid (50 μL) was added, and the reaction was stirred at RT for 2 hours. The sample was concentrated, and the residue was partitioned between ethyl acetate and saturated sodium bicarbonate. The organic layer was separated, washed with water and then with brine, and then dried over sodium sulfate. The sample was concentrated and purified by chromatography to provide pure product 33a (1 g).

Preparation of (2S,3R,4S,5S,6R)-2-(4-chloro-5-(4-ethylbenzyl)-2-(methoxy-d₃)phenyl)-6-(hydroxymethyl)-2-methoxytetrahydro-2H-pyran-3,4,5-triol (34a)

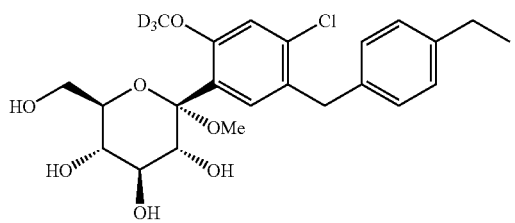

To a solution of 1-bromo-4-chloro-5-(4-ethylbenzyl)-2-(methoxy-d₃)benzene (0.5 g, 1.46 mmol) in toluene/tetrahydrofuran (7.5 mL, 2:1) at −78° C. was added dropwise n-butyllithium (0.65 mL, 2.5 M in hexane, 1.62 mmol), and the mixture was stirred for 45 min. The mixture was added dropwise into a solution of (3R,4S,5R,6R)-3,4,5-tris(trimethylsilyloxy)-6-((trimethylsilyloxy)methyl)tetrahydro-2H-pyran-2-one (1.03 g) in toluene (7.5 mL) at −78° C. The mixture was stirred for 2.5 hours at −78° C., and the reaction was quenched by addition of methanesulfonic acid (6.14 mL, 3.68 mmol, 0.6 M in methanol). The reaction was stirred overnight as the temperature rose to 20° C. The reaction was quenched by addition of saturated sodium bicarbonate and was extracted with ethyl acetate. The combined ethyl acetate fractions were washed with brine and dried over sodium sulfate. The sample was concentrated to obtain crude product 34a (0.6 g), which was used in the next step without further purification.

Preparation of (2S,3R,4R,5S,6R)-2-(4-chloro-5-(4-ethylbenzyl)-2-(methoxy-d₃)phenyl)-6-(hydroxymethyl)tetrahydro-2H-pyran-3,4,5-triol (35a)

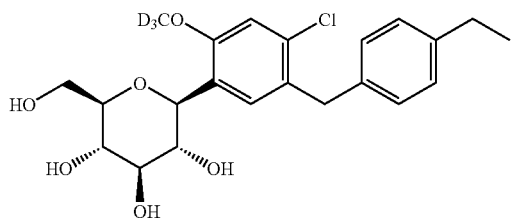

To a stirred solution of the crude (2S,3R,4S,5S,6R)-2-(4-chloro-5-(4-ethylbenzyl)-2-(methoxy-d₃)phenyl)-6-(hydroxymethyl)-2-methoxytetrahydro-2H-pyran-3,4,5-triol (0.6 g, 1.3 mmol) in methylene chloride/acetonitrile (6 mL, 1:1) at −15° C. was added triethylsilane (0.42 mL, 2.6 mmol). Boron trifluoride etherate (0.26 mL, 2.1 mmol) was added while the reaction temperature was maintained between −5° C.~−10° C. The stirred solution was allowed to warm to 0° C. over 5 hours, and then the reaction was quenched by addition of saturated aqueous sodium bicarbonate. The solvent was removed under reduced pressure, and the residue was partitioned between ethyl acetate and water (50 mL, 1:1). The aqueous layer was extracted with ethyl acetate (2×20 mL), and the combined organic phases were washed with brine, then with water, and dried over sodium sulfate. The sample was purified by preparative HPLC-MS to obtain compound 35a as a yellow gel (131 mg). ¹H-NMR (CD₃OD, 400 MHz): δ 7.36 (s, 1H), 7.06-7.09 (m, 4H), 7.00 (s, 1H), 4.62-4.64 (m, 1H), 4.01-4.04 (d, J=15.2 Hz, 1H), 3.96-3.99 (d, J=15.2 Hz, 1H), 3.84-3.87 (m, 1H), 3.64-3.68 (m, 1H), 3.44-3.48 (m, 2H), 3.37-3.38 (m, 2H), 2.56-2.61 (q, J=7.6 Hz, 2H), 1.18-1.21 (t, J=7.6 Hz, 3H); MS ESI (m/z): 470 (M+45)⁻.

Example 15

This example illustrates the preparation of compound 35b according to the approach provided in Scheme 14. In this example, R is ethoxy.

Preparation of (2S,3R,4R,5S,6R)-2-(4-chloro-5-(4-ethoxybenzyl)-2-(methoxy-d₃)phenyl)-6-(hydroxymethyl)tetrahydro-2H-pyran-3,4,5-triol (35b)

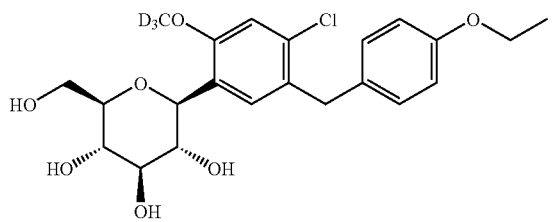

Compound 35b was prepared using methods analogous to those described in Example 14 above by using (4-ethoxyphenyl)magnesium bromide instead of (4-ethylphenyl)magnesium bromide. ¹H-NMR (CD₃OD, 400 MHz): δ 7.32 (s, 1H) 7.05-7.07 (d, J=8 Hz, 2H), 6.96 (s, 1H), 6.76-6.78 (d, J=8.0 Hz, 2H), 4.60-4.62 (m, 1H), 3.82-4.00 (m, 5H), 3.61-3.66 (m, 1H), 3.36-3.45 (m, 4H), 1.32-1.36 (t, J=6.8 Hz, 3H); MS ESI (m/z): 486 (M+45)⁻.

Example 16

This example illustrates the preparation of compound 43 according to the approach provided in Scheme 16. The general method is applicable to other compounds of the present invention.

Scheme 16

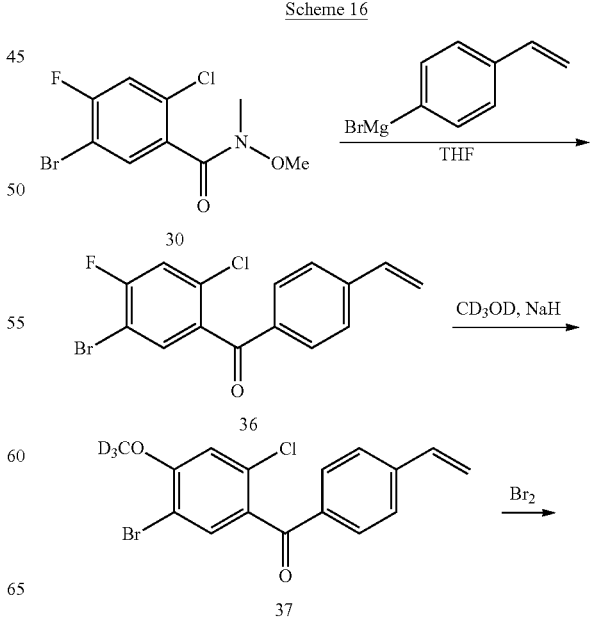

-continued

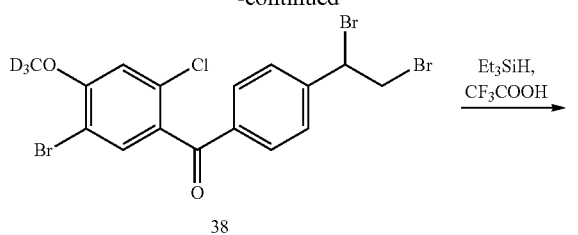
38

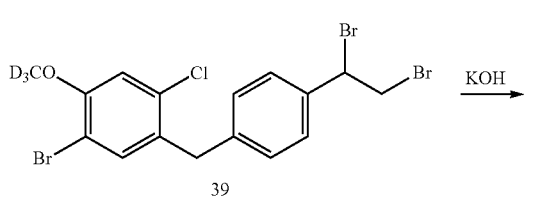
39

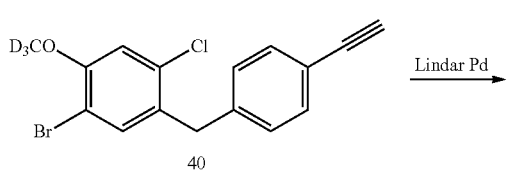
40

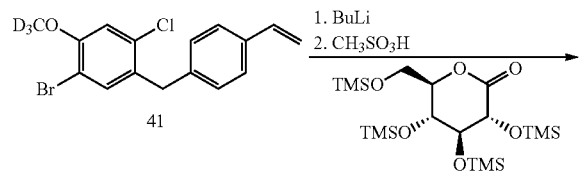
41

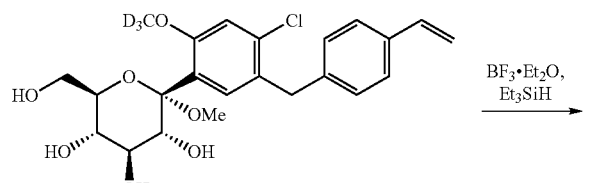
42

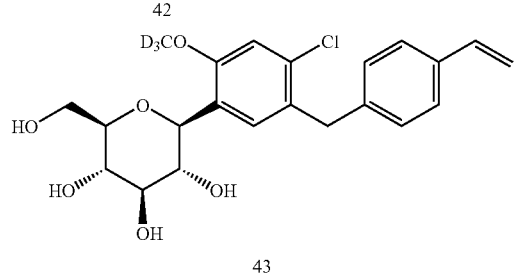
43

Preparation of (5-bromo-2-chloro-4-(methoxy-d$_3$)phenyl)(4-vinylphenyl)methanone (37)

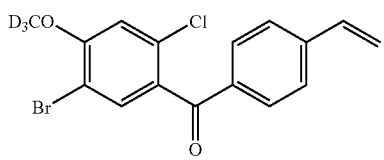

Compound 37 was prepared by using methods analogous to those described in Example 14 above for the preparation of compound 31a by using (4-vinylphenyl)magnesium bromide instead of (4-ethylphenyl)magnesium bromide.

Preparation of (5-bromo-2-chloro-4-(methoxy-d$_3$) phenyl)(4-(1,2-dibromoethyl)phenyl)methanone (38)

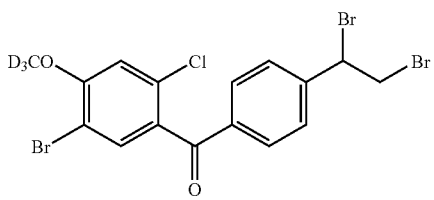

To a solution of (5-bromo-2-chloro-4-(methoxy-d$_3$)phenyl)(4-vinylphenyl)methanone (1.3 mmol) in chloroform (4 mL) at 0° C. was added dropwise a solution of bromine in carbon tetrachloride (0.5 M, 4 mL, 2 mmol), and the mixture was stirred for 2 hours. The reaction was quenched by addition of saturated sodium bisulfate and diluted with dichloromethane. The organic layer was separated, washed with water, then with brine, and dried over sodium sulfate. The sample was concentrated to give the crude product 38, which was used for the next step without further purification.

Preparation of 1-bromo-4-chloro-5-(4-(1,2-dibromoethyl)benzyl)-2-(methoxy-d$_3$)benzene (39)

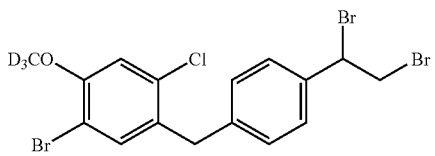

Compound 39 was obtained by reduction of (5-bromo-2-chloro-4-(methoxy-d$_3$)phenyl)(4-(1,2-dibromoethyl)phenyl) methanone (38) by using methods analogous to those described in Example 14 above for the preparation of 1-bromo-4-chloro-5-(4-ethylbenzyl)-2-(methoxy-d$_3$)benzene (33a).

Preparation of 1-bromo-4-chloro-5-(4-ethynylbenzyl)-2-(methoxy-d$_3$)benzene (40)

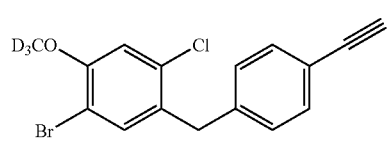

To a solution of 1-bromo-4-chloro-5-(4-(1,2-dibromoethyl)benzyl)-2-(methoxy-d$_3$)benzene (0.487 g, 0.974 mmol) in ethanol (5 mL) was added powdered potassium hydroxide (0.27 g, 4.82 mmol), and the mixture was stirred at reflux for 2 hours. The sample was cooled and partitioned between diethyl ether and water, and the water layer was extracted twice with diethyl ether. The combined organic layers were washed with water, then with brine, and dried over sodium sulfate. The sample was concentrated to give the crude product 40 (357 mg, containing 20 mol % alkene), which was used for the next step without further purification.

Preparation of 1-bromo-4-chloro-2-(methoxy-$d_3$)-5-(4-vinylbenzyl)benzene (41)

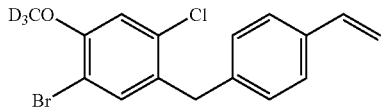

A mixture of 1-bromo-4-chloro-5-(4-ethynylbenzyl)-2-(methoxy-$d_3$)benzene (357 mg, 1.06 mmol) and Lindar catalyst (35 mg, 10 wt %) in ethyl acetate (5 mL) was evacuated and backfilled with hydrogen gas three times. The mixture was stirred at RT for 3 hours, and the catalyst was filtered. The filtrate was concentrated and then purified by chromatography (petroleum ether:ethyl acetate, 100:1) to provide compound 41 (339 mg).

Preparation of (2S,3R,4R,5S,6R)-2-(4-chloro-5-(4-vinylbenzyl)-2-(methoxy-$d_3$)phenyl)-6-(hydroxymethyl)tetrahydro-2H-pyran-3,4,5-triol (43)

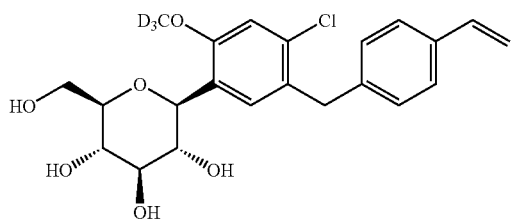

Compound 43 was prepared from 1-bromo-4-chloro-2-(methoxy-$d_3$)-5-(4-vinylbenzyl)benzene (41) by using methods analogous to those described in Example 14 above for the preparation of (2S,3R,4R,5S,6R)-2-(4-chloro-5-(4-ethylbenzyl)-2-(methoxy-$d_3$)phenyl)-6-(hydroxymethyl)tetrahydro-2H-pyran-3,4,5-triol (35a) from 1-bromo-4-chloro-5-(4-ethylbenzyl)-2-(methoxy-$d_3$)benzene (33a). $^1$H-NMR (CD$_3$OD, 400 MHz): δ 7.30-7.36 (m, 3H), 7.13-7.15 (m, 2H), 7.00 (s, 1H), 6.65-6.72 (dd, J=10.8 and 17.6 Hz, 1H), 5.69-5.73 (d, J=16 Hz, 1H), 5.14-5.17 (d, J=11.2 Hz, 1H), 4.60-4.64 (m, 1H), 4.04-4.07 (d, J=15.2 Hz, 1H), 3.98-4.02 (d, J=15.6 Hz, 1H), 3.83-3.85 (m, 1H), 3.63-3.67 (m, 1H), 3.42-3.48 (m, 2H), 3.37-3.40 (m, 2H); MS ESI (m/z): 468 (M+45)$^-$.

Example 17

This example illustrates the preparation of compound 45 according to the approach provided in Scheme 17. The general method is applicable to other compounds of the present invention.

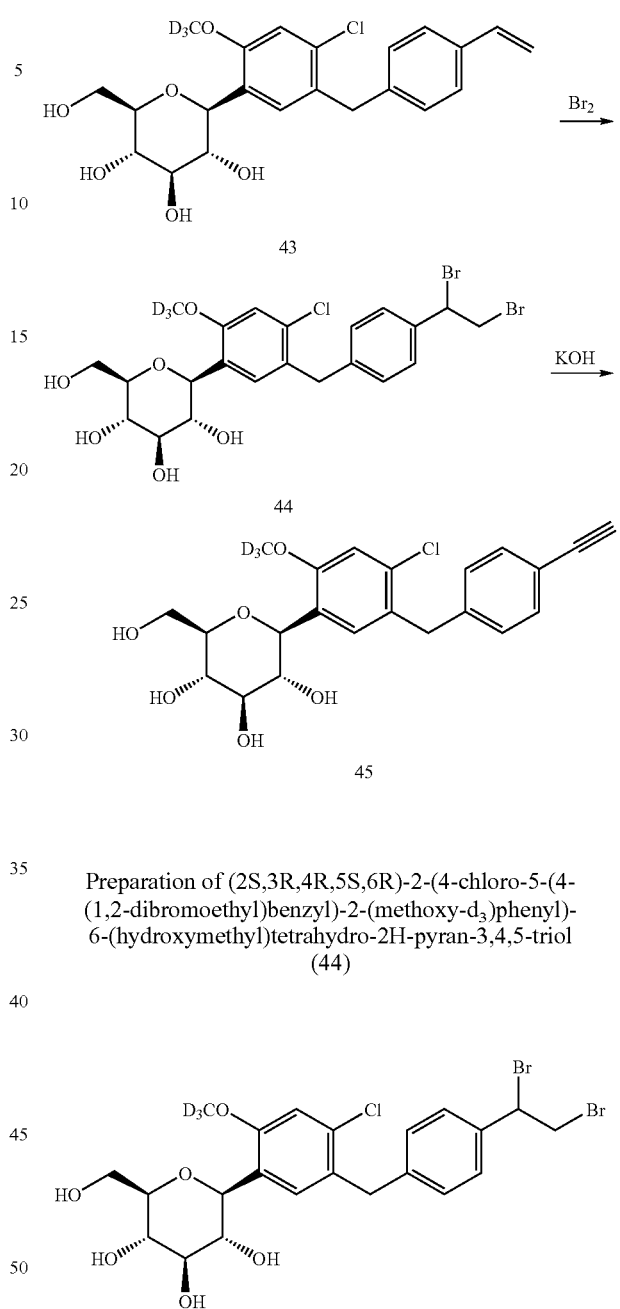

Preparation of (2S,3R,4R,5S,6R)-2-(4-chloro-5-(4-(1,2-dibromoethyl)benzyl)-2-(methoxy-$d_3$)phenyl)-6-(hydroxymethyl)tetrahydro-2H-pyran-3,4,5-triol (44)

To a solution of (2S,3R,4R,5S,6R)-2-(4-chloro-5-(4-vinylbenzyl)-2-(methoxy-$d_3$)phenyl)-6-(hydroxymethyl)tetrahydro-2H-pyran-3,4,5-triol (43) (95 mg, 0.225 mmol) in chloroform (2 mL) at 0° C. was added dropwise a solution of bromine in chloroform (0.5 M in carbon tetrachloride, 0.68 mL, 0.337 mmol), and the mixture was stirred for 3 hours. Thin layer chromatography indicated the presence of the starting alkene, and a solution of bromine in chloroform (0.5 M in carbon tetrachloride, 0.5 mL, 0.25 mmol) was added. The mixture was stirred for an additional 2 hours, then the reaction was quenched by addition of saturated sodium bisulfate, and the mixture was diluted with dichloromethane. The organic layer was separated, washed with water and then with brine, and dried over sodium sulfate. The sample was concentrated to give the crude product 44, which was used for the next step without further purification.

Preparation of (2S,3R,4R,5S,6R)-2-(4-chloro-5-(4-ethynylbenzyl)-2-(methoxy-d₃)phenyl)-6-(hydroxymethyl)tetrahydro-2H-pyran-3,4,5-triol (45)

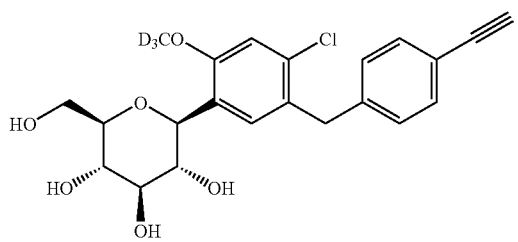

To a solution of the crude (2S,3R,4R,5S,6R)-2-(4-chloro-5-(4-(1,2-dibromoethyl)benzyl)-2-(methoxy-d₃)phenyl)-6-(hydroxymethyl)tetrahydro-2H-pyran-3,4,5-triol (~0.225 mmol) in ethanol (2 mL) was added powdered potassium hydroxide (38 mg, 0.675 mmol), and the mixture was refluxed for 6.5 hours. The sample was concentrated, the residue was partitioned between ethyl acetate and water, and the aqueous layer was extracted twice with ethyl acetate. The combined organic layers were washed with water and then with brine, and dried over sodium sulfate. The sample was concentrated and purified by preparative HPLC-MS to obtain compound 45 (8 mg). $^1$H-NMR (400 MHz, CD₃OD): δ 7.38 (s, 1H), 7.34-7.36 (d, J=8.4 Hz, 2H), 7.16-7.18 (m, J=8.4 Hz, 2H), 7.02 (s, 1H), 4.63-4.65 (m, 1H), 4.07-4.11 (d, J=16 Hz, 1H), 4.02-4.07 (d, J=15.6 Hz, 1H), 3.84-3.87 (m, 1H), 3.64-3.69 (m, 1H), 3.45-3.47 (m, 2H), 3.42 (s, 1H), 3.38-3.39 (m, 2H); MS ESI (m/z): 466 (M+45)⁻.

Example 18

This example illustrates the preparation of compound 49 according to the approach provided in Scheme 18. The general method is applicable to other compounds of the present invention.

Scheme 18

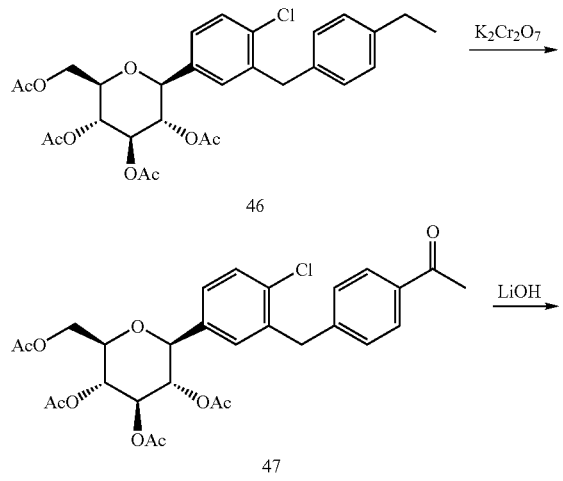

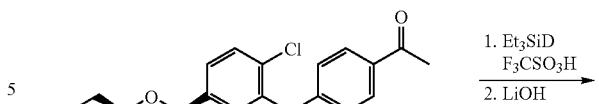

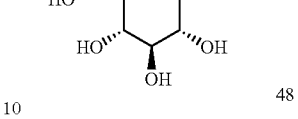

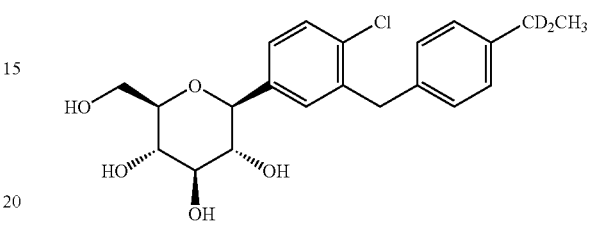

Preparation of (2R,3R,4R,5S,6S)-2-(acetoxymethyl)-6-(3-(4-acetylbenzyl)-4-chlorophenyl)tetrahydro-2H-pyran-3,4,5-triyl triacetate (47)

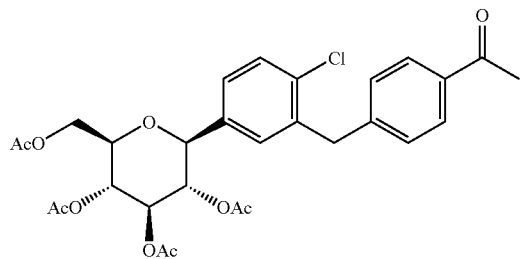 [SMILES: CC(=O)OC[C@H]1O[C@@H](c2ccc(Cl)c(Cc3ccc(C(C)=O)cc3)c2)[C@H](OC(C)=O)[C@@H](OC(C)=O)[C@@H]1OC(C)=O]

To a stirred solution of (2R,3R,4R,5S,6S)-2-(acetoxymethyl)-6-(4-chloro-3-(4-ethylbenzyl)phenyl)tetrahydro-2H-pyran-3,4,5-triyl triacetate (10 g, 10.8 mmol) (prepared using methods analogous to those described in US20040138439) in acetic acid (130 mL) at 120° C. was added potassium chromate (6.3 g, 21.4 mmol) in one portion. The mixture was stirred for 22 hours at 120° C. The solvents were removed under reduced pressure, ethyl acetate was added, and the solid was filtered. The organic layer was washed with saturated aqueous sodium bicarbonate and then with brine, and then dried over sodium sulfate. The sample was concentrated, and the resulting residue was purified by silica gel chromatography (3:1 petroleum ether:ethyl acetate) to give pure product 47 as a solid (2.3 g). $^1$H-NMR (CDCl₃, 400 MHz): δ 7.90 (d, J=8.0 Hz, 2H), 7.39 (d, J=8.4 Hz, 1H), 7.26 (d, J=8.4 Hz, 2H), 7.22 (dd, J=8.4, 2.2 Hz, 1H), 7.17 (d, J=2.0 Hz, 1H), 5.31 (t, J=9.4 Hz, 1H), 5.22 (t, J=9.8 Hz, 1H), 5.09 (t, J=9.4 Hz, 1H), 4.35 (d, J=10.0 Hz, 1H), 4.29 (dd, J=12.4, 4.8 Hz, 1H), 4.18-4.13 (m, 3H), 3.85-3.81 (m, 1H), 2.60 (s, 3H), 2.09 (s, 3H), 2.07 (s, 3H), 2.01 (s, 3H), 1.75 (s, 3H); MS ESI: 575 [M+H]⁺, 619 [M+HCO₂]⁻.

Preparation of 1-(4-(2-chloro-5-((2S,3R,4R,5S,6R)-3,4,5-trihydroxy-6-(hydroxymethyl)tetrahydro-2H-pyran-2-yl)benzyl)phenyl)ethanone (48)

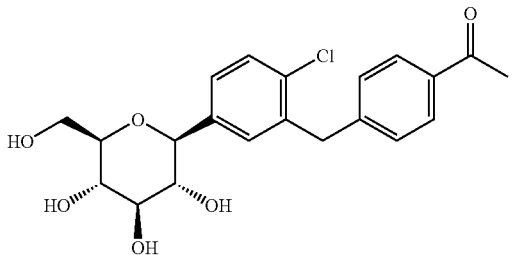 [SMILES: CC(=O)c1ccc(Cc2cc([C@@H]3O[C@H](CO)[C@@H](O)[C@H](O)[C@H]3O)ccc2Cl)cc1]

To a solution of (2R,3R,4R,5S,6S)-2-(acetoxymethyl)-6-(3-(4-acetylbenzyl)-4-chlorophenyl)tetrahydro-2H-pyran-3,4,5-triyl triacetate (95 mg, 0.17 mmol) in a mixture of tetrahydrofuran/methanol/water (2.4 mL, 2:3:1) was added lithium hydroxide monohydrate (11.2 mg, 0.27 mmol). After stirring overnight at RT, volatiles were removed under reduced pressure. The residue was partitioned between water and ethyl acetate (3×), and the combined organic phases were washed with brine, dried over sodium sulfate, and concentrated to give crude product 48 (68 mg), which was used in the next step without further purification. MS ESI: 407 [M+H]+, 451 [M+HCO2]−.

Preparation of (2S,3R,4R,5S,6R)-2-(4-chloro-3-(4-(ethyl-1,1-d2)benzyl)phenyl)-6-(hydroxymethyl)tetrahydro-2H-pyran-3,4,5-triol (49)

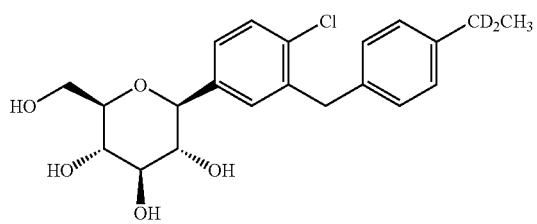

To a stirred solution of 1-(4-(2-chloro-5-((2S,3R,4R,5S,6R)-3,4,5-trihydroxy-6-(hydroxymethyl)tetrahydro-2H-pyran-2-yl)benzyl)phenyl)ethanone (57.4 mg, 0.14 mmol) in trifluoroacetic acid (1 mL) was added triethylsilane-d (52 mg, 0.44 mmol, 97 atom % D). A catalytic amount of trifluoromethanesulfonic acid was added, and the reaction mixture was stirred for 6.5 hours at RT. Volatiles were removed under reduced pressure, the residue was taken up with water, and the aqueous layer was extracted with ethyl acetate (3×). The combined organic layers were washed with brine, dried over sodium sulfate, and concentrated to obtain crude product with one trifluoroacetate group remaining on the molecule (93 mg). The residue was dissolved in tetrahydrofuran/methanol/water (1.5 mL, 2:3:1), and lithium hydroxide monohydrate (7 mg, 0.167 mmol) was added. After stirring at RT for 2 hours, volatiles were removed under reduced pressure. The residue was taken up with water and ethyl acetate, the organic layer was separated, and the aqueous layer was extracted with ethyl acetate (3×). The combined organic phases were washed with brine, dried over sodium sulfate, concentrated, and purified by preparative HPLC to give compound 49 (28 mg). $^1$H-NMR (400 MHz, CD$_3$OD): δ 7.36-7.33 (m, 2H), 7.28 (dd, J=8.0, 2.0 Hz, 1H), 7.09 (s, 4H), 4.09 (d, J=15.0 Hz, 1H), 4.09 (d, J=9.6 Hz, 1H), 4.03 (d, J=15.0 Hz, 1H), 3.88 (d, J=12.4 Hz, 1H), 3.71-3.67 (m, 1H), 3.48-3.38 (m, 3H), 3.29 (t, J=8.8 Hz, 1H), 1.18 (s, 3H); MS ESI: 412 [M+NH$_4$]$^+$, 439 [M+HCO$_2$]$^-$.

Example 19

Preparation of (2S,3R,4R,5S,6R)-2-(4-chloro-3-(4-hydroxybenzyl)phenyl)-6-(hydroxymethyl)tetrahydro-2H-pyran-2-d-3,4,5-triol (50)

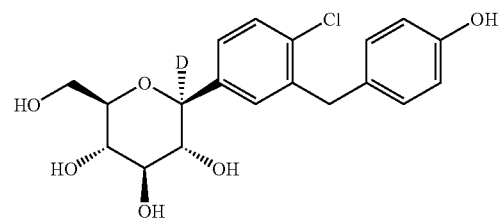

This example illustrates the preparation of compound 50 (See Scheme 19).

Scheme 19

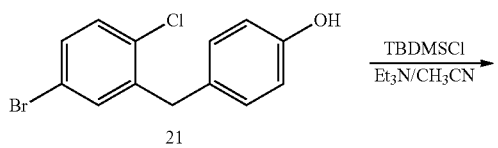

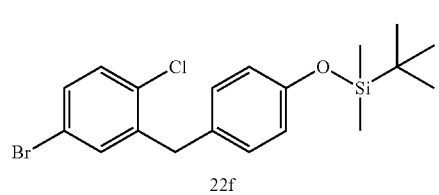

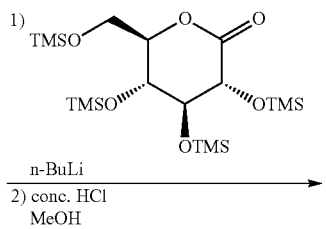

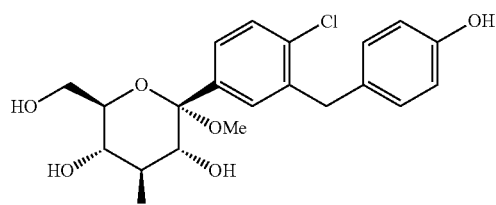 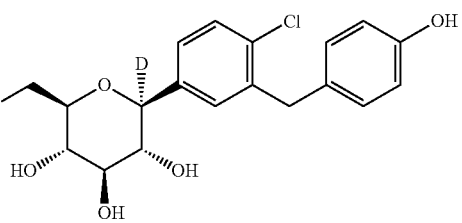

23f → 50

Et₃SiD
BF₃·Et₂O

Preparation of (4-(5-bromo-2-chlorobenzyl)phenoxy)(tert-butyl)dimethylsilane (22f)

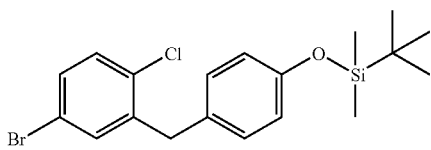 [SMILES: CC(C)(C)[Si](C)(C)Oc1ccc(Cc2cc(Br)ccc2Cl)cc1]

To a stirred suspension of 4-(5-bromo-2-chlorobenzyl)phenol (60 g, 0.202 mol) and tert-butylchlorodimethylsilane (37.9 g, 0.252 mol) in acetonitrile (300 mL) was added dropwise triethylamine (54.4 mL, 0.390 mol) so that the reaction temperature did not exceed 5° C. After the addition was completed, the reaction mixture was stirred for 2 hours at 10~15° C. This reaction mixture was filtered, and the filter cake was washed with petroleum ether (2×50 mL). The combined organic layers were evaporated under reduced pressure (30° C.), and the residue was dissolved in petroleum ether (300 mL). The solution was washed with water (100 mL×2) and evaporated, and the residue was dissolved in ethanol (180 mL) at 35° C. with stirring. This solution was cooled to 5~10° C. and kept for 4 h. The solids were filtered, the filter cake was washed with cold ethanol (0~5° C., 60 mL) and then dried under vacuum at 25° C. overnight to give 22f as a white solid (72 g, 86.6% yield; HPLC purity 99%, retention time 6.6 min). ¹H-NMR (CDCl₃, 400 MHz): δ 7.21~7.28 (m, 3H), 7.06 (d, J=8.0 Hz, 2H), 6.82 (d, J=8.0 Hz, 2H), 4.00 (s, 2H), 1.00 (s, 9H), 0.21 (s, 6H); MS ESI (m/z) 411 [M+1]⁺, calc. 410.

Preparation of (2S,3R,4S,5S,6R)-2-(4-chloro-3-(4-hydroxybenzyl)phenyl)-6-(hydroxymethyl)-2-methoxytetrahydro-2H-pyran-3,4,5-triol (231)

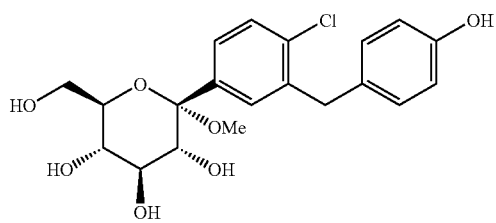 [SMILES: CO[C@@]1(c2ccc(Cl)c(Cc3ccc(O)cc3)c2)O[C@H](CO)[C@@H](O)[C@H](O)[C@H]1O]

To a solution of (4-(5-bromo-2-chlorobenzyl)phenoxy)(tert-butyl)dimethylsilane (50 g, 0.122 mol) in anhydrous toluene/tetrahydrofuran (300 mL, 2:1) at −65° C. was added dropwise n-BuLi (2.5 M in hexane, 58.5 mL), and the reaction was stirred for an additional 30 minutes at −65° C. The mixture was transferred to a solution of (3R,4S,5R,6R)-3,4,5-tris(trimethylsilyloxy)-6-((trimethylsilyloxy)methyl)tetrahydro-2H-pyran-2-one (74 g, 0.158 mol) in toluene (200 mL) at −65° C. The mixture was stirred at −65° C. for 2 hours until starting material was consumed. The reaction was quenched with hydrochloric acid (7.6 mL, 0.091 mol) in methanol (100 mL), and the mixture was allowed to warm to RT overnight. The reaction mixture was quenched by the addition of 5% sodium bicarbonate until the pH reached 7.5, and the organic phase was separated. The aqueous phase was extracted with ethyl acetate (300 mL×2), and the combined organic phases were washed with saturated bicarbonate (100 mL), then with water (100 mL), then with brine (100 mL), and dried over sodium sulfate. After removal of the volatiles, the residue was dried under vacuum to give 23f as a crude glassy product (50 g; HPLC purity 84%, retention time 2.23 min), which was used in the next step without further purification. MS ESI (m/z) 411 [M+1]⁺, 455 [M+45]⁻, calc. 410.

Preparation of (2S,3R,4R,5S,6R)-2-(4-chloro-3-(4-hydroxybenzyl)phenyl)-6-(hydroxymethyl)tetrahydro-2H-pyran-2-d-3,4,5-triol (50)

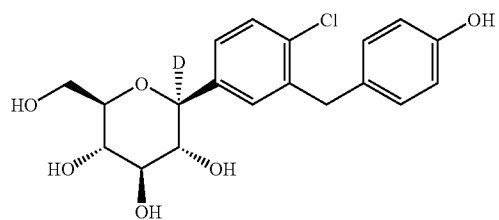

To a solution of (2S,3R,4S,5S,6R)-2-(4-chloro-3-(4-hydroxybenzyl)phenyl)-6-(hydroxymethyl)-2-methoxytetrahydro-2H-pyran-3,4,5-triol (102.7 mg, 0.25 mmol) in dichloromethane (1.0 mL) and acetonitrile (1.0 mL) at −40° C. under argon was added triethylsilane-d (0.16 mL, 1.0 mmol, 97 atom % D). Then boron trifluoride etherate (0.095 mL, 0.75 mmol) was added while maintaining the reaction temperature below −10° C., and the reaction solution was stirred for another 1.5 hours. The reaction was quenched by addition of 5% sodium bicarbonate until reaching pH 7.5. The organic phase was separated, and the aqueous phase was extracted with ethyl acetate (3×10 mL). The combined organic phases were washed with brine (2×20 mL) and dried over anhydrous sodium sulfate. The sample was concentrated under reduced pressure to provide a pale solid product, which was purified by preparative HPLC to give compound 50 as a white solid (62.3 mg, 65% yield, HPLC purity=99%). ¹H-NMR (CD₃OD, 400 MHz): δ 7.24-7.34 (m, 3H), 7.01 (d, J=8.4 Hz, 2H), 6.66 (d, J=8.4 Hz, 2H), 4.03 (d, J=15.6 Hz, 1H), 3.95 (d, J=15.6 Hz, 1H), 3.86 (d, J=11.6 Hz, 1H), 3.68-3.69 (m, 1H), 3.36-3.44 (m, 3H), 3.26-3.30 (m, 1H); MS ESI (m/z) 382 [M+1]⁺, calc. 381.

Example 20

This example illustrates the preparation of compound 54 according to the approach provided in Scheme 20. The general method is applicable to other compounds of the present invention.

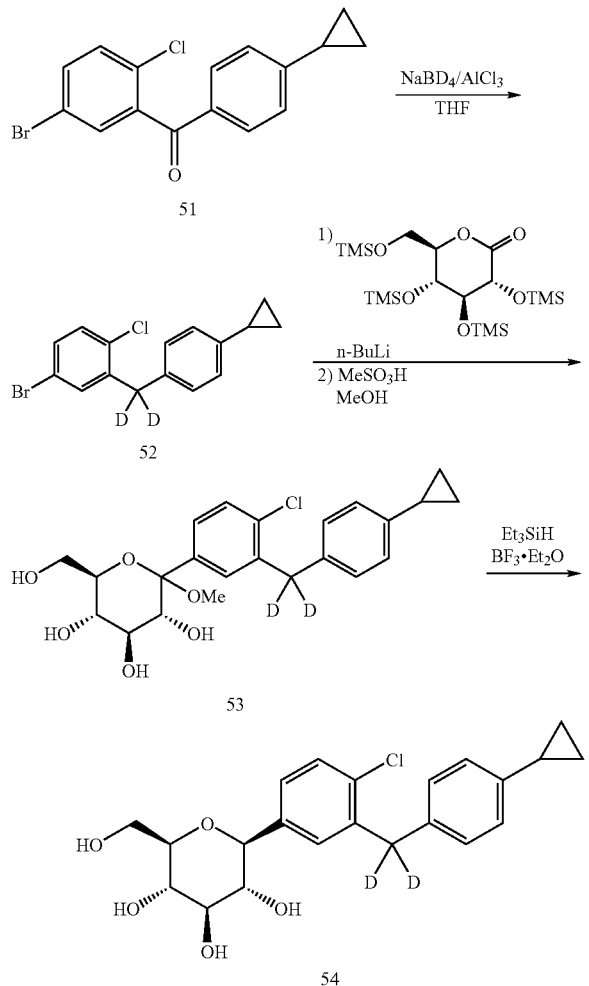

Preparation of 4-bromo-1-chloro-2-((4-cyclopropylphenyl)methyl-d₂)benzene (52)

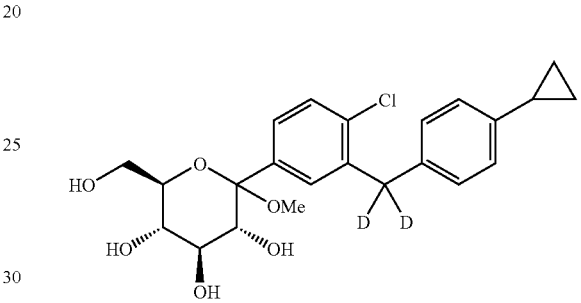

To a solution of (5-bromo-2-chlorophenyl)(4-cyclopropylphenyl)methanone (310 mg, 0.9 mmol) (prepared using methods analogous to those described in Example 1 above by using cyclopropylbenzene instead of phenetole) in anhydrous THF (15 mL) at 0° C. was added sodium borodeuteride (194 mg, 4.6 mmol, 99 atom % D). Then aluminum trichloride (617 mg, 4.6 mmol) was added in portions, and the mixture was stirred for 30 minutes at 0° C. The mixture was heated to 70° C. and stirred overnight. Then the mixture was cooled to 0° C., and the reaction was slowly quenched with ice-water. The aqueous layer was extracted with ethyl acetate, and the combined organic layers were washed with saturated sodium bicarbonate, then with brine and then with water, and dried over anhydrous sodium sulfate. The sample was concentrated and the residue was purified by column chromatography to give compound 52 as a yellow oil (78 mg).

Preparation of (3R,4S,5S,6R)-2-(4-chloro-3-((4-cyclopropylphenyl)methyl-d₂)phenyl)-6-(hydroxymethyl)-2-methoxytetrahydro-2H-pyran-3,4,5-triol (53)

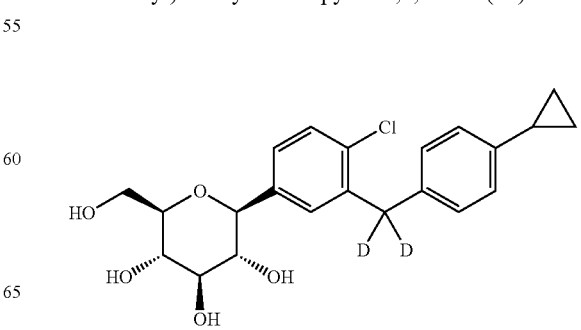

To a solution of 4-bromo-1-chloro-2-((4-cyclopropylphenyl)methyl-d₂)benzene (78 mg, 0.3 mmol) in dry THF/toluene (2:1, 1 mL) at −60° C. under argon was slowly added dropwise a solution of n-butyllithium in hexane (2.5 M, 0.14 mL), and the mixture was stirred for 30 minutes at −60° C. A solution of (3R,4S,5R,6R)-3,4,5-tris(trimethylsilyloxy)-6-((trimethylsilyloxy)methyl)tetrahydro-2H-pyran-2-one (170 mg, 0.4 mmol) in toluene (0.5 mL) was slowly added dropwise to maintain the reaction temperature below −55° C., and the mixture was stirred for 2 hours at −60° C. The reaction mixture was quenched by the addition of methanol (0.7 mL) containing methanesulfonic acid (0.06 mL). The reaction was stirred overnight at RT and then treated with aqueous sodium hydrogen carbonate solution. The organic layer was separated, and the aqueous phase was extracted with ethyl acetate. The combined organic extracts were dried over sodium sulfate and concentrated to give the crude residue 53 (130 mg), which was used for the next step without further purification.

Preparation of (2S,3R,4R,5S,6R)-2-(4-chloro-3-((4-cyclopropylphenyl)methyl-d₂)phenyl)-6-(hydroxymethyl)tetrahydro-2H-pyran-3,4,5-triol (54)

To a solution of the crude residue (3R,4S,5S,6R)-2-(4-chloro-3-((4-cyclopropylphenyl)methyl-d₂)phenyl)-6-(hydroxymethyl)-2-methoxytetrahydro-2H-pyran-3,4,5-triol (130 mg) in acetonitrile/dichloromethane (1:1, 1 mL) at −40° C. was added triethylsilane (0.2 mL, 1.2 mmol). Then boron trifluoride etherate (0.14 mL, 1.1 mmol) was added, and the reaction mixture was stirred for 6 hr at RT. Saturated aqueous sodium bicarbonate was added, and the solvent was removed under reduced pressure. The residue was extracted with ethyl acetate (3×), and the combined organic phases were washed with brine and then with water, and then dried over sodium sulfate. The sample was concentrated under reduced pressure, and the residue was purified by preparative HPLC-MS to obtain compound 54 as a white powder (10.76 mg, 11% yield for two steps). $^1$H-NMR (CD₃OD, 400 MHz): δ 7.34~7.25 (m, 3H), 7.04 (d, J=8 Hz, 2H), 6.94 (d, J=8 Hz, 2H), 4.06 (d, J=9.2 Hz, 1H), 3.87~3.84 (m, 1H), 3.70~3.65 (m, 1H), 3.44~3.38 (m, 1H), 3.37~3.345 (m, 2H), 3.27~3.25 (m, 1H), 1.86~1.81 (m, 1H), 0.92~0.87 (m, 2H), 0.63~0.59 (m, 1H); MS ESI (m/z): 424 [M+18]⁺, 451 [M+45]⁻, calc. 406.

Example 21

This example illustrates the preparation of compound 57 according to the approach provided in Scheme 21. The general method is applicable to other compounds of the present invention.

Scheme 21

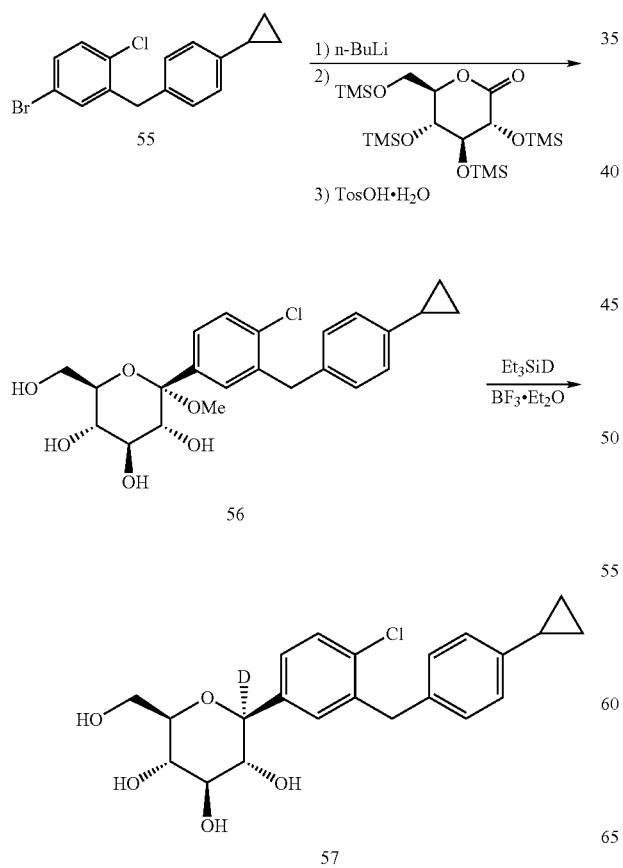

Preparation of (2S,3R,4S,5S,6R)-2-(4-chloro-3-(4-cyclopropylbenzyl)phenyl)-6-(hydroxymethyl)-2-methoxytetrahydro-2H-pyran-3,4,5-triol (56)

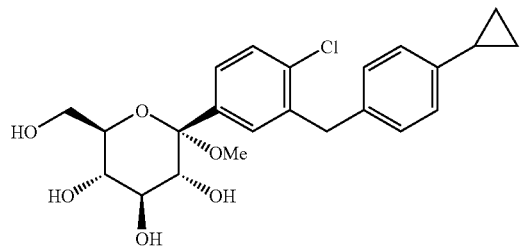 [SMILES: CO[C@@]1(c2ccc(Cl)c(Cc3ccc(C4CC4)cc3)c2)O[C@H](CO)[C@@H](O)[C@H](O)[C@H]1O]

To a stirred solution of 4-bromo-1-chloro-2-(4-cyclopropylbenzyl)benzene (6.6 g, 20.5 mmol) in dry THF/toluene (90 mL, 1:2) at −78° C. under argon was added dropwise n-BuLi (9.84 mL, 24.62 mmol, 2.5 N in hexane) over 10 minutes, and then the mixture was stirred for 30 minutes at −70° C. A solution of (3R,4S,5R,6R)-3,4,5-tris(trimethylsilyloxy)-6-((trimethylsilyloxy)methyl)tetrahydro-2H-pyran-2-one (12.4 g, 26.6 mmol) in anhydrous toluene (30 mL) was added dropwise over 5 minutes, and the reaction solution was stirred for 1 hour at −65° C. The reaction was quenched by addition of saturated aq. ammonium chloride (100 mL) at 0° C., the organic layer was separated, and the aqueous layer was extracted with toluene (30 mL). The combined organic phases were concentrated under reduced pressure, and the residue was dissolved in methanol (200 mL). The solution was cooled with an ice/water bath to 0° C., and then 4-methylbenzenesulfonic acid hydrate (2.43 g, 15.4 mmol) was added in one portion. The resulting solution was stirred at 25° C. for 18 hours. LC-MS showed the reaction was complete. Saturated aqueous sodium bicarbonate (50 mL) was added, and the mixture was concentrated under reduced pressure to remove most of the methanol. The residue was treated with water (100 mL) and ethyl acetate (100 mL), the organic layer was separated, and the aqueous layer was extracted with ethyl acetate (100 mL). The combined organic phases were dried over sodium sulfate and concentrated under reduced pressure to give crude product 56 as a white solid (8.0 g, 89.6% yield), which was used for the next step without further purification.

Preparation of (2S,3R,4R,5S,6R)-2-(4-chloro-3-(4-cyclopropylbenzyl)phenyl)-6-(hydroxymethyl)tetrahydro-2H-pyran-2-d-3,4,5-triol (57)

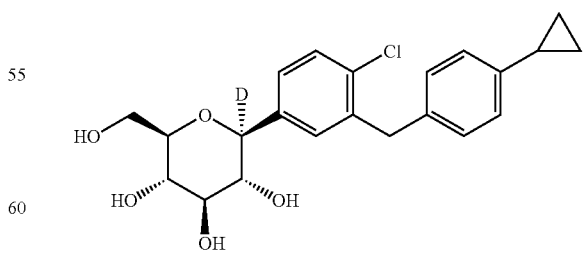

To a solution of crude (2S,3R,4S,5S,6R)-2-(4-chloro-3-(4-cyclopropylbenzyl)phenyl)-6-(hydroxymethyl)-2-methoxytetrahydro-2H-pyran-3,4,5-triol (0.25 g, 0.574 mmol) in anhydrous dichloromethane (2 mL) and acetonitrile (2 mL) at −30° C. was added triethylsilane-d (0.1 g, 0.86 mmol). Boron fluoride etherate (0.12 g, 0.86 mmol) was added dropwise while maintaining the temperature below −20° C. The resulting solution was stirred at −20° C. for 3 hours. Saturated aqueous sodium bicarbonate (10 mL) was added dropwise at 0° C., and the resulting solution was stirred at 25° C. for 30 min. The solution was concentrated under reduced pressure, and the resulting yellow syrup was treated with water (5 mL) and ethyl acetate (10 mL). The organic layer was separated, and the aqueous layer was extracted with ethyl acetate (10 mL). The combined organic phases were dried over sodium sulfate and concentrated. The residue was purified via preparative HPLC-MS to give compound 57 (30 mg, 12.9%) as a white solid. HPLC retention time: 3.70 min; Waters XTerra C18, 5 μm pore size, 2.1×50 mm column; 1.0 mL/min, 8 min gradient; mobile phase: solvent A: 0.045% formic acid in acetonitrile, solvent B: 0.1% formic acid in Milli-Q water. $^1$H-NMR (CD$_3$OD, 400 MHz): δ 7.24-7.34 (m, 3H), 7.04-7.06 (d, J=8 Hz, 2H), 6.93-6.95 (d, J=8 Hz, 2H), 3.98-4.08 (m, 2H), 3.84-3.87 (m, 1H), 3.65-3.69 (m, 1H), 3.36-3.47 (m, 3H), 3.25-3.27 (m, 1H), 1.83-1.85 (m, 1H), 0.87-0.92 (m, 2H), 0.59-0.62 (m, 2H); MS ESI (m/z): (m/z): 405 (M+45)$^-$.

Example 22

This example illustrates the preparation of compound 62 according to the approach provided in Scheme 22. The general method is applicable to other compounds of the present invention.

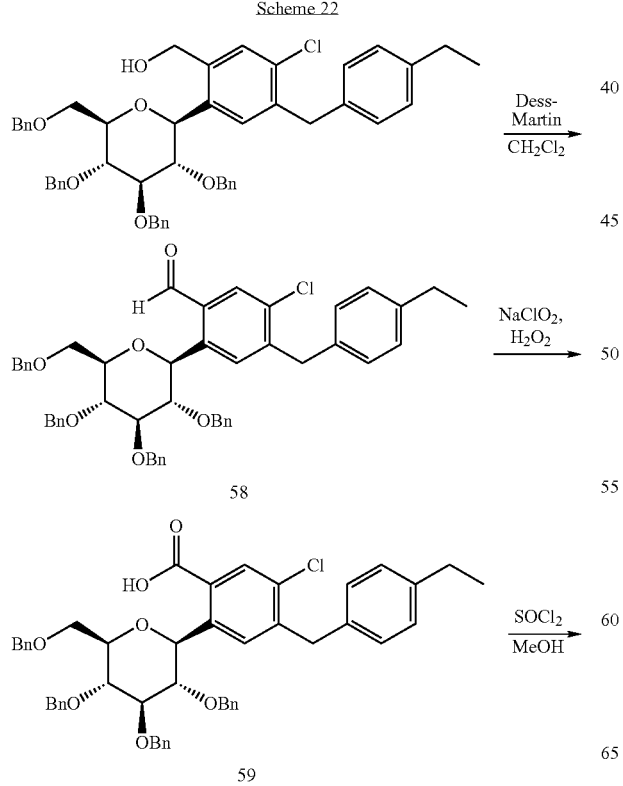

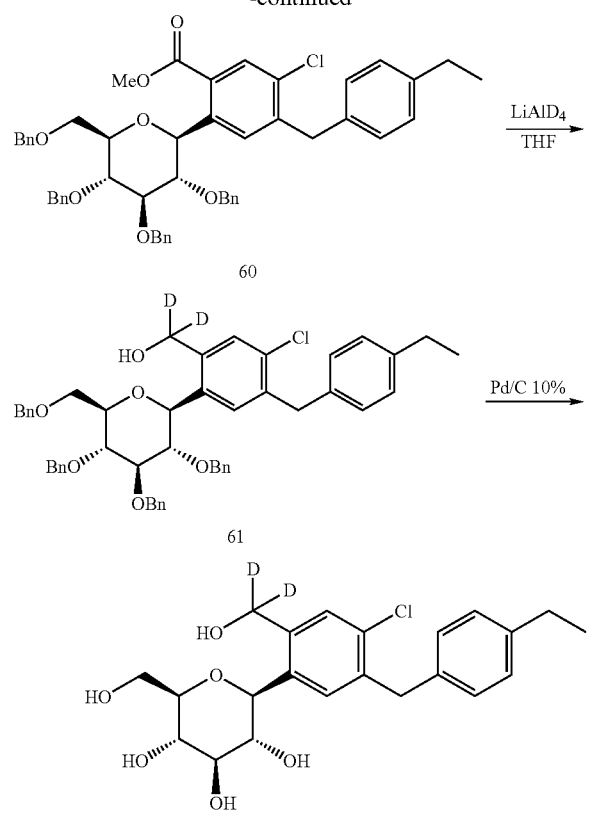

Preparation of 5-chloro-4-(4-ethylbenzyl)-2-((2S,3S, 4R,5R,6R)-3,4,5-tris(benzyloxy)-6-(benzyloxymethyl)tetrahydro-2H-pyran-2-yl)benzaldehyde (58)

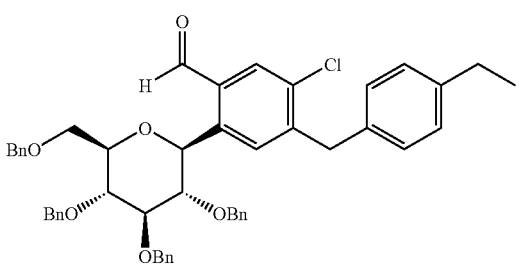 [SMILES: CCc1ccc(Cc2cc([C@@H]3O[C@H](COCc4ccccc4)[C@@H](OCc4ccccc4)[C@H](OCc4ccccc4)[C@H]3OCc3ccccc3)c(C=O)cc2Cl)cc1]

To a cold (0° C.) stirred suspension of Dess-Martin periodinane (1.24 g, 2.92 mmol) in dichloromethane (20 mL) was added (5-chloro-4-(4-ethylbenzyl)-2-((2S,3S,4R,5R,6R)-3, 4,5-tris(benzyloxy)-6-(benzyloxymethyl)tetrahydro-2H-pyran-2-yl)phenyl)methanol (1.76 g, 2.25 mmol) (prepared as described in U.S. Ser. No. 12/060,767) in dichloromethane (3 mL). The mixture was stirred for 2 hours at 0° C., and the reaction was quenched with 2N sodium hydroxide (5 mL). The organic phase was separated, and the aqueous phase was extracted with ethyl acetate. The organic phases were combined, washed with saturated sodium bicarbonate, then with water and then with brine, and then dried over anhydrous sodium sulfate. The combined filtrate was concentrated under Preparation of 5-chloro-4-(4-ethylbenzyl)-2-((2S,3S, 4R,5R,6R)-3,4,5-tris(benzyloxy)-6-(benzyloxymethyl)tetrahydro-2H-pyran-2-yl)benzoic acid (59)

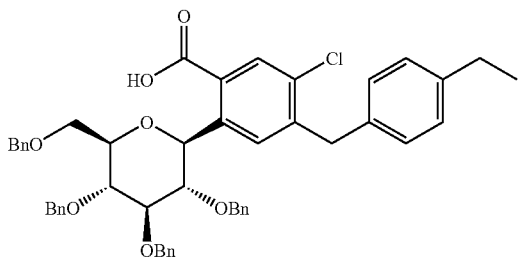 [SMILES: CCc1ccc(Cc2cc([C@@H]3O[C@H](COCc4ccccc4)[C@@H](OCc4ccccc4)[C@H](OCc4ccccc4)[C@H]3OCc3ccccc3)c(C(=O)O)cc2Cl)cc1]

To a solution of 5-chloro-4-(4-ethylbenzyl)-2-((2S,3S,4R, 5R,6R)-3,4,5-tris(benzyloxy)-6-(benzyloxymethyl)tetrahydro-2H-pyran-2-yl)benzaldehyde (0.826 g, 1.1 mmol) in t-BuOH/water (3:1, 17 mL) was added hydrogen peroxide (30%, 5.29 mL, 46.7 mmol) and sodium perchlorate (0.14 g, 1.1 mmol), and the solution was stirred overnight at RT. The volatiles were removed under reduced pressure, and the residue was quenched with water. The aqueous phase was extracted with ethyl acetate, and the organic phases were combined, washed with water and then with brine, and then dried over anhydrous sodium sulfate. After removal of the volatiles, 0.802 g of crude solid product was obtained. MS ESI$^-$ (m/z): 841 (M+45)$^-$.

Preparation of methyl 5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzoate (60)

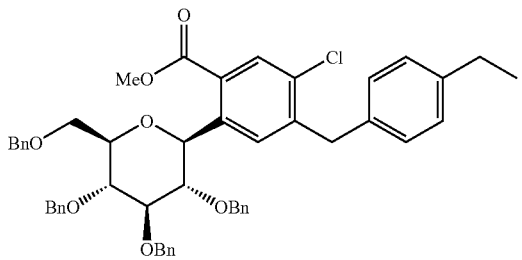 [SMILES: CCc1ccc(Cc2cc([C@@H]3O[C@H](COCc4ccccc4)[C@@H](OCc4ccccc4)[C@H](OCc4ccccc4)[C@H]3OCc3ccccc3)c(C(=O)OC)cc2Cl)cc1]

To a cold (0° C.) stirred solution of 5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzoic acid (0.15 g, 0.188 mmol) in methanol (10 mL) was added dropwise sulfurous dichloride (0.034 g, 0.021 mL). The mixture was heated to reflux and kept refluxing overnight. The volatiles were removed under reduced pressure, and the residue was quenched with water. The organic phase was separated, and the aqueous phase was extracted with ethyl acetate. The organic phases were combined, washed with saturated sodium bicarbonate, then with water and then with brine, and dried over anhydrous sodium sulfate. After removal of the volatiles, 153 mg of crude solid product was obtained.

Preparation of (5-chloro-4-(4-ethylbenzyl)-2-((2S, 3S,4R,5R,6R)-3,4,5-tris(benzyloxy)-6-(benzyloxymethyl)tetrahydro-2H-pyran-2-yl)phenyl)methan-d$_2$-ol (61)

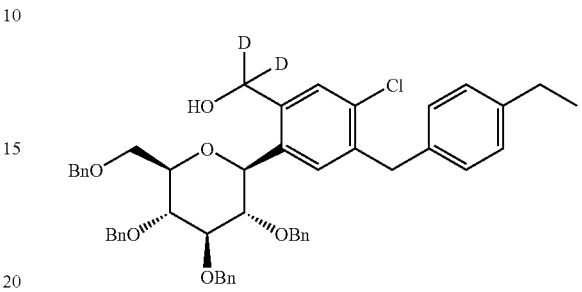

To a cold (0° C.) stirred solution of methyl 5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzoate (0.06 g, 0.074 mmol) in dry THF (10 mL) was added lithium aluminum deuteride (LiAlD$_4$) (4 mg, 0.9 mmol), and the solution was stirred for 1.5 hours at 0° C. Water (3 mL) was added dropwise to the reaction, and the mixture was kept stirring for another 0.5 hours. Sodium hydroxide (15% aqueous, 2 mL) was added, and the reaction mixture was stirred for 1 hour. The mixture was filtered, and the solvent was concentrated under reduced pressure to give 20 mg of product. MS ESI$^+$ (m/z): 802 (M+18)$^+$.

Preparation of (2S,3R,4R,5S,6R)-2-(4-chloro-5-(4-ethylbenzyl)-2-(hydroxy(methyl-d$_2$))phenyl)-6-(hydroxymethyl)tetrahydro-2H-pyran-3,4,5-triol (62)

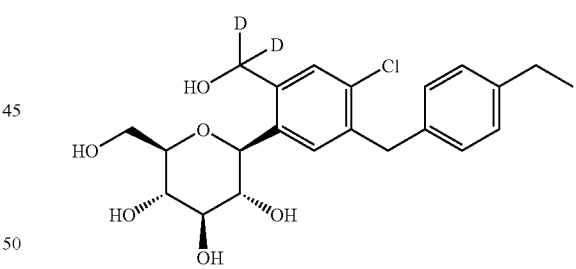

To a stirred solution of methyl (5-chloro-4-(4-ethylbenzyl)-2-((2S,3S,4R,5R,6R)-3,4,5-tris(benzyloxy)-6-(benzyloxymethyl)tetrahydro-2H-pyran-2-yl)phenyl)methan-d$_2$-ol (0.02 g, 0.026 mmol) in methanol (2 mL) was added dichlorobenzene (0.02 mL) and palladium over charcoal (10%) (5 mg). The mixture was degassed five times and charged with hydrogen, and the resulting suspension was stirred under an atmosphere of hydrogen for 2 hours at RT. The reaction mixture was filtered, concentrated and purified by preparative TLC (ethyl acetate:ethanol=8:1) to give 3 mg of product. $^1$H-NMR (CD$_3$OD, 300 MHz): δ 7.35-7.54 (m, 3H), 7.04 (s, 4H), 4.40-4.43 (d, J=9 Hz, 1H), 4.02-4.04 (d, J=5.7 Hz, 2H), 3.83-3.86 (d, J=11.4 Hz, 1H), 3.68-3.70 (m, 1H), 3.33-3.48 (m, 4H), 2.52-2.60 (q, J=7.5 Hz, 2H), 1.13-1.18 (t, J=7.5 Hz, 3H); MS ESI$^-$ (m/z): 469 (M+45)$^-$.

Example 23

This example illustrates the preparation of compound 65 according to the approach provided in Scheme 23. The general method is applicable to other compounds of the present invention.

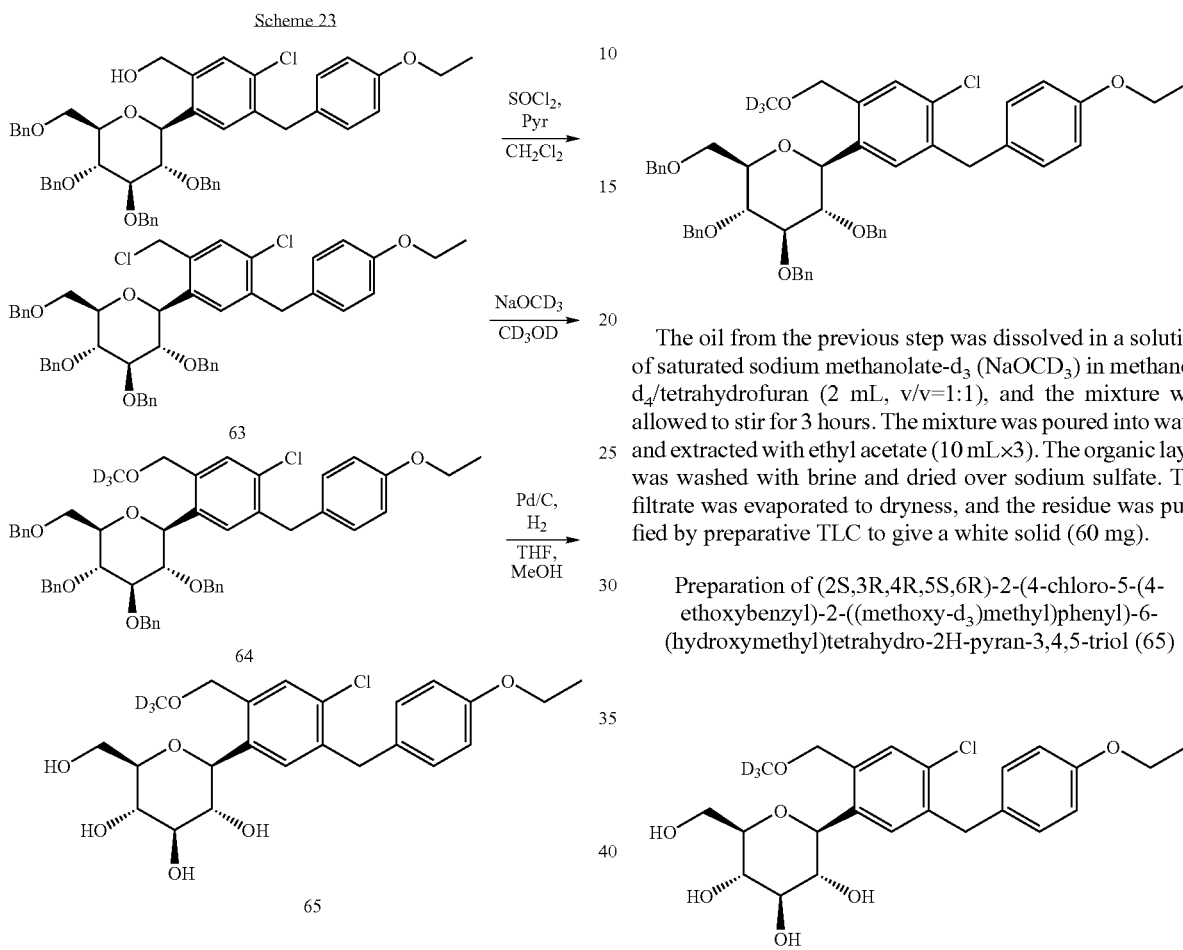

Preparation of (2R,3R,4R,5S,6S)-3,4,5-tris(benzyloxy)-2-(benzyloxymethyl)-6-(4-chloro-2-(chloromethyl)-5-(4-ethoxybenzyl)phenyl)tetrahydro-2H-pyran (63)

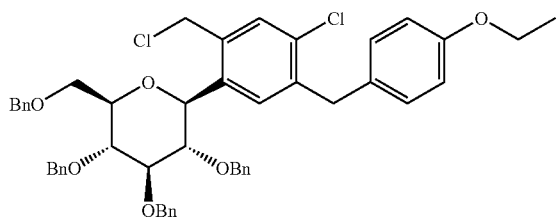 [SMILES: CCOc1ccc(Cc2cc([C@@H]3O[C@H](COCc4ccccc4)[C@@H](OCc4ccccc4)[C@H](OCc4ccccc4)[C@H]3OCc3ccccc3)c(CCl)cc2Cl)cc1]

Thionyl chloride (0.1 mL) was added dropwise into a solution of (5-chloro-4-(4-ethoxybenzyl)-2-((2S,3S,4R,5R,6R)-3,4,5-tris(benzyloxy)-6-(benzyloxymethyl)tetrahydro-2H-pyran-2-yl)phenyl)methanol (100 mg, 0.13 mmol) in methylene chloride (2 mL) at 0° C., and the mixture was allowed to stir for 2 hours at RT. The reaction mixture was evaporated to dryness, and the residual oil was used for the next step without further purification.

Preparation of (2R,3R,4R,5S,6S)-3,4,5-tris(benzyloxy)-2-(benzyloxymethyl)-6-(4-chloro-5-(4-ethoxybenzyl)-2-((methoxy-$d_3$)methyl)phenyl)tetrahydro-2H-pyran (64)

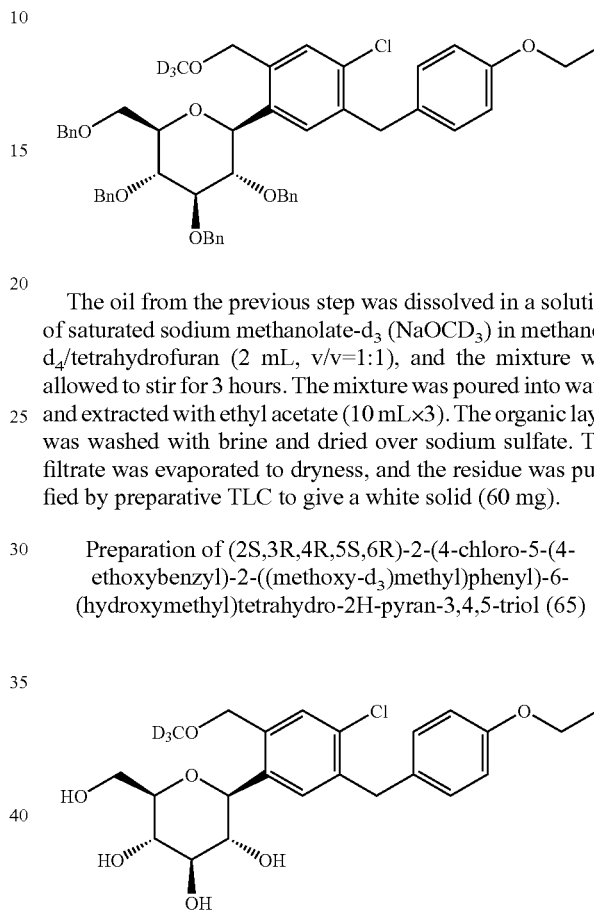

The oil from the previous step was dissolved in a solution of saturated sodium methanolate-$d_3$ (NaOCD$_3$) in methanol-$d_4$/tetrahydrofuran (2 mL, v/v=1:1), and the mixture was allowed to stir for 3 hours. The mixture was poured into water and extracted with ethyl acetate (10 mL×3). The organic layer was washed with brine and dried over sodium sulfate. The filtrate was evaporated to dryness, and the residue was purified by preparative TLC to give a white solid (60 mg).

Preparation of (2S,3R,4R,5S,6R)-2-(4-chloro-5-(4-ethoxybenzyl)-2-((methoxy-$d_3$)methyl)phenyl)-6-(hydroxymethyl)tetrahydro-2H-pyran-3,4,5-triol (65)

To a solution of (2R,3R,4R,5S,6S)-3,4,5-tris(benzyloxy)-2-(benzyloxymethyl)-6-(4-chloro-5-(4-ethoxybenzyl)-2-((methoxy-$d_3$)methyl)phenyl)tetrahydro-2H-pyran (60 mg) in tetrahydrofuran:methanol (v/v=2:1) (6 mL) was added 1,2-dichlorobenzene (0.1 mL) and Pd/C (10%, 30 mg), and the mixture was kept for 4 hours under hydrogen atmosphere at RT (about 25° C.). The mixture was filtered, and the filtrate was evaporated to dryness. The resulting yellow oil was purified by preparative HPLC to give the title compound (20 mg). $^1$H-NMR (400 MHz, CDOD$_3$): δ 7.41 (2H, m), 7.08 (2H, m), 6.79 (3H, m), 4.67 (1H, d, J=12 Hz), 4.49 (1H, d, J=12.4 Hz), 4.41 (1H, d, J=9.2 Hz), 4.00 (4H, m), 3.85 (1H, m), 3.65 (1H, m), 3.41 (4H, m), 1.34 (3H, t, J=7.2 Hz); MS ESI$^+$ (m/z): 456 [M+1]$^+$, 473 [M+18]$^+$ 911 [2M+1]$^+$; MS ESI$^-$ (m/z): 500 [M+45]$^-$, 955 [2M+45]$^-$, calc. 455.18.

Example 24

This example illustrates the preparation of compound 68 according to the approach provided in Scheme 24. The general method is applicable to other compounds of the present invention.

Scheme 24

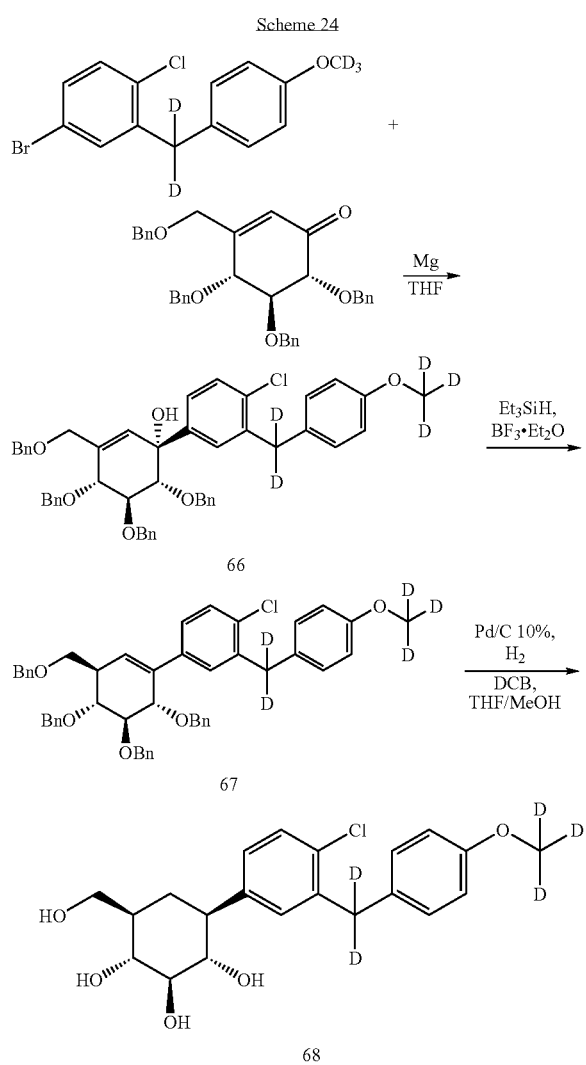

Preparation of (1R,4R,5S,6R)-4,5,6-tris(benzyloxy)-3-(benzyloxymethyl)-1-(4-chloro-3-((4-(methoxy-d₃)phenyl)methyl-d₂)phenyl)cyclohex-2-enol (66)

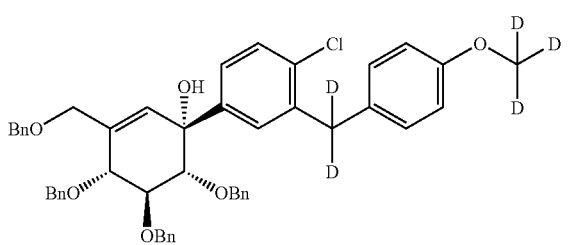 [SMILES: [2H]C([2H])([2H])Oc1ccc(C([2H])([2H])c2cc([C@]3(O)C=C(COCc4ccccc4)[C@@H](OCc4ccccc4)[C@H](OCc4ccccc4)[C@H]3OCc3ccccc3)ccc2Cl)cc1]

To magnesium powder (114 mg, 4.76 mmol) under argon atmosphere was added a portion of a solution of 4-bromo-1-chloro-2-((4-(methoxy-d₃)phenyl)methyl-d₂)benzene (0.3 g, 0.95 mmol) in dry THF (2 mL), and 1,2-dibromoethane (0.05 mL). The mixture was heated to reflux, and after reaction initiation (exothermic), the remaining portion of a solution of 4-bromo-1-chloro-2-((4-(methoxy-d₃)phenyl)methyl-d₂)benzene (700 mg, 2.22 mol) in dry THF (2 mL) was added dropwise. The mixture was allowed to react for 1 hour under gentle reflux until most of the magnesium was consumed. The above Grignard reagent was added dropwise into a solution of (4R,5S,6R)-4,5,6-tris(benzyloxy)-3-(benzyloxymethyl)cyclohex-2-enone (1.13 g, 2.11 mmol) in dry THF (2 mL) under argon at RT (about 25° C.). After 3 hours, saturated aqueous ammonium chloride (10 mL) was added into the mixture to quench the reaction. The mixture was extracted with ethyl acetate (3×15 mL), and the organic layer was washed with brine (3×10 mL), dried over Na₂SO₄, and filtered. The filtrate was evaporated to dryness to give the crude target compound as a yellow oil (755 mg, 46% yield). MS ESI⁺ (m/z): 789 (M+18).

Preparation of ((1R,2S,3S,6R)-6-(benzyloxymethyl)-4-(4-chloro-3-((4-(methoxy-d₃)phenyl)methyl-d₂)phenyl)cyclohex-4-ene-1,2,3-triyl)tris(oxy)tris(methylene)tribenzene (67)

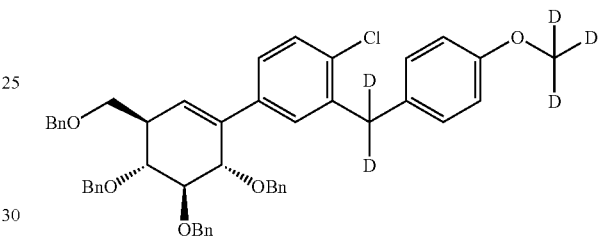

To a cooled (−25° C.) solution of (1R,4R,5S,6R)-4,5,6-tris(benzyloxy)-3-(benzyloxymethyl)-1-(4-chloro-3-((4-(methoxy-d₃)phenyl)methyl-d₂)phenyl)cyclohex-2-enol (755 mg, 0.98 mmol) in methylene chloride (5 mL) was added dropwise triethylsilane (3 eq, 0.47 mL) followed by borontrifluoride etherate (2 eq, 0.25 mL) slowly. The reaction mixture was allowed to stir 2 hours at −25° C., quenched by saturated ammonium chloride (5 mL), and the aqueous layer was extracted with methylene chloride (3×10 mL). The organic layers were combined, washed with brine (3×10 mL), and dried over anhydrous sodium sulfate. The sample was concentrated under reduced pressure to provide a yellow oil, which was purified by preparative TLC (elution with petroleum ether:ethyl acetate=10:1) to give the title compound as a white solid (140 mg; 19% yield). MS ESI⁺ (m/z): 773 (M+18).

Preparation of (1R,2R,3S,4S,6R)-4-(4-chloro-3-((4-(methoxy-d₃)phenyl)methyl-d₂)phenyl)-6-(hydroxymethyl)cyclohexane-1,2,3-triol (68)

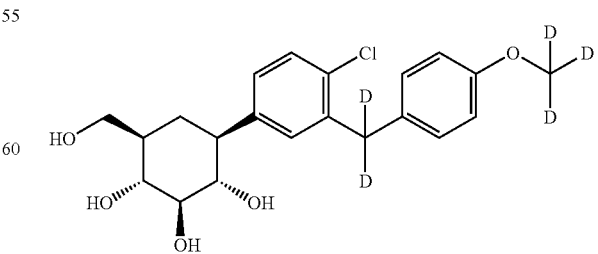

To a solution of ((1R,2S,3S,6R)-6-(benzyloxymethyl)-4-(4-chloro-3-((4-(methoxy-d₃)phenyl)methyl-d₂)phenyl)cyclohex-4-ene-1,2,3-triyl)tris(oxy)tris(methylene)tribenzene (60 mg, 0.079 mmol) in tetrahydrofuran/methanol (1:1 v/v, 4 mL) was added palladium over charcoal (10%, 10 mg), and the mixture was stirred for 1.5 hours under hydrogen atmosphere. The mixture was filtered, and the filtrate was concentrated under reduced pressure to provide a yellow oil. The residue was purified by preparative HPLC to give title compound as a white solid (9 mg; 28% yield). $^1$H-NMR (CD$_3$OD, 400 MHz): δ 7.30-7.32 (d, J=8.0 Hz, 1H), 7.11-7.15 (m, 4H), 6.82-6.84 (d, J=9.2 Hz, 1H), 3.77 (dd, J=3.6, 10.8 Hz, 1H), 3.60 (dd, J=6.4, 10.8 Hz, 1H), 3.46 (t, J=8.4 Hz, 1H), 3.33 (m, 2H), 2.59 (m, 1H), 1.83 (dt, J=3.6, 10.4 Hz, 1H), 1.66 (m, 1H), 1.39-1.43 (t, J=12.8 Hz, 1H); MS ESI$^+$ (m/z): 398 [M+1]$^+$, 415 [M+18]$^+$, 420 [M+23]$^+$; MS ESI$^-$ (m/z) 442 [M+45]$^-$, calc. 397.17.

Example 25

This example illustrates the preparation of compound 70.

Preparation of ((1R,2S,3S,6R)-6-(benzyloxymethyl)-4-(4-chloro-3-(4-ethylbenzyl)phenyl)cyclohex-4-ene-6-d-1,2,3-triyl)tris(oxy)tris(methylene)tribenzene (69)

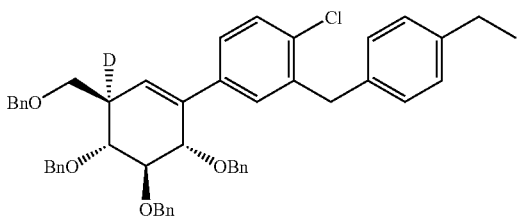 [SMILES: [2H][C@]1(COCc2ccccc2)C=C(c2ccc(Cl)c(Cc3ccc(CC)cc3)c2)[C@H](OCc2ccccc2)[C@@H](OCc2ccccc2)[C@@H]1OCc1ccccc1]

To a cold solution (−30° C.) of (1R,4R,5S,6R)-4,5,6-tris(benzyloxy)-3-(benzyloxymethyl)-1-(4-chloro-3-(4-ethylbenzyl)phenyl)cyclohex-2-enol (1.086 g, 1.4 mmol) (prepared using methods analogous to those described in the preceding example) in methylene chloride (10 mL) was added dropwise triethylsilane-d (500 mg, 4.2 mmol) followed by boron trifluoride etherate (403 mg, 0.28 mmol). The reaction mixture was allowed to stir 2 hours at −30° C. and was quenched with saturated ammonium chloride (5 mL). The aqueous layer was extracted with methylene chloride (3×10 mL), and the organic layer was combined, washed with brine (3×10 mL), and dried over anhydrous sodium sulfate. The sample was concentrated under reduced pressure to provide a yellow oil, which was purified by preparative TLC (elution with petroleum ether:ethyl acetate=6:1) to give the title product as a white solid (0.542 g; 51% yield).

Preparation of (1R,2R,3S,4S,6R)-4-(4-chloro-3-(4-ethylbenzyl)phenyl)-6-(hydroxymethyl)cyclohexane-6-d-1,2,3-triol (70)

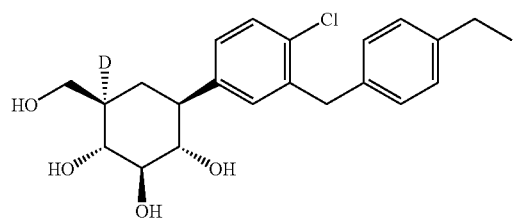 [SMILES: [2H][C@]1(CO)C[C@@H](c2ccc(Cl)c(Cc3ccc(CC)cc3)c2)[C@H](O)[C@@H](O)[C@@H]1O]

To a solution of ((1R,2S,3S,6R)-6-(benzyloxymethyl)-4-(4-chloro-3-(4-ethylbenzyl)phenyl)cyclohex-4-ene-6-d-1,2,3-triyl)tris(oxy)tris(methylene)tribenzene (150 mg, 0.200 mmol) in tetrahydrofuran:methanol (2:1 v/v, 3 mL) was added palladium (10% on carbon, 12 mg), and the mixture was stirred for 3 hours under a hydrogen atmosphere. The mixture was filtered, and the filtrate was concentrated under reduced pressure to provide a yellow oil. The residue was purified by preparative HPLC to give the title compound as a white solid (36.6 mg; 46.7% yield). $^1$H-NMR (CD$_3$OD, 400 Hz): δ 7.32 (d, J=8.4 Hz, 1H), 7.14 (m, 6H), 4.06 (s, 2H), 3.77 (d, J=1, 0.8 Hz, 1H), 3.59 (d, J=10.0 Hz, 1H), 3.46 (m, 1H), 2.59 (m, 3H), 1.82 (dd, J=13.6, 4 Hz, 1H), 1.22 (t, J=7.6 Hz, 3H); MS ESI$^+$ (m/z): 392 [M+1]$^+$, 409 [M+18]$^+$, 413 [M+23]$^+$, MS ESI$^-$ (m/z): 436 [M+45]$^-$, calc. 391.17.

Example 26

Preparation of (2S,3R,4R,5S,6R)-2-(4-chloro-3-((4-hydroxyphenyl)methyl-d$_2$)phenyl)-6-(hydroxymethyl)tetrahydro-2H-pyran-3,4,5-triol (71)

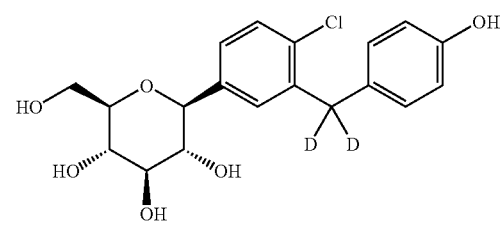 [SMILES: [2H]C([2H])(c1ccc(O)cc1)c1cc([C@@H]2O[C@H](CO)[C@@H](O)[C@H](O)[C@H]2O)ccc1Cl]

To a solution of (2S,3R,4R,5S,6R)-2-(4-chloro-3-((4-(methoxy-d$_3$)phenyl)methyl-d$_2$)phenyl)-6-(hydroxymethyl)tetrahydro-2H-pyran-3,4,5-triol (19) (1 g, 2.50 mmol) in dichloromethane, was added dropwise tribromoborane (1.25 g, 2.00 mmol) at −78° C. The solution was warmed to 0° C. for 1 hour. The solution was quenched with ice-water, and the dichloromethane was removed under reduced pressure. Ethyl acetate was added, and the extracts were washed with brine, dried over sodium sulfate, and concentrated. The product was purified by preparative LC-MS to give 357 mg of title compound. $^1$H-NMR (CD$_3$OD, 400 MHz): δ 7.24-7.34 (m, 3H), 7.06-7.09 (m, 2H), 6.76-6.80 (m, 2H), 4.09-4.11 (d, J=9.6 Hz, 1H), 3.87-3.90 (m, 1H), 3.71-3.72 (m, 1H), 3.36-3.46 (m, 3H), 3.25-3.27 (1H, m); MS ESI$^-$ (m/z): 427 (M+45)$^-$.

Example 27

This example illustrates the preparation of compound 76 according to the approach provided in Scheme 25. The general method is applicable to other compounds of the present invention.

Scheme 25

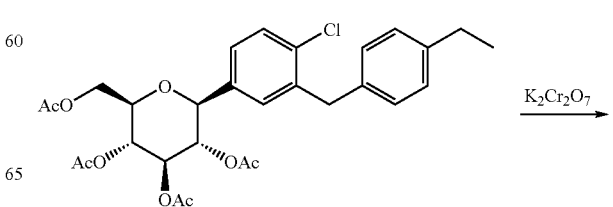

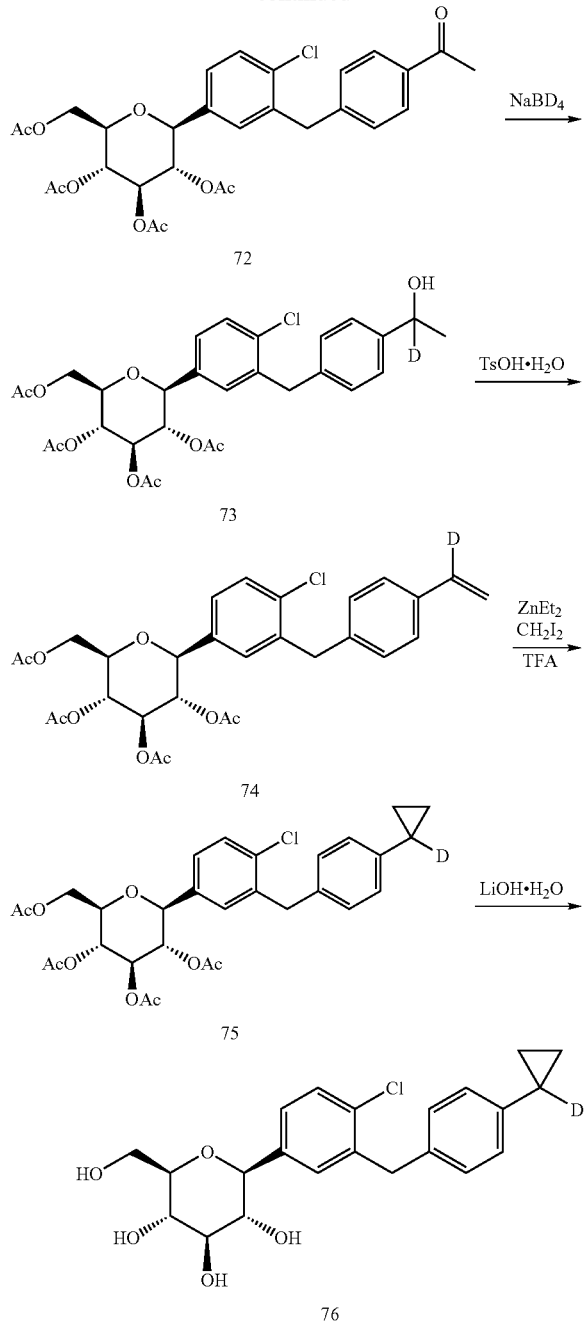

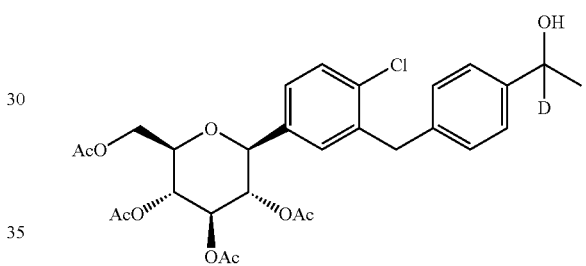

To a stirred solution of (2R,3R,4R,5S,6S)-2-(acetoxymethyl)-6-(4-chloro-3-(4-ethylbenzyl)phenyl)tetrahydro-2H-pyran-3,4,5-triyl triacetate (10 g, 10.8 mmol) in acetic acid (130 mL) at 120° C. was added potassium chromate (6.3 g, 21.4 mmol) in one portion. The mixture was stirred for 22 hours at this temperature, and the reaction was cooled to RT. The volatiles were removed under reduced pressure, ethyl acetate was added, and the solids were filtered off. The organic layer was washed with a saturated solution of sodium bicarbonate and then with brine, and dried over sodium sulfate. Concentration of the organic solution and purification of the resulting residue by silica gel column (3:1 petroleum ether:ethyl acetate) gave 2.3 g of title compound as a white solid. $^1$H NMR (400 MHz, CDCl$_3$): δ 7.90 (d, J=8.0 Hz, 2H), 7.39 (d, J=8.4 Hz, 1H), 7.26 (d, J=8.4 Hz, 2H), 7.22 (dd, J=8.4, 2.2 Hz, 1H), 7.17 (d, J=2.0 Hz, 1H), 5.31 (t, J=9.4 Hz, 1H), 5.22 (t, J=9.8 Hz, 1H), 5.09 (t, J=9.4 Hz, 1H), 4.35 (d, J=10.0 Hz, 1H), 4.29 (dd, J=12.4, 4.8 Hz, 1H), 4.18-4.13 (m, 3H), 3.85-3.81 (m, 1H), 2.60 (s, 3H), 2.09 (s, 3H), 2.07 (s, 3H), 2.01 (s, 3H), 1.75 (s, 3H); MS ESI (m/z): 575 [M+H]$^+$, 619 [M+HCO$_2$]$^-$.

Preparation of (2R,3R,4R,5S,6S)-2-(acetoxymethyl)-6-(4-chloro-3-(4-(1-hydroxyethyl-1-d)benzyl)phenyl)tetrahydro-2H-pyran-3,4,5-triyl triacetate (73)

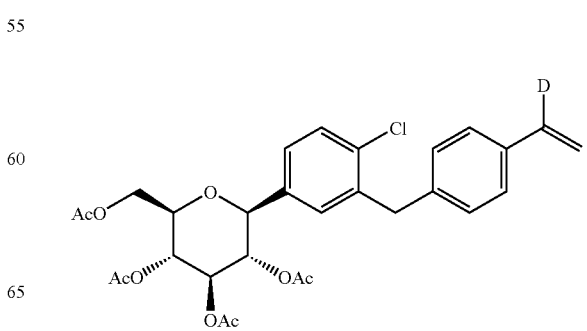

To a cooled (0° C.) solution of (2R,3R,4R,5S,6S)-2-(acetoxymethyl)-6-(3-(4-acetylbenzyl)-4-chlorophenyl)tetrahydro-2H-pyran-3,4,5-triyl triacetate (4.53 g, 7.88 mmol) in THF (30 mL) was added sodium borodeuteride (0.535 g, 13.4 mmol, 97% atom D) in one portion, followed by addition of methanol (1.2 mL) dropwise. The reaction mixture was warmed to room temperature, and stirred for 2.5 hours, and a saturated solution of ammonium chloride was added. The resulting mixture was extracted with ethyl acetate (3×), and the combined organic phases were washed with brine and dried over sodium sulfate. Concentration of the organic solution provided 4.55 g of crude product as a white solid. MS ESI (m/z): 591 [M+NH$_4$]$^+$, 596 [M+Na]$^+$.

Preparation of (2R,3R,4R,5S,6S)-2-(acetoxymethyl)-6-(4-chloro-3-(4-(vinyl-1-d)benzyl)phenyl)tetrahydro-2H-pyran-3,4,5-triyl triacetate (74)

Preparation of (2R,3R,4R,5S,6S)-2-(acetoxymethyl)-6-(3-(4-acetylbenzyl)-4-chlorophenyl)tetrahydro-2H-pyran-3,4,5-triyl triacetate (72)

A solution of (2R,3R,4R,5S,6S)-2-(acetoxymethyl)-6-(4-chloro-3-(4-(1-hydroxyethyl-1-d)benzyl)phenyl)tetrahydro-2H-pyran-3,4,5-triyl triacetate (4.55 g, 7.87 mmol) and p-toluenesulfonic acid monohydrate (0.15 g, 0.79 mmol) in toluene (100 mL) was stirred for 1 hour at 120° C. Water was added, the organic layer was separated, and the aqueous layer was extracted with ethyl acetate. The combined organic phases were washed with 1 M aqueous sodium hydroxide and then with brine, and dried over sodium sulfate. Concentration of the organic solution and purification of the resulting residue by silica gel column (5:1 petroleum ether:ethyl acetate) gave 2.25 g of the title compound as a white solid. MS ESI (m/z): 577 [M+NH$_4$]$^+$, 582 [M+Na]$^+$.

Preparation of (2R,3R,4R,5S,6S)-2-(acetoxymethyl)-6-(4-chloro-3-(4-(cyclopropyl-1-d)benzyl)phenyl)tetrahydro-2H-pyran-3,4,5-triyl triacetate (75)

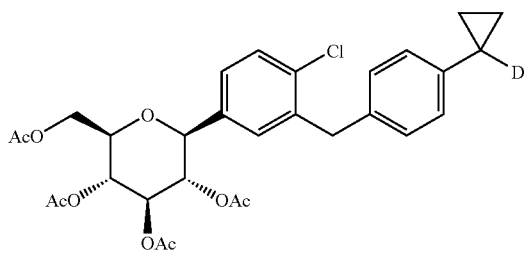 [SMILES: [2H]C1(c2ccc(Cc3cc([C@@H]4O[C@H](COC(C)=O)[C@@H](OC(C)=O)[C@H](OC(C)=O)[C@H]4OC(C)=O)ccc3Cl)cc2)CC1]

To a cooled (0° C.) solution of diethylzinc (1 M in hexane, 9.8 mL, 9.8 mmol) in dichloromethane (8 mL) under argon was added dropwise trifluoroacetic acid (0.73 mL, 9.83 mmol) in dichloromethane (4 mL). After stirring for 20 minutes, diiodomethane (0.79 mL, 9.8 mmol) in dichloromethane (4 mL) was added dropwise. After stirring for another 20 minutes, (2R,3R,4R,5S,6S)-2-(acetoxymethyl)-6-(4-chloro-3-(4-(vinyl-1-d)benzyl)phenyl)tetrahydro-2H-pyran-3,4,5-triyl triacetate (2.2 g, 3.93 mmol) in dichloromethane (8 mL) was added over 15 minutes, and the mixture was warmed to RT and stirred for 18.5 hours. A saturated solution of ammonium chloride was added, the mixture was extracted 3 times with dichloromethane, and the combined organic phases were washed with brine and dried over sodium sulfate. Concentration of the organic solution provided 2.65 g of crude product as a white solid. MS ESI (m/z): 595 [M+NH$_4$]$^+$, 600 [M+Na]$^+$.

Preparation of (2S,3R,4R,5S,6R)-2-(4-chloro-3-(4-(cyclopropyl-1-d)benzyl)phenyl)-6-(hydroxymethyl)tetrahydro-2H-pyran-3,4,5-triol (76)

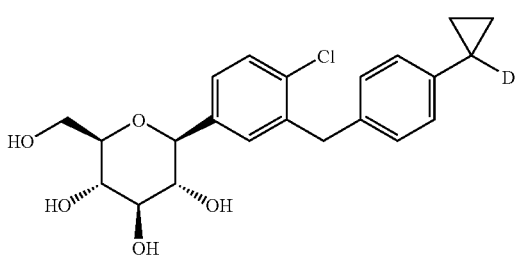 [SMILES: [2H]C1(c2ccc(Cc3cc([C@@H]4O[C@H](CO)[C@@H](O)[C@H](O)[C@H]4O)ccc3Cl)cc2)CC1]

To a solution of (2R,3R,4R,5S,6S)-2-(acetoxymethyl)-6-(4-chloro-3-(4-(cyclopropyl-1-d)benzyl)phenyl)tetrahydro-2H-pyran-3,4,5-triyl triacetate (2.62 g, 4.56 mmol) in a mixture of tetrahydrofuran/methanol/H$_2$O (13 mL, 2:3:1) was added lithium hydroxide monohydrate (62 mg, 1.48 mmol). After stirring overnight at RT, the volatiles were removed under reduced pressure. The residue was taken up with water and ethyl acetate, the organic layer was separated, and the aqueous layer was extracted 3 times with ethyl acetate. The combined organic phases were washed with brine and dried over sodium sulfate. Concentration of the organic solution and purification of the resulting residue by silica gel column (1:2 to 1:4 petroleum ether:ethyl acetate) gave 0.98 g of the title compound as a white solid. $^1$H-NMR (400 MHz, CDCl$_3$): δ 7.37-7.34 (m, 2H), 7.30 (d, J=8.0 Hz, 1H), 7.07 (d, J=8.0 Hz, 2H), 6.96 (d, J=8.0 Hz, 2H), 4.12-4.00 (m, 3H), 3.89 (d, J=10.8 Hz, 1H), 3.72 (dd, J=12.0, 5.2 Hz, 1H), 3.52-3.38 (m, 3H), 3.33 (t, J=9.0 Hz, 1H), 0.94-0.89 (m, 2H), 0.64-0.61 (m, 2H); MS ESI (m/z): 406 [M+H]$^+$, 428 [M+Na]$^+$, 450 [M+HCO$_2$]$^-$.

Example 28

Preparation of (1R,2R,3S,4R,5R,6S)-4-(4-chloro-3-(4-ethylbenzyl)phenyl)-6-(hydroxymethyl)cyclohexane-6-d-1,2,3,5-tetraol (77)

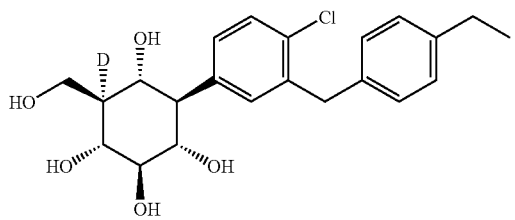

To a solution of ((1R,2S,3S,6R)-6-(benzyloxymethyl)-4-(4-chloro-3-(4-ethylbenzyl)phenyl)cyclohex-4-ene-6-d-1,2,3-triyl)tris(oxy)tris(methylene)tribenzene (69) (30 mg, 0.04 mmol) in tetrahydrofuran:methanol (2:1, v/v, 3 mL) was added 1,2-dichlorobenzene (11.5 mg, 0.08 mmol) and palladium (10% on carbon, 15 mg), and the mixture was stirred for 2 hours under a hydrogen atmosphere at RT. The mixture was filtered and the filtrate was concentrated under reduced pressure to provide crude product as a yellow oil. The product was purified by preparative HPLC to give the title compound as a white solid (3.65 mg; 22.9% yield). $^1$H-NMR (CD$_3$OD, 400 MHz): δ 7.35 (d. J=8 Hz, 1H, 7.14 (m, 6H), 4.07 (s, 2H), 3.93 (s, 2H), 3.67 (d, J=10.4 Hz, 1H), 3.45 (m, 2H), 2.58 (m, 3H), 1.21 (t, J=7.2 Hz, 3H); MS ESI$^+$ (m/z): 408 [M+1]$^+$, 425 [M+18]$^+$, 815 [2M+1]$^+$; MS ESI$^-$ (m/z): 452 [M+45]$^-$, calc. 407.16.

Example 29

This example illustrates the preparation of compound 81.

Preparation of 2-(2,2-difluoroethoxy)ethyl 4-methylbenzenesulfonate (78)

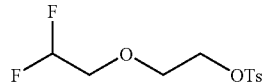

To a cooled (0° C.) solution of 4.6 N sodium hydroxide (20.6 mL) was slowly added 2-(2,2-difluoroethoxy)ethanol (4 g, 31.7 mmol) in THF (10 mL) at a rate that maintained the temperature below 5° C. The mixture was stirred for 10 minutes, and TsCl (6.1 g, 32 mmol) in THF (10.6 mL) was slowly added at a rate that maintained the temperature below 5° C. The mixture was stirred for 30 minutes below 5° C., and then diluted with water. The aqueous layer was extracted with EtOAc (2×20 mL), and the combined organic layers were washed with aqueous NH$_4$Cl (30 mL), then with brine (30 mL), and dried over anhydrous sodium sulfate. Concentration under reduced pressure gave the crude product, which was purified by silica column chromatography (elution with PE:EtOAc=4:1) to give the title compound (10 g, yield 81.9%). $^1$H-NMR (CDCl$_3$, 400 MHz): δ 7.78 (d, J=8.4 Hz, 2H), 7.33 (d, J=8 Hz, 2H), 5.77 (ttt, J=4, 5.52 Hz, 1H), 4.16 (t, J=4.4 Hz, 2H), 3.74 (t, J=4.8 Hz, 2H), 3.62 (dt, J=4, 14 Hz, 2H), 2.44 (s, 3H).

Preparation of 4-bromo-1-chloro-2-(4-(2-(2,2-difluoroethoxy)ethoxy)benzyl)benzene (79)

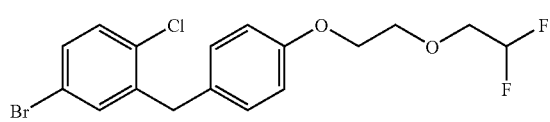 [SMILES: FC(F)COCCOc1ccc(Cc2cc(Br)ccc2Cl)cc1]

2-(2,2-difluoroethoxy)ethyl 4-methylbenzenesulfonate (3 g, 10.7 mmol), 4-(5-bromo-2-chlorobenzyl)phenol (3.8 g, 12.8 mmol), and Cs$_2$CO$_3$ (8.7 g, 26.8 mmol) were suspended in DMF (8 mL) at 50° C. The mixture was stirred for 24 hours at this temperature. The mixture was diluted with water and the aqueous layer was extracted with PE two times. The combined organic layers were washed with brine, concentrated and purified by flash chromatography (PE/EtOAc=50:1) to obtain a yellow solid (4 g, yield 91.9%), which was used in the next step without further purification.

Preparation of (3R,4S,5S,6R)-2-(4-chloro-3-(4-(2-(2,2-difluoroethoxy)ethoxy)benzyl)phenyl)-6-(hydroxymethyl)-2-methoxytetrahydro-2H-pyran-3,4,5-triol (80)

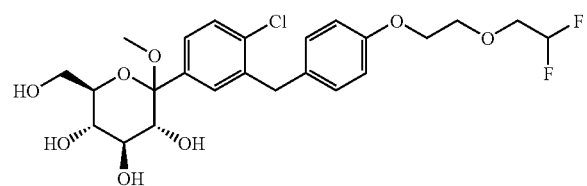 [SMILES: COC1(c2ccc(Cl)c(Cc3ccc(OCCOCC(F)F)cc3)c2)O[C@H](CO)[C@@H](O)[C@H](O)[C@H]1O]

To a cold (−60° C.) solution of 4-bromo-1-chloro-2-(4-(2-(2,2-difluoroethoxy)ethoxy)benzyl)benzene (4 g, 9.9 mmol) in dry THF/toluene (2:1, 18 mL) was slowly added dropwise a solution of n-butyllithium in hexane (2.5 M, 4.7 mL), and the pale yellow solution was stirred for 30 minutes at −60° C. A solution of (3R,4S,5R,6R)-3,4,5-tris(trimethylsilyloxy)-6-((trimethylsilyloxy)methyl)tetrahydro-2H-pyran-2-one (6 g, 12.8 mmol) in toluene (15 mL) was added dropwise at a rate that maintained the temperature below −55° C., and the mixture was stirred for 2 hr at −60° C. The reaction mixture was quenched by addition of MeOH (24 mL) containing methanesulfonic acid (2 mL). The reaction was stirred overnight at RT, and then aqueous sodium hydrogen carbonate solution (30 mL) was added. The organic layer was separated, the aqueous phase was extracted with ethyl acetate (30 mL) and the combined organic extracts were dried over sodium sulfate. The product was concentrated to give a residue (5.4 g), which was used in the next step without further purification.

Preparation of (2S,3R,4R,5S,6R)-2-(4-chloro-3-(4-(2-(2,2-difluoroethoxy)ethoxy)benzyl)phenyl)-6-(hydroxymethyl)tetrahydro-2H-pyran-2-d-3,4,5-triol (81)

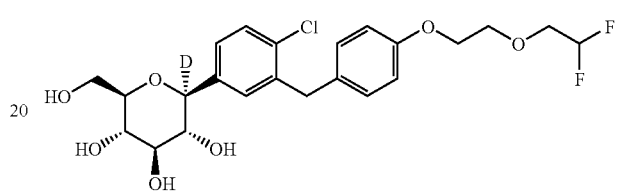

The residue (250 mg, 0.5 mmol) from the previous step was dissolved in acetonitrile/dichloromethane (1:1, 1.6 mL), and the resulting solution was cooled to −40° C. Triethylsilane-d (113 mg, 1.0 mmol, 97 atom % D) and boron trifluoride etherate (0.1 mL, 0.8 mmol) were added quickly, and the mixture was stirred for 6 hours at RT. Saturated aqueous sodium bicarbonate was added, and the solvent was removed under reduced pressure. The residue was extracted with ethyl acetate (3×), and the combined organic phases were washed with brine and then with water, and dried over sodium sulfate. The solvent was removed under reduced pressure and the residue was purified by preparative LC-MS to obtain the title compound as a white powder (108 mg, yield 45.7%). $^1$H-NMR (CD$_3$OD, 400 MHz): δ 7.38~7.28 (m, 3H), 7.12 (d, J=8.4 Hz, 2H), 6.85 (d, J=8.8 Hz, 2H), 5.97 (ttt, J=4, 5.6 Hz, 1H), 4.12~4.10 (m, 2H), 4.04 (d, J=8.8 Hz, 2H), 3.91-3.88 (m, 3H), 3.78 (dt, J=4, 14 Hz, 2H), 3.73-3.68 (m, 1H), 3.49-3.44 (m, 1H), 3.42-3.40 (m, 1H), 3.32-3.30 (m, 1H); MS ESI (m/z): 490 [M+1]$^+$, 507 [M+18]$^+$, 534 [M+45]$^-$, calc. 489.

Example 30

This example illustrates the preparation of compound 82 according to the approach provided in Scheme 26. The general method is applicable to other compounds of the present invention.

Scheme 26

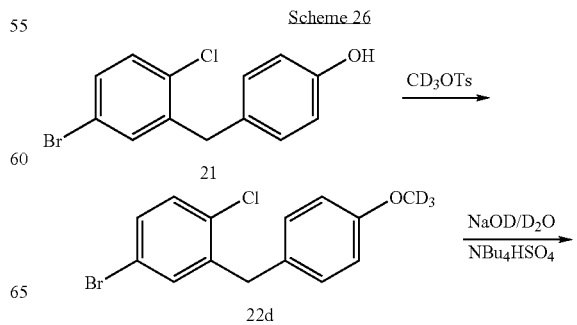

-continued

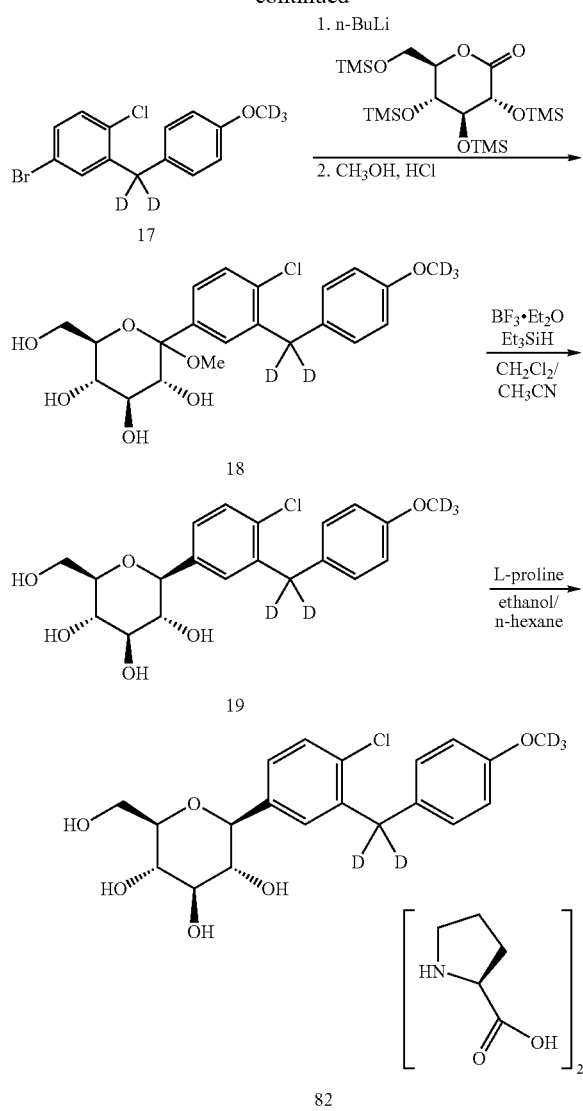

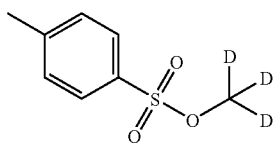
82

Preparation of methyl-d$_3$ 4-methylbenzenesulfonate

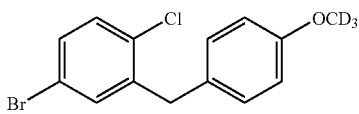

Methanol-d$_4$ (20 g, 554 mmol, 99.8 atom % D) dissolved in tetrahydrofuran (100 mL) was slowly added to a cooled (0° C.) solution of 4.6 N sodium hydroxide (365 mL) and maintained at a temperature below 5° C., and 4-methylbenzene-1-sulfonyl chloride (126 g, 665 mmol) in tetrahydrofuran (100 mL) was slowly added to the above solution while keeping the temperature below 5° C. The mixture was stirred for 1 hour. The reaction mixture was separated and extracted with ethyl acetate. The combined organic layers were washed with saturated ammonium chloride and brine, dried over anhydrous sodium sulfate, and concentrated to give a white solid (104 g, ~91% yield).

Preparation of 4-bromo-1-chloro-2-(4-(methoxy-d$_3$) benzyl)benzene (22d)

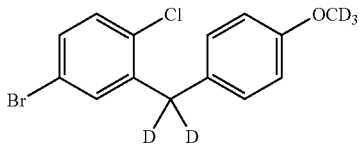

To a solution of 4-(5-bromo-2-chlorobenzyl)phenol (150 g) in acetone (1 L), was added methyl-d$_3$ 4-methylbenzenesulfonate (104.3 g) and potassium carbonate (210 g, 1.5 mol), and the mixture was heated to 80° C. for 16 hours. The mixture was filtered, and the filtrate was evaporated under reduced pressure to give a residue. The residue was dissolved in water (1 L) and ethyl acetate (1 L), the ethyl acetate layer was separated, and the water layer was extracted with ethyl acetate (2×1 L). The combined organic layers were washed with brine, dried over sodium sulfate, and concentrated to give 146 g white solid (91% yield).

Preparation of 4-bromo-1-chloro-2-((4-(methoxy-d$_3$) phenyl)methyl-d$_2$)benzene (17)

1. Preparation of sodium deuteroxide in deuterium oxide (30%)

Deuterium oxide (171 g, D, 99.9%) in a four-neck flask was cooled with an ice bath, and sodium hydride (61 g, 60% dispersion in mineral oil) was added portion-wise over 1 hour while venting off the hydrogen deuteride. The mixture was allowed to warm to 25° C. and stirred for 10 minutes.

2. Preparation of 4-bromo-1-chloro-2-((4-(methoxy-d$_3$)phenyl)methyl-d$_2$)benzene Method A: To the above solution of sodium deuteroxide in deuterium oxide (30%) was added hexane (10 mL), and the mixture was stirred until it turned clear. Tetrabutylammonium bisulfate (14 g, 0.04 mol) and 4-bromo-1-chloro-2-(4-(methoxy-d$_3$)benzyl)benzene (120 g, 0.38 mol) in hexane (500 mL) were added. The flask was sealed and stirred for 24 hours at 25° C. The color of the reaction mixture turned to yellow, and an even dispersion was observed. An aliquot was analyzed using $^1$H NMR (acetone-d$_6$, 400 MHz): from the ratio of the integrals of the peak at 4.03 ppm (methylene, CH$_2$) to the peak at 6.87-6.91 ppm (aromatic), the D/H ratio was calculated to be 95%. The organic layer was decanted, and the aqueous layer was extracted with hexane (2×100 mL). The aqueous layer was recycled to pre-enrich other batches. The combined organic layers were washed with aqueous ammonium chloride (100 mL), dried over sodium sulfate, and concentrated under reduced pressure to give a colorless oil (140 g). $^1$H-NMR (acetone-d$_6$, 400 MHz): δ 7.37-7.46 (m, 3H), 7.17-7.20 (m, 2H), 6.87-6.91 (m, 2H), 4.03 (m, 0.11H).

Method B: To a solution of sodium deuteroxide (1.3 g, 12.6 mmol, 40%, in deuterium oxide), was added tetrabutylammonium bisulfate (210 mg, 0.62 mmol), mineral oil (400 mg, white, light, Sigma-Aldrich), and 4-bromo-1-chloro-2-(4-(methoxy-d$_3$)benzyl)benzene (1 g, 3.1 mmol) in hexane (5 mL). The flask was sealed, and the mixture was vigorously stirred for 24 hours at 25° C. The color of the reaction mixture turned to yellow. The catalyst appeared to be well dispersed in the reaction mixture. The organic layer was decanted, and the aqueous layer was extracted with hexane (2×20 mL). The combined organic layers were washed with aqueous ammonium chloride (10 mL), dried over sodium sulfate, and concentrated under reduced pressure to give a colorless oil (1 g). From the ratio of the integrals of the peak at 4.03-4.53 ppm (methylene) to the peak at 6.87-6.90 (aromatic), the D/H ratio was calculated to be 94%. $^1$H-NMR (acetone-d$_6$, 400 MHz): δ 7.37-7.45 (m, 3H), 7.10-7.20 (m, 2H), 6.87-6.90 (m, 2H), 4.03-4.53 (m, 0.12H).

3. Second Round Deuteration

The above procedure was repeated using the crude product and fresh reagent. An aliquot was analyzed using $^1$H NMR (DMSO-d$_6$, 400 MHz). From the ratio of the integrals of the peak at 3.95 ppm (methylene CH$_2$) to the peak at 6.84~6.88 ppm (aromatic), the D/H ratio was calculated to be 99%. The reaction was worked up as described above to give an oil (170 g). This product was purified by re-crystallization in hexane to give a white solid (94 g, 78% yield). $^1$H-NMR (DMSO-d$_6$, 400 MHz): δ 7.37~7.50 (m, 3H), 7.11~7.15 (m, 2H), 6.84~6.88 (m, 2H), 3.95 (m, 0.02H).

Preparation of (3R,4S,5S,6R)-2-(4-chloro-3-((4-(methoxy-d$_3$)phenyl)methyl-d$_2$)phenyl)-6-(hydroxymethyl)-2-methoxytetrahydro-2H-pyran-3,4,5-triol (18)

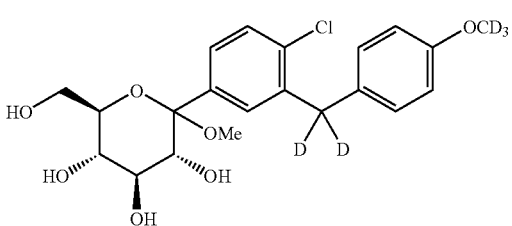

A cold (−78° C.) solution of n-butyllithium (227 mL, 2.5 M in hexane, 0.568 mol) was added dropwise under argon to a cold (−78° C.) solution of 4-bromo-1-chloro-2-((4-(methoxy-d$_3$)phenyl)methyl-d$_2$)benzene (150 g, 0.474 mol) in dry tetrahydrofuran, toluene (900 mL, 1:2) at such a rate as to keep the temperature below −70° C., and the mixture was stirred for 40 min. The reaction mixture was transferred to a stirred, cold (−78° C.) solution of (3R,4S,5R,6R)-3,4,5-tris(trimethylsilyloxy)-6-((trimethylsilyloxy)methyl)tetrahydro-2H-pyran-2-one in toluene (900 mL) at a rate that maintained the reaction temperature below −70° C. The mixture was stirred for 3 hours at −78° C. Hydrochloric acid (36~38%, 87 mL, 1.04 mol) in methanol (600 mL) was slowly added, and the reaction temperature was maintained so as not to exceed −45° C. The reaction mixture was gradually warmed to 25° C. and stirred for 16 hours. The reaction was neutralized with saturated sodium bicarbonate to pH 7.5, the organic phase was separated, and the aqueous phase was extracted with ethyl acetate (2×3000 mL). The combined organic phases were washed with brine (2×2000 mL) and dried over sodium sulfate. After removal of the volatiles, the residues were dried under vacuum at 40° C. to give 215 g of off-white solid which was used for the next step without further purification. Purity (HPLC): 9.46 minutes, 69.9% (UV); MS ES$^+$ (m/z): 430 [M+1]$^+$.

Preparation of (2S,3R,4R,5S,6R)-2-(4-chloro-3-((4-(methoxy-d$_3$)phenyl)methyl-d$_2$)phenyl)-6-(hydroxymethyl)tetrahydro-2H-pyran-3,4,5-triol (19)

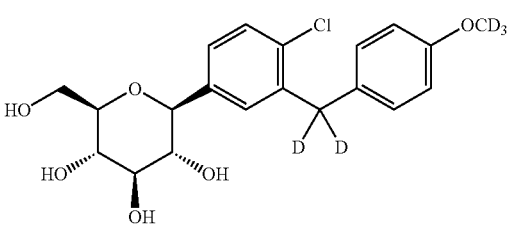

To a −45° C. solution of the above crude product (215 g, ~0.501 mmol) in anhydrous acetonitrile/dichloromethane (2.58 L, 1:1) was added triethylsilane (232 g, 2.00 mol), followed by addition of boron trifluoride etherate (190 mL, 1.50 mol) and the mixture was stirred for 2 hours at −10° C. The reaction was quenched with saturated aqueous bicarbonate to pH 7.5. The volatiles were removed under reduced pressure, and the residues were extracted with ethyl acetate (2×3000 mL). The combined organic phases were washed with brine (2×2000 mL) and were dried over sodium sulfate. The reaction mixture was concentrated to give 190 g of a white solid which was used for the next step without further purification. Purity (HPLC) 8.88 minutes, 69.7% (UV); MS ES$^+$ (m/z): 400 [M+1]$^+$.

Preparation of (2S,3R,4R,5S,6R)-2-(4-chloro-3-((4-(methoxy-d$_3$)phenyl)methyl-d$_2$)phenyl)-6-(hydroxymethyl)tetrahydro-2H-pyran-3,4,5-triol, bis(L-proline) complex (82)

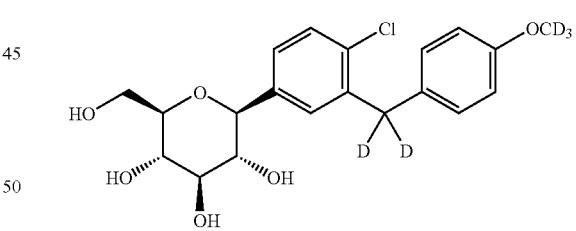

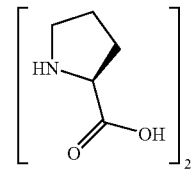

A 5 L 4-neck flask was charged with (2S,3R,4R,5S,6R)-2-(4-chloro-3-((4-(methoxy-d$_3$)phenyl)methyl-d$_2$)phenyl)-6-(hydroxymethyl)tetrahydro-2H-pyran-3,4,5-triol (190 g, 82% pure) and L-proline (109 g, 0.950 mole), and then ethanol (1400 mL) and water (120 mL) were added to the flask. After refluxing for 30 minutes with rapid mechanical stirring, n-hexane (1900 mL) was added dropwise. After the addition was complete, the reaction was cooled slowly to 25° C. and then cooled to 5° C. After stirring for 3 hours at 5° C., the reaction was filtered. The filter cake was washed with n-hexane (2×300 mL) and dried under vacuum at 65° C. to give 176 g of a white solid. Then 175 g of this crude solid was dissolved in 95% ethanol/water (525 mL) at 75° C. with mechanical stirring. After the reaction solution was clear, the reaction was cooled slowly to 25° C. and stirred for another 5 hours. The reaction mixture was filtered, and the filter cake was washed with ethanol (2×50 mL) and dried under vacuum at 65° C. to afford a white solid (145 g, 66.1% yield). Purity (HPLC) 99.3% (UV). HPLC retention time: 15.43 min; Waters XTerra C18, 5 μm pore size, 2.1×50 mm column; 1.0 mL/min, 8 min gradient; mobile phase: solvent A: 0.045% formic acid in acetonitrile, solvent B: 0.1% formic acid in Milli-Q water. $^1$H-NMR (CD$_3$OD, 400 MHz): δ 7.34~7.25 (m, 3H), 7.08 (d, J=8.8 Hz, 2H), 6.78 (d, J=8.8 Hz, 2H), 4.10 (d, J=9.2 Hz, 1H), 4.01~3.97 (m, 2H), 3.90 (d, J=12.4 Hz, 1H), 3.73~3.69 (m, 1H), 3.49~3.37 (m, 5H), 3.30~3.21 (m, 3H), 2.36~2.27 (m, 2H), 2.17~2.09 (m, 2H), 2.02~1.95 (m, 4H).

Example 31

This example illustrates the preparation of compound 83 according to the approach provided in Scheme 27. The general method is applicable to other compounds of the present invention.

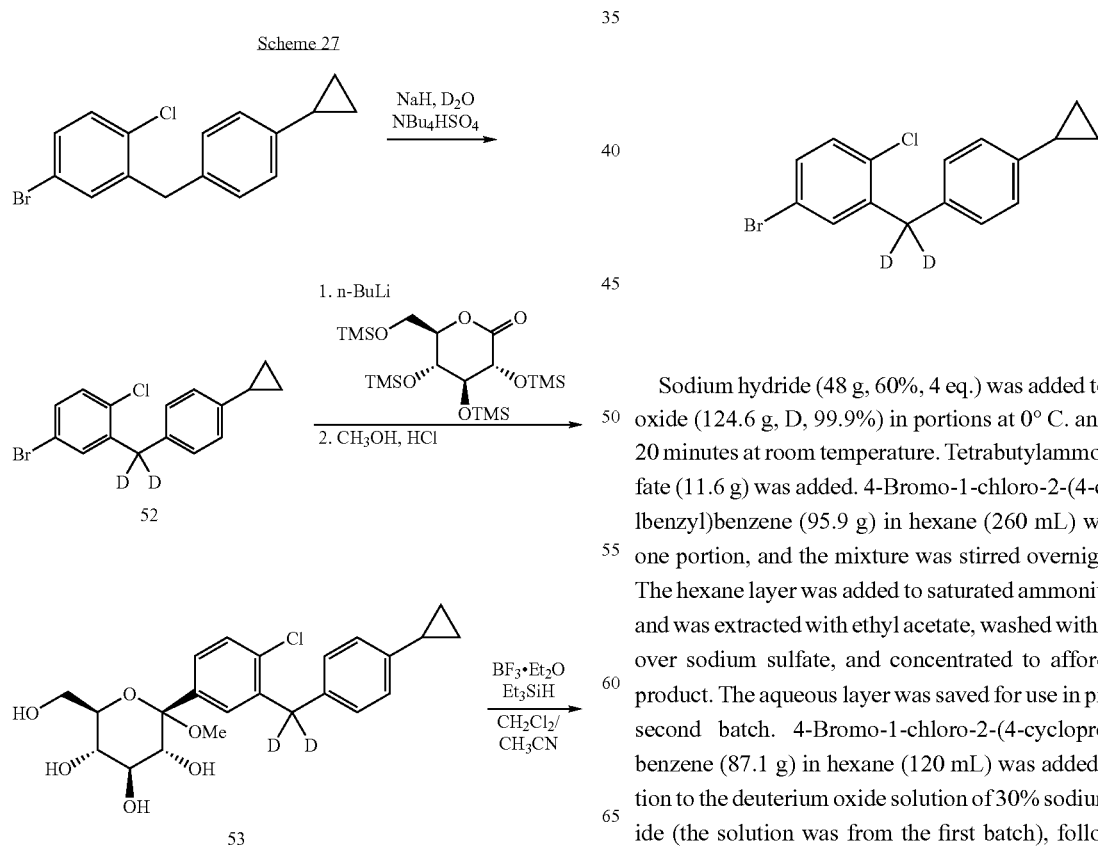

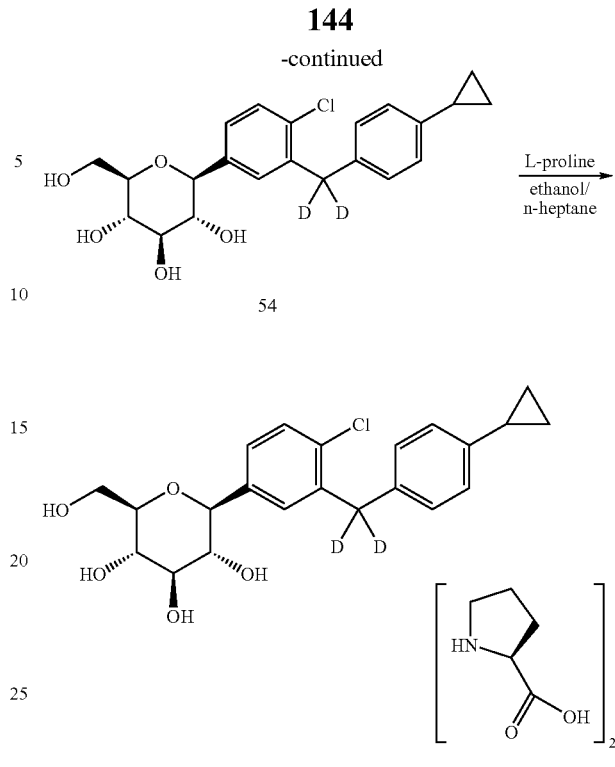

Preparation of 4-bromo-1-chloro-2-((4-cyclopropylphenyl)methyl-d$_2$)benzene (52)

Sodium hydride (48 g, 60%, 4 eq.) was added to deuterium oxide (124.6 g, D, 99.9%) in portions at 0° C. and stirred for 20 minutes at room temperature. Tetrabutylammonium bisulfate (11.6 g) was added. 4-Bromo-1-chloro-2-(4-cyclopropylbenzyl)benzene (95.9 g) in hexane (260 mL) was added in one portion, and the mixture was stirred overnight at 25° C. The hexane layer was added to saturated ammonium chloride and was extracted with ethyl acetate, washed with brine, dried over sodium sulfate, and concentrated to afford the crude product. The aqueous layer was saved for use in preparing the second batch. 4-Bromo-1-chloro-2-(4-cyclopropylbenzyl)benzene (87.1 g) in hexane (120 mL) was added in one portion to the deuterium oxide solution of 30% sodium deuteroxide (the solution was from the first batch), followed by the addition of 5 mL of mineral oil (400 mg, white, light, Sigma- Aldrich). The mixture was stirred overnight at room temperature. The work-up was the same as to the first batch. Sodium hydride (91.6 g, 60%, 4 eq.) was added to deuterium oxide (237.8 g) at 0° C. in portions. The reaction stirred for 20 minutes at room temperature, and tetrabutylammonium bisulfate (22.1 g) was added. The crude product from the above two batches (183 g) in hexane (300 mL) was added in one portion. The mixture was then stirred overnight at room temperature. The organic layer was separated, and the aqueous layer was extracted with ethyl acetate. The combined organic layers were washed with brine, dried over sodium sulfate, and concentrated to afford the crude product, which was then purified by column chromatography to afford almost quantitative target compound. The D incorporation ratio was about 98.5% from $^1$H NMR.

Preparation of (2S,3R,4S,5S,6R)-2-(4-chloro-3-((4-cyclopropylphenyl)methyl-d$_2$)phenyl)-6-(hydroxymethyl)-2-methoxytetrahydro-2H-pyran-3,4,5-triol (53)

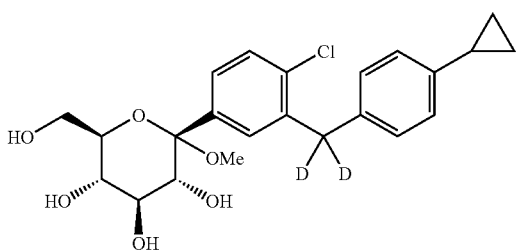 [SMILES: [2H]C([2H])(c1ccc(C2CC2)cc1)c1cc([C@]2(OC)O[C@H](CO)[C@@H](O)[C@H](O)[C@H]2O)ccc1Cl]

A cold (−78° C.) solution of n-butyllithium (163 mL, 2.5 M in hexane, 0.408 mol) was added dropwise under argon to a cold (−78° C.) solution of 4-bromo-1-chloro-2-((4-cyclopropylphenyl)methyl-d$_2$)benzene (100 g, 0.340 mol) in dry tetrahydrofuran/toluene (660 mL, 1:2) at such a rate as to keep the temperature below −70° C. The mixture was stirred for 40 minutes. The reaction mixture was transferred to a stirred, cold (−78° C.) solution of (3R,4S,5R,6R)-3,4,5-tris(trimethylsilyloxy)-6-((trimethylsilyloxy)methyl)tetrahydropyran-2-one (206 g, 0.442 mol) in toluene (660 mL) at a rate that maintained the reaction temperature below −70° C. The mixture was stirred for 3 hours at −78° C. until starting material was consumed. Hydrochloric acid (36~38%, 62.3 mL, 0.747 mol) in methanol (440 mL) was slowly added, and the reaction temperature was maintained so as not to exceed −45° C. The reaction mixture was gradually warmed to 25° C. and stirred for 16 hours. The reaction was neutralized with saturated sodium bicarbonate to pH 7.5, the organic phase was separated, and the aqueous phase was extracted with ethyl acetate (2×1200 mL). The combined organic phases were washed with brine (2×2000 mL) and dried over sodium sulfate. After removal of the volatiles, the residues were dissolved in hot toluene (200 mL), and then this solution was poured into n-hexane (2000 mL) with fast stirring. After stirring for 1 hour, the reaction mixture was filtered. The filter cake was dried under vacuum to give 118 g of white solid, which was used for the next step without further purification. Purity (HPLC) 13.97 minutes, 76% (UV); MS ES$^+$ (m/z): 437 [M+1]$^+$.

Preparation of (2S,3R,4R,5S,6R)-2-(4-chloro-3-((4-cyclopropylphenyl)methyl-d$_2$)phenyl)-6-(hydroxymethyl)tetrahydro-2H-pyran-3,4,5-triol (54)

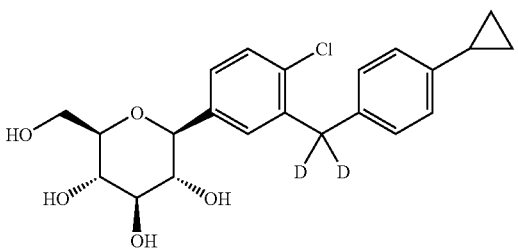

To a −45° C. solution of the above crude product (118 g, 0.270 mmol) in anhydrous acetonitrile/dichloromethane (1.42 L, 1:1) was added triethylsilane (126 g, 1.08 mol) followed by addition of boron trifluoride etherate (103 mL, 0.812 mol). The mixture was stirred for 2 hours at −10° C. The reaction was quenched with saturated aqueous bicarbonate to pH 7.5. The volatiles were removed under reduced pressure, and the residues were extracted with ethyl acetate (2×1500 mL). The combined organic phases were washed with brine (2×1000 mL) and were dried over sodium sulfate. The reaction mixture was concentrated to give 105 g of a white solid which was used for the next step without further purification. Purity (HPLC) 12.72 minutes, 76.0% (UV); MS ES$^+$ (m/z): 407 [M+1]$^+$.

Preparation of (2S,3R,4R,5S,6R)-2-(4-chloro-3-((4-cyclopropylphenyl)methyl-d$_2$)phenyl)-6-(hydroxymethyl)tetrahydro-2H-pyran-3,4,5-triol, bis(L-proline) complex (83)

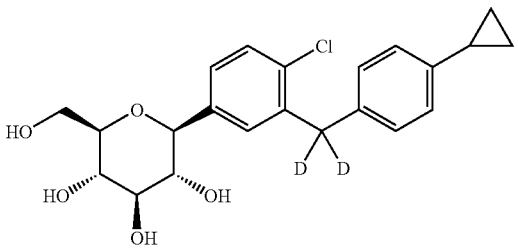 [SMILES: [2H]C([2H])(c1ccc(C2CC2)cc1)c1cc([C@@H]2O[C@H](CO)[C@@H](O)[C@H](O)[C@H]2O)ccc1Cl]
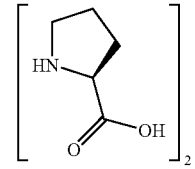

A 5 L 4-neck flask was charged with (2S,3R,4R,5S,6R)-2-(4-chloro-3-((4-cyclopropylphenyl)methyl-d$_2$)phenyl)-6-(hydroxymethyl)tetrahydro-2H-pyran-3,4,5-triol (105 g, 76% pure) and L-proline (59.5 g, 0.517 mol), and ethanol (798 mL) and water (42 mL) were added to the flask. After refluxing for 30 minutes with rapid mechanical stirring, n-heptane (1050 mL) was added dropwise. After the addition was complete, the reaction was cooled slowly to 25° C. and stirred for another 5 hours. The reaction mixture was then filtered. The filter cake was washed with n-heptane (2×300 mL) and then dried under vacuum at 55° C. to give 118 g of a white solid. This crude solid was dissolved in 95% ethanol/water (354 mL) at 75° C. with mechanical stirring. After the reaction solution was clear, n-heptane (590 mL) was added dropwise to it. After the addition was complete, the reaction was cooled slowly to 25° C. and stirred for another 5 hours. The reaction mixture was filtered, and the filter cake was washed with n-heptane (2×200 mL) and dried under vacuum at 65° C. to give 105 g of a white solid. This solid was recrystallized with 95% ethanol/water four times and dried under vacuum at 65° C. to give a white solid (73 g, 58.4% yield). Purity (HPLC) 99.0% (UV). HPLC retention time: 15.43 min; Waters XTerra C18, 5 μm pore size, 2.1×50 mm column; 1.0 mL/min, 8 min gradient; mobile phase: solvent A: 0.045% formic acid in acetonitrile, solvent B: 0.1. % formic acid in Milli-Q water. $^1$H-NMR (CD$_3$OD, 400 MHz): δ 7.34~7.25 (m, 3H), 7.08 (d, J=8.4 Hz, 2H), 6.79 (d, J=8.4 Hz, 2H), 4.10 (d, J=9.6 Hz, 1H), 4.05~3.97 (m, 2H), 3.87~3.84 (m, 1H), 3.70~3.65 (m, 1H), 3.49~3.37 (m, 5H), 3.32~3.21 (m, 3H), 2.36~2.27 (m, 2H), 2.17~2.08 (m, 2H), 2.01~1.95 (m, 4H), 1.87~1.84 (m, 1H), 0.92~0.87 (m, 2H), 0.63~0.59 (m, 2H).

Example 32

Preparation of (2S,3R,4R,5S,6R)-2-(4-chloro-3-((4-((E)-prop-1-enyl)phenyl)methyl-d$_2$)phenyl)-6-(hydroxymethyl)tetrahydro-2H-pyran-3,4,5-triol (84)

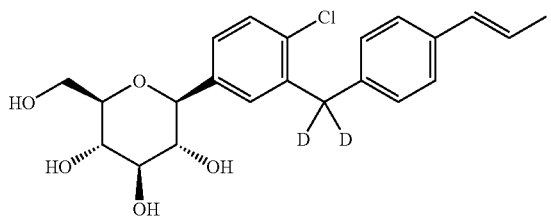 [SMILES: [2H]C([2H])(c1ccc(/C=C/C)cc1)c1cc([C@@H]2O[C@H](CO)[C@@H](O)[C@H](O)[C@H]2O)ccc1Cl]

This product was separated by preparative HPLC-MS from the mother liquid of 83. It is the major by-product of the reaction. HPLC-MS method: Method 3, retention time: 14.5 minutes, purity 99%; MS ES$^+$ (m/z): 407 [M+1]$^+$. $^1$H-NMR (CD$_3$OD, 400 MHz): δ 7.34~7.25 (m, 3H), 7.10 (d, J=8.4 Hz, 2H), 6.79 (d, J=8.4 Hz, 2H), 6.34 (d, J=16.0 Hz, 1H), 6.22~6.17 (m, 1H), 4.08 (d, J=9.6 Hz, 1H), 3.87~3.84 (m, 1H), 3.70~3.65 (m, 1H), 3.46~3.25 (m, 4H), 1.84~1.80 (m, 3H).

Example 33

Preparation of (2S,3R,4R,5S,6R)-2-(4-chloro-3-((4-cyclopropylphenyl)methyl-d$_2$)phenyl)-6-(hydroxymethyl)tetrahydro-2H-pyran-3,4,5-triol, L-phenylalanine complex (1:1) (85)

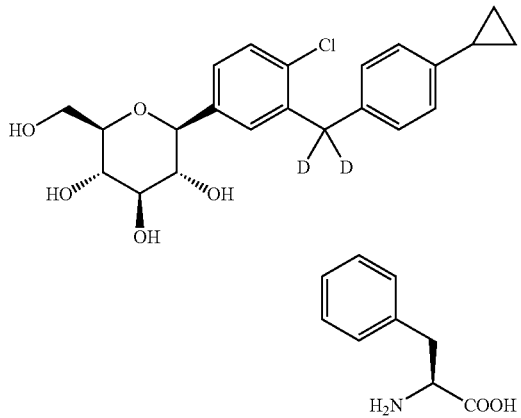 [SMILES: [2H]C([2H])(c1ccc(C2CC2)cc1)c1cc([C@@H]2O[C@H](CO)[C@@H](O)[C@H](O)[C@H]2O)ccc1Cl ; N[C@@H](Cc1ccccc1)C(=O)O]

A solution of L-phenylalanine (0.54 g, 3.3 mmol) and (2S,3R,4R,5S,6R)-2-(4-chloro-3-((4-cyclopropylphenyl)methyl-2)phenyl)-6-(hydroxymethyl)tetrahydro-2H-pyran-3,4,5-triol (1.36 g, 3.1 mmol, purity: 92%) in ethanol and water (20 mL, 1:1) was heated to 80° C. and became clear. The reaction mixture was cooled to 25° C. and was stirred for 24 hours. The reaction was then filtered, and the filter cake was washed with ethanol and hexane (20 mL, 1:1) and dried under vacuum at 40° C. to provide a white solid (3 g). The solid was dissolved in ethanol and water (40 mL, 20:1) at 75° C. After it was clear, the mixture was cooled slowly to 25° C. with stirring and stirred for 16 hours. This reaction mixture was filtered, and the filter cake was washed with pre-cooled ethanol/water (20 mL, 1:1) and dried under vacuum at 45° C. to give 830 mg of white solid. $^1$H-NMR (methanol-d$_4$, 400 MHz): δ 7.28-7.37 (m, 8H), 7.07-7.09 (m, 2H), 6.97-6.99 (m, 2H), 4.60 (s, 1H), 4.09-4.11 (m, 1H), 3.87-3.91 (m, 1H), 3.78-3.81 (m, 1H), 3.68-3.72 (m, 1H), 3.36-3.47 (m, 4H), 3.28-3.30 (m, 2H), 2.98-3.04 (m, 1H), 1.83-1.90 (m, 1H), 0.90-0.96 (m, 2H), 0.61-0.66 (m, 2H); purity (HPLC): 97% (UV).

Example 34

This example illustrates the preparation of compound 86 according to the approach provided in Scheme 28. The general method is applicable to other compounds of the present invention.

Scheme 28

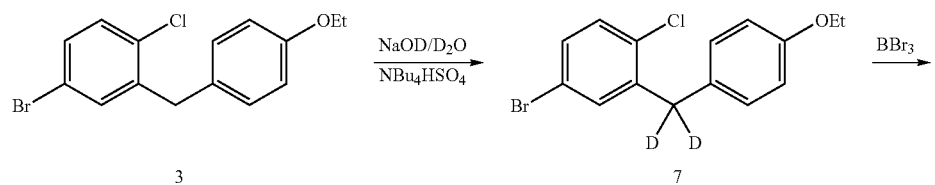

3  7

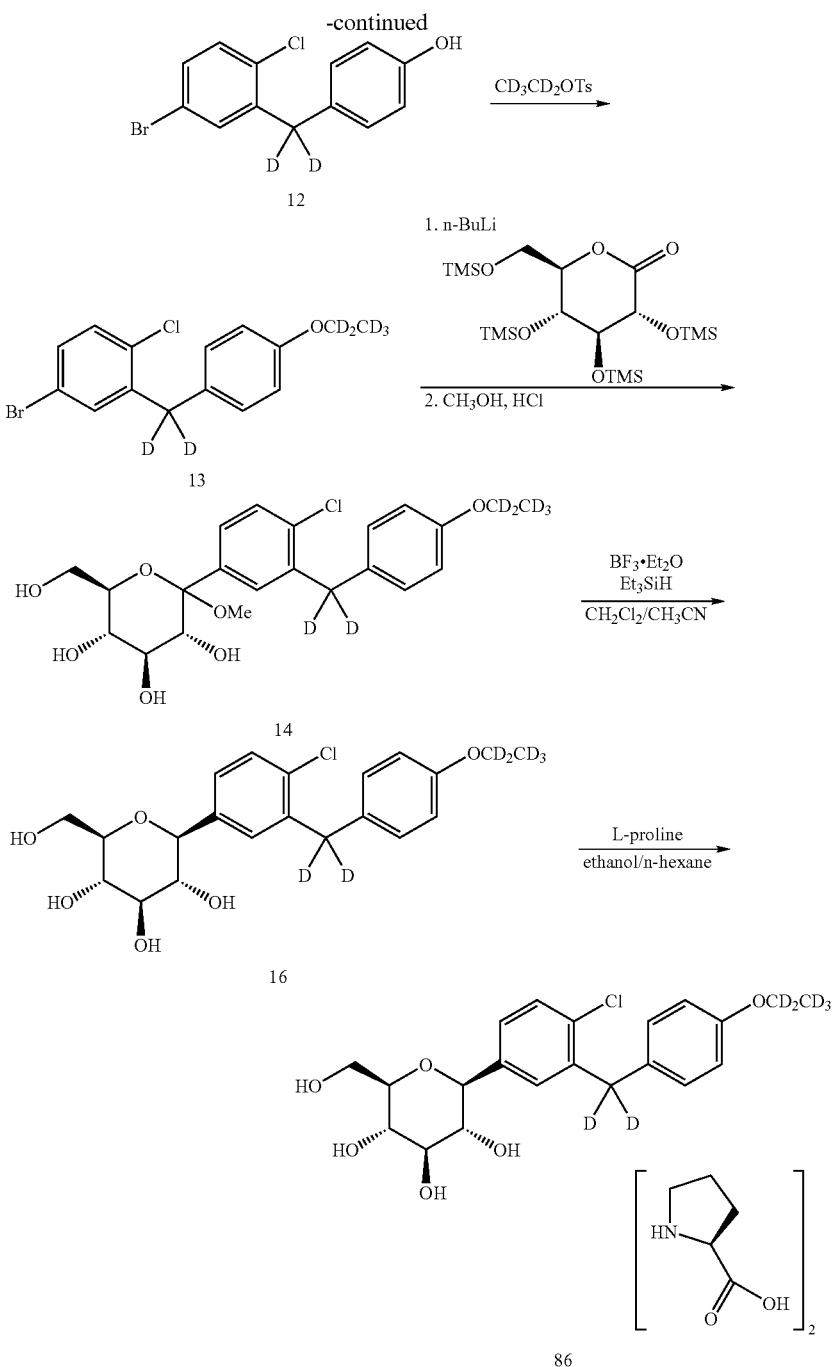

Preparation of 4-bromo-1-chloro-2-((4-ethoxyphenyl)methyl-d₂)benzene (7)

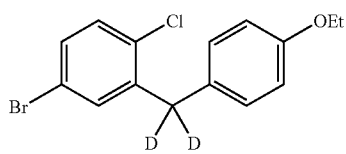 [SMILES: [2H]C([2H])(c1ccc(OCC)cc1)c1cc(Br)ccc1Cl]

Deuterium oxide (50.4 g, D, 99.9%) in a four-neck flask was cooled with an ice bath, and sodium hydride (21 g, 60% dispersion in mineral oil) was added to the above portion-wise over 1 hour while venting off the hydrogen deuteride. The mixture was allowed to warm to 25° C. and stirred for 10 minutes. To the solution of sodium deuteroxide in deuterium oxide (30%) was added hexane (10 mL), and the mixture was stirred until it turned clear. Tetrabutylammonium bisulfate (9.2 g, 0.04 mol) and 4-bromo-1-chloro-2-(4-ethoxybenzyl) benzene (50 g, 135 mmol) in hexane (250 mL) were added. The flask was sealed and stirred for 24 hours at 25° C. The color of the reaction turned to a yellow suspension. The hexane layer was added to fresh deuterium oxide (50.4 g, 99.9% D) solution of sodium deuteroxide (40%, in deuterium oxide), tetrabutylammonium bisulfate (9.2 g, 0.04 mol), and mineral oil (20 g, Sigma-Aldrich). The mixture was stirred overnight at room temperature. The aqueous layer was removed and used in the preparation of a second batch. The second batch of 4-bromo-1-chloro-2-(4-ethoxybenzyl)benzene (50 g, 135 mmol) was treated according to the above procedure. The combined organic layers were washed with saturated aqueous ammonium chloride, dried over sodium sulfate, and concentrated to afford the crude product (144 g).

Preparation of 4-((5-bromo-2-chlorophenyl)methyl-$d_2$)phenol (12)

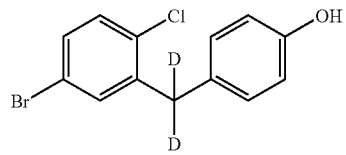 [SMILES: [2H]C([2H])(c1ccc(O)cc1)c1cc(Br)ccc1Cl]

4-bromo-1-chloro-2-((4-ethoxyphenyl)methyl-$d_2$)benzene (144 g, 306.7 mmol, crude) was dissolved in dichloromethane (500 mL) and cooled to −60° C. before boron tribromide (38 mL, 402 mol) was added to the solution. The mixture was slowly warmed to 25° C. and stirred for 3 hours. The above mixture was poured into ice water and extracted with dichloromethane. The organic layer was washed sequentially with saturated aqueous sodium bicarbonate, water, and brine. The organic layer was then dried over sodium sulfate and concentrated to give a yellow solid. The solid was suspended in 500 mL hexane, and the solution was stirred for 1 hour. The suspension was filtered to give a white solid. The product was again suspended in 500 mL hexane, and the above steps repeated to afford pure product (86 g, 85% yield). $^1$H-NMR (chloroform-d, 400 MHz): δ 7.24-7.32 (m, 3H), 7.07-7.09 (m, 2H), 6.79-6.82 (m, 2H), 4.77 (s, 1H), 4.02 (s, 0.03H); purity (HPLC) 99.7% (UV).

Preparation of ethyl-$d_5$ 4-methylbenzenesulfonate

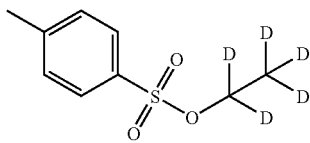 [SMILES: [2H]C([2H])([2H])C([2H])([2H])OS(=O)(=O)c1ccc(C)cc1]

Ethanol-$d_6$ (6 g, 115 mmol, 99.5 atom % D, Aldrich) dissolved in tetrahydrofuran (20 mL) was slowly added to a cooled solution of 4.6 N sodium hydroxide (75 mL) and maintained at a temperature below 5° C. Then 4-methylbenzene-1-sulfonyl chloride (26.3 g, 138 mmol) in tetrahydrofuran (20 mL) was slowly added to the above solution while the temperature was kept below 5° C. The mixture was stirred for 1 hour. The reaction mixture was then separated and extracted with ethyl acetate. The combined organic layers were washed with saturated ammonium chloride and brine, dried over anhydrous sodium sulfate, and concentrated to afford a colorless oil (18 g, ~78% yield).

Preparation of 4-bromo-1-chloro-2-((4-(ethoxy-$d_5$)phenyl)methyl-$d_2$)benzene (13)

4-((5-bromo-2-chlorophenyl)methyl-$d_2$)phenol (25 g, 83.4 mmol), ethyl-$d_5$ 4-methylbenzenesulfonate (15 g, 73 mmol), and potassium carbonate (30 g, 219 mmol) were dissolved in acetone (100 mL) at 25° C. and then refluxed for 16 hours. The volatiles were evaporated under reduced pressure. Ammonium chloride was added, and the mixture was extracted with ethyl acetate. The combined organic layers were washed with ammonium chloride and brine, dried over sodium sulfate, and then concentrated to give a residue. The residue was purified by column chromatography to afford a white solid (22 g, 92.8% yield). $^1$H-NMR (chloroform-d, 400 MHz): δ 7.24-7.29 (m, 3H), 7.10-7.13 (m, 2H), 6.85-6.87 (m, 2H).

Preparation of (3R,4S,5S,6R)-2-(4-chloro-3-((4-(ethoxy-$d_5$)phenyl)methyl-$d_2$)phenyl)-6-(hydroxymethyl)-2-methoxytetrahydro-2H-pyran-3,4,5-triol (14)

A 5 L 4-neck flask was charged with 4-bromo-1-chloro-2-((4-(ethoxy-$d_5$)phenyl)methyl-$d_2$)benzene (22.6 g, 0.068 mol), anhydrous toluene (80 mL) and tetrahydrofuran (40 mL). After stirring for 10 minutes and cooling to −65° C. under argon, n-butyllithium (35.4 mL, 2.5 M) was added dropwise, and the reaction temperature was maintained so as not to exceed −60° C. After the addition was complete, the reaction was stirred for another 1 hour at −60° C. to −65° C. A cold (−65° C.) solution of (3R,4S,5R,6R)-3,4,5-tris(trimethylsilyloxy)-6-((trimethylsilyloxy)methyl)tetrahydro-2H- pyran-2-one (34.9 g, 0.074 mole) in anhydrous toluene (120 mL) was transferred to the above reaction solution. After the addition was complete, the reaction was stirred for another 2 hours at −60° C. to −65° C. and then quenched by the addition of a solution of methanesulfonic acid (13.2 mL) in methanol (265 mL). During the quench, the reaction temperature was maintained so as not to exceed −30° C. After the addition was complete, the reaction was stirred for another 24 hours. The reaction was neutralized with saturated aqueous sodium carbonate to pH 8.0. The aqueous layer was extracted with ethyl acetate (3×500 mL), and the combined organic layers were washed with brine (2×500 mL) and dried over anhydrous sodium sulfate. The sample was concentrated under reduced pressure to provide the title compound as a brown oil. This crude product was used for the next step without purification. HPLC-MS method: Method 2, retention time 2.99 min., purity: 80%; MS ES⁺ (m/z): 490 (M+45)⁻.

Preparation of (2S,3R,4R,5S,6R)-2-(4-chloro-3-((4-(ethoxy-d₅)phenyl)methyl-d₂)phenyl)-6-(hydroxymethyl)tetrahydro-2H-pyran-3,4,5-triol (16)

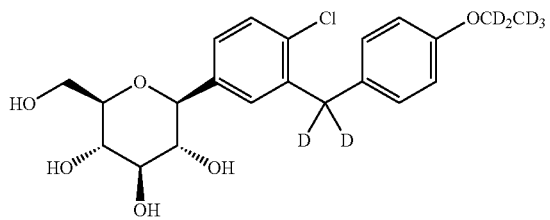

To a solution of the above crude product (30.3 g, 68.1 mmol) in dichloromethane/acetonitrile (500 mL, 1:1) was added triethylsilane (43.5 mL, 272.4 mmol) followed by addition of boron trifluoride etherate (25.9 mL, 204.3 mmol) at −40° C. under argon. After stirring for 2 hours below −15° C., the reaction was quenched by addition of saturated sodium carbonate to pH 7.5. The reaction mixture was evaporated, and the residue was dissolved in ethyl acetate (400 mL) and water (400 mL). The organic layer was washed with brine, dried over anhydrous sodium sulfate, and concentrated under reduced pressure to provide a yellow solid (24 g). This crude product was used for the next step without purification. HPLC-MS method: Method 2, retention time 2.86 min., purity: 70%; MS ES⁺ (m/z): 460 (M+45)⁻.

Preparation of (2S,3R,4R,5S,6R)-2-(4-chloro-3-((4-(ethoxy-d₅)phenyl)methyl-d₂)phenyl)-6-(hydroxymethyl)tetrahydro-2H-pyran-3,4,5-triol, bis(L-proline) complex (86)

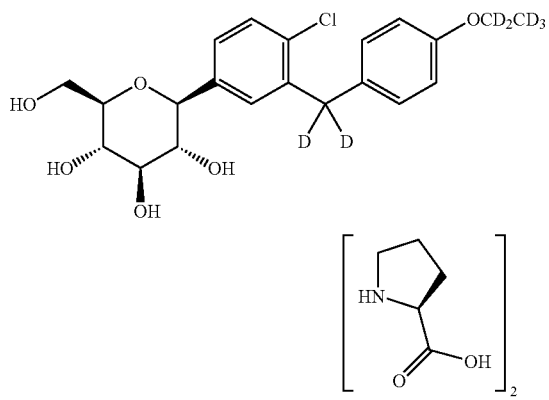

A solution of L-proline (13.3 g, 106 mmol) and the above crude product (24 g) in ethanol and water (232 mL, 20:1) was heated to 80° C. After 30 minutes, hexane (232 mL) was added. After the addition was complete, the reaction mixture was cooled to 25° C. and stirred for 3 hours. Then it was filtered, and the filter cake was washed with ethanol and hexane (100 mL, 20:1), and dried under vacuum at 40° C. to provide a white solid (18 g). The solid was dissolved in ethanol and water (60 mL, 20:1) at 75° C. After the solution became clear, hexane (60 mL) was added. The mixture was cooled slowly to 25° C. with stirring and stirred for 16 hours. The reaction mixture was filtered. The filter cake was washed with pre-cooled ethanol/water (95%, 10 mL) and dried under vacuum at 45° C. to give 15 g of white solid. HPLC-MS method: Method 2, retention time 2.86 min., purity: 95%. ¹H-NMR (methanol-d₄, 400 MHz): δ 7.30-7.37 (m, 3H), 7.10-7.12 (d, J=8.0 Hz, 2H), 6.80-6.82 (d, J=8.0 Hz, 2H), 4.09-4.11 (m, 1H), 3.97-4.0 (m, 2H), 3.87-3.91 (m, 1H), 3.71-3.72 (m, 1H), 3.22-3.47 (m, 9H), 2.30-2.35 (m, 2H), 2.11-2.16 (m, 2H), 1.98-2.03 (m, 4H); MS ES⁺ (m/z): 460 (M+45)⁻.

Example 35

This example illustrates the preparation of compounds 87 and 88 according to the approach provided in Scheme 29. The general method is applicable to other compounds of the present invention.

Scheme 29

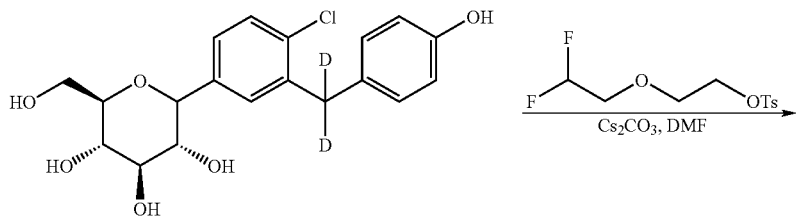

-continued

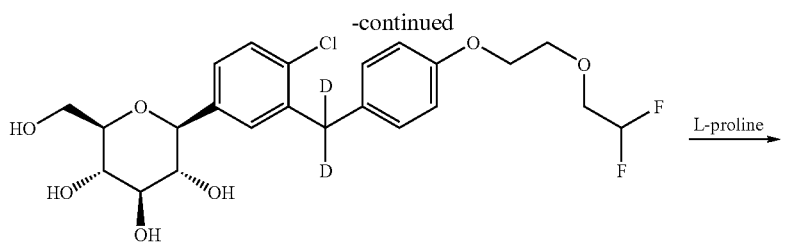

87

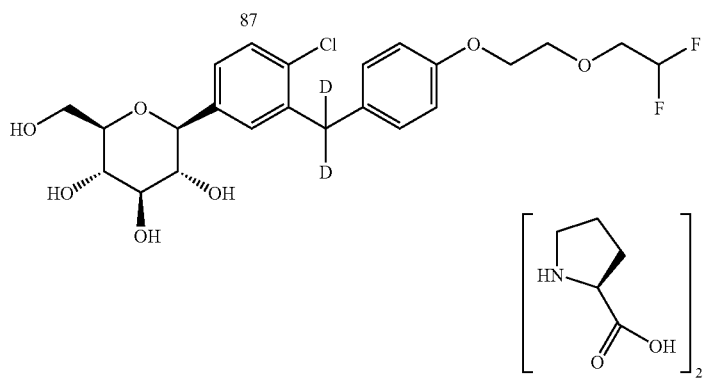

88

Preparation of (2S,3R,4R,5S,6R)-2-(4-chloro-3-((4-(2-(2,2-difluoroethoxy)ethoxy)phenyl)methyl-d₂)phenyl)-6-(hydroxymethyl)-tetrahydro-2H-pyran-3,4,5-triol (87)

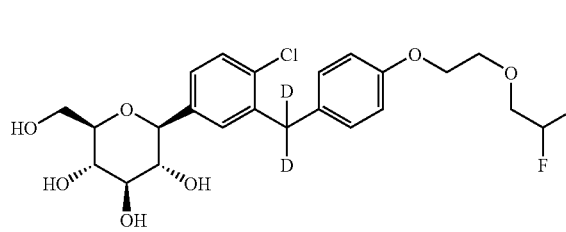

To a stirred suspension of (2S,3R,4R,5S,6R)-2-(4-chloro-3-((4-hydroxyphenyl)methyl-d₂)phenyl)-6-(hydroxymethyl)tetrahydro-2H-pyran-3,4,5-triol (100 mg, 0.3 mmol) in N,N-dimethylformamide (5 mL) and cesium carbonate (211 mg, 0.7 mmol) was added 2-(2,2-difluoroethoxy)ethyl 4-methylbenzenesulfonate (900 mg, 0.3 mmol). The mixture was stirred for 2 hours at 80° C. The solution was diluted with water, and the aqueous layer was extracted with ethyl acetate. The combined organic layers were washed with brine prior to drying over sodium sulfate and being concentrated. The residue was purified by preparative HPLC-MS to give 60 mg of white solid (47% yield). HPLC-MS method: Method 2, retention time 2.61 minutes, purity: 95%. ¹H-NMR (methanol-d₄, 400 MHz): δ 7.24~7.34 (m, 3H), 7.09-7.11 (d, J=8.8 Hz, 2H), 6.76-6.80 (d, J=8.8 Hz, 2H), 5.80-6.10 (m, 1H), 4.05-4.09 (m, 3H), 3.85-3.87 (m, 3H), 3.65-3.78 (m, 3H), 3.36-3.46 (m, 3H), 3.25-3.27 (1H, m); MS ES⁺ (m/z): 535 (M+45)⁻.

Preparation of (2S,3R,4R,5S,6R)-2-(4-chloro-3-((4-(2-(2,2-difluoroethoxy)ethoxy)phenyl)methyl-d₂)phenyl)-6-(hydroxymethyl)-tetrahydro-2H-pyran-3,4,5-triol, bis(L-proline) complex (88)

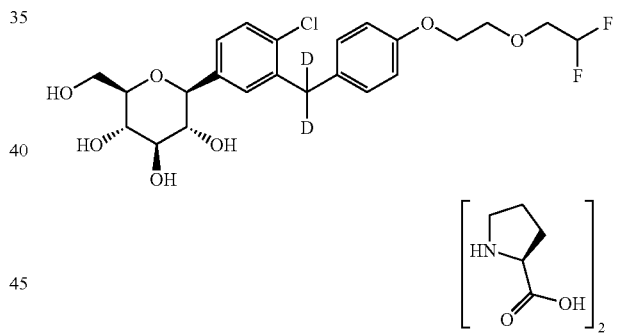

A solution of L-proline (15.6 g, 135 mmol) and (2S,3R,4R,5S,6R)-2-(4-chloro-3-((4-(2-(2,2-difluoroethoxy)ethoxy)phenyl)methyl-d₂)phenyl)-6-(hydroxymethyl)tetrahydro-2H-pyran-3,4,5-triol (35 g, 68 mmol) in ethanol and water (200 mL, 20:1) was heated to 80° C. After 30 minutes, hexane (200 mL) was added. After the addition was complete, the reaction mixture was cooled to 25° C. and stirred for 3 hours. The reaction was filtered. The filter cake was washed with ethanol and hexane (200 mL, 20:1) and dried under vacuum at 40° C. to provide a white solid (39 g). The sample was dissolved in ethanol and water (200 mL, 20:1) at 75° C. After the solution became clear, hexane (200 mL) was added. The mixture was cooled slowly to 25° C. with stirring and stirred for 16 hours. The reaction mixture was filtered, and the filter cake was washed with pre-cooled ethanol/water (20 mL, 95%) and dried under vacuum at 45° C. to give 20 g of white solid. ¹H-NMR (methanol-d₄, 400 MHz): δ 7.28-7.37 (m, 3H), 7.13-7.15 (m, 2H), 6.85-6.87 (m, 2H), 5.82-6.11 (tt, J=4.0 Hz, J=55.6 Hz, 1H), 4.10-4.12 (m, 3H), 3.97-4.00 (m, 2H), 3.89-3.91 (m, 3H), 3.68-3.82 (m, 3H), 3.37-3.47 (m, 5H), 3.21-3.31 (m, 3H), 2.27-2.36 (m, 2H), 2.09-2.18 (m, 2H), 1.96-2.03 (m, 4H). HPLC-MS method: Method 2, retention time 2.61 minutes, purity: 97%; MS ES$^+$ (m/z): 535 (M+45)$^-$.
Example 36
This example illustrates the preparation of compound 95 according to the approach provided in Scheme 30. The general method is applicable to other compounds of the present invention.
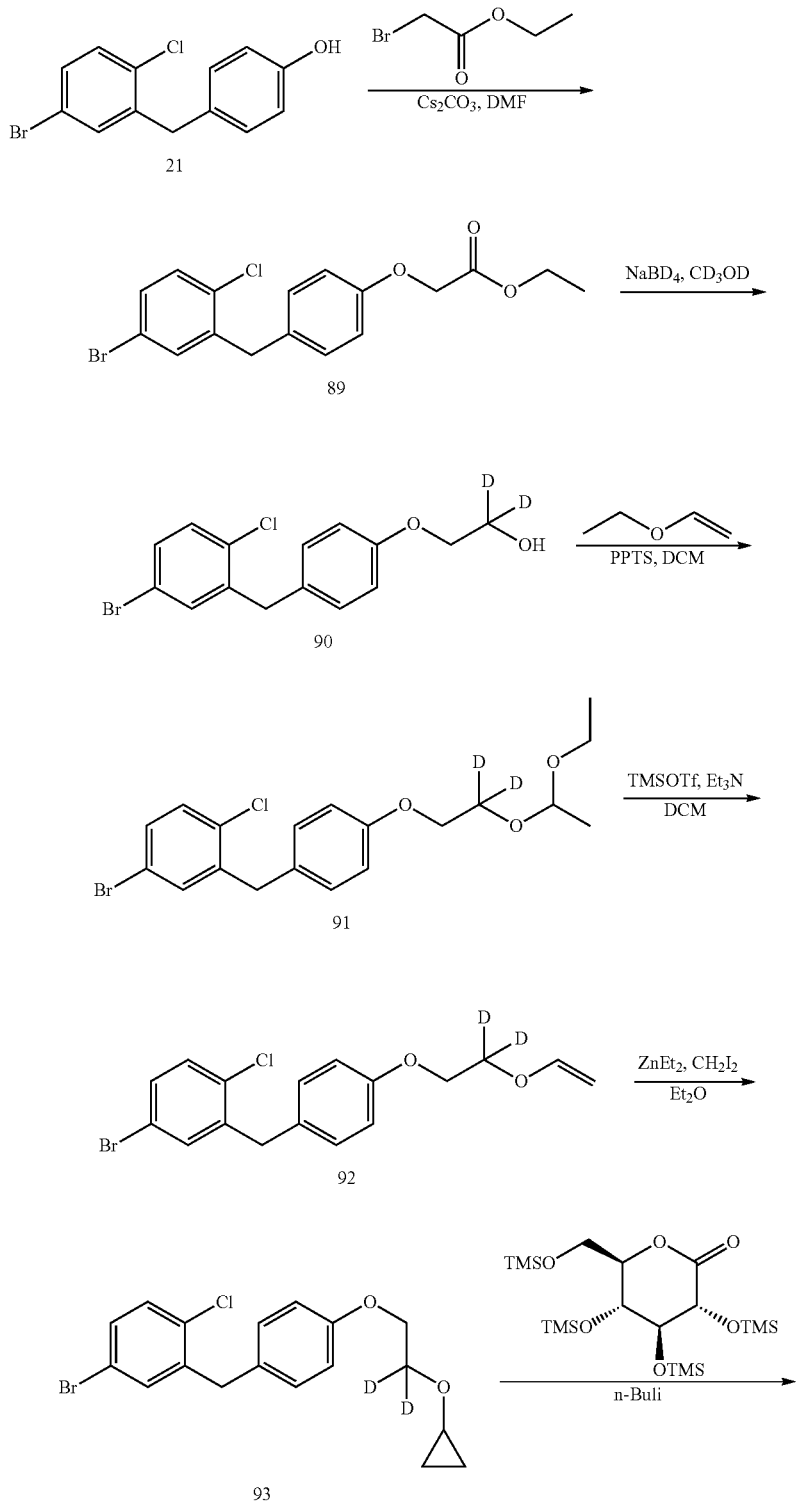

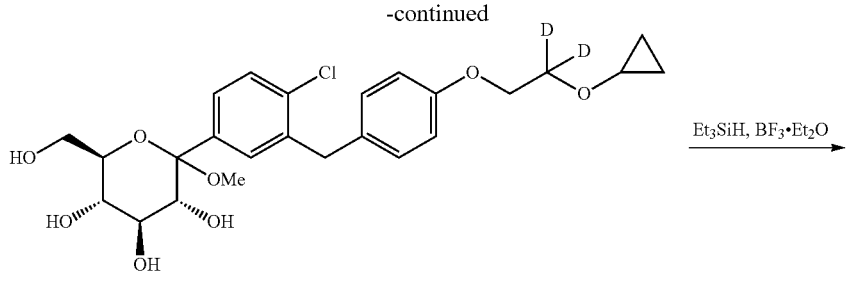

94

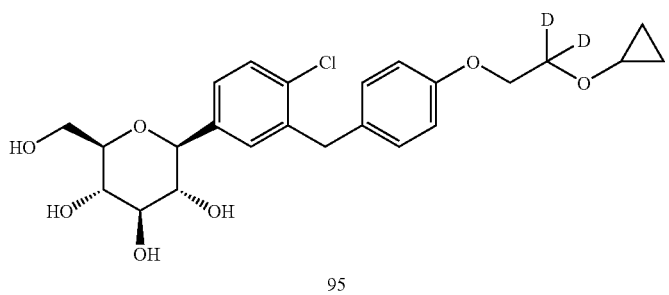 [SMILES: [2H]C([2H])(COc1ccc(Cc2cc([C@@H]3O[C@H](CO)[C@@H](O)[C@H](O)[C@H]3O)ccc2Cl)cc1)OC1CC1]

95

Preparation of ethyl 2-(4-(5-bromo-2-chlorobenzyl)phenoxy)acetate (89)

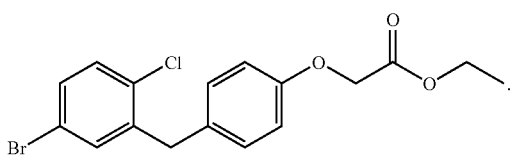 [SMILES: CCOC(=O)COc1ccc(Cc2cc(Br)ccc2Cl)cc1 ; "."]

To a stirred suspension of 4-(5-bromo-2-chlorobenzyl)phenol (5.0 g, 16.8 mmol) in N,N-dimethylformamide (20 mL) and cesium carbonate (11.0 g, 33.6 mmol) was added ethyl 2-bromoacetate (2.8 mL, 25.2 mmol). The mixture was stirred overnight at 80° C. The solution was diluted with water, and the aqueous layer was extracted with ethyl acetate. The combined organic layers were washed with brine prior to drying over sodium sulfate and concentrated under reduced pressure. The residue was purified by column chromatography to give 5.0 g of white solid (78% yield).

Preparation of 2-(4-(5-bromo-2-chlorobenzyl)phenoxy)ethan-1,1-$d_2$-ol (90)

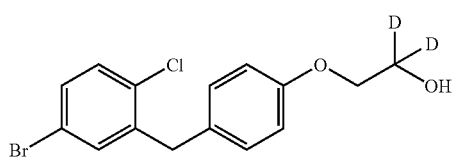 [SMILES: [2H]C([2H])(O)COc1ccc(Cc2cc(Br)ccc2Cl)cc1]

Methanol-$d_4$ (0.3 mL, 6.5 mmol, Aldrich, 99.8 atom % D) was slowly added into a solution of ethyl 2-(4-(5-bromo-2-chlorobenzyl)phenoxy)acetate (1.0 g, 2.6 mmol) and sodium borohydride-$d_4$ (0.3 g, 6.5 mmol, Isotec, 98 atom % D) in tetrahydrofuran (20 mL) at 65° C. The solution was stirred for 1.5 hours at 65° C. before the mixture was quenched with saturated ammonium chloride solution. The aqueous layer was extracted with ethyl acetate. The organic phases were combined and washed with brine prior to drying over sodium sulfate. After removal of the volatiles, 0.8 g of colorless oil was obtained (89% yield). $^1$H-NMR (CDCl$_3$, 400 MHz): δ 7.27-7.32 (m, 3H), 7.12-7.14 (d, J=8.4 Hz, 2H), 6.89-6.91 (d, J=8.4 Hz, 2H), 4.09 (s, 2H), 4.02 (s, 2H).

Preparation of 4-bromo-1-chloro-2-(4-(2-(1-ethoxyethoxy)ethoxy-2,2-$d_2$)-benzyl)benzene (91)

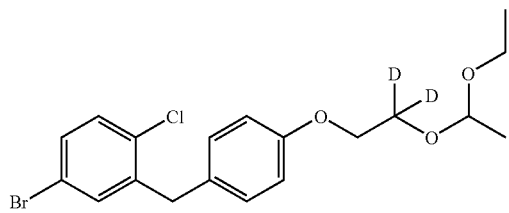 [SMILES: [2H]C([2H])(COc1ccc(Cc2cc(Br)ccc2Cl)cc1)OC(C)OCC]

Ethyl vinyl ether (1.1 mL, 11.6 mmol) and pyridinium p-toluenesulfonate (23.3 mg, 0.1 mmol) were added to a solution of 2-(4-(5-bromo-2-chlorobenzyl)-phenoxy)ethan-1,1-$d_2$-ol (0.8 g, 2.3 mmol) in dry dichloromethane (23 mL), and the mixture was stirred at room temperature for 2.5 hours. Solid sodium bicarbonate (6 g) was added and stirred for 30 minutes. The insoluble materials were filtered off, and the filtrate was dried over sodium sulfate and concentrated. The residue was purified by preparative TLC to afford 0.8 g of colorless oil (84% yield). $^1$H-NMR (CDCl$_3$, 400 MHz): δ 7.27-7.32 (m, 3H), 7.12-7.14 (d, J=8.4 Hz, 2H), 6.89-6.91 (d, J=8.4 Hz, 2H), 4.82-4.87 (q, J=5.2 Hz, 1H), 4.09 (s, 2H), 4.02 (s, 2H), 3.68-3.76 (m, 1H), 3.50-3.58 (m, 1H), 1.37-1.38 (d, J=5.2 Hz, 3H), 1.22-1.26 (t, J=7.2 Hz, 3H).

Preparation of 4-bromo-1-chloro-2-(4-(2-(vinyloxy)
ethoxy-2,2-d$_2$)-benzyl)benzene (92)

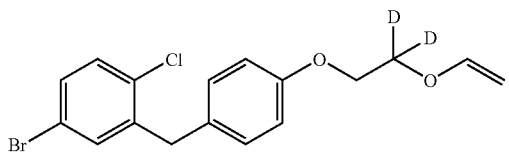 [SMILES: [2H]C([2H])(COc1ccc(Cc2cc(Br)ccc2Cl)cc1)OC=C]

To a solution of 4-bromo-1-chloro-2-(4-(2-(1-ethoxyethoxy)ethoxy-2,2-d$_2$)-benzyl)benzene (360 mg, 2.5 mmol) in anhydrous dichloromethane (10 mL) at 0° C. under nitrogen was added fresh distilled triethylamine (0.14 mL, 1.0 mmol), followed by trimethylsilyl trifluoromethanesulfonate (0.2 mL, 1.0 mmol) over 5 minutes. After 1 hour, 1.0 M sodium hydroxide (1.4 mL) was added, followed by ethyl acetate (10 mL). The organic layer was separated prior to drying over sodium sulfate and concentrated to give an oil. The residue was purified by preparative TLC to afford 0.3 g of colorless oil (83% yield). $^1$H-NMR (CDCl$_3$, 400 MHz): δ 7.27-7.32 (m, 3H), 7.12-7.14 (d, J=8.4 Hz, 2H), 6.89-6.91 (d, J=8.4 Hz, 2H), 6.50-6.60 (m, 1H), 4.20-6.30 (m, 1H), 4.08-4.09 (m, 1H), 4.09 (s, 2H), 4.02 (s, 2H).

Preparation of 4-bromo-1-chloro-2-(4-(2-cyclopropoxy(ethoxy-2,2-d$_2$))-benzyl)benzene (93)

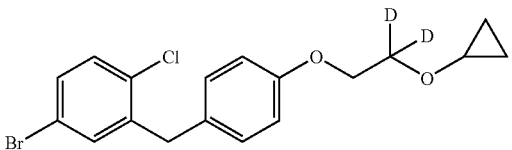 [SMILES: [2H]C([2H])(COc1ccc(Cc2cc(Br)ccc2Cl)cc1)OC1CC1]

Diethylzinc (2.5 mL, 1N in hexane, 2.5 mmol) was added to ethoxyethane (10 mL) and cooled to 0° C. Diiodomethane (1.2 mL, 2.5 mmol) was added dropwise to the above solution. The mixture was stirred at 0° C. for 30 minutes before a solution of 4-bromo-1-chloro-2-(4-(2-(vinyloxy)ethoxy-2,2-d$_2$)-benzyl)benzene (370 mg, 1.0 mmol) in ethoxyethane (5 mL) was added dropwise. The mixture was then warmed slowly to 25° C. and stirred overnight. Then the mixture was quenched with saturated ammonium chloride solution, and the organic layers were purified by preparative TLC to give 0.1 g of colorless oil (33% yield). $^1$H-NMR (CDCl$_3$, 400 MHz): δ 7.27-7.32 (m, 3H), 7.12-7.14 (d, J=8.4 Hz, 2H), 6.89-6.91 (d, J=8.4 Hz, 2H), 4.09 (s, 2H), 4.02 (s, 2H), 3.30-3.50 (m, 1H), 0.63-0.65 (m, 2H), 0.51-0.52 (m, 1H).

Preparation of (3R,4S,5S,6R)-2-(4-chloro-3-(4-(2-cyclopropoxy(ethoxy-2,2-d$_2$))benzyl)phenyl)-6-(hydroxymethyl)-2-methoxytetrahydro-2H-pyran-3,4,5-triol (94)

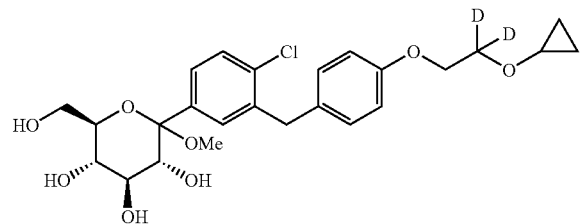 [SMILES: [2H]C([2H])(COc1ccc(Cc2cc(C3(OC)O[C@H](CO)[C@@H](O)[C@H](O)[C@H]3O)ccc2Cl)cc1)OC1CC1]

To a cold (−65° C.) solution of 4-bromo-1-chloro-2-(4-(2-cyclopropoxy(ethoxy-2,2-d$_2$))benzyl)benzene (100 mg, 0.26 mmol) in anhydrous toluene/tetrahydrofuran (3 mL, v/v=2:1) was added dropwise n-butyllithium (2.5 M in hexane, 0.13 mL), and the pale yellow mixture was stirred for 30 minutes at −65° C. The mixture was transferred to a cold (−65° C.) solution of (3R,4S,5R,6R)-3,4,5-tris(trimethylsilyloxy)-6-((trimethylsilyloxy)methyl)tetrahydro-2H-pyran-2-one (158 mg, 0.34 mmol) in toluene (2 mL). The mixture was stirred at −65° C. for 2 hours. The reaction was quenched with methanesulfonic acid (0.03 mL, 0.55 mmol) in methanol (0.5 mL), and the mixture was allowed to warm to 20° C. and stirred overnight. The reaction was then further quenched with saturated sodium bicarbonate. The organic phase was separated, and the aqueous phase was extracted with ethyl acetate. The organic phases were combined and washed with saturated sodium bicarbonate, water, and brine prior to drying over sodium sulfate. After removal of the volatiles, 150 mg of crude solid product was obtained.

Preparation of (2S,3R,4R,5S,6R)-2-(4-chloro-3-(4-(2-cyclopropoxy(ethoxy-2,2-d$_2$))benzyl)phenyl)-6-(hydroxymethyl)tetrahydro-2H-pyran-3,4,5-triol (95)

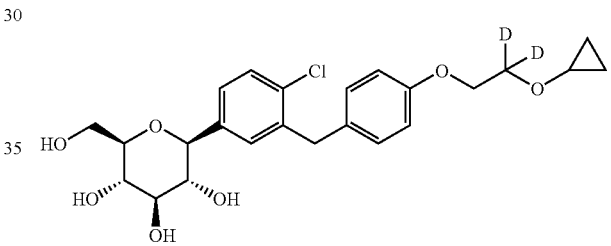

To a cold (−15° C.) solution of the crude product from the previous step (150 mg, ~0.26 mmol) in 1:1 anhydrous acetonitrile/dichloromethane (2 mL), was added triethylsilane (0.16 mL, 1.0 mmol). Boron trifluoride diethyl etherate (0.12 mL, 0.91 mmol) was added dropwise, and after the addition was complete, the mixture was stirred for 4 hours at −10° C. The reaction was quenched with saturated aqueous sodium bicarbonate. The volatiles were removed under reduced pressure, and the residue was extracted with ethyl acetate and washed with water and then with brine prior to drying over sodium sulfate. The product was filtered, concentrated to a solid, and purified by preparative HPLC-MS (HPLC-MS method: Method 2, retention time 3.0 min) to give 20 mg pure product (purity: 95%). $^1$H-NMR (methanol-d$_4$, 400 MHz): δ 7.24-7.34 (m, 3H), 7.11-7.13 (d, J=8.4 Hz, 2H), 6.84-6.86 (d, J=8.4 Hz, 2H), 4.04-4.11 (m, 4H), 3.80-3.85 (m, 1H), 3.62-3.70 (m, 1H), 3.31-3.43 (m, 6H), 0.50-0.58 (m, 4H); MS ES$^+$ (m/z): 511 (M+45)$^-$.

Example 37

This example illustrates the preparation of compound 101a according to the approach provided in Scheme 31. The general method is applicable to other compounds of the present invention. In this example, R$^k$ is H and R$^W$ is CD$_3$.

Scheme 31
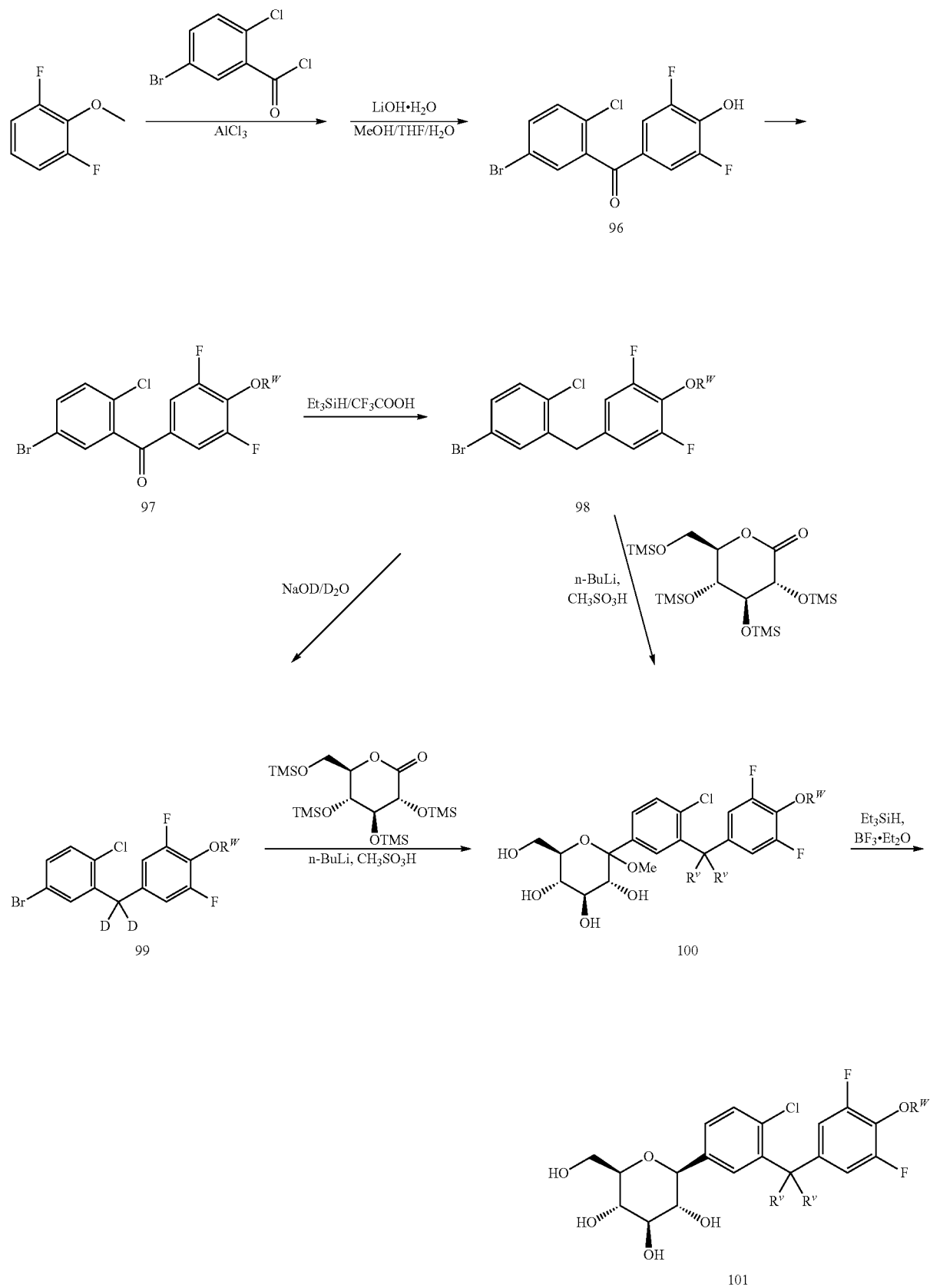

Preparation of (5-bromo-2-chlorophenyl)(3,5-difluoro-4-hydroxyphenyl)-methanone (96)

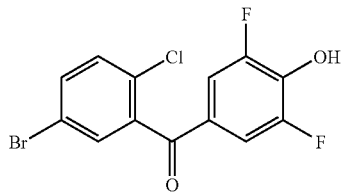 [SMILES: O=C(c1cc(F)c(O)c(F)c1)c1cc(Br)ccc1Cl]

To a solution of 5-bromo-2-chlorobenzoic acid (3.2 g, 13.5 mmol) in dichloromethane (40 mL), oxalyl dichloride (1.7 mL, 27.1 mmol) was added. Then N,N-dimethylformamide (50 mL) was added dropwise. After the vigorous evolution of gas ceased, the mixture was stirred at 25° C. overnight prior to removal of the volatiles under reduced pressure. The residue was dissolved in dichloromethane (20 mL) and cooled to 0° C. Aluminum trichloride (2.7 g, 20.4 mmol) was added in portions, and the mixture was stirred for 10 minutes. Then 1,3-difluoro-2-methoxybenzene (2.0 g, 13.8 mmol) was added, and the mixture was stirred at 0° C. for 2 hours. Then the reaction was allowed to warm to 25° C. overnight. The reaction was quenched with ice-water (30 mL) and extracted with dichloromethane (2×20 mL). The combined organic layers were washed with sodium hydroxide (2 M), water, hydrochloric acid (10%), and brine prior to drying over sodium sulfate. Crude product was obtained after dichloromethane was removed under reduced pressure. The sample was dissolved in tetrahydrofuran/methanol/water (30 mL, v/v/v=2:3:1), and lithium hydroxide monohydrate (700 mg) was added. The mixture was stirred for 1 hour at 25° C. The solvent was removed under reduced pressure. The aqueous layer was extracted with ethyl acetate (3×30 mL), and the extracts were washed with brine, dried over sodium sulfate, and concentrated to a crude product under reduced pressure. The residue was purified by silica column chromatography to give 1.46 g of white solid (30% yield, purity: 95%). $^1$H-NMR (CDCl$_3$, 400 MHz): δ 7.59-7.62 (m, 1H), 7.49-7.50 (m, 1H), 7.36-7.42 (m, 3H); HPLC-MS method: Method 2, retention time 3.81 min; MS ES$^+$ (m/z): 345 (M−1)$^-$.

Preparation of (5-bromo-2-chlorophenyl)(3,5-difluoro-4-(methoxy-d$_3$)phenyl)-methanone (97a)

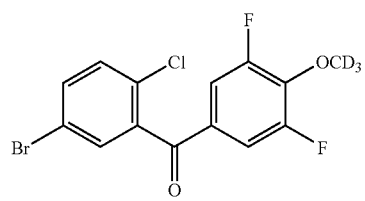

To a solution of (5-bromo-2-chlorophenyl)(3,5-difluoro-4-hydroxyphenyl)methanone (500 mg, 1.4 mmol) in acetone (5 mL), was added methyl-d$_3$ 4-methylbenzene-sulfonate (314 mg, 1.5 mmol) and potassium carbonate (580 mg, 4.1 mmol), and the mixture was stirred overnight at 25° C. The solvent was removed under reduced pressure, and the residue was dissolved in N,N-dimethylformamide (5 mL) and heated to 70° C. After 2 hours, water (10 mL) and ethyl acetate (20 mL) were added. The ethyl acetate layer was separated, and the aqueous layer was extracted with ethyl acetate (2×20 mL). The combined organic layers were washed with brine and concentrated to give 1.3 g of crude product, which was used for the next step without further purification.

Preparation of 5-(5-bromo-2-chlorobenzyl)-1,3-difluoro-2-(methoxy-d$_3$)benzene (98a)

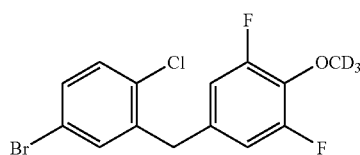

To a solution of (5-bromo-2-chlorophenyl)(3,5-difluoro-4-(methoxy-d$_3$)phenyl)-methanone (1.3 g, 3.5 mmol) in trifluoroacetic acid (10 mL) was added triethylsilane (1.3 mL, 8.1 mmol), and the mixture was stirred for 10 minutes at 25° C. Trifluoro-methanesulfonic acid (50 μL, cat.) was added, and the reaction briefly boiled. The mixture was stirred overnight at 25° C. and the volatiles were removed under reduced pressure. The residue was dissolved in ethyl acetate (20 mL), washed with saturated sodium carbonate, then with brine, dried over sodium sulfate, and concentrated to give a crude product. The crude product was purified by flash column chromatography to give 669 mg of product. $^1$H-NMR (CDCl$_3$, 400 MHz): δ 7.27-7.37 (m, 3H), 6.70-6.75 (m, 2H), 3.95 (s, 2H).

Preparation of (2S,3R,4S,5S,6R)-2-(4-chloro-3-(3,5-difluoro-4-(methoxy-d$_3$)-benzyl)phenyl)-6-(hydroxymethyl)-2-methoxytetrahydro-2H-pyran-3,4,5-triol (100a)

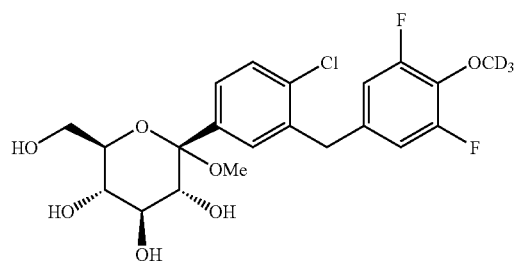

To a cold (−65° C.) solution of 5-(5-bromo-2-chlorobenzyl)-1,3-difluoro-2-(methoxy-d$_3$)benzene (200 mg, 0.57 mmol) in anhydrous toluene/tetrahydrofuran (3 mL, v/v=1:2) was added dropwise n-butyllithium (2.5 M in hexane, 0.3 mL, 0.8 mmol), and the orange solution was stirred for 30 min. The mixture was transferred to a cold (−65° C.) solution of (3R,4S,5R,6R)-3,4,5-tris(trimethylsilyloxy)-6-((trimethylsilyloxy)methyl)tetrahydro-2H-pyran-2-one (373 mg, 0.8 mmol) in toluene (3 mL). The mixture was stirred at −65° C. for 2 hours, and the reaction was quenched with methanesulfonic acid (80 μL) in methanol (1.6 mL). The mixture was allowed to warm to 20° C. and was stirred overnight. The reaction was quenched with saturated sodium bicarbonate, the organic layer was separated, and the aqueous layer was extracted with ethyl acetate (2×20 mL). The combined organic layers were washed with saturated sodium bicarbonate, water, and brine prior to drying over sodium sulfate to give a crude solid (200 mg) after removal of the volatiles. HPLC-MS method: Method 2, retention time 2.97 minutes, purity: 40%; MS ES+ (m/z): 508 (M+45)−.

Preparation of (2S,3R,4R,5S,6R)-2-(4-chloro-3-(3,5-difluoro-4-(methoxy-d$_3$)benzyl)phenyl)-6-(hydroxymethyl)tetrahydro-2H-pyran-3,4,5-triol (101a)

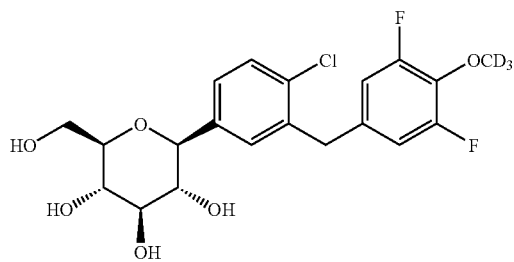

To a cold (−78° C.) solution of (2S,3R,4S,5S,6R)-2-(4-chloro-3-(3,5-difluoro-4-(methoxy-d$_3$)benzyl)phenyl)-6-(hydroxymethyl)-2-methoxytetrahydro-2H-pyran-3,4,5-triol (200 mg, 0.4 mmol, crude product from previous step) in acetonitrile/dichloromethane (4 mL, v/v=1:1) was added triethylsilane (0.3 mL, 1.6 mmol), followed by addition of boron trifluoride diethyl etherate (0.2 mL, 1.2 mmol). During the addition, the temperature was maintained between −60° C. and −40° C. The stirred solution was allowed to warm to 25° C. slowly over 1 hour. The reaction was quenched with saturated aqueous sodium bicarbonate (1 mL). The volatiles were removed under reduced pressure, and the residue was extracted with ethyl acetate (2×20 mL), washed with water and brine, dried over sodium sulfate, filtered, and concentrated to a solid. The solid was then purified by preparative HPLC-MS (HPLC-MS method: Method 2, retention time 2.80 min.) to give 4 mg of pure product (purity: 95%). $^1$H-NMR (methanol-d$_4$, 400 MHz): δ 7.33-7.41 (m, 3H), 6.78-6.84 (m, 2H), 4.03-4.16 (m, 3H), 3.88-3.91 (m, 1H), 3.70-3.74 (m, 1H), 3.42-3.51 (m, 3H), 3.29-3.33 (1H, m); MS ES+ (m/z): 478 (M+45)−.

Example 38

This example illustrates the preparation of compound 101b according to the approach provided in Scheme 31. In this example, R$^v$ is H and R$^w$ is CD$_2$CD$_3$.

Preparation of (5-bromo-2-chlorophenyl)(3,5-difluoro-4-(ethoxy-d$_5$)-phenyl)methanone (97b)

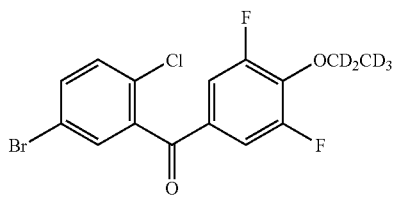

To a solution of (5-bromo-2-chlorophenyl)(3,5-difluoro-4-hydroxyphenyl)methanone (300 mg, 0.9 mmol) in acetone (5 mL) was added ethyl-d$_5$ 4-methylbenzenesulfonate (184 mg, 0.9 mmol) and potassium carbonate (348 mg, 2.5 mmol), and the mixture was heated to 70° C. overnight. The volatiles were removed under reduced pressure, and the residue was dissolved in ethyl acetate (15 mL). The organic layer was washed with brine and concentrated to give 385 mg of crude product, which was used in the next step without further purification.

Preparation of 5-(5-bromo-2-chlorobenzyl)-2-(ethoxy-d$_5$)-1,3-difluorobenzene (98b)

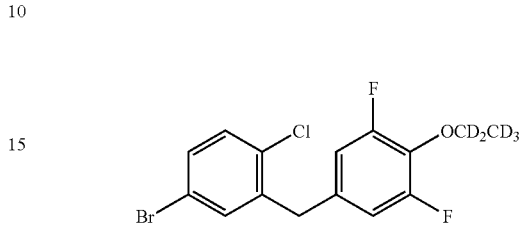

To a solution of (5-bromo-2-chlorophenyl)(3,5-difluoro-4-(ethoxy-d$_5$)phenyl)-methanone (385 mg, 1.0 mmol) in trifluoroacetic acid (3 mL) was added triethylsilane (0.3 mL, 2.0 mmol), and the mixture was stirred for 10 minutes at 25° C. Trifluoromethanesulfonic acid (50 μL, cat.) was added, and the reaction was briefly boiled. The mixture was stirred overnight at 25° C. The volatiles were removed under reduced pressure, and the residue was dissolved in ethyl acetate (20 mL). The ethyl acetate layer was washed with saturated sodium carbonate and brine, dried over sodium sulfate, and concentrated to give a crude product. 235 mg of pure product as colorless oil was obtained by silica column chromatography (74% two-step yield). $^1$H-NMR (CDCl$_3$, 400 MHz): δ 7.27-7.37 (m, 3H), 6.70-6.75 (m, 2H), 3.95 (s, 2H).

Preparation of (2S,3R,4S,5S,6R)-2-(4-chloro-3-(3,5-difluoro-4-(ethoxy-d$_5$)-benzyl)phenyl)-6-(hydroxymethyl)-2-methoxytetrahydro-2H-pyran-3,4,5-triol (100b)

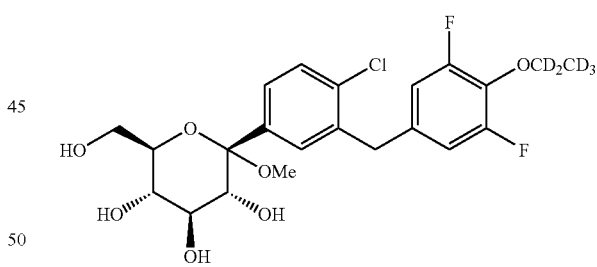

To a cold (−65° C.) solution of 5-(5-bromo-2-chlorobenzyl)-2-(ethoxy-d$_5$)-1,3-difluorobenzene (230 mg, 0.6 mmol) in anhydrous toluene/tetrahydrofuran (3 mL, v/v=1:2) was added dropwise n-butyllithium (2.5 M in hexane, 0.3 mL, 0.8 mmol), and the orange solution was stirred for 30 min. The mixture was transferred to a cold (−65° C.) solution of (3R,4S,5R,6R)-3,4,5-tris(trimethylsilyloxy)-6-((trimethylsilyloxy)methyl)tetrahydro-2H-pyran-2-one (353 mg, 0.8 mmol) in toluene (3 mL). The mixture was stirred at −65° C. for 2 hours. The reaction was quenched with methanesulfonic acid (80 μL) in methanol (1.6 mL), and the mixture was allowed to warm to 20° C. and stirred overnight. The reaction was quenched with saturated sodium bicarbonate. The organic layer was separated, and the aqueous layer was extracted with ethyl acetate (2×20 mL). The organic phases were combined and washed with saturated sodium bicarbonate, water, and brine prior to drying over sodium sulfate. After removal of the volatiles, 393 mg of crude solid product was obtained. HPLC-MS method: Method 1, retention time 1.83 minutes, purity: 60%; MS ES+ (m/z): 524 (M+45)−.

Preparation of (2S,3R,4R,5S,6R)-2-(4-chloro-3-(3,5-difluoro-4-(ethoxy-$d_5$)benzyl)phenyl)-6-(hydroxymethyl)tetrahydro-2H-pyran-3,4,5-triol (101b)

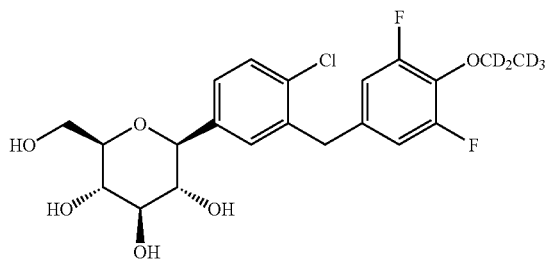

To a cold (−78° C.) solution of (2S,3R,4S,5S,6R)-2-(4-chloro-3-(3,5-difluoro-4-(ethoxy-d)benzyl)phenyl)-6-(hydroxymethyl)-2-methoxytetrahydro-2H-pyran-3,4,5-triol (393 mg, ~0.8 mmol, crude product from the previous step) in acetonitrile/dichloromethane (4 mL, v/v=1:1) was added triethylsilane (0.5 mL, 3.1 mmol), followed by addition of boron trifluoride diethyl etherate (0.3 mL, 8.1 mmol). During the addition, the temperature was maintained between −60° C. and −40° C. The stirred solution was allowed to warm to 25° C. slowly over 1 hour. The reaction was quenched with saturated aqueous sodium bicarbonate. The volatiles were removed under reduced pressure, and the residue was extracted with ethyl acetate (2×20 mL), washed with water and then with brine, dried over sodium sulfate, filtered, and concentrated to a solid. The solid was purified by preparative HPLC-MS (HPLC-MS method: Method 2, retention time 3.05 min., purity: 95%) to give 85 mg pure product (64% yield). $^1$H-NMR (methanol-$d_4$, 400 MHz): δ 7.33-7.41 (m, 3H), 6.78-6.84 (m, 2H), 4.03-4.16 (m, 3H), 3.88-3.91 (m, 1H), 3.70-3.74 (m, 1H), 3.42-3.51 (m, 3H), 3.29-3.33 (m, 1H); MS ES− (m/z): 494 (M+45)−.

Example 39

This example illustrates the preparation of compound 101c according to the approach provided in Scheme 31. In this example, R$^v$ is D and R$^w$ is CH$_3$.

Preparation of (5-bromo-2-chlorophenyl)(3,5-difluoro-4-methoxyphenyl)-methanone (97c)

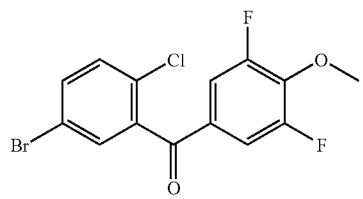 [SMILES: COc1c(F)cc(C(=O)c2cc(Br)ccc2Cl)cc1F]

To a solution of (5-bromo-2-chlorophenyl)(3,5-difluoro-4-hydroxyphenyl)methanone (600 mg, 1.7 mmol) in acetone (5 mL) was added iodomethane (50 μL, 2.6 mmol) and potassium carbonate (470 mg, 3.4 mmol), and the mixture was stirred overnight at 25° C. After the volatiles were removed under reduced pressure, the residue was dissolved in ethyl acetate (30 mL), washed with brine, and concentrated to give 629 mg of crude product, which was used in the next step without further purification.

Preparation of 5-(5-bromo-2-chlorobenzyl)-1,3-difluoro-2-methoxybenzene (98c)

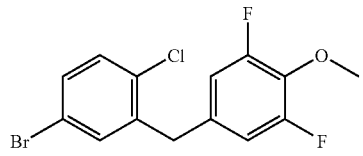 [SMILES: COc1c(F)cc(Cc2cc(Br)ccc2Cl)cc1F]

To a solution of (5-bromo-2-chlorophenyl)(3,5-difluoro-4-methoxy-phenyl)methanone (629 mg, 1.7 mmol) in trifluoroacetic acid (6 mL) was added triethylsilane (1.1 mL, 6.9 mmol), and the mixture was stirred for 10 minutes at 25° C. Trifluoromethane-sulfonic acid (50 μL) was added, and the reaction was briefly boiled. The mixture was stirred overnight at 25° C. before the volatiles were removed under reduced pressure. The residue was dissolved in ethyl acetate (20 mL) and was washed with saturated sodium carbonate and brine, dried over sodium sulfate, and concentrated to give a crude product. 573 mg of pure product was obtained by column chromatography (94.8% yield).

Preparation of 5-((5-bromo-2-chlorophenyl)methyl-$d_2$)-1,3-difluoro-2-methoxybenzene (99c)

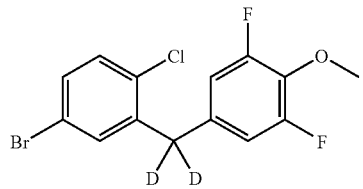 [SMILES: [2H]C([2H])(c1cc(F)c(OC)c(F)c1)c1cc(Br)ccc1Cl]

To a solution of sodium deuteroxide (123 mg, 40% in deuterium oxide) and deuterium oxide (41 mg) was added mineral oil (100 mg) followed by addition of tetrabutylammonium hydrogen sulfate (20 mg). 5-(5-Bromo-2-chlorobenzyl)-1,3-difluoro-2-methoxybenzene in hexane (1 mL) was added to the above solution, and the mixture was stirred at 25° C. overnight. From $^1$H-NMR, the D ratio was 95%. The hexane layer was washed with ammonium chloride (aq.) and concentrated under reduced pressure. 71 mg of pure product was obtained by column chromatography (70% yield).

Preparation of (2S,3R,4S,5S,6R)-2-(4-chloro-3-((3,5-difluoro-4-methoxyphenyl)methyl-$d_2$)phenyl)-6-(hydroxymethyl)-2-methoxytetrahydro-2H-pyran-3,4,5-triol (100c)

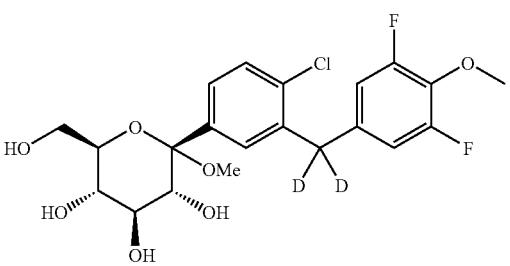 [SMILES: [2H]C([2H])(c1cc(F)c(OC)c(F)c1)c1cc([C@]2(OC)O[C@H](CO)[C@@H](O)[C@H](O)[C@H]2O)ccc1Cl]

To a cold (−65° C.) solution of 5-((5-bromo-2-chlorophenyl)methyl-d$_2$)-1,3-difluoro-2-methoxybenzene (71 mg, 0.2 mmol) in anhydrous toluene/tetrahydrofuran (1.5 mL, v/v=1:2) was added dropwise n-butyllithium (2.5 M in hexane, 0.1 mL, 0.3 mmol), and the pale yellow solution was stirred for 30 minutes. The mixture was transferred to a cold (−65° C.) solution of (3R,4S,5R,6R)-3,4,5-tris(trimethylsilyloxy)-6-((trimethylsilyloxy)methyl)tetrahydro-2H-pyran-2-one (113 mg, 0.3 mmol) in toluene (1.5 mL). The mixture was stirred at −65° C. for 2 hours. The reaction was quenched with methanesulfonic acid (27 µL) in methanol (0.5 mL), and the mixture was allowed to warm to 20° C. and stirred overnight. The reaction was quenched with saturated sodium bicarbonate (2 mL). The organic layer was separated, and the aqueous phase was extracted with ethyl acetate (2×10 mL). The organic phases were combined, washed with saturated sodium bicarbonate, then with water and then with brine, and then dried over sodium sulfate. After removal of the volatiles, 70 mg of crude solid product was obtained. HPLC-MS method: Method 2, retention time 2.96 minutes, purity 50%; MS ES$^+$ (m/z): 507 (M+45)$^-$.

Preparation of (2S,3R,4R,5S,6R)-2-(4-chloro-3-((3,5-difluoro-4-methoxyphenyl)methyl-d$_2$)phenyl)-6-(hydroxymethyl)tetrahydro-2H-pyran-3,4,5-triol (101c)

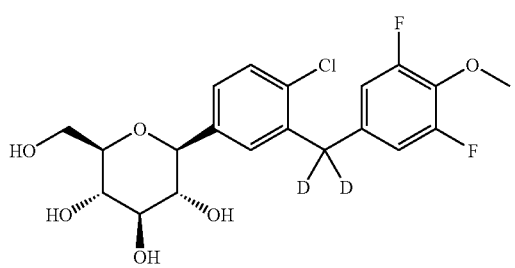 [SMILES: [2H]C([2H])(c1cc(F)c(OC)c(F)c1)c1cc([C@@H]2O[C@H](CO)[C@@H](O)[C@H](O)[C@H]2O)ccc1Cl]

To a cold (−78° C.) solution of (2S,3R,4S,5S,6R)-2-(4-chloro-3-((3,5-difluoro-4-methoxyphenyl)methyl-d$_2$)phenyl)-6-(hydroxymethyl)-2-methoxytetrahydro-2H-pyran-3,4,5-triol (70 mg, ~0.15 mmol, crude product from the previous step) in acetonitrile/dichloromethane (2 mL, v/v 1:1) was added triethylsilane (0.13 mL, 0.8 mmol), followed by addition of boron trifluoride diethyl etherate (70 µL, 0.6 mmol). During the addition, the temperature was maintained between −60° C. and −40° C. The reaction was allowed to warm to room temperature over 1 hour. The reaction was quenched with saturated aqueous sodium bicarbonate (0.5 mL), and the volatiles were removed under reduced pressure. The residue was extracted with ethyl acetate (2×20 mL), washed with water and then with brine, and dried over sodium sulfate. The sample was filtered and concentrated to give a white foam. The foam was purified by preparative HPLC-MS. (HPLC-MS method: Method 2, retention time 2.81 minutes, 95% pure) to give 17 mg of a white solid (26% yield). $^1$H-NMR (methanol-d$_4$, 400 MHz): δ 7.33-7.41 (m, 3H), 6.78-6.84 (m, 2H), 4.14-4.16 (m, 1H), 3.81-3.91 (m, 4H), 3.70-3.74 (m, 1H), 3.39-3.51 (m, 3H), 3.29-3.33 (1H, m); MS ES$^+$ (m/z): 477 (M+45)$^-$.

Example 40

This example illustrates the preparation of compound 101d according to the approach provided in Scheme 31. In this example, R$^v$ is D and R$^w$ is CD$_3$.

Preparation of 5-((5-bromo-2-chlorophenyl)methyl-d$_2$)-1,3-difluoro-2-(methoxy-d$_3$)benzene (99d)

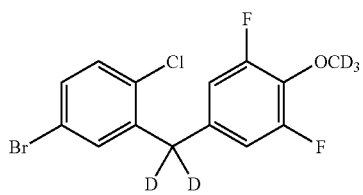

To a solution of sodium deuteroxide (695 mg, 40% in deuterium oxide) and deuterium oxide (234 mg), was added mineral oil (500 mg) followed by addition of tetrabutylammonium hydrogen sulfate (100 mg). 5-(5-Bromo-2-chlorobenzyl)-1,3-difluoro-2-(methoxy-d$_3$)benzene in hexane (6 mL) was added, and the mixture was stirred at 25° C. overnight. From $^1$H-NMR, D ratio was 95%. The hexane layer was washed with ammonium chloride (aq.) and concentrated under reduced pressure. 411 mg of pure product was obtained by column chromatography (68% yield).

Preparation of (2S,3R,4S,5S,6R)-2-(4-chloro-3-((3,5-difluoro-4-(methoxy-d$_3$)phenyl)methyl-d$_2$)phenyl)-6-(hydroxymethyl)-2-methoxytetrahydro-2H-pyran-3,4,5-triol (100d)

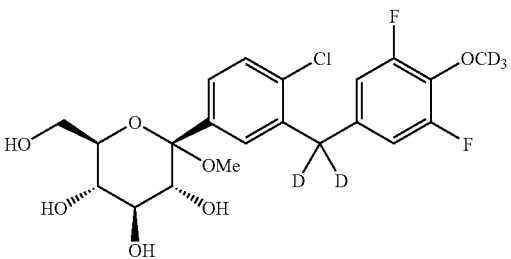

To a cold (−65° C.) solution of 5-((5-bromo-2-chlorophenyl)methyl-d$_2$)-1,3-difluoro-2-(methoxy-d$_3$)benzene (411 mg, 1.2 mmol) in anhydrous toluene/tetrahydrofuran (4.5 mL, v/v=1:2) was added dropwise n-butyllithium (2.5 M in hexane, 0.6 mL, 1.5 mmol), and the orange solution was stirred for 30 minutes at −65° C. The mixture was transferred to a cold (−65° C.) solution of 3R,4S,5R,6R)-3,4,5-tris(trimethylsilyloxy)-6-((trimethylsilyloxy)methyl)tetrahydro-2H-pyran-2-one (747 mg, 1.6 mmol) in toluene (4.5 mL). The mixture was stirred at −65° C. for 2 hours. The reaction was quenched with methanesulfonic acid (0.2 mL) in methanol (4 mL), and the mixture was allowed to warm to 20° C. and stirred overnight. The reaction was further quenched with saturated sodium bicarbonate (2 mL). The organic phase was separated, and the aqueous phase was extracted with ethyl acetate (2×20 mL). The organic phases were combined, washed sequentially with saturated sodium bicarbonate, water, and brine, and then dried over sodium sulfate. After removal of the volatiles, 609 mg of crude solid product was obtained. HPLC-MS method: Method 2, retention time 2.98 min., purity 78%. MS ES$^+$ (m/z): 510 (M+45)$^-$.

Preparation of (2S,3R,4R,5S,6R)-2-(4-chloro-3-((3,5-difluoro-4-(methoxy-d₃)phenyl)methyl-d₂)phenyl)-6-(hydroxymethyl)tetrahydro-2H-pyran-3,4,5-triol (101d)

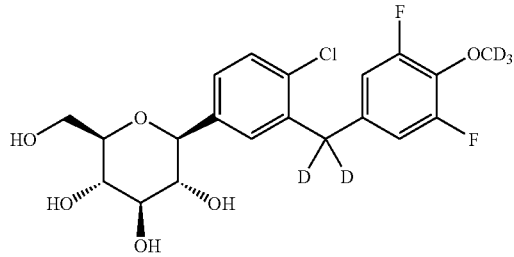

To a cold (−78° C.) solution of (2S,3R,4S,5S,6R)-2-(4-chloro-3-((3,5-difluoro-4-(methoxy-d₃)phenyl)methyl-d₂)phenyl)-6-(hydroxymethyl)-2-methoxytetrahydro-2H-pyran-3,4,5-triol (609 mg, ~1.3 mmol, crude product) in acetonitrile/dichloromethane (4 mL, v/v=1:1) was added triethylsilane (0.8 mL, 5.2 mmol), followed by addition of boron trifluoride diethyl etherate (0.5 mL, 4.0 mmol). During the addition, the temperature was maintained between −60° C. and −40° C. The stirred solution was allowed to warm to 25° C. slowly over 1 hour. The reaction was quenched with saturated aqueous sodium bicarbonate (2 mL). The volatiles were removed under reduced pressure. The residue was extracted with ethyl acetate (2×20 mL), washed with water and brine, and then dried over sodium sulfate. The sample was filtered and concentrated to a white foam. 66.91 mg pure product was obtained by preparative HPLC-MS (HPLC-MS method: Method 2, retention time 2.80 minutes, purity 95%) (12% yield). ¹H-NMR (methanol-d₄, 400 MHz): δ 7.34-7.41 (m, 3H), 6.78-6.82 (m, 2H), 4.14-4.17 (m, 1H), 3.89-3.92 (m, 1H), 3.71-3.75 (m, 1H), 3.40-3.52 (m, 3H), 3.30-3.33 (1H, m); MS ES⁺ (m/z): 480 (M+45)⁻.

Example 41

This example illustrates the preparation of compound 101e according to the approach provided in Scheme 31. In this example, R$^v$ is D and R$^w$ is CD₂CD₃.

Preparation of 5-((5-bromo-2-chlorophenyl)methyl-d₂)-1,3-difluoro-2-(ethoxy-d₅)benzene (99e)

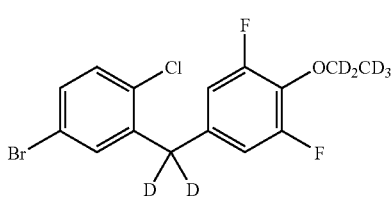

To a solution of sodium deuteroxide (383 mg, 40% in deuterium oxide) and deuterium oxide (96 mg) was added mineral oil (200 mg) and tetrabutylammonium hydrogen sulfate (34 mg). 5-(5-Bromo-2-chlorobenzyl)-2-(ethoxy-d₅)-1,3-difluorobenzene in hexane (3 mL) was added, and the mixture was stirred at 25° C. overnight. From ¹H-NMR, the D ratio was 95%. The hexane layer was washed with ammonium chloride (aq.) and concentrated under reduced pressure. 181 mg of pure product as a colorless oil was obtained by silica column chromatography (74% yield).

Preparation of (3R,4S,5S,6R)-2-(4-chloro-3-((3,5-difluoro-4-(ethoxy-d₅)phenyl)methyl-d₂)phenyl)-6-(hydroxymethyl)-2-methoxytetrahydro-2H-pyran-3,4,5-triol (100e)

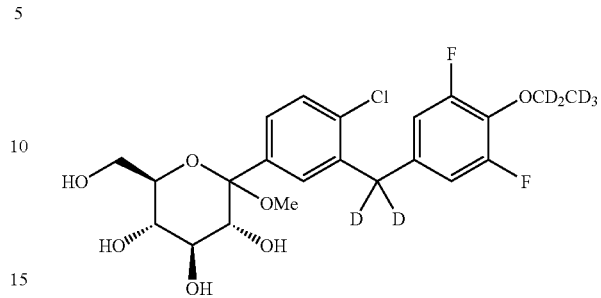

To a cold (−65° C.) solution of 5-((5-bromo-2-chlorophenyl)methyl-d₂)-1,3-difluoro-2-(ethoxy-d₅)benzene (181 mg, 0.5 mmol) in anhydrous toluene/tetrahydrofuran (3 mL, v/v=1:2) was added dropwise n-butyllithium (2.5 M in hexane, 0.2 mL, 0.6 mmol), and the orange solution was stirred for 30 minutes at −65° C. The mixture was transferred to a cold (−65° C.) solution of (3R,4S,5R,6R)-3,4,5-tris(trimethylsilyloxy)-6-((trimethylsilyloxy)methyl)tetrahydro-2H-pyran-2-one (327 mg, 0.6 mmol) in toluene (3 mL). The mixture was stirred at −65° C. for 2 hours. The reaction was quenched with methanesulfonic acid (80 μL) in methanol (1.6 mL), and the mixture was allowed to warm to 20° C. and stirred overnight. The reaction was quenched with saturated sodium bicarbonate. The organic phase was separated, and the aqueous phase was extracted with ethyl acetate (2×20 mL). The organic phases were combined, washed sequentially with saturated sodium bicarbonate, water, and brine, and then dried over sodium sulfate. After removal of the volatiles, 266 mg of crude solid product was obtained. HPLC-MS method: Method 2, retention time 3.19 min., purity 53%. MS ES⁺ (m/z): 526 (M+45)⁻.

Preparation of (2S,3R,4R,5S,6R)-2-(4-chloro-3-((3,5-difluoro-4-(ethoxy-d₅)phenyl)methyl-d₂)phenyl)-6-(hydroxymethyl)tetrahydro-2H-pyran-3,4,5-triol (101e)

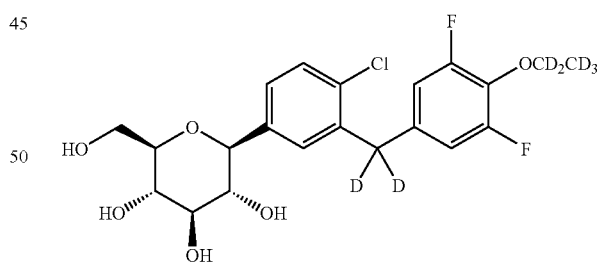

To a cold (−78° C.) solution of (3R,4S,5S,6R)-2-(4-chloro-3-((3,5-difluoro-4-(ethoxy-d₅)phenyl)methyl-d₂)phenyl)-6-(hydroxymethyl)-2-methoxytetrahydro-2H-pyran-3,4,5-triol (266 mg, ~0.6 mmol, crude product from the previous step) in acetonitrile/dichloromethane (3 mL, v/v 1:1) was added triethylsilane (0.4 mL, 2.4 mmol), followed by addition of boron trifluoride diethyl etherate (0.2 mL, 1.6 mmol). During the addition, the temperature was maintained between −60° C. and −40° C. The stirred solution was allowed to warm to 25° C. slowly over 1 hour. The reaction was quenched with saturated aqueous sodium bicarbonate (1 mL). The volatiles were removed under reduced pressure, and the residue was extracted with ethyl acetate (2×10 mL). The extracts were washed with water and then with brine prior to drying over sodium sulfate. The sample was filtered and concentrated to give a white foam, and 35.74 mg of pure product was obtained by preparative HPLC-MS. (HPLC-MS method: Method 2, retention time 3.03 minutes, purity 95%) (14% yield). $^1$H-NMR (methanol-$d_4$, 400 MHz): δ 7.33-7.41 (m, 3H), 6.78-6.84 (m, 2H), 4.14-4.16 (m, 1H), 3.89-3.92 (m, 1H), 3.70-3.74 (m, 1H), 3.41-3.50 (m, 3H), 3.29-3.33 (1H, m); MS ES$^-$ (m/z): 496 (M+45)$^-$.

Example 42

This example illustrates the preparation of compound 102.

Preparation of (2S,3R,4R,5S,6R)-2-(4-chloro-3-((3,5-difluoro-4-hydroxyphenyl)methyl-$d_2$)phenyl)-6-(hydroxymethyl)tetrahydro-2H-pyran-3,4,5-triol (102)

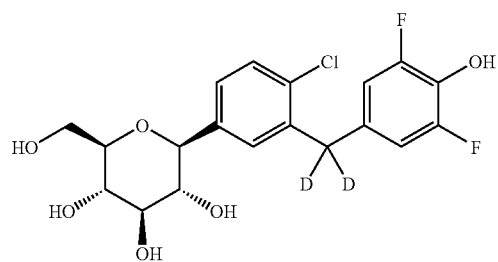 [SMILES: [2H]C([2H])(c1cc(F)c(O)c(F)c1)c1cc([C@@H]2O[C@H](CO)[C@@H](O)[C@H](O)[C@H]2O)ccc1Cl]

To a solution of (2S,3R,4R,5S,6R)-2-(4-chloro-3-((3,5-difluoro-4-(methoxy-$d_3$)phenyl)methyl-$d_2$)phenyl)-6-(hydroxymethyl)tetrahydro-2H-pyran-3,4,5-triol (84 mg, 0.19 mmol) in dichloromethane (5 mL) at −78° C., boron tribromide (0.8 mL, 2 M in dichloromethane) was added dropwise. The mixture was allowed to warm to 0° C. over 2 hours. Sodium carbonate and ice-water (10 mL) were then added to quench the reaction. The volatiles were removed under reduced pressure. The aqueous layer was extracted with ethyl acetate (20 mL) and was washed with brine and concentrated under reduced pressure to give 230 mg of crude product. The sample was purified by preparative HPLC-MS. (HPLC-MS method: Method 2, retention time 2.24 minutes, purity 95%) to give 3 mg pure product. $^1$H-NMR (methanol-$d_4$, 400 MHz): δ 7.32-7.40 (m, 3H), 6.73-6.75 (m, 2H), 4.12-4.15 (m, 1H), 3.88-3.91 (m, 1H), 3.70-3.74 (m, 1H), 3.41-3.50 (m, 3H), 3.29-3.33 (m, 1H); MS ES$^+$ (m/z): 417 (M−1)$^-$.

Example 43

This example illustrates the preparation of compound 105a according to the approach provided in Scheme 32. The general method is applicable to other compounds of the present invention. In this example, R$^v$ is D, R$^m$ is cyclopropyl, R$^p$ is H.

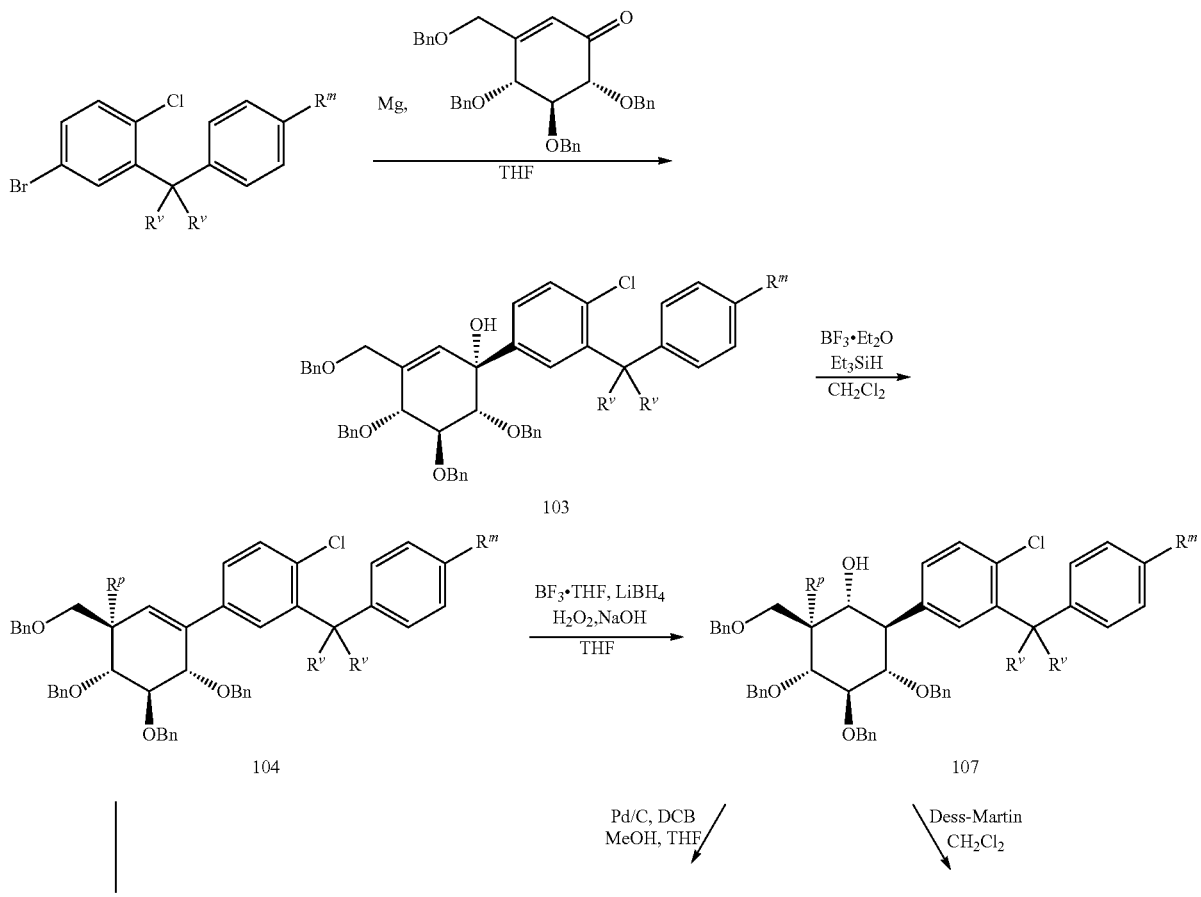

-continued

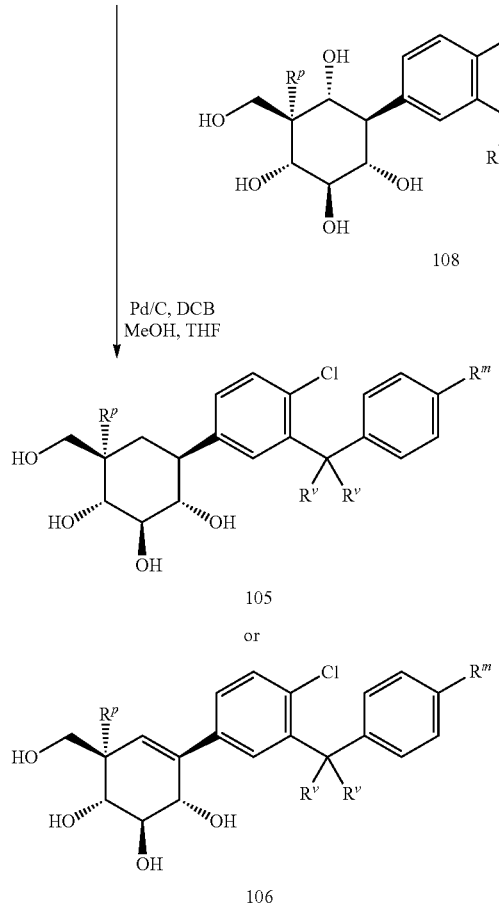

105 or

106

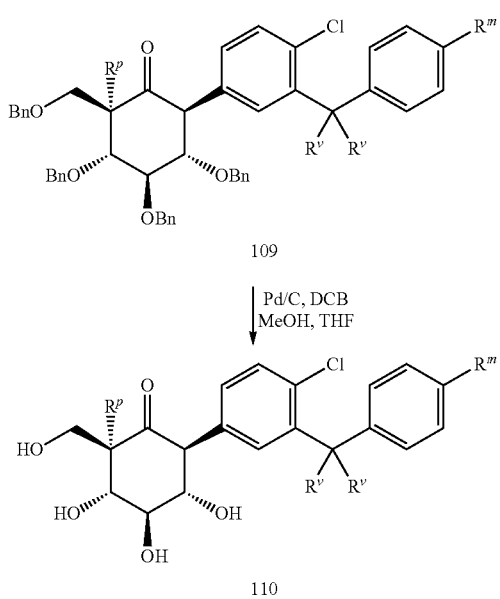

109

110

Preparation of 4-bromo-1-chloro-2-((4-cyclopropylphenyl)methyl-d$_2$)benzene (52)

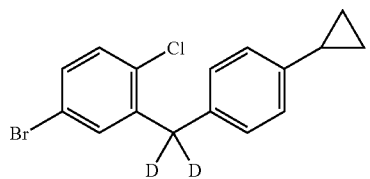 [SMILES: [2H]C([2H])(c1ccc(C2CC2)cc1)c1cc(Br)ccc1Cl]

To a stirred solution of (5-bromo-2-chlorophenyl)(4-cyclopropylphenyl)methanone (500 mg, 1.50 mmol) in trifluoroacetic acid (5 mL) triethyl(silane-d) (500 mg, 4.27 mmol, Aldrich, 97 atom % D) and trifluoromethanesulfonic acid (0.01 mL, cat.) were added sequentially at 25° C. After stirring for about 2 hours, the reaction mixture was poured onto ice-water and extracted with methylene chloride (3×10 mL). The combined organic layers were washed with water and brine, dried over sodium sulfate, and concentrated to give a residue. The residue was purified by preparative TLC (petroleum ether:ethyl acetate=10:1) to give 469 mg of title compound as white solid (97% yield). $^1$H-NMR (CDCl$_3$, 400 MHz): δ 7.27-7.30 (m, 2H), 7.23-7.25 (m, 1H), 7.06 (dd, J=8 Hz, 4H), 1.86-1.92 (m, 1H), 0.93-1.00 (m, 2H), 0.67-0.71 (m, 1H).

Preparation of (1R,4R,5S,6R)-4,5,6-tris(benzyloxy)-3-(benzyloxymethyl)-1-(4-chloro-3-((4-cyclopropylphenyl)methyl-d$_2$)phenyl)cyclohex-2-enol (103a)

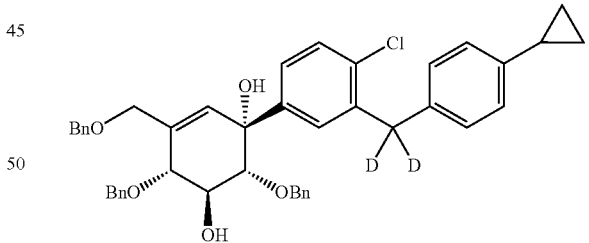

Under argon, Mg powder (89.4 mg, 3.73 mmol) was charged into a three-necked flask, followed by addition of a portion of the solution of 4-bromo-1-chloro-2-((4-cyclopropylphenyl)methyl-d$_2$)benzene (0.3 g, 0.90 mmol) in anhydrous tetrahydrofuran (3 mL), and 1,2-dibromoethane (0.05 mL). The mixture was then heated to reflux. After the reaction was initiated (an exotherm and consumption of Mg were observed), the rest of the solution of 4-bromo-1-chloro-2-((4-cyclopropylphenyl)methyl-d$_2$)benzene (0.7 g, 2.1 mmol) in anhydrous tetrahydrofuran (7 mL) was added dropwise. The mixture was then allowed to react for another 1 hour with gentle refluxing until most of Mg was consumed. The above Grignard reagent was added dropwise into the solution of (4R,5S,6R)-4,5,6-tris(benzyloxy)-3-(benzyloxymethyl)cyclohex-2-enone (1.49 g, 2.7 mmol) in anhydrous tetrahydrofuran (5 mL) under argon at 25° C. The reaction stirred for 3 hours. The reaction mixture was quenched with saturated aqueous ammonium chloride (10 mL) and then extracted with ethyl acetate (3×50 mL). The organic layers were combined, washed with brine, dried over sodium sulfate, and concentrated to give a residue as yellow oil (3.5 g). HPLC-MS method: Method 2, retention time 6.68 minutes, purity 73%; MS ES$^+$ (m/z): 796 (M+18)$^+$.

Preparation of ((1R,2S,3S,6R)-6-(benzyloxymethyl)-4-(4-chloro-3-((4-cyclopropylphenyl)methyl-d$_2$)phenyl)cyclohex-4-ene-1,2,3-triyl)tris(oxy)tris(methylene)tribenzene (104a)

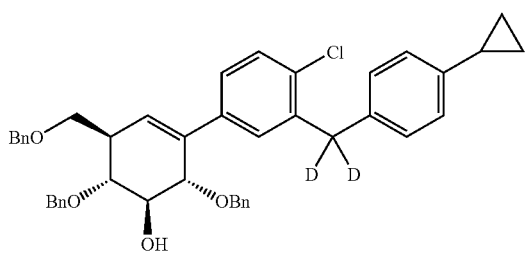 [SMILES: [2H]C([2H])(c1ccc(C2CC2)cc1)c1cc(C2=C[C@H](COCc3ccccc3)[C@@H](OCc3ccccc3)[C@H](O)[C@H]2OCc2ccccc2)ccc1Cl]

To a cooled solution (−25° C.) of (1R,4R,5S,6R)-4,5,6-tris(benzyloxy)-3-(benzyloxymethyl)-1-(4-chloro-3-((4-cyclopropylphenyl)methyl-d$_2$)phenyl)cyclohex-2-enol (300 mg, crude, ~0.26 mmol) in methylene chloride (4 mL), triethylsilane (90.56 mg, 0.78 mmol) followed by borontrifluoride ethyl ether complex (73.8 mg, 0.52 mmol) was added dropwise slowly. The reaction mixture was allowed to stir 2 hours at this temperature. The reaction was then quenched with saturated aqueous ammonium chloride (5 mL) and extracted with methylene chloride (3×20 mL). The organic layers were combined, washed with brine, dried over sodium sulfate, and concentrated to give a residue as yellow oil. The residue was purified by preparative TLC (petroleum ether:ethyl acetate=10:1) to give a white solid (120 mg, 61% yield). HPLC-MS method: Method 2, retention time 6.47 minutes, purity 89%; MS ES$^+$ (m/z): 763 (M+1)$^+$, 780 (M+18)$^+$.

Preparation of (1R,2R,3S,4S,6R)-4-(4-chloro-3-((4-cyclopropylphenyl)methyl-d$_2$)phenyl)-6-(hydroxymethyl)cyclohexane-1,2,3-triol (105a)

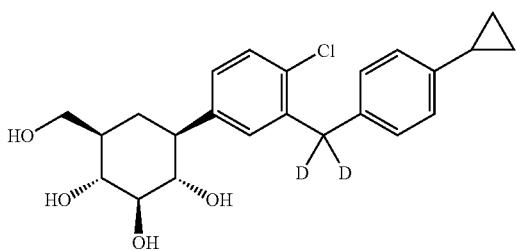

To a solution of ((1R,2S,3S,6R)-6-(benzyloxymethyl)-4-(4-chloro-3-((4-cyclopropylphenyl)methyl-d$_2$)phenyl)cyclohex-4-ene-1,2,3-triyl)tris(oxy)tris(methylene)tribenzene (20 mg, 0.026 mmol) in tetrahydrofuran/methanol (v:v=2:1, 6 mL), palladium 10% on carbon (20 mg) was added and stirred for 1.5 hours under hydrogen atmosphere. The mixture was then filtered, and the filtrate was concentrated to a residue as yellow oil. The residue was purified by preparative HPLC-MS to give 6.5 mg as white solid (61% yield). $^1$H-NMR (CD$_3$OD, 400 MHz): δ 7.29-7.33 (m, 1H), 7.07-7.15 (m, 4H), 6.97-6.99 (m, 2H), 3.75-3.79 (m, 1H), 3.57-3.62 (m, 1H), 3.43-3.48 (m, 1H), 2.39 (b, 1H), 1.84-1.89 (m, 1H), 0.90-0.95 (m, 1H), 0.62-0.65 (m, 1H). HPLC-MS method: Method 2, retention time 3.30 minutes, purity 96.5%. MS ES$^+$ (m/z): 405 (M+1)$^+$, 422 (M+18)$^+$; MS ES$^+$ (m/z): 449 (M+45).

Example 44

This example illustrates the preparation of compound 105b according to the approach provided in Scheme 32. In this example, R$^v$ is D, R$^m$ is n-propyl, R$^p$ is H.

Preparation of (1R,2R,3S,4S,6R)-4-(4-chloro-3-((4-propylphenyl)methyl-d$_2$)phenyl)-6-(hydroxymethyl)cyclohexane-1,2,3-triol (105b)

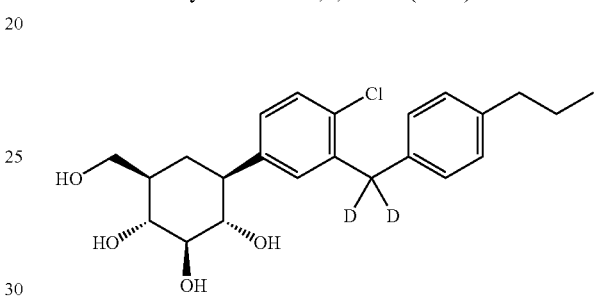

Compound 105b was prepared from 104a using the hydrogenation process described in Example 43 for the preparation of 105a, except that the reaction time was prolonged from 1.5 hours to 5 hours. $^1$H-NMR (CD$_3$OD. 400 MHz): δ 7.31-7.33 (m, 1H), 7.07-7.17 (m, 6H), 3.77 (dd, J=10.6, 4 Hz, 1H), 3.60-3.61 (m, 1H), 3.44-3.46 (m, 1H), 2.54-2.57 (m, 3H), 1.81-1.85 (m, 1H), 1.60-1.66 (m, 3H), 1.39-1.42 (m, 1H), 0.94 (t, J=7.6 Hz, 3H). HPLC-MS method: Method 2, retention time 3.56 minutes, purity 91%. MS ES$^+$ (m/z): 407 (M+1)$^+$, 424 (M+18)$^+$, 429 (M+23)$^+$; MS ES$^+$ (m/z): 451 (M+45)$^-$.

Example 45

This example illustrates the preparation of compound 106a according to the approach provided in Scheme 32. In this example, R$^v$ is D, R$^m$ is cyclopropyl, R$^p$ is H.

Preparation of (1R,2S,3S,6R)-4-(4-chloro-3-((4-cyclopropylphenyl)methyl-d$_2$)phenyl)-6-(hydroxymethyl)cyclohex-4-ene-1,2,3-triol (106a)

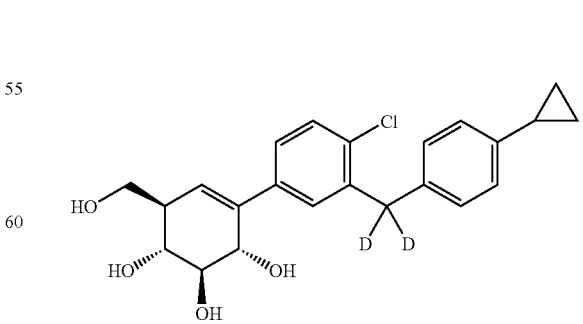

Compound 106a was prepared from 104a using the hydrogenation process described in Example 43 for the preparation of 105a, except that the reaction time was shortened from 1.5 hours to 0.5 hours. $^1$H-NMR (CD$_3$OD, 400 MHz): δ 7.23-7.33 (m, 3H), 7.08 (d, J=8.0 Hz, 2H), 6.98 (d, J=8.0 Hz, 2H), 5.86 (s, 1H), 4.50-4.52 (m, 1H), 3.88 (dd, J=10.4, 4.0 Hz, 1H), 3.52-3.68 (m, 3H), 2.38-2.40 (m, 1H), 1.84-1.89 (m, 1H), 0.90-1.03 (m, 2H), 0.62-0.64 (m, 2H). HPLC-MS method: Method 2, retention time 3.32 minutes, purity 98.3%. MS ES$^+$ (m/z): 403 (M+1)$^+$, 420 (M+18)$^+$, 425 (M+23)$^+$; MS ES$^+$ (m/z): 447 (M+45)$^-$.

Example 46

This example illustrates the preparation of compound 108c according to the approach provided in Scheme 32. In this example, R$^v$ is D, R$^m$ is ethyl, R$^p$ is H.

Preparation of (1R,2S,3R,4R,5S,6R)-3,4,5-tris(benzyloxy)-2-(benzyloxymethyl)-6-(4-chloro-3-((4-ethylphenyl)methyl-d$_2$)phenyl)cyclohexanol (107c)

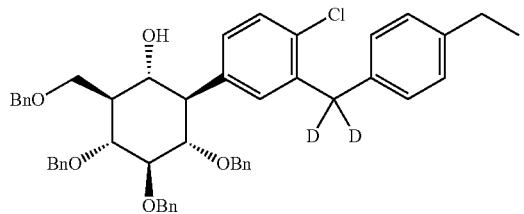 [SMILES: [2H]C([2H])(c1ccc(CC)cc1)c1cc([C@@H]2[C@@H](O)[C@H](COCc3ccccc3)[C@@H](OCc3ccccc3)[C@H](OCc3ccccc3)[C@H]2OCc2ccccc2)ccc1Cl]

To a cooled solution (0° C.) of ((1R,2S,3S,6R)-6-(benzyloxymethyl)-4-(4-chloro-3-((4-ethylphenyl)methyl-d$_2$)phenyl)cyclohex-4-ene-1,2,3-triyl)tris(oxy)tris(methylene)tribenzene (80 mg, 0.11 mmol; prepared using methods analogous to those described in Example 43) in anhydrous tetrahydrofuran (2 mL), borane-tetrahydrofuran complex (1 M in tetrahydrofuran, 0.32 mL, 0.32 mmol) was added dropwise followed by lithium borohydride (2 M in tetrahydrofuran, 0.05 mL, 0.025 mmol) under argon. The reaction mixture was then warmed to 70-80° C. for about 40 minutes with vigorous refluxing. Hydrogen peroxide (70.9 mg, 2.1 mmol, 30%) was added to the mixture followed by aqueous sodium hydroxide (3 M in water, 0.14 mL, 0.41 mmol) at 0° C. The mixture was extracted with ethyl acetate (3×10 mL), and the combined the organic layers were washed with brine (2×10 mL), dried over sodium sulfate, and concentrated to a residue. The residue was purified by preparative TLC (petroleum ether:ethyl acetate=6:1) to give 45 mg of white solid (55% yield). HPLC-MS method: Method 2, retention time 4.82 minutes, purity 33%. MS ES$^+$ (m/z): 769 (M+1)$^+$, 786 (M+18)$^+$.

Preparation of (1R,2R,3S,4R,5R,6S)-4-(4-chloro-3-((4-ethylphenyl)methyl-d$_2$)phenyl)-6-(hydroxymethyl)cyclohexane-1,2,3,5-tetraol (108c)

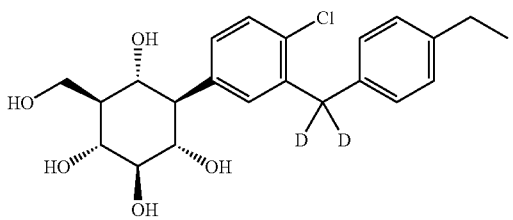 [SMILES: [2H]C([2H])(c1ccc(CC)cc1)c1cc([C@H]2[C@H](O)[C@@H](O)[C@H](O)[C@@H](CO)[C@@H]2O)ccc1Cl]

Compound 108c was prepared from 107c using the hydrogenation process described in Example 43 for the preparation of 105a. $^1$H-NMR (CD$_3$OD, 400 MHz): δ 7.35 (d, J=8.4 Hz, 1H), 7.09-7.20 (m, 6H), 3.93 (d, J=3.2 Hz, 2H), 3.668 (m, 1H), 3.35-3.49 (m, 3H), 2.56-2.63 (m, 3H), 1.5 (m, 1H), 1.21 (t, J=7.6 Hz, 3H). HPLC-MS method: Method 2, retention time 2.86 minutes, purity 91%. MS ES$^+$ (m/z): 409 (M+1)$^+$, 426 (M+18)$^+$, 431 (M+23)$^+$; MS ES$^-$ (m/z): 453 (M+45)$^-$.

Example 47

This example illustrates the preparation of compound 108d according to the approach provided in Scheme 32. In this example, R$^v$ is D, R$^m$ is ethyl, R$^p$ is D.

Preparation of ((1R,2S,3S,6R)-6-(benzyloxymethyl)-4-(4-chloro-3-((4-ethylphenyl)methyl-d$_2$)phenyl)-cyclohex-4-ene-6-d-1,2,3-triyl)tris(oxy)tris(methylene)tribenzene (104d)

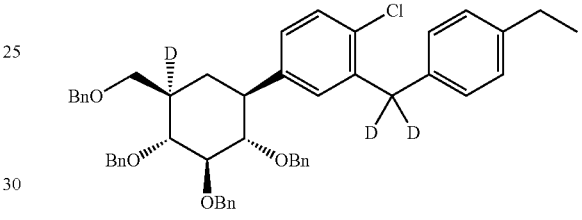

To a cooled solution (−25° C.) of (1R,4R,5S,6R)-4,5,6-tris(benzyloxy)-3-(benzyloxymethyl)-1-(4-chloro-3-((4-ethylphenyl)methyl-d$_2$)phenyl)cyclohex-2-enol (100 mg, 0.13 mmol; prepared using methods analogous to those described in Example 43) in methylene chloride (2 mL), triethyl(silane-d) (45.8 mg, 0.39 mmol) and boron trifluoride ethyl ether complex (36.9 mg, 0.26 mmol) were added sequentially in a slow, dropwise manner. The reaction mixture was allowed to stir 2 hours at the same temperature. The reaction was then quenched with saturated aqueous ammonium chloride (5 mL) and extracted with methylene chloride (3×10 mL). The organic layers were combined, washed with brine, dried over sodium sulfate, and concentrated to give a yellow oil. The residue was purified by preparative TLC (petroleum ether: ethyl acetate=10:1) to give 70 mg of white solid (71% yield). HPLC-MS method: Method 2, retention time 6.45 minutes, purity 69%. MS ES$^+$ (m/z): 752 (M+1)$^+$, 769 (M+18)$^+$.

Preparation of (1R,2S,3R,4R,5S,6R)-3,4,5-tris(benzyloxy)-2-(benzyloxymethyl)-6-(4-chloro-3-((4-ethylphenyl)methyl-d$_2$)phenyl)-cyclohexan-2-d-ol (107d)

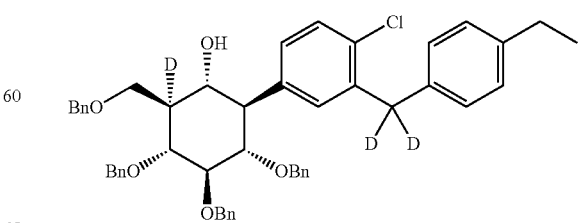

Compound 107d was prepared from 104d using the hydroboronation process described in Example 46 for the preparation of 107c. HPLC-MS method: Method 2, retention time 4.85 minutes, purity 28%. MS ES+ (m/z): 770 (M+1)+, 787 (M+18)+, 792 (M+23)+.

Preparation of (1R,2R,3S,4R,5R,6S)-4-(4-chloro-3-((4-ethylphenyl)methyl-d$_2$)phenyl)-6-(hydroxymethyl)cyclohexane-6-d-1,2,3,5-tetraol (108d)

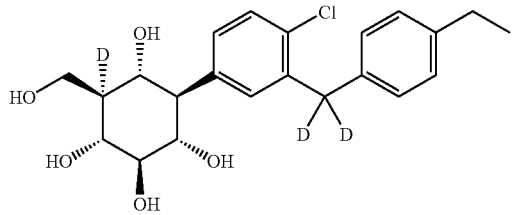

Compound 108d was prepared from 107d using the hydrogenation process described in Example 43 for the preparation of 105a. $^1$H-NMR (CD$_3$OD, 400 MHz): δ 7.35 (d, J=8.4 Hz, 1H), 7.09-7.20 (m, 6H), 3.93 (s, 2H), 3.66 (d, J=6.4 Hz, 1H), 3.41-3.50 (m, 3H), 2.56-2.63 (m, 3H), 1.62-1.64 (m, 1H), 0.92 (t, J=7.2 Hz, 3H). HPLC-MS method: Method 2, retention time 2.90 minutes, purity 99%. MS ES+ (m/z): 410 (M+1)+, 427 (M+18)+; MS ES+ (m/z): 454 (M+45)−.

Example 48

This example illustrates the preparation of compound 108e according to the approach provided in Scheme 32. In this example, R$^v$ is H, R$^m$ is —OCD$_3$, R$^p$ is H.

Preparation of (1R,2R,3S,4R,5R,6S)-4-(4-chloro-3-(4-(methoxy-d$_3$)benzyl)phenyl)-6-(hydroxymethyl)cyclohexane-1,2,3,5-tetraol (108e)

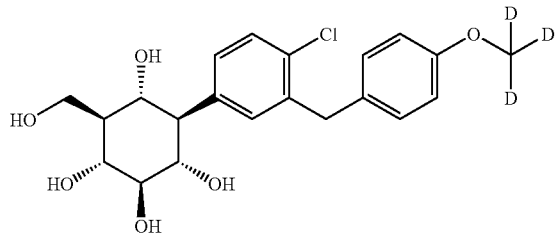 [SMILES: [2H]C([2H])([2H])Oc1ccc(Cc2cc([C@H]3[C@H](O)[C@@H](O)[C@H](O)[C@@H](CO)[C@@H]3O)ccc2Cl)cc1]

Compound 108e was prepared using procedures analogous to those described in Example 46 for the preparation of 108c. $^1$H-NMR (CD$_3$OD, 400 MHz): δ 7.24 (d, J=8.0 Hz, 1H), 7.14-7.18 (m, 4H), 6.82 (d, J=8.4 Hz, 2H), 4.04 (s, 2H), 3.93 (d, J=3.2 Hz, 2H), 3.65 (t, J=10.4 Hz, 1H), 3.33-3.51 (m, 3H), 2.56 (t, J=10.4 Hz, 1H), 1.55 (m, 1H). HPLC-MS method: Method 2, retention time 2.34 minutes, purity 99%. MS ES+ (m/z): 412 (M+1)+, 429 (M+18)+, 434 (M+23)+; MS ES+ (m/z) 456 (M+45)−.

Example 49

This example illustrates the preparation of compound 108f according to the approach provided in Scheme 32. In this example, R$^v$ is D, R$^m$ is —OCD$_3$, R$^p$ is H.

Preparation of (1R,2R,3S,4R,5R,6S)-4-(4-chloro-3-((4-(methoxy-d$_3$)phenyl)methyl-d$_2$)phenyl)-6-(hydroxymethyl)cyclohexane-1,2,3,5-tetraol (108f)

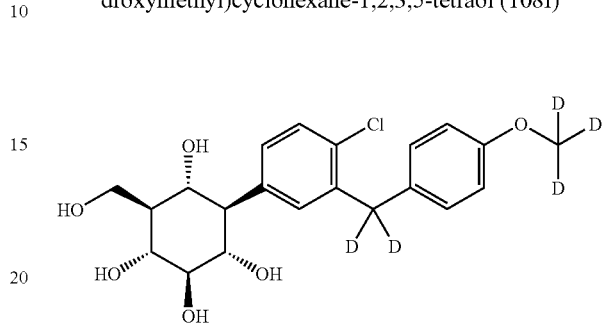

Compound 108f was prepared using procedures analogous to those described in Example 46 for the preparation of 108c. The title compound was obtained as a white solid. $^1$H-NMR (CD$_3$OD, 400 MHz): δ 7.23-7.30 (m, 1H), 7.10-7.13 (m, 4H), 6.89-6.91 (m, 2H), 4.01 (s, 2H), 3.66 (t, J=10.4 Hz, 1H), 3.41-3.51 (m, 2H), 2.56 (t, J=10.8 Hz, 1H), 1.55 (m, 1H). HPLC-MS method: Method 2, retention time 2.33 minutes, purity 96%. MS ES+ (m/z): 414 (M+1)+, 431 (M+18)+, 436 (M+23)+; MS ES+ (m/z): 458 (M+45)−.

Example 50

This example illustrates the preparation of compound 108g according to the approach provided in Scheme 32. In this example, R$^v$ is D, R$^m$ is cyclopropyl, R$^p$ is H.

Preparation of (1R,2R,3S,4R,5R,6S)-4-(4-chloro-3-((4-cyclopropylphenyl)methyl-d$_2$)phenyl)-6-(hydroxymethyl)cyclohexane-1,2,3,5-tetraol (108g)

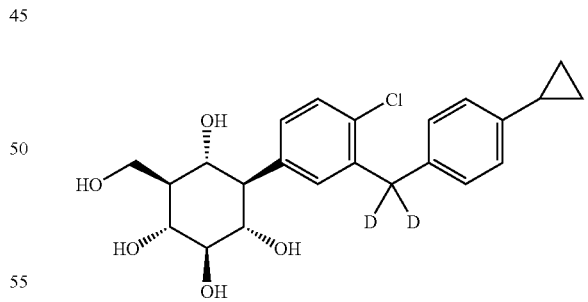

Compound 108g was prepared using procedures analogous to those described in Example 46 for the preparation of 108c. The title compound was obtained as a white solid. $^1$H NMR (CD$_3$OD, 400 MHz): δ 7.34 (d, J=8.4 Hz, 1H), 7.10-7.18 (m, 4H), 6.97 (d, J=8 Hz, 2H), 3.93 (d, J=3.6 Hz, 2H), 3.66 (t, J=10.4 Hz, 1H), 3.41-3.51 (m, 2H), 2.55 (t, J=10.8 Hz, 1H), 1.84-1.88 (m, 1H), 1.52-1.57 (m, 1H), 0.90-0.95 (m, 1H), 0.61-0.65 (m, 1H). HPLC-MS method: Method 2, retention time 2.88 minutes, purity 99%. MS ES+ (m/z): 421 (M+1)+, 438 (M+18)+, 443 (M+23)+; MS ES+ (m/z): 465 (M+45)−.

Example 51

This example illustrates the preparation of compound 108h according to the approach provided in Scheme 32. In this example, $R^v$ is D, $R^m$ is n-propyl, $R^p$ is H.

Preparation of (1R,2R,3S,4R,5R,6S)-4-(4-chloro-3-((4-propylphenyl)methyl-d$_2$)phenyl)-6-(hydroxymethyl)cyclohexane-1,2,3,5-tetraol (108h)

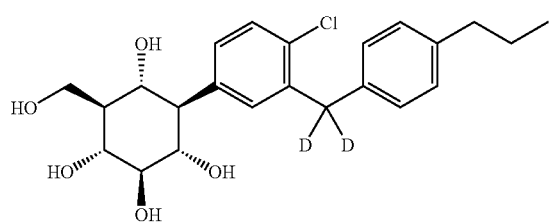 [SMILES: [2H]C([2H])(c1ccc(CCC)cc1)c1cc([C@H]2[C@H](O)[C@@H](O)[C@H](O)[C@@H](CO)[C@@H]2O)ccc1Cl]

Compound 108h was prepared using procedures analogous to those described in Example 46 for the preparation of 108c. The title compound was obtained as a white solid. $^1$H-NMR (CD$_3$OD, 400 MHz): δ 7.35 (d, J=7.6 Hz, 1H), 7.14-7.20 (m, 4H), 7.08 (d, J=8.0 Hz, 2H), 3.93 (d, J=3.2 Hz, 2H), 3.67 (t, J=10.4 Hz, 1H), 3.41-3.51 (m, 2H), 2.53-2.58 (m, 3H), 1.55-1.65 (m, 3H), 0.94 (t, J=7.2 Hz). HPLC-MS method: Method 2, retention time 3.16 minutes, purity 91%. MS ES$^+$ (m/z): 423 (M+1)$^+$, 440 (M+18)$^+$, 445 (M+23)$^+$; MS ES$^-$ (m/z): 467 (M+45)$^-$.

Example 52

This example illustrates the preparation of compound 110e according to the approach provided in Scheme 32. In this example, $R^v$ is H, $R^m$ is —OCD$_3$, and $R^p$ is H.

Preparation of (2R,3R,4R,5S,6S)-3,4,5-tris(benzyloxy)-2-(benzyloxymethyl)-6-(4-chloro-3-(4-(methoxy-d$_3$)benzyl)phenyl)cyclohexanone (109e)

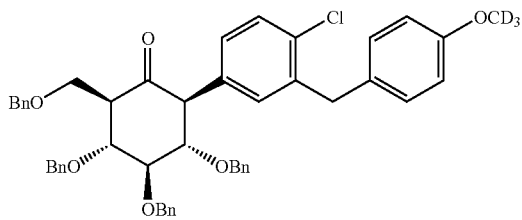

To a solution of (1R,2S,3R,4R,5S,6R)-3,4,5-tris(benzyloxy)-2-(benzyloxymethyl)-6-(4-chloro-3-(4-(methoxy-d$_3$)benzyl)phenyl)cyclohexanol (45 mg, 0.06 mmol) in dichloromethane (1 mL), Dess-Martin periodinane (36.8 mg, 0.09 mmol) was added slowly at 0° C. The reaction then stirred for 2 hours at the same temperature. The reaction mixture was quenched with 1 M sodium hydroxide solution, extracted with dichloromethane (3×10 mL), dried over sodium sulfate, and evaporated to a residue. The residue was purified by preparative TLC (petroleum ether:ethyl acetate=8:1) to give 25 mg of yellow oil (56% yield). HPLC-MS method: Method 2, retention time 6.48 minutes, purity 93%. MS ES$^+$ (m/z): 770 (M+1)$^+$, 787 (M+18)$^+$.

Preparation of (2S,3S,4R,5R,6R)-2-(4-chloro-3-(4-(methoxy-d$_3$)benzyl)phenyl)-3,4,5-trihydroxy-6-(hydroxymethyl)cyclohexanone (110e)

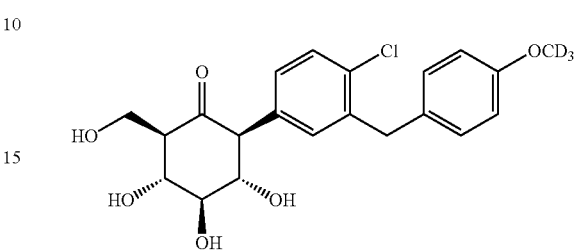

To a solution of (2R,3R,4R,5S,6S)-3,4,5-tris(benzyloxy)-2-(benzyloxymethyl)-6-(4-chloro-3-(4-(methoxy-d$_3$)benzyl)phenyl)cyclohexanone (25 mg, 0.032 mmol) in tetrahydrofuran/methanol (v:v=2:1, 6 mL), palladium 10% on carbon (25 mg) was added and stirred for over 1.5 hours under hydrogen atmosphere. Then the mixture was filtered, and the filtrate was concentrated to dryness as yellow oil. The residue was purified by preparative HPLC-MS to give 3.4 mg of white solid (26% yield). $^1$H-NMR (CD$_3$OD, 400 MHz): δ 7.34 (d, J=8.4 Hz, 1H), 7.13 (d, J=8.8 Hz, 2H), 7.02 (m, 2H), 6.84 (m, 2H), 4.03 (s, 2H), 3.99 (m, 1H), 3.88 (m, 1H), 3.79 (m, 2H), 3.63 (m, 2H), 2.73 (m, 1H). HPLC-MS method: Method 2, retention time 3.16 minutes, purity: 93%. MS ES$^+$ (m/z): 410 (M+1)$^+$, 427 (M+18)$^+$, 432 (M+23)$^+$; MS ES$^+$ (m/z): 454 (M+45)$^-$.

Example 53

This example illustrates the preparation of compound 110g according to the approach provided in Scheme 32. In this example, $R^v$ is D, $R^m$ is cyclopropyl, and $R^p$ is H.

Preparation of (2S,3S,4R,5R,6R)-2-(4-chloro-3-((4-cyclopropylphenyl)methyl-d$_2$)phenyl)-6-(hydroxymethyl)cyclohexanone (110g)

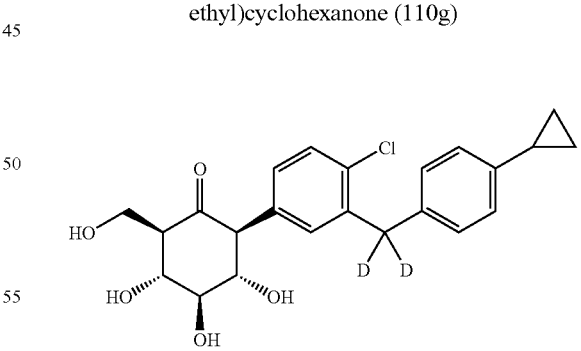

Compound 110g was prepared using procedures analogous to those described in Example 52 for the preparation of 110e. The title compound was obtained as a white solid. $^1$H-NMR (CD$_3$OD, 400 MHz): δ 7.31 (d, J=7.6 Hz, 1H), 6.93-7.07 (m, 6H), 3.94-3.97 (m, 1H), 3.83-3.87 (m, 1H), 3.74-3.79 (m, 2H), 3.55-3.65 (m, 2H), 2.64 (s, 1H), 1.83 (s, 1H), 0.87-3.92 (m, 2H), 0.58-0.62 (m, 2H). HPLC-MS method: Method 2, retention time 2.97 minutes, purity 96%. MS ES$^+$ (m/z): 419 (M+1)$^+$, 436 (M+18)$^+$; MS ES$^+$ (m/z): 463 (M+45)$^-$.

Example 54

This example illustrates the preparation of compound 110h according to the approach provided in Scheme 32. In this example, $R^v$ is D, $R^m$ is n-propyl, and $R^p$ is H.

Preparation of (2S,3S,4R,5R,6R)-2-(4-chloro-3-((4-propylphenyl)methyl-$d_2$)phenyl)-6-(hydroxymethyl)cyclohexanone (110h)

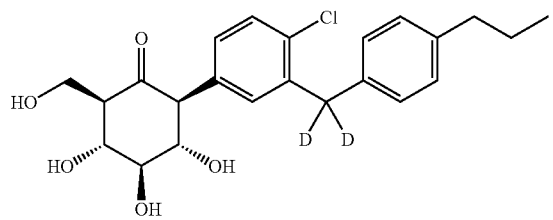 [SMILES: [2H]C([2H])(c1ccc(CCC)cc1)c1cc([C@@H]2C(=O)[C@H](CO)[C@@H](O)[C@H](O)[C@H]2O)ccc1Cl]

Compound 110h was prepared using procedures analogous to those described in Example 52 for the preparation of 110e. The title compound was obtained as a white solid. $^1$H-NMR (CD$_3$OD, 400 MHz): δ 7.33 (d, J=8.4 Hz, 1H), 6.99-7.11 (m, 6H), 3.95-3.99 (m, 1H), 3.84-3.89 (m, 1H), 3.76-3.81 (m, 2), 3.56-3.66 (m, 2H), 3.70-3.74 (m, 1H), 2.51-2.55 (m, 2H), 1.58-1.64 (m, 2H), 0.90-0.94 (m, 3H). HPLC-MS method: Method 2, retention time 3.21 minutes, purity 95%. MS ES$^+$ (m/z) 421 (M+1)$^+$, 438 (M+18)$^+$; MS ES$^+$ (m/z): 465 (M+45)$^-$.

Example 55

This example illustrates the preparation of compound 115 according to the approach provided in Scheme 33. The general method is applicable to other compounds of the present invention.

Scheme 33

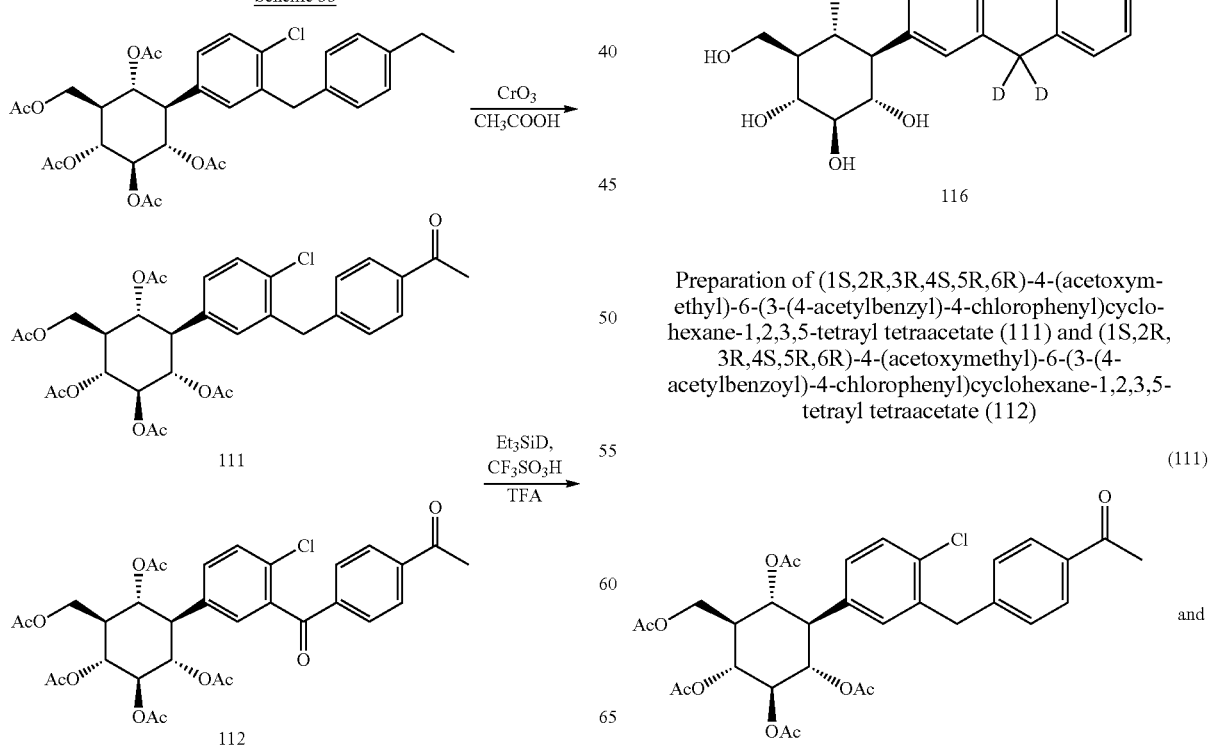

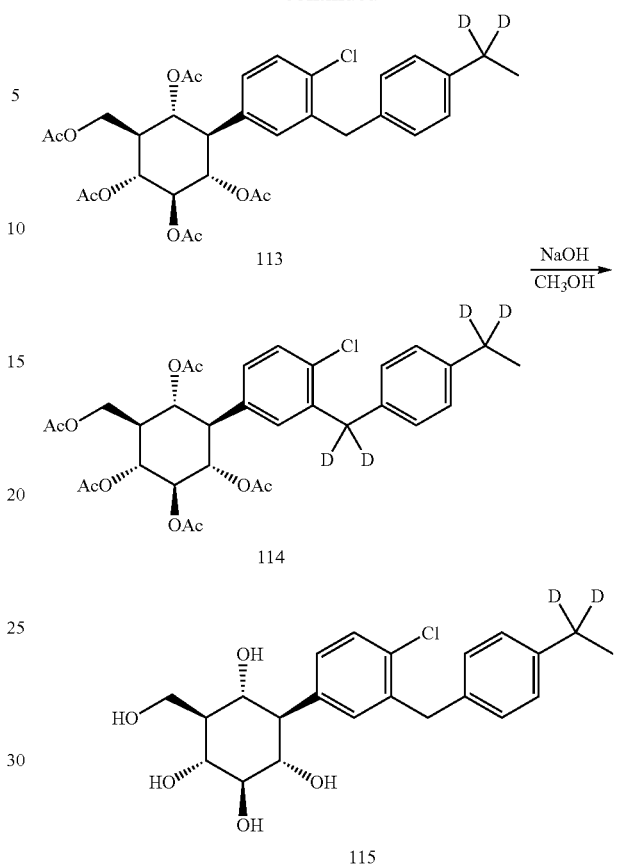

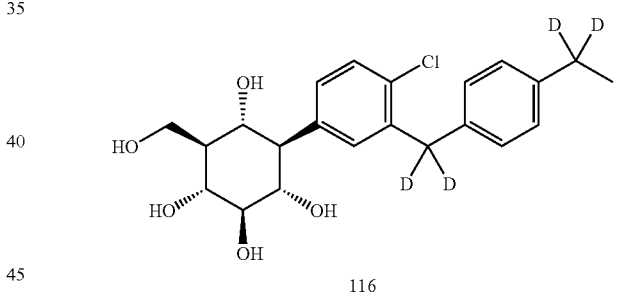

Preparation of (1S,2R,3R,4S,5R,6R)-4-(acetoxymethyl)-6-(3-(4-acetylbenzyl)-4-chlorophenyl)cyclohexane-1,2,3,5-tetrayl tetraacetate (111) and (1S,2R,3R,4S,5R,6R)-4-(acetoxymethyl)-6-(3-(4-acetylbenzoyl)-4-chlorophenyl)cyclohexane-1,2,3,5-tetrayl tetraacetate (112)

189
-continued (112)

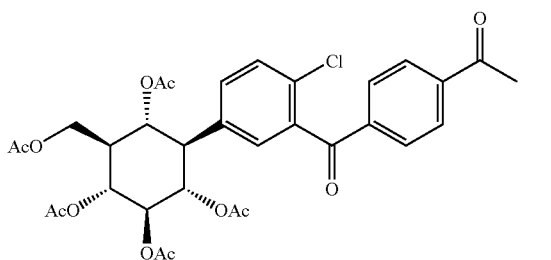

To a solution of (1S,2R,3R,4S,5R,6R)-4-(acetoxymethyl)-6-(4-chloro-3-(4-ethyl-benzyl)phenyl)cyclohexane-1,2,3,5-tetrayl tetraacetate (600 mg, 0.97 mmol; prepared as described in US20090156516) in acetic acid (2 mL), chromium(VI) oxide (487 mg, 4.87 mmol) was added at 25° C. The reaction mixture was allowed to stir for 6 hours and was monitored by HPLC-MS. The mixture was poured onto ice-water and extracted with methylene chloride (3×20 mL). The organic layers were combined, washed with brine, dried over sodium sulfate, and concentrated to dryness. The residue was purified by preparative HPLC-MS to give 250 mg of white solid. $^1$H-NMR (CDCl$_3$, 400 MHz): δ 7.89 (d, J=8.4 Hz, 1H), 7.24-7.32 (m, 3H), 7.07-7.10 (m, 2H), 5.30-5.40 (m, 3H), 5.22 (t, J=9.6 Hz, 1H), 4.13 (s, 2H), 3.96-4.08 (m, 2H), 3.77 (s, 1H), 3.01 (t, J=11.2 Hz, 1H), 2.68 (s, 3H), 2.08 (s, 3H), 2.07 (s, 3H), 2.01 (s, 3H), 1.71 (s, 3H), 1.70 (s, 3H); MS ES$^+$ (m/z): 631 (M+1)$^+$, 648 (M+18)$^+$. $^1$H NMR (CDCl$_3$, 400 MHz): δ 7.81-8.04 (m, 4H), 7.24-7.40 (m, 3H), 5.20-5.41 (m, 3H), 3.96-4.05 (m, 2H), 3.71 (s, 1H), 3.10 (t, J=11.2 Hz, 1H), 2.65 (s, 3H), 1.99-2.04 (m, 9H), 1.82 (s, 3H), 1.80 (s, 3H); MS ES$^+$ (m/z): 645 (M+1)$^+$, 662 (M+18)$^+$.

Preparation of (1R,2R,3S,4R,5R,6S)-4-(4-chloro-3-(4-(ethyl-1,1-d$_2$)benzyl)phenyl)-6-(hydroxymethyl)cyclohexane-1,2,3,5-tetraol (115)

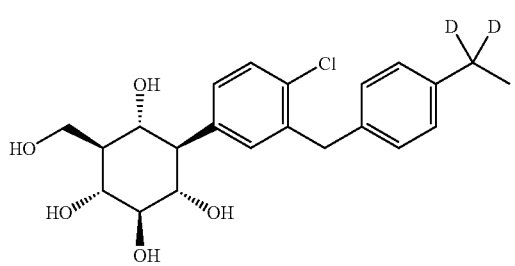 [SMILES: [2H]C([2H])(C)c1ccc(Cc2cc([C@H]3[C@H](O)[C@@H](O)[C@H](O)[C@@H](CO)[C@@H]3O)ccc2Cl)cc1]

To a solution of (1S,2R,3R,4S,5R,6R)-4-(acetoxymethyl)-6-(3-(4-acetylbenzoyl)-4-chlorophenyl)cyclohexane-1,2,3,5-tetrayl tetraacetate (111) (250 mg, 0.40 mmol) in trifluoroacetic acid (2 mL), triethyl(silane-d) (141 mg, 1.20 mmol, Aldrich, 97 atom % D) and trifluoromethanesulfonic acid (0.01 mL, cat.) were added sequentially at 25° C. The mixture was allowed to stir for 3 hours, and then the mixture was poured onto ice-water and extracted with ethyl acetate (3×10 mL). The organic layers were combined, washed with brine,

190 dried over sodium sulfate, and concentrated to dryness. The residue was dissolved in methanol (5 mL), and sodium hydroxide powder (40 mg, 1 mmol) was added. The mixture was heated to reflux for 2 hours and then cooled to 25° C. The mixture was diluted with water and extracted with ethyl acetate (3×20 mL). The organic layer was washed with brine, dried over sodium sulfate, and concentrated to dryness. The residue was purified by preparative HPLC-MS to give 107 mg of white solid (66% yield). $^1$H-NMR (CD$_3$OD, 400 MHz): δ 7.35 (d, J=8.0 Hz, 1H), 7.09-7.20 (m, 6H), 4.07 (s, 2H), 3.93 (d, J=3.2 Hz, 2H), 3.67 (t, J=10.4 Hz, 1H), 3.41-3.49 (m, 2H). 2.56 (t, J=10.8 Hz, 1H), 1.55 (m, 1H), 1.20 (s, 3H). HPLC-MS method: Method 2, retention time 2.88 minutes, purity 99%. MS ES$^+$ (m/z): 409 (M+1)$^+$, 426 (M+18)$^+$, 431 (M+23)$^+$; MS ES$^-$ (m/z): 453 (M+45)$^-$.

Example 56

This example illustrates the preparation of compound 116 according to the approach provided in Scheme 33.

Preparation of (1R,2R,3S,4R,5R,6S)-4-(4-chloro-3-((4-(ethyl-1,1-d$_2$)phenyl)methyl-d$_2$)phenyl)-6-(hydroxymethyl)cyclohexane-1,2,3,5-tetraol (116)

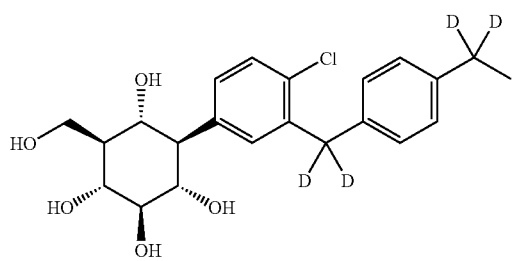 [SMILES: [2H]C([2H])(C)c1ccc(C([2H])([2H])c2cc([C@H]3[C@H](O)[C@@H](O)[C@H](O)[C@@H](CO)[C@@H]3O)ccc2Cl)cc1]

Compound 116 was prepared from (1S,2R,3R,4S,5R,6R)-4-(acetoxymethyl)-6-(3-(4-acetylbenzoyl)-4-chlorophenyl)cyclohexane-1,2,3,5-tetrayl tetraacetate (112) using the procedure described in Example 55 for the preparation of 115. The title compound was obtained as a white solid. $^1$H-NMR (CD$_3$OD, 400 MHz): δ 7.35 (d, J=8.0 Hz, 1H), 7.09-7.20 (m, 6H), 3.93 (d, J=3.6 Hz, 2H), 3.67 (t, J=10.8 Hz, 1H), 3.41-3.51 (m, 2H), 2.55 (t, J=10.8 Hz, 1H), 1.55-1.58 (m, 1H), 1.20 (s, 3H). HPLC-MS method: Method 2, retention time 2.93 minutes, purity 98%. MS ES$^+$ (m/z): 411 (M+1)$^+$, 428 (M+18)$^+$, 433 (M+23)$^+$; MS ES$^+$ (m/z): 455 (M+45)$^-$.

Example 57

This example illustrates the preparation of compounds 126 and 127 according to the approach provided in Scheme 34. The general method is applicable to other compounds of the present invention.

Scheme 34
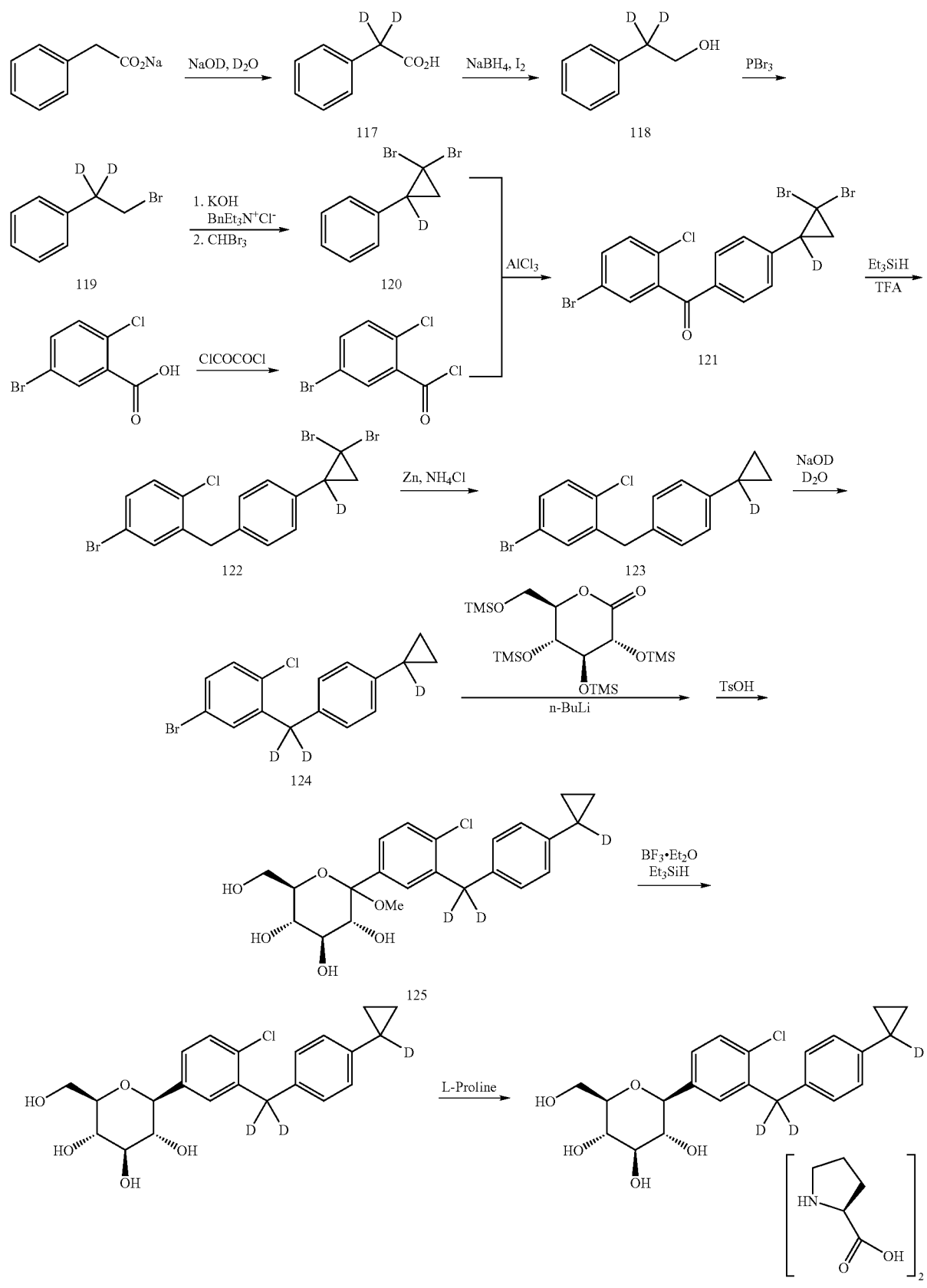

Preparation of 2-phenylacetic-2,2-d₂ acid (117)

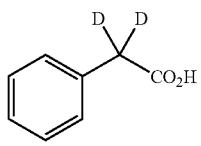 [SMILES: [2H]C([2H])(C(=O)O)c1ccccc1]

The following procedure uses methods analogous to those described in *Carbohydr. Res.*, 142:165, 1985. Deuterium oxide (70 g, 3.5 mol, 99 atom % D) in 500 mL of three-necked flask was cooled to about 0° C. with an ice bath. Sodium hydride (17 g, 60% dispersion in mineral oil, 0.425 mol) was added in portions. After completion of the addition, the mixture was warmed to 25° C. and stirred for 1 hour. Sodium phenylacetate (60 g, 0.379 mol) was added in one portion. The mixture was then warmed to 80° C. and stirred for 21 hours. The water was removed in vacuum, and the resulting residue was dried at 80° C. in vacuum for about 4 hours. Analysis of $^1$H-NMR showed that the D/H ratio was about 90%. Deuterium oxide (42 g, 2.1 mol) was added to the above residue, and the mixture was stirred at 80° C. for 14 hours before being diluted with 100 mL of water. The solution was neutralized to pH 3~4 with 3 M hydrochloric acid, and the mixture was extracted three times with dichloromethane. The combined organic layers were washed with water, dried over sodium sulfate, and concentrated to give 57 g of crude product as white solid. $^1$H-NMR showed that the deuterated incorporation ratio was about 97%. $^1$H-NMR (400 MHz, methanol-d₄): δ 7.34~7.23 (m, 5H), 3.59 (s, 0.06H).

Preparation of 2-phenylethan-2,2-d₂-ol (118)

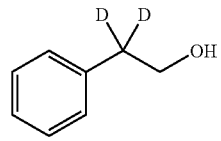

The following procedure uses methods analogous to those described in *J. Org. Chem.* 69:2362-6, 2004. To a cooled (0° C.) solution of 2-phenylacetic-2,2-d₂ acid (52.35 g, 0.379 mol) and sodium borohydride (34.4 g, 0.91 mol) in anhydrous tetrahydrofuran (1 L) was added dropwise iodine (96.2 g, 0.379 mol) in tetrahydrofuran (0.2 L) over 2 hours. After completion of the addition, the mixture was heated to reflux for 13.5 hours. The reaction mixture was then cooled to ambient temperature. Methanol was added until the solution became clear. The reaction solution was stirred for 30 minutes, and the solvent was removed in vacuum. The resulting residue was dissolved in 900 g of 18% aqueous sodium hydroxide. The solution was stirred for 2.5 hours and was extracted with ethyl acetate. The combined organic layers were washed with water, dried over anhydrous sodium sulfate, and concentrated in vacuum to afford 55.2 g of crude product.

Preparation of (2-bromoethyl-1,1-d₂)benzene (119)

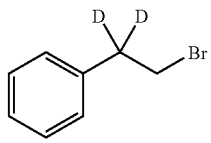

The following procedure uses methods analogous to those described in *J. Am. Chem. Soc.* 128: 8087-94, 2006. To a cooled (0° C.) mixture of 2-phenylethan-2,2-d₂-ol (52.36 g, 0.422 mol) in toluene (200 mL) was added phosphorous tribromide (13.6 mL, 0.143 mol). After completion of the addition, the mixture was allowed to reflux for 2 hours and then cooled to ambient temperature. The organic phase was washed twice with aqueous solution of sodium subsulfite and sodium bicarbonate, dried over sodium sulfate, and the solvent was evaporated to give 75 g of crude product as a colorless liquid (95% yield).

Preparation of (2,2-dibromocyclopropyl-1-d)benzene (120)

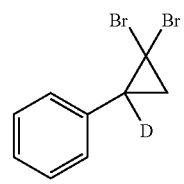 [SMILES: [2H]C1(c2ccccc2)CC1(Br)Br]

The mixture of (2-bromoethyl-1,1-d₂)benzene (70.9 g, 0.379 mol), potassium hydroxide (51.9 g, 82%), benzylethylammonium chloride (0.86 g), and dichloromethane (350 mL) was stirred at reflux temperature for 19 hours before additional potassium hydroxide (13 g, 82%) was added. After stirring for another 5 hours, additional potassium hydroxide (26 g, 82%) was added, followed by addition of bromoform (43.1 mL, 0.49 mol). After completion of the addition, the reaction mixture was refluxed for 12 hours before an additional portion of potassium hydroxide (5 g, 82%) was added. The mixture was stirred for another 12 hours. The mixture was then filtered through a thin silica-layer. The filtrate was concentrated, and the resulting residue was purified by flash chromatography (100% petroleum ether) to give 54 g (51% yield) of title compound as colorless oil.

Preparation of (5-bromo-2-chlorophenyl)(4-(2,2-dibromocyclopropyl-1-d)phenyl)methanone (121)

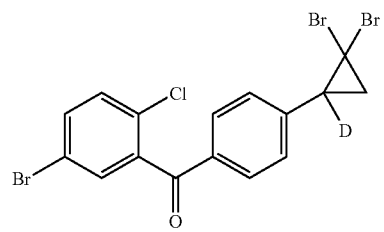 [SMILES: [2H]C1(c2ccc(C(=O)c3cc(Br)ccc3Cl)cc2)CC1(Br)Br]

To a stirred solution of 3-bromo-2-chlorobenzoic acid (50.5 g, 0.215 mol) and oxalyl chloride (23.9 mL, 0.279 mol) in 200 mL of dichloromethane was added 0.3 mL of N,N-dimethylformamide. The reaction mixture was stirred for 16 hours prior to removal of the volatiles under reduced pressure using a rotary evaporator. The resulting 3-bromo-2-chlorobenzoyl chloride was dissolved in dichloromethane (200 mL) and cooled to 0° C. (2,2-Dibromocyclopropyl-1-d)benzene (54 g, 0.195 mol) was then added, followed by addition of aluminum chloride (36.4 g, 0.273 mol) over 20 minutes. After completion of the addition, the mixture was warmed to 25° C., stirred for 1.5 hours, and then poured over ice water. The mixture was extracted three times with dichloromethane. The combined organic portions were washed with 1 N hydrochloric acid, water, and 1 M sodium hydroxide, dried over sodium sulfate, and concentrated in vacuum. The resulting residue was purified by flash chromatography (petroleum ether:ethyl acetate=50:1-10:1) to give 75 g (77% yield) of title compound as colorless oil.

Preparation of 4-bromo-1-chloro-2-(4-(2,2-dibromocyclopropyl-1-d)benzyl)benzene (122)

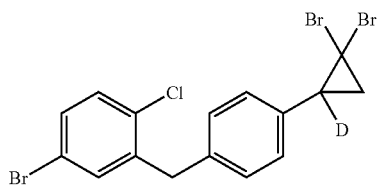 [SMILES: [2H]C1(c2ccc(Cc3cc(Br)ccc3Cl)cc2)CC1(Br)Br]

To a stirred solution of (5-bromo-2-chlorophenyl)(4-(2,2-dibromocyclopropyl-1-d)phenyl)methanone (74 g, 0.15 mol) in trifluoroacetic acid (210 mL) was added a catalytic amount of trifluoromethanesulfonic acid (3 drops). The reaction mixture was stirred at 25° C. for 5 hours, and white solids were formed. The white solids were filtered, washed with methanol (60 mL), and dried in vacuum to yield 64.1 g (89% yield) of title compound.

Preparation of 4-bromo-1-chloro-2-(4-(cyclopropyl-1-d)benzyl)benzene (123)

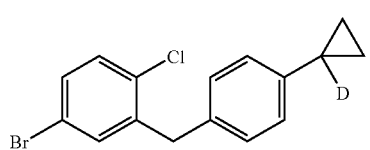 [SMILES: [2H]C1(c2ccc(Cc3cc(Br)ccc3Cl)cc2)CC1]

The mixture of 4-bromo-1-chloro-2-(4-(2,2-dibromocyclopropyl-1-d)benzyl)benzene (63.6 g, 0.132 mol), zinc dust (64 g, 0.978 mol), ammonium chloride (63.6 g, 1.2 mol), and methanol (510 mL) was warmed to reflux for 8 hours. The mixture was filtered, and the solids were washed with ethyl acetate. The filtrate was concentrated in vacuum, and the resulting white solids were taken up with ethyl acetate (500 mL) and water (250 mL). The water layer was separated, and the organic layer was washed with water (250 mL) and dried over sodium sulfate. The mixture was concentrated to afford the crude product, which was purified by flash chromatography (100% petroleum ether) to afford 25 g (59% yield) of title compound as white solid.

Preparation of 4-bromo-1-chloro-2-((4-(cyclopropyl-1-d)phenyl)methyl-$d_2$)benzene (124)

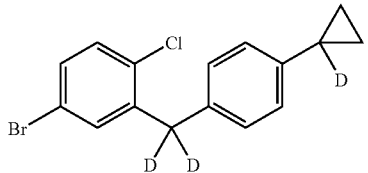 [SMILES: [2H]C1(c2ccc(C([2H])([2H])c3cc(Br)ccc3Cl)cc2)CC1]

To cooled (0° C.) deuterium oxide (24 g, 99 atom % D) was added sodium hydride (9 g, 60% dispersion in mineral oil, 0.225 mol) in portions. After completion of the addition, the mixture was warmed to 25° C. and stirred for about 1 hour. Tetrabutylammonium hydrogen sulfate (2.16 g, 6.12 mmol) and hexane (5 mL) were then added, followed by addition of 4-bromo-1-chloro-2-(4-(cyclopropyl-1-d)benzyl)benzene (20 g, 62 mmol) in hexane (30 mL). After 16 hours, the mixture was diluted with water and extracted with ethyl acetate. The combined extracts were washed with brine, dried over sodium sulfate, and concentrated to give crude product. The above crude product was run through a second round using the same conditions as for Compound (123). $^1$H-NMR showed that the deuteration ratio was about 96%. $^1$H-NMR (CDCl$_3$, 400 MHz,): δ 7.33-7.25 (m, 3H), 7.14-7.10 (m, 2H), 7.08-7.04 (m, 2H), 4.04 (s, 0.08H), 1.10-0.97 (m, 2H), 0.74-0.70 (m, 2H).

Preparation of (3R,4S,5S,6R)-2-(4-chloro-3-((4-(cyclopropyl-1-d)phenyl)methyl-$d_2$)phenyl)-6-(hydroxymethyl)-2-methoxytetrahydro-2H-pyran-3,4,5-triol (125)

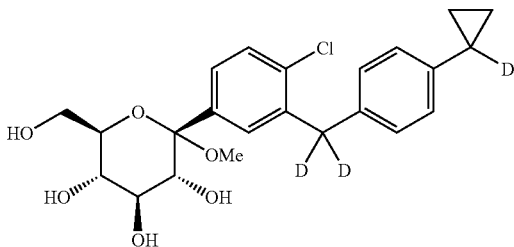 [SMILES: [2H]C1(c2ccc(C([2H])([2H])c3cc([C@]4(OC)O[C@H](CO)[C@@H](O)[C@H](O)[C@H]4O)ccc3Cl)cc2)CC1]

To a stirred −78° C. solution of 4-bromo-1-chloro-2-((4-(cyclopropyl-1-d)phenyl)methyl-$d_2$)benzene (16 g, 49.3 mmol) in anhydrous tetrahydrofuran/toluene (120 mL, 1:2) under argon was added n-butyllithium (23.7 mL, 59.3 mmol, 2.5 M in hexane) dropwise. The mixture was stirred for 1 hour before (3R,4S,5R,6R)-3,4,5-tris(trimethylsilyloxy)-6-((trimethylsilyloxy)methyl)tetrahydro-2H-pyran-2-one (27.6 g, 59.2 mmol) in toluene (120 mL) was added at −78° C. The reaction mixture was stirred for another 1 hour at the same temperature prior to quenching with water (50 mL). The mixture was extracted with ethyl acetate. The combined extracts were washed with saturated solution of ammonium chloride and brine, dried over sodium sulfate, and concentrated to a residue. The resulting residue was dissolved in methanol (470 mL) and cooled to 0° C. with an ice bath. p-Toluenesulfonic acid monohydrate (7.06 g, 37.1 mmol) was added in several portions. The reaction solution was then warmed to 25° C. and stirred for 18 hours. A saturated solution of sodium bicarbonate (100 mL) was then added. The mixture was concentrated in vacuum, and the resulting mixture was extracted three times with ethyl acetate (3×100 mL). The combined extracts were washed with water, dried over sodium sulfate, and concentrated in vacuum to provide 22.6 g of crude product as oil. HPLC-MS method: Method 2, retention time 3.30 minutes, purity 58%. MS ES$^+$ (m/z): 482 (M+45)$^-$.

Preparation of (2S,3R,4R,5S,6R)-2-(4-chloro-3-((4-(cyclopropyl-1-d)phenyl)methyl-d$_2$)phenyl)-6-(hydroxymethyl)tetrahydro-2H-pyran-3,4,5-triol (126)

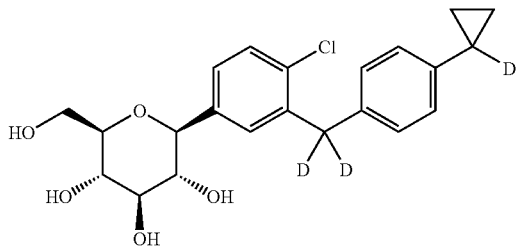

To a stirred −10° C. solution of (3R,4S,5S,6R)-2-(4-chloro-3-((4-(cyclopropyl-1-d)phenyl)methyl-d$_2$)phenyl)-6-(hydroxymethyl)-2-methoxytetrahydro-2H-pyran-3,4,5-triol (14.78 g, 19.6 mmol) in 130 mL of 1:1 dichloromethane/acetonitrile was added triethylsilane (11.8 mL, 74 mmol), followed by addition of boron trifluoride etherate (6.4 mL, 50.5 mmol). After stirring for about 4 hours at −10 to 0° C., the reaction was quenched with saturated solution of sodium bicarbonate. The mixture was extracted with ethyl acetate. The combined organic layers were washed with brine, dried over sodium sulfate, and concentrated. The resulting residue was purified by flash chromatography to afford 7.4 g (53% yield) of title product. $^1$H-NMR (CDCl$_3$, 400 MHz): δ 7.38-7.34 (m, 2H), 7.30 (dd, J=8.0, 2.4 Hz, 1H), 7.08 (d, J=8.0 Hz, 2H), 6.96 (d, J=8.0 Hz, 2H), 4.11 (d, J=9.6 Hz, 1H), 3.89 (dd, J=12.0, 1.6 Hz, 1H), 3.72 (dd, J=12.0, 5.4 Hz, 1H), 3.50-3.38 (m, 3H), 3.33 (t, J=9.0 Hz, 1H), 0.92-0.89 (m, 2H), 0.64-0.60 (m, 2H). HPLC-MS method: Method 2, retention time 3.16 minutes, purity 67%. MS ES$^+$ (m/z): 408 [M+H]$^+$, 430 [M+Na]$^+$; MS ES$^-$ (m/z): 452 [M+HCO$_2$]$^-$.

Preparation of (2S,3R,4R,5S,6R)-2-(4-chloro-3-((4-(cyclopropyl-1-d)phenyl)methyl-d$_2$)phenyl)-6-(hydroxymethyl)tetrahydro-2H-pyran-3,4,5-triol, bis(L-proline) complex (127)

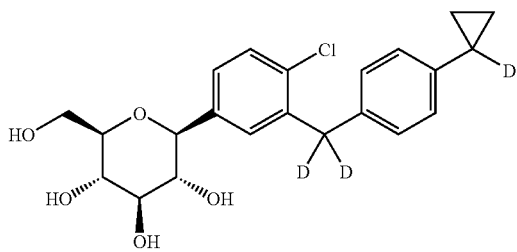 [SMILES: [2H]C1(c2ccc(C([2H])([2H])c3cc([C@@H]4O[C@H](CO)[C@@H](O)[C@H](O)[C@H]4O)ccc3Cl)cc2)CC1]

To a stirred solution of (2S,3R,4R,5S,6R)-2-(4-chloro-3-((4-(cyclopropyl-1-d)phenyl)methyl-d$_2$)phenyl)-6-(hydroxymethyl)tetrahydro-2H-pyran-3,4,5-triol (5.57 g, 67% HPLC pure) in ethanol (38 mL) was added L-proline (2.76 g, 24 mmol), followed by addition of water (2 mL). After reflux for 1 hour, n-hexane (50 mL) was added. Then the mixture was allowed to cool to 0 to 5° C. slowly. The formed white solids were filtered, washed with hexane, and dried in vacuum.

First recrystallization: To a 80° C. stirred solution of above crude co-crystals in ethanol (10 mL) and water (0.9 mL) was added n-hexane (10 mL). The mixture was then cooled to 25° C. and stored at 0° C. for 16 hours. The formed white solids were filtered, washed with hexane, and dried in vacuum to give 4.77 g of title co-crystals (93.1% HPLC pure, 225 nm).

Second recrystallization: To an 80° C. stirred solution of above co-crystals in ethanol (8 mL) and water (0.72 mL) was added n-hexane (8 mL). The mixture was then cooled to 25° C. and stored at 0° C. for about 3 hours. The formed white solids were filtered, washed with hexane, and dried in vacuum to give 2.95 g of title co-crystals (95.9% HPLC pure, 225 nm). $^1$H-NMR (CD$_3$OD, 400 MHz): δ 7.37-7.34 (m, 2H), 7.29 (dd, J=8.4, 2.4 Hz, 1H), 7.09 (d, J=8.4 Hz, 2H), 6.97 (d, J=8.4 Hz, 2H), 4.11 (d, J=9.6 Hz, 1H), 4.00 (dd, J=8.8, 6.4 Hz, 2H), 3.89 (dd, J=12.0, 1.6 Hz, 1H), 3.71 (dd, J=12.0, 5.2 Hz, 1H), 3.50-3.36 (m, 5H), 3.34~3.21 (m, 3H), 2.26~2.36 (m, 2H), 2.17~2.08 (m, 2H), 2.02~1.94 (m, 4H), 0.93-0.90 (m, 2H), 0.64-0.61 (m, 2H). HPLC-MS method: Method 2, retention time 3.16 minutes, purity 95%. MS ES$^+$ (m/z): 408 [M+H]$^+$, 430 [M+Na]$^+$; MS ES$^-$ (m/z): 452 [M+HCO$_2$]$^-$.

Example 58

The following reference compounds were prepared to help evaluate the biological properties of compounds of the invention.

Preparation of (2S,3R,4R,5S,6R)-2-(4-chloro-3-(4-ethoxybenzyl)phenyl)-6-(hydroxymethyl)tetrahydro-2H-pyran-3,4,5-triol (Ref. A)

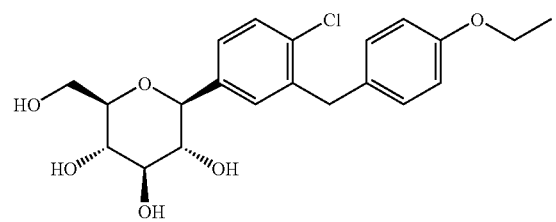 [SMILES: CCOc1ccc(Cc2cc([C@@H]3O[C@H](CO)[C@@H](O)[C@H](O)[C@H]3O)ccc2Cl)cc1]

Reference compound A was prepared according to methods analogous to those described in Example 1 by using triethylsilane instead of triethylsilane-d.

Preparation of (2S,3R,4R,5S,6R)-2-(4-chloro-3-(4-methoxybenzyl)phenyl)-6-(hydroxymethyl)tetrahydro-2H-pyran-3,4,5-triol (Ref. B)

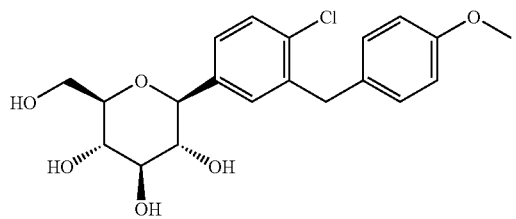 [SMILES: COc1ccc(Cc2cc([C@@H]3O[C@H](CO)[C@@H](O)[C@H](O)[C@H]3O)ccc2Cl)cc1]

Reference compound B was prepared according to methods analogous to those described above for the preparation of reference compound A by using ethylbenzene instead of phenetole as starting material.

Preparation of (2S,3R,4R,5S,6R)-2-(4-chloro-3-(4-cyclopropylbenzyl)phenyl)-6-(hydroxymethyl)tetrahydro-2H-pyran-3,4,5-triol (Ref. C)

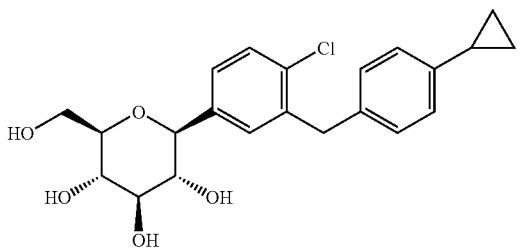 [SMILES: OC[C@H]1O[C@@H](c2ccc(Cl)c(Cc3ccc(C4CC4)cc3)c2)[C@H](O)[C@@H](O)[C@@H]1O]

Reference compound C was prepared according to methods analogous to those described in Example 21 by using triethylsilane instead of triethylsilane-d.

Preparation of (2S,3R,4R,5S,6R)-2-(4-chloro-3-(4-hydroxybenzyl)phenyl)-6-(hydroxymethyl)tetrahydro-2H-pyran-3,4,5-triol (Ref. D)

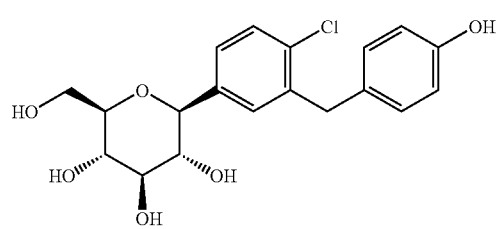 [SMILES: OC[C@H]1O[C@@H](c2ccc(Cl)c(Cc3ccc(O)cc3)c2)[C@H](O)[C@@H](O)[C@@H]1O]

Reference compound D was prepared according to methods analogous to those described in Example 19 by using triethylsilane instead of triethylsilane-d.

Preparation of (2S,3R,4R,5S,6R)-2-(4-chloro-3-((4-ethoxyphenyl)(hydroxy)methyl)phenyl)-6-(hydroxymethyl)tetrahydro-2H-pyran-3,4,5-triol (Ref. E)

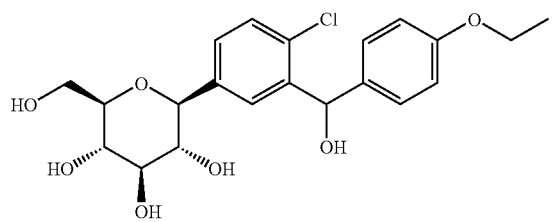 [SMILES: CCOc1ccc(C(O)c2cc([C@@H]3O[C@H](CO)[C@@H](O)[C@H](O)[C@H]3O)ccc2Cl)cc1]

Reference compound E was isolated from rat urine by preparative HPLC after dosing at 250 mg/kg. $^1$H NMR (400 MHz, CD$_3$OD): δ 7.80 (s, 0.75H), 7.77 (s, 0.25H), 7.30-7.34 (m, 2H), 7.23 (d, J=8.8 Hz, 2H), 6.81 (d, J=8.8 Hz, 2H), 6.06 (s, 0.25H), 6.04 (s, 0.75H), 4.15 (d, J=9.2 Hz, 1H), 3.98 (q, J=14 and 7.2 Hz, 2H), 3.87 (m, 1H), 3.68 (m, 1H), 3.47~3.37 (m, 3H), 3.26 (m, 1H), 1.33 (t, J=6.8 Hz, 3H); MS ESI (m/z): 425 (M+H).

Preparation of (2S,3R,4R,5S,6R)-2-(4-chloro-3-(4-(2-(2,2-difluoroethoxy)ethoxy)benzyl)phenyl)-6-(hydroxymethyl)tetrahydro-2H-pyran-3,4,5-triol (Ref. F)

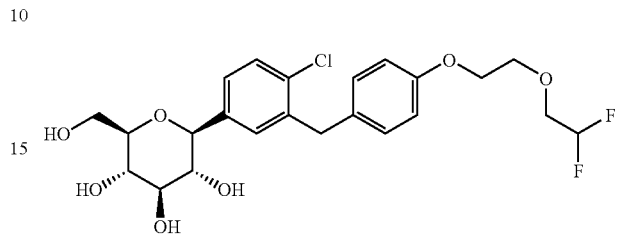

Reference compound F was prepared according to the method described in US 2009/0118201.

Preparation of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol (Ref. G)

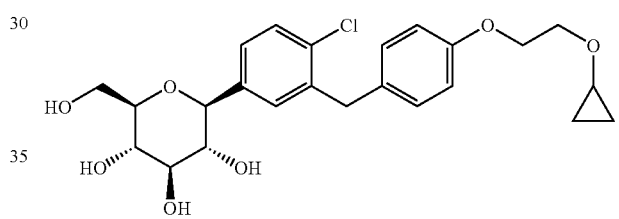

Reference compound G was prepared according to the method described in US 2009/0118201.

Example 59

Effects on In Vitro SGLT Inhibition

To test SGLT inhibition by the compounds of the invention, the following in vitro and in vivo tests were employed.

Preparation of Human SGLT2 Expression Vector

A full-length cDNA clone expressing human SGLT2 (GenScript Corporation) was subcloned into Hind III and Not I sites of the pEAK15 expression vector. Clones harboring the cDNA inserts were identified by restriction analysis.

Preparation of a Cell Line Stably Expressing Human SGLT2

A plasmid containing human SGLT2 was linearized with Nsi I and purified by agarose gel electrophoresis. Using Lipofectamine 2000 Transfection Reagent (Invitrogen Corporation), DNA was transfected into HEK293.ETN cells and cultured in Dulbecco's Modified Eagle Medium (DMEM) containing 10% fetal bovine serum (FBS) at 37° C. under 5% CO$_2$ for 24 hours. Transfectants were selected in the same growth medium supplemented with puromycin (Invitrogen Corporation) for two weeks. Puromycin-resistant cells were recovered and seeded on a fresh 96-well plate (single cell per well) and cultured in the presence of puromycin until cells became confluent. Puromycin-resistant clones were evaluated for SGLT2 activity in the methyl-α-D-[U-$^{14}$C]glucopyranoside uptake assay described below. The clone that exhibited the highest signal-to-background ratio was used for the methyl-α-D-[U-$^{14}$C]glucopyranoside uptake assay.

Preparation of Human SGLT1 Expressing Cells

Full-length human SGLT1 cDNA in the pDream2.1 expression vector was obtained from GenScript Corporation and propagated in *Escherichia coli* strain DH5α using Luria-Bertani (LB) medium containing ampicillin. Plasmid DNA was isolated using the QIAGEN Plasmid Midi Kit (QIAGEN Inc.). Human SGLT1 expression plasmid DNA was transfected into COS-7 cells (American Type Culture Collection) using Lipofectamine 2000 Transfection Reagent according to a manufacturer suggested protocol. Transfected cells were stored in DMEM containing 10% dimethyl sulfoxide (DMSO) at −80° C.

Methyl-α-D-[U-$^{14}$C]Glucopyranoside Uptake Assay

Cells expressing SGLT1 or SGLT2 were seeded on 96-well ScintiPlate scintillating plates (PerkinElmer, Inc.) in DMEM containing 10% FBS (1×10$^5$ cells per well in 1001 medium) incubated at 37° C. under 5% CO$_2$ for 48 hours prior to the assay. Cells were washed twice with 150 μl of either sodium buffer (137 mM NaCl, 5.4 mM KCl, 2.8 mM CaCl$_2$, 1.2 mM MgCl$_2$, 10 mM tris(hydroxymethyl)aminomethane/N-2-hydroxyethylpiperazine-N'-ethanesulfonic acid [Tris/Hepes], pH 7.2) or sodium-free buffer (137 mM N-methyl-glucamine, 5.4 mM KCl, 2.8 mM CaCl$_2$, 1.2 mM MgCl$_2$, 10 mM Tris/Hepes, pH 7.2). Test compound in 50 μl each of sodium or sodium-free buffer containing 40 μCi/ml methyl-α-D-[U-$^{14}$C]glucopyranoside (Amersham Biosciences/GE Healthcare) and 25% human serum was added per well of a 96-well plate and incubated at 37° C. with shaking for either 2 hours (SGLT1 assay) or 1.5 hours (SGLT2 assay). Cells were washed twice with 150 μl of wash buffer (137 mM N-methylglucamine, 10 mM Tris/Hepes, pH 7.2) and methyl-α-D-[U-$^{14}$C]glucopyranoside uptake was quantified using a TopCount scintillation counter (PerkinElmer, Inc.). Sodium-dependent glucopyranoside uptake was measured by subtracting the values obtained with sodium-free buffer from those obtained using sodium buffer (average of triplicate determinations). The IC$_{50}$ for SGLT2 and SGLT1 were determined, and the selectivity for SGLT2 inhibition was calculated by dividing the SGLT1 IC$_{50}$ by the SGLT2 IC$_{50}$. As shown in Table 1, compounds of the invention exhibited increased selectivity for SGLT2 inhibition versus non-deuterated reference compounds.

TABLE 1

| Compound | SGLT2 IC$_{50}$ (μM) | SGLT1 IC$_{50}$ (μM) | Selectivity |
|---|---|---|---|
| Ref A | 0.0032 | 3.14 | 981 |
| 24c | 0.0025 | 3.17 | 1268 |
| Ref B | 0.0019 | 0.54 | 284 |
| 19 | 0.0008 | 0.82 | 1025 |

Example 60

Effects on In Vitro Cytochrome P450 (CYP) Inhibition

P450-Glo™ CYP Screening Kits for CYP1A2, CYP3A4 and CYP2C19 were purchased from Promega. Compound stock solutions were made in acetonitrile, and serial dilutions were made in water containing 1% acetonitrile. Assays were performed according to the manufacturer suggested protocols in 96-well OptiPlates (PerkinElmer, catalog #6005509). Luminescence was quantified using a Victor 3 spectrophotometer (PerkinElmer). As shown in Table 2, compounds of the invention exhibited decreased CYP1A2, CYP3A4 and/or CYP2C19 inhibition versus non-deuterated reference compounds.

TABLE 2

| | IC$_{50}$ (μM) | | |
|---|---|---|---|
| Compound | 1A2 | 3A4 | 2C19 |
| Ref A | 426.0 | ~400 | 61.1 |
| 5 | 500-1000 | 500-1000 | 104.3 |
| 9 | ~500 | ~1000 | 50-100 |
| 24c | 500-1000 | 500-1000 | 168.2 |
| Ref B | >1000 | 250.0 | 195.1 |
| 19 | >1000 | >1000 | 355 |
| 24d | >1000 | ~1000 | 119.9 |

Example 61

Effects on Urinary Glucose Excretion in SD Rats

Each test compound was dissolved in 30% PEG400 and administered orally to overnight-fasted SD rats by gavage at the dose level of 1 mg/kg. Control rats were given 30% PEG400 only. One hour post dosing, glucose solution (2 g/kg, 10 mL/kg) was administered by oral gavage. Urine was collected within metabolic cages from 0 to 4 hours, and 4 to 24 hours post-dosing for urine volume and glucose measurement. Food was removed 16 hours before dosing and then provided 4 hours after dosing. Water was supplied ad libitum. The concentration of urinary glucose was determined at 4 hours and 24 hours post-dose using a biochemistry analyzer. Results were recorded for the periods 0-4 hours, 4-24 hours and 0-24 hours, and expressed as a percentage of the urinary glucose excretion (UGE) seen with reference compound A, which was run as a positive control in all experiments. As shown in Table 3, compounds of the invention exhibited increased UGE in rats versus non-deuterated reference compounds.

TABLE 3

| Compound | Urinary Glucose Excretion in Rats (mg) (% relative to Ref A) (mean ± SD) | | |
|---|---|---|---|
| | 0-4 h | 4-24 h | 0-24 h |
| Ref A | (100%) | (100%) | (100%) |
| 5 | | 2457 ± 369 (110%) | 2650 ± 385 (109%) |
| Ref B | 233 ± 35 (122%) | 1657 ± 354 (74%) | 1889 ± 361 (78%) |
| 19 | | | 2096 ± 332 (83%) |
| 24d | 251 ± 44 (131%) | 1983 ± 167 (89%) | 2234 ± 199 (92%) |
| 24e | 236 ± 48 (162%) | 2288 ± 287 (97%) | 2525 ± 266 (101%) |

Example 62

Effects on Urinary Glucose Excretion in Beagle Dogs

Each test compound was dissolved in 10% PEG400 and administered orally to overnight-fasted beagle dogs by gavage at the dose level of 0.03 mg/kg. Control dogs were given 10% PEG400 only. One hour post dosing, glucose solution (2 g/kg, 5 mL/kg) was administered by oral gavage. Urine was collected within metabolic cages from 0 to 8 hours, and 8 to 24 hours post-dosing for urine volume and glucose measurement. Food was removed 16 hours before dosing and then provided 3 hours after dosing. Water was supplied ad libitum. The concentration of urinary glucose was determined at 8 hours and 24 hours post-dose using a biochemistry analyzer.

Results were recorded for the periods 0-8 hours, 8-24 hours and 0-24 hours, and expressed as a percentage of the urinary glucose excretion (UGE) seen with reference compound A, which was run as a positive control in all experiments. As shown in Table 4, compounds of the invention exhibited a substantial increase in UGE in dogs versus non-deuterated reference compound during the initial 0-8 hours period after administration.

TABLE 4

| Compound | Urinary Glucose Excretion in Dogs (mg) (% relative to Ref A) (mean ± SD) | | |
|---|---|---|---|
| | 0-8 h | 8-24 h | 0-24 h |
| Ref A | (100%) | (100%) | (100%) |
| 5 | 3765 ± 808 (175%) | 8910 ± 1700 (94%) | 12676 ± 2150 (109%) |
| 9 | 3396 ± 442 (158%) | 6832 ± 2555 (72%) | 10228 ± 895 (88%) |
| 16 | 4362 ± 818 (114%) | 10995 ± 1987 (95%) | 15357 ± 2514 (99%) |

TABLE 4-continued

| Compound | Urinary Glucose Excretion in Dogs (mg) (% relative to Ref A) (mean ± SD) | | |
|---|---|---|---|
| | 0-8 h | 8-24 h | 0-24 h |
| 24c | 3472 ± 622 (161%) | 8491 ± 1569 (90%) | 11964 ± 2190 (103%) |

In a separate experiment, shown in Table 4A, compounds of the invention exhibited a similar increase in UGE in dogs versus non-deuterated reference compounds during the initial 0-8 hours period after administration (19) or during both periods after administration (87).

TABLE 4A

| Compound | Urinary Glucose Excretion in Dogs (mg) (mean ± SD) | | |
|---|---|---|---|
| | 0-8 h | 8-24 h | 0-24 h |
| Ref B | 3322 ± 464 | 13404 ± 1888 | 16726 ± 1507 |
| 19 | 3412 ± 544 | 12516 ± 485 | 15928 ± 321 |
| Ref F | 1927 ± 307 | 11511 ± 5327 | 13438 ± 5237 |
| 87 | 2426 ± 493 | 14432 ± 1150 | 16858 ± 674 |

Example 63

Effects on Pharmacokinetic Parameters in SD Rats

The pharmacokinetic study of each test compound was conducted in 4 Sprague-Dawley rats following a single oral administration of 3 mg/kg of the compound. The dose was prepared by dissolving test article in appropriate volume of 30% PEG400. The plasma samples were collected from the orbital plexus at 0.083, 0.25, 0.50, 1.0, 2.0, 4.0, 6.0, 8.0, 12 and 24 hours post dose, and the plasma concentrations were determined by a developed LC-MS/MS method. A non-compartmental pharmacokinetic analysis (WinNonlin 5.0.1, Pharsight Corp., Mountain View, Calif., USA) was performed on the plasma concentrations for each rat to determine the following parameters: $C_{max}$, $T_{max}$, AUC, $T_{1/2}$, MRT, CL/F, and Vz/F. As shown in Table 5, when compared with non-deuterated reference compounds, compounds of the invention exhibited substantial improvement in pharmacokinetic parameters, including increased $t_{max}$, $C_{max}$, $AUC_{0-t}$, and/or $t_{1/2}$, and decreased clearance.

TABLE 5

| | Pharmacokinetic Parameters in Rats (mean ± SD) | | | | |
|---|---|---|---|---|---|
| Cpd | $t_{max}$ (h) | $C_{max}$ (ng/mL) | $AUC_{0-t}$ (ng·h/mL) | $t_{1/2}$ (h) | CL/F (mL/h/kg) |
| Ref A | 0.88 ± 0.75 | 1603 ± 425 | 11297 ± 2598 | 4.52 ± 0.98 | 270 ± 68.1 |
| 9 | 1.69 ± 0.59 | 1830 ± 365 | 15324 ± 2377 | 5.14 ± 1.28 | 192 ± 36.2 |
| 16 | 1.00 ± 0.71 | 2683 ± 471 | 21021 ± 4372 | 5.70 ± 0.63 | 138 ± 28.5 |
| 24a | 0.88 ± 0.75 | 2923 ± 393 | 20319 ± 1614 | 4.56 ± 0.64 | 144 ± 13.0 |
| 24c | 1.38 ± 0.75 | 2285 ± 697 | 21177 ± 1885 | 6.05 ± 0.85 | 133 ± 10.3 |
| Ref B | 0.56 ± 0.31 | 1638 ± 326 | 5245 ± 715 | 3.55 ± 1.80 | 568 ± 75.1 |
| 24d | 1.19 ± 0.94 | 1494 ± 428 | 6680 ± 350 | 6.34 ± 2.79 | 431 ± 37.0 |
| Ref C | 3.00 ± 1.15 | 1049 ± 230 | 9769 ± 2184 | 4.28 ± 0.80 | 312 ± 81.6 |
| 54 | 2.00 ± 0.00 | 1274 ± 138 | 10588 ± 1600 | 6.08 ± 1.92 | 264 ± 28.1 |
| Ref G | 1.88 ± 1.55 | 594 ± 85.8 | 4235 ± 405 | 3.39 ± 0.68 | 705 ± 69.2 |
| 95 | 2.13 ± 1.44 | 710 ± 76.4 | 5242 ± 328 | 4.83 ± 1.42 | 552 ± 44.8 |

Example 63A

Effects on Pharmacokinetic Parameters in Beagle Dogs

The pharmacokinetic study of each test compound was conducted in three Beagle dogs following a single oral administration of 1 mg/kg of the compound. The dose was prepared by dissolving test article in appropriate volume of 30% PEG400. The plasma samples were collected from the cephalic vein pre-dose and at 0.25, 0.50, 1.0, 2.0, 4.0, 6.0, 8.0, 12 and 24 hours post dose, and the plasma concentrations were determined by a developed LC-MS/MS method. A non-compartmental pharmacokinetic analysis (WinNonlin 5.0.1, Pharsight Corp., Mountain View, Calif., USA) was performed on the plasma concentrations for each rat to determine the following parameters: $C_{max}$, $T_{max}$, AUC, $T_{1/2}$, MRT, CL/F, and Vz/F. As shown in Table 5A, when compared with non-deuterated reference compound, compounds of the invention exhibited substantial improvement in pharmacokinetic parameters, including increased $t_{max}$, $C_{max}$, $AUC_{0-t}$, and decreased clearance.

205

TABLE 5A

| | Pharmacokinetic Parameters in Dogs (mean ± SD) | | | |
|---|---|---|---|---|
| Cpd | $t_{max}$ (h) | $C_{max}$ (ng/mL) | $AUC_{0-t}$ (ng · h/mL) | CL/F (mL/h/kg) |
| Ref F | 0.4 ± 0.1 | 889 ± 65.4 | 4924 ± 484 | 190 ± 17.5 |
| 87 | 0.6 ± 0.4 | 1578 ± 282 | 8875 ± 1435 | 111 ± 19.7 |

Example 64

Effects on Metabolism in SD Rats

Each test compound was dissolved in 30% PEG400 and administered orally to male SD rats by gavages at the dose level of 50 mg/kg (when using co-crystals, the weight calculation was based on free drug) for five consecutive days. Control rats were given 30% PEG400 only. All rats were housed in metabolic cages individually. Food and water were supplied ad libitum. Clinical observations (with attention to diarrhea symptoms) were performed twice daily. Food and water consumption were determined daily. Urine was collected pre-determined intervals: pre-dose, 0-4 hours, 4-8 hours, and 8-24 hours post-dose. Metabolites were analyzed and identified by LC/MS. The structures of the metabolites were confirmed by re-synthesis or isolation from the urine by preparative HPLC and NMR analysis. On day 6, all animals were sacrificed and gross necropsy was performed. The urine from two rats for each test compound was collected and pooled. The samples were diluted (1 mL urine in 4 mL of methanol) and analyzed by LC-MS: Waters 2695 Separations Module equipped with a Waters 2996 Photodiode Array Detector and a Waters Micromass ZQ Detector; Waters XTerra C18 3.5 µm, 20 mm×2.1 mm column, 1.0 mL/min, detection at 190-400 nm; 1.7 min gradient 10-50% A, followed by 1.8 min gradient 50-95% A, hold 1 min at 95% A; solvent A: 100% acetonitrile+0.045% formic acid; solvent B: Milli-Q water+0.1% formic acid. The urine samples were analyzed from 0-4 hours, 4-8 hours, 8-24 hours and 0-24 hours after administration. The ratio of metabolites was highly consistent within each time for each rat. The metabolites were identified by mass then re-synthesized to confirm their identity and the relative distribution was assayed using HPLC. As evident from Table 6, when compared with non-deuterated reference compounds, compounds of the invention exhibited decreased conversion of parent compound into metabolites. See also FIGS. 1, 2A-2C, 3A-3D, and 4A-4C.

TABLE 6

| | Distribution of Metabolites in Urine (% of total) | | |
|---|---|---|---|
| Compound | Peak 1 (Parent) | Peak 2 (Ref E) | Peak 3 (Ref D) |
| Ref A | 40% | 16% | 44% |
| 9 | 55% | 12% | 32% |
| 24c | 45% | 21% | 24% |
| Ref B | 72% | n.d. | 28% |
| 19 | 87% | n.d. | 13% |

Figure 5:
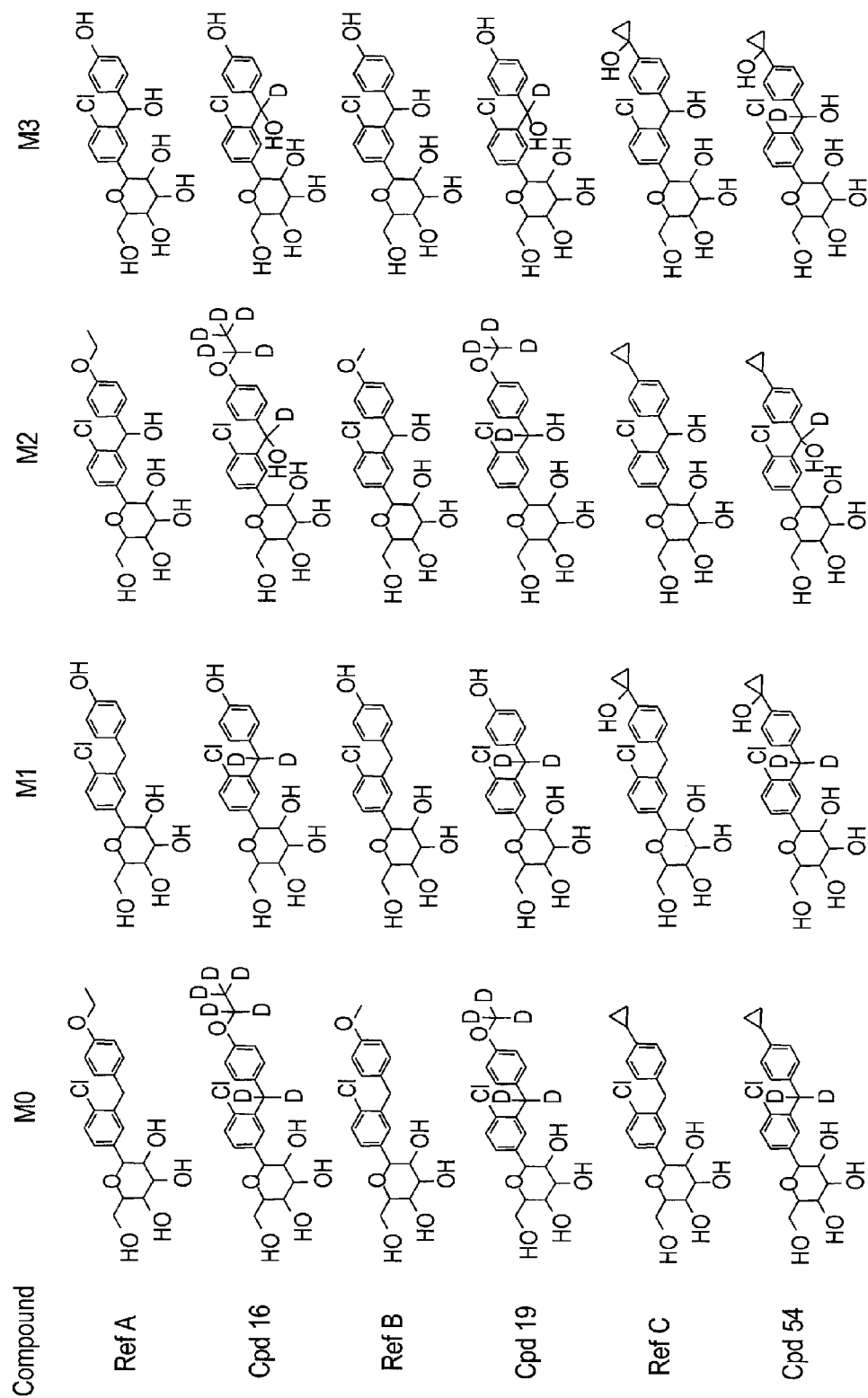
FIG. 5 summarizes additional metabolic studies on Compounds 16, 19, 54, and Reference Compounds A, B, and C.

FIG. 5 summarizes additional metabolic studies on Compounds 16, 19, 54, and Reference Compounds A, B, and C. These data were obtained according to the procedure described below.

FIGS. 6 and 7 illustrate that mass spectrometry is also useful in obtaining data concerning the metabolic pathway of the compounds of the invention. These methods were carried out as follows. LC-MS analyses were performed on a Waters 2695 Separations Module equipped with a Waters 2996 Photodiode Array Detector (190-400 nm) and a Waters Micromass ZQ Detector using Waters Masslynx. The sample (1 mL) was eluted through a Sepax GP C18 5 mm, 250 mm×4.6 mm ID column at 35° C. using a 25 min gradient and a 5 min hold from 5% A (0.05% formic acid in acetonitrile) and 95% B (0.1% formic acid in Milli-Q water) to 85% A and 15% B. Mass data were obtained in electrospray ionization mode (+ and −). The Total Ion Counts (TIC) peaks were used to determine the ratio of metabolites to the parent compound. The samples were prepared in the following way. SD rats were dosed orally with the test compound as a solution in 30% PEG-400 at 50 mg/kg, and the urine was collected over 24 hours at regular time intervals. Before analysis, the individual time point samples for each animal were pooled to generate one 0 to 24-h urine sample. A quantitative amount of methanol was added to urine samples, and the samples were centrifuged; the supernatant was injected directly onto LC-MS. The data presented in FIG. 6 represents LC/MS total ion counts. In FIG. 7, data is represented as mass/charge ratios (m/z).

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

What is claimed is:

1. A composition comprising a compound having the structure:

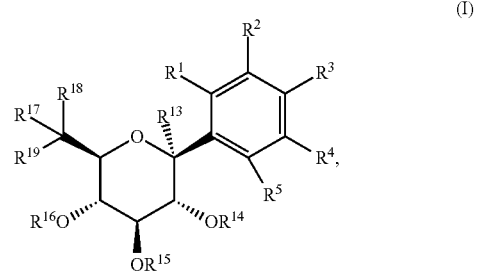

(I)

or any stereoisomer or tautomer thereof, or any pharmaceutically acceptable salt thereof, wherein
each $R^1$, $R^2$, $R^3$, $R^4$ and $R^5$ is, independently, —H, -D, halo, cyano, nitro, a substituent that is optionally deuterated, or group Q:

(Q)

[structure: benzene ring with R6, R7, R8, R9, R10 substituents and a carbon bearing R11, R12 attached]

each $R^6$, $R^7$, $R^8$, $R^9$, and $R^{10}$ is, independently, —H, -D, halo, cyano, nitro, or a substituent that is optionally deuterated;

each $R^{14}$, $R^{15}$, and $R^{16}$ is, independently, —H or a substituent that is optionally deuterated; and each $R^{11}$, $R^{12}$, $R^{13}$, $R^{17}$ and $R^{18}$ is, independently, —H, -D, or halogen; and $R^{19}$ is —H, -D, halo, cyano, or a substituent that is optionally deuterated;

wherein one of $R^1$, $R^2$, $R^3$, $R^4$ and $R^5$ is group Q; and at least one of $R^1$-$R^{19}$ is -D or comprises -D, wherein said composition has an isotopic enrichment factor for deuterium of at least 5 for said compound.

2. The composition of claim 1, wherein one of $R^1$, $R^2$, $R^3$, $R^4$ and $R^5$ is group Q;

one of the remaining groups $R^1$, $R^2$, $R^3$, $R^4$ and $R^5$ represents hydrogen, deuterium, halo, cyano, nitro, amino, hydroxy, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ cycloalkenyl, $C_1$-$C_6$ alkoxy, $C_3$-$C_{10}$ cycloalkoxy, ($C_1$-$C_6$ alkoxy)$C_1$-$C_6$ alkoxy, $C_5$-$C_7$ cycloalkenyloxy, aryl, heteroaryl, aryloxy, heteroaryloxy, ($C_2$-$C_4$ alkenyl)$C_1$-$C_3$ alkoxy, ($C_2$-$C_4$ alkynyl)$C_1$-$C_3$ alkoxy, (aryl)$C_1$-$C_3$ alkoxy, (heteroaryl)$C_1$-$C_3$ alkoxy, ($C_3$-$C_{10}$ cycloalkyl)$C_1$-$C_3$ alkyl, ($C_3$-$C_{10}$ cycloalkyl)$C_1$-$C_3$ alkoxy, ($C_5$-$C_{10}$ cycloalkenyl)$C_1$-$C_3$ alkyl, ($C_5$-$C_{10}$ cycloalkenyl)$C_1$-$C_3$ alkoxy, ($C_1$-$C_4$ alkoxy)$C_1$-$C_3$ alkyl, ($C_3$-$C_7$ cycloalkoxy)$C_1$-$C_3$ alkyl, ($C_3$-$C_7$ cycloalkoxy)$C_2$-$C_4$ alkenyl, ($C_3$-$C_7$ cycloalkoxy)$C_2$-$C_4$ alkynyl, ($C_3$-$C_7$ cycloalkoxy)$C_1$-$C_3$ alkoxy, ($C_1$-$C_4$ alkylamino)$C_1$-$C_3$ alkyl, di-($C_1$-$C_3$ alkylamino)$C_1$-$C_3$ alkyl, tri-($C_1$-$C_4$ alkyl)silyl-$C_1$-$C_6$ alkyl, tri-($C_1$-$C_4$ alkyl)silyl-$C_2$-$C_6$ alkenyl, tri-($C_1$-$C_4$ alkyl)silyl-$C_2$-$C_6$ alkynyl, tri-($C_1$-$C_4$ alkyl)silyl-$C_1$-$C_6$ alkoxy, ($C_3$-$C_7$ cycloalkyl)$C_2$-$C_5$ alkenyl, ($C_3$-$C_7$ cycloalkyl)$C_3$-$C_5$ alkenyloxy, ($C_3$-$C_7$ cycloalkyl)$C_3$-$C_5$ alkynyloxy, ($C_5$-$C_8$ cycloalkenyl)$C_3$-$C_5$ alkenyloxy, ($C_5$-$C_8$ cycloalkenyl)$C_3$-$C_5$ alkynyloxy, $C_3$-$C_6$ cycloalkylidenmethyl, ($C_1$-$C_4$ alkyl)carbonyl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, ($C_1$-$C_4$ alkoxy)carbonyl, $C_1$-$C_4$ alkylamino, di-($C_1$-$C_3$ alkyl)amino, ($C_1$-$C_4$ alkyl)carbonylamino, arylcarbonylamino, heteroarylcarbonylamino, $C_1$-$C_4$ alkylsulfonylamino, arylsulfonylamino, $C_1$-$C_4$ alkylthio, $C_1$-$C_4$ alkylsulfinyl, $C_1$-$C_4$ alkylsulfonyl, $C_3$-$C_{10}$ cycloalkylthio, $C_3$-$C_{10}$ cycloalkylsulfinyl, $C_3$-$C_{10}$ cycloalkylsulfonyl, $C_5$-$C_{10}$ cycloalkenylthio, $C_5$-$C_{10}$ cycloalkenylsulfinyl, $C_5$-$C_{10}$ cycloalkenylsulfonyl, arylthio, arylsulfinyl or arylsulfonyl;

two of the remaining groups $R^1$, $R^2$, $R^3$, $R^4$ and $R^5$ each independently represent hydrogen, deuterium, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkoxy or $C_3$-$C_{10}$ cycloalkoxy; and one of the remaining groups $R^1$, $R^2$, $R^3$, $R^4$ and $R^5$ represents hydrogen or deuterium;

one of the groups $R^6$, $R^7$, $R^8$, $R^9$ and $R^{10}$ represents hydrogen, deuterium, halo, cyano, nitro, amino, hydroxy, $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, $C_1$-$C_6$ alkoxy, $C_3$-$C_{10}$ cycloalkoxy, ($C_1$-$C_6$ alkoxy)$C_1$-$C_6$ alkoxy, ($C_1$-$C_3$ alkoxy)$C_3$-$C_7$ cycloalkoxy, $C_5$-$C_7$ cycloalkenyloxy, aryl, heteroaryl, aryloxy, heteroaryloxy, ($C_2$-$C_4$ alkenyl)$C_1$-$C_3$ alkoxy, ($C_2$-$C_4$ alkynyl)$C_1$-$C_3$ alkoxy, (aryl)$C_1$-$C_3$ alkoxy, (heteroaryl)$C_1$-$C_3$ alkoxy, ($C_3$-$C_{10}$ cycloalkyl)$C_1$-$C_3$ alkyl, ($C_3$-$C_{10}$ cycloalkyl)$C_1$-$C_3$ alkoxy, ($C_5$-$C_{10}$ cycloalkenyl)$C_1$-$C_3$ alkyl, ($C_5$-$C_{10}$ cycloalkenyl)$C_1$-$C_3$ alkoxy, ($C_1$-$C_4$ alkoxy)$C_1$-$C_3$ alkyl, ($C_3$-$C_7$ cycloalkoxy)$C_1$-$C_3$ alkyl, ($C_3$-$C_7$ cycloalkoxy)$C_2$-$C_4$ alkenyl, ($C_3$-$C_7$ cycloalkoxy)$C_2$-$C_4$ alkynyl, ($C_3$-$C_7$ cycloalkoxy)$C_1$-$C_3$ alkoxy, ($C_1$-$C_4$ alkylamino)$C_1$-$C_3$ alkyl, di-($C_1$-$C_3$ alkylamino)$C_1$-$C_3$ alkyl, tri-($C_1$-$C_4$ alkyl)silyl-$C_1$-$C_6$ alkyl, tri-($C_1$-$C_4$ alkyl)silyl-$C_2$-$C_6$ alkenyl, tri-($C_1$-$C_4$ alkyl)silyl-$C_2$-$C_6$ alkynyl, tri-($C_1$-$C_4$ alkyl)silyl-$C_1$-$C_6$ alkoxy, ($C_3$-$C_7$ cycloalkyl)$C_2$-$C_5$ alkenyl, ($C_3$-$C_7$ cycloalkyl)$C_3$-$C_5$ alkenyloxy, ($C_3$-$C_7$ cycloalkyl)$C_3$-$C_5$ alkynyloxy, ($C_5$-$C_8$ cycloalkenyl)$C_3$-$C_5$ alkenyloxy, ($C_5$-$C_8$ cycloalkenyl)$C_3$-$C_5$ alkynyloxy, $C_3$-$C_6$ cycloalkylidenmethyl, ($C_1$-$C_4$ alkyl)carbonyl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, ($C_1$-$C_4$ alkoxy)carbonyl, $C_1$-$C_4$ alkylamino, di-($C_1$-$C_3$ alkyl)amino, ($C_1$-$C_4$ alkyl)carbonylamino, arylcarbonylamino, heteroarylcarbonylamino, $C_1$-$C_4$ alkylsulfonylamino, arylsulfonylamino, $C_1$-$C_4$ alkylthio, $C_1$-$C_4$ alkylsulfinyl, $C_1$-$C_4$ alkylsulfonyl, $C_3$-$C_{10}$ cycloalkylthio, $C_3$-$C_{10}$ cycloalkylsulfinyl, $C_3$-$C_{10}$ cycloalkylsulfonyl, $C_5$-$C_{10}$ cycloalkenylthio, $C_5$-$C_{10}$ cycloalkenylsulfinyl, $C_5$-$C_{10}$ cycloalkenylsulfonyl, arylthio, arylsulfinyl or arylsulfonyl;

two of the remaining groups $R^6$, $R^7$, $R^8$, $R^9$ and $R^{10}$ each independently represent hydrogen, deuterium, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkoxy or $C_3$-$C_{10}$ cycloalkoxy; and two of the remaining groups $R^6$, $R^7$, $R^8$, $R^9$ and $R^{10}$ each independently represent hydrogen or deuterium;

$R^{14}$, $R^{15}$ and $R^{16}$ each independently represent hydrogen, ($C_1$-$C_{18}$ alkyl)carbonyl, ($C_1$-$C_{18}$ alkyl)oxycarbonyl, arylcarbonyl, aryl-($C_1$-$C_3$ alkyl)carbonyl, ($C_3$-$C_{10}$ cycloalkyl)carbonyl, $C_1$-$C_6$ alkyl, $C_2$-$C_6$ alkenyl, $C_2$-$C_6$ alkynyl, ($C_5$-$C_7$ cycloalkenyl)$C_1$-$C_3$ alkyl, (aryl)$C_1$-$C_3$ alkyl, (heteroaryl)$C_1$-$C_3$ alkyl, $C_3$-$C_7$ cycloalkyl, $C_5$-$C_7$ cycloalkenyl, aryl, heteroaryl, ($C_3$-$C_7$ cycloalkyl)$C_1$-$C_3$ alkyl, ($C_5$-$C_7$ cycloalkenyl)$C_1$-$C_3$ alkyl, (aryl)$C_1$-$C_3$ alkyl, (heteroaryl)$C_1$-$C_3$ alkyl, $C_1$-$C_4$ alkylsulfonyl, arylsulfonyl, (aryl)$C_1$-$C_3$ alkylsulfonyl, trimethylsilyl or t-butyldimethylsilyl;

$R^{19}$ represents hydroxy, ($C_1$-$C_{18}$ alkyl)carbonyloxy, ($C_1$-$C_{18}$ alkyl)oxycarbonyloxy, arylcarbonyloxy, aryl-($C_1$-$C_3$ alkyl)carbonyloxy, ($C_3$-$C_{10}$ cycloalkyl)carbonyloxy, hydrogen, deuterium, halo, $C_1$-$C_6$ alkyl, $C_2$-$C_6$ alkenyl, $C_2$-$C_6$ alkynyl, ($C_3$-$C_{10}$ cycloalkyl)$C_1$-$C_3$ alkyl, ($C_5$-$C_7$ cycloalkenyl)$C_1$-$C_3$ alkyl, (aryl)$C_1$-$C_3$ alkyl, (heteroaryl)$C_1$-$C_3$ alkyl, $C_1$-$C_6$ alkoxy, $C_2$-$C_6$ alkenyloxy, $C_2$-$C_6$ alkynyloxy, $C_3$-$C_7$ cycloalkoxy, $C_5$-$C_7$ cycloalkenyloxy, aryloxy, heteroaryloxy, ($C_3$-$C_7$ cycloalkyl)$C_1$-$C_3$ alkoxy, ($C_5$-$C_7$ cycloalkenyl)$C_1$-$C_3$ alkoxy, (aryl)$C_1$-$C_3$ alkoxy, (heteroaryl)$C_1$-$C_3$ alkoxy, aminocarbonyl, hydroxycarbonyl, ($C_1$-$C_4$ alkyl)aminocarbonyl, di-($C_1$-$C_3$ alkyl)aminocarbonyl, ($C_1$-$C_4$ alkoxy)carbonyl, (aminocarbonyl)C$_1$-C$_3$ alkyl, (C$_1$-C$_4$ alkyl)aminocarbonyl-(C$_1$-C$_3$)alkyl, di-(C$_1$-C$_3$ alkyl)aminocarbonyl-(C$_1$-C$_3$) alkyl, (hydroxycarbonyl)C$_1$-C$_3$ alkyl, (C$_1$-C$_4$ alkoxy)carbonyl-(C$_1$-C$_3$)alkyl, (C$_3$-C$_7$ cycloalkoxy)C$_1$-C$_3$ alkyl, (C$_5$-C$_7$ cycloalkenyloxy)C$_1$-C$_3$ alkyl, (aryloxy) C$_1$-C$_3$ alkyl, (heteroaryloxy)C$_1$-C$_3$ alkyl, C$_1$-C$_4$ alkylsulfonyloxy, arylsulfonyloxy, (aryl)C$_1$-C$_3$ alkylsulfonyloxy, trimethylsilyloxy, t-butyldimethylsilyloxy, or cyano,
wherein alkyl, alkenyl, alkynyl, cycloalkyl and cycloalkenyl groups or portions optionally may be partly or completely substituted with fluorine or deuterium and may be mono- or disubstituted by identical or different substituents selected from chlorine, hydroxy, C$_1$-C$_3$ alkoxy and C$_1$-C$_3$ alkyl, and in cycloalkyl and cycloalkenyl groups or portions one or two methylene groups are optionally replaced independently of one another by NR$^a$, O, S, CO, SO or SO$_2$; R$^a$ independently represents hydrogen, C$_1$-C$_4$ alkyl or (C$_1$-C$_4$ alkyl)carbonyl, wherein alkyl groups or portions optionally may be partly or completely substituted with fluorine or deuterium.

3. The composition of claim 1, wherein said composition further comprises an amino acid.

4. The composition of claim 1, wherein R$^{11}$ and R$^{12}$ are both -D.

5. The composition of claim 1, wherein R$^{13}$ is -D.

6. The composition of claim 1, wherein one of R$^1$, R$^2$, R$^3$, or R$^5$ is halogen.

7. The composition of claim 6, wherein R$^3$ is —Cl.

8. The composition of claim 1, wherein R$^4$ is Q.

9. The composition of claim 1, wherein
each R$^1$, R$^2$, R$^3$, R$^4$ and R$^5$ is, independently, —H, -D, group Q, halogen, or an optionally deuterated substituent selected from hydroxyl, optionally substituted alkyl, haloalkyl, optionally substituted alkoxyalkyl, optionally substituted alkoxy, haloalkoxy, optionally substituted alkenyl, optionally substituted alkynyl, optionally substituted cycloalkyl, or optionally substituted alkcycloalkyl;
each R$^6$, R$^7$, R$^8$, R$^9$, R$^{10}$ is, independently, —H, -D, halogen, or an optionally deuterated substituent selected from hydroxyl, optionally substituted carbamoyl, optionally substituted alkyl, haloalkyl, optionally substituted alkoxyalkyl, optionally substituted alkoxy, haloalkoxy, optionally substituted alkenyl, optionally substituted alkynyl, optionally substituted cycloalkyl, or optionally substituted alkcycloalkyl; and
each R$^{14}$, R$^{15}$, and R$^{16}$ is, independently, —H, optionally substituted alkyl, haloalkyl, optionally substituted alkoxyalkyl, optionally substituted alkoxy, haloalkoxy, optionally substituted alkenyl, optionally substituted alkynyl, optionally substituted cycloalkyl, optionally substituted alkcycloalkyl, —C(O)R$^A$, —C(O)OR$^A$, or —C(O)NR$^A$R$^B$, wherein each R$^A$ and R$^B$ is, independently, hydrogen, deuterium, or an optionally deuterated substituent selected from optionally substituted alkyl, optionally substituted alkenyl, optionally substituted cycloalkyl, and optionally substituted aryl.

10. The composition of claim 9, wherein R$^4$ is Q and R$^8$ is -D, halogen, or an optionally deuterated substituent selected from hydroxyl, optionally substituted alkyl, haloalkyl, optionally substituted alkoxyalkyl, optionally substituted alkoxy, haloalkoxy, optionally substituted alkenyl, optionally substituted alkynyl, optionally substituted cycloalkyl, or optionally substituted alkcycloalkyl.

11. The composition of claim 10, wherein R$^2$ is H; R$^3$ is halogen; R$^5$, R$^6$, R$^7$, R$^9$, and R$^{10}$ are H; and R$^{14}$, R$^{15}$, and R$^{16}$ are, independently, selected from H, —C(O)R$^A$, —C(O)OR$^A$, or —C(O)NR$^A$R$^B$.

12. The composition of claim 11, wherein R$^3$ is —Cl.

13. The composition of claim 11, wherein R$^{11}$ and R$^{12}$ are both -D.

14. The composition of claim 11, wherein R$^{13}$ is -D.

15. The composition of claim 11, wherein R$^8$ is a deuterated substituent.

16. A composition comprising a compound selected from the group consisting of:

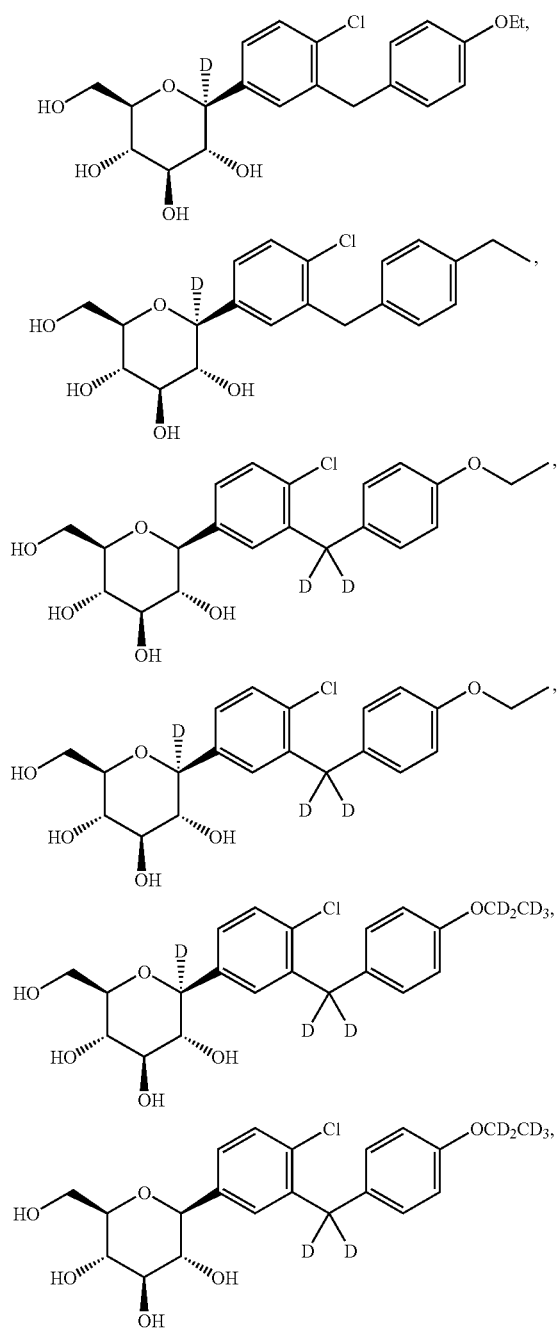

211
-continued
212
-continued
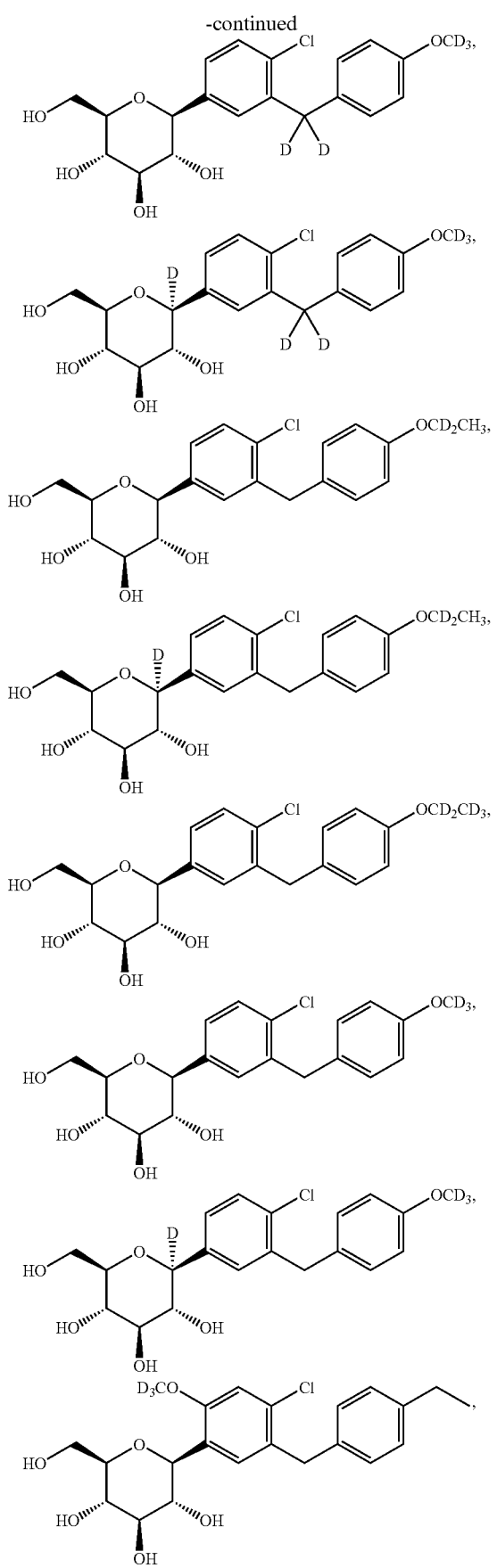
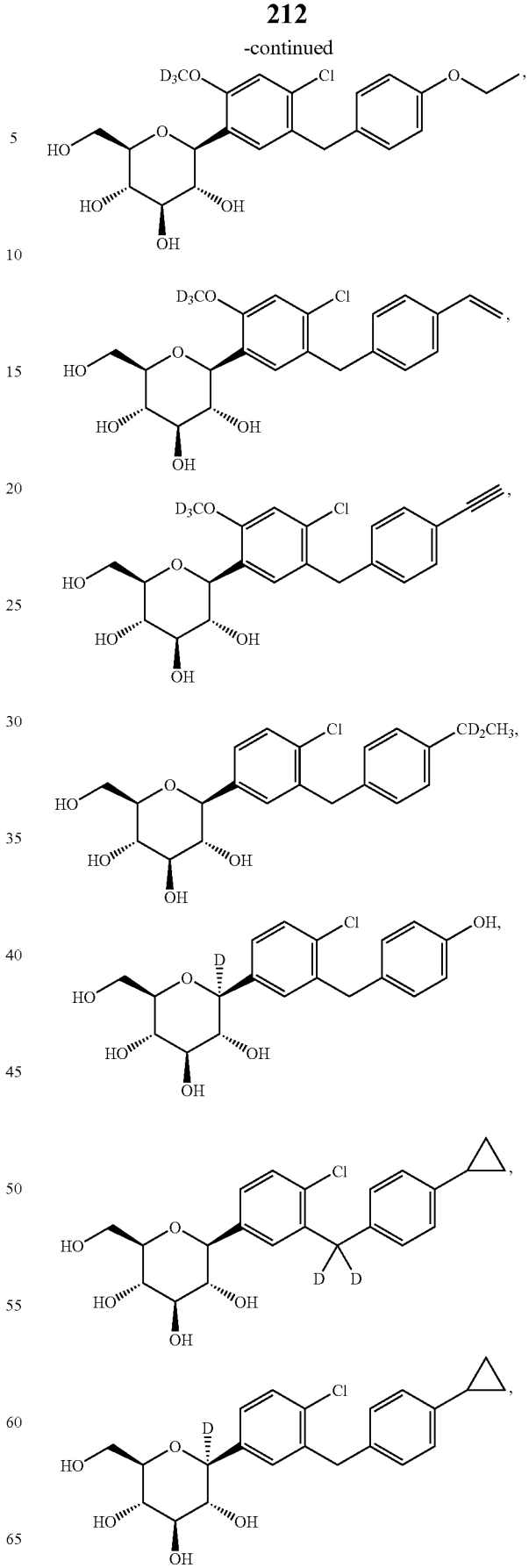

213
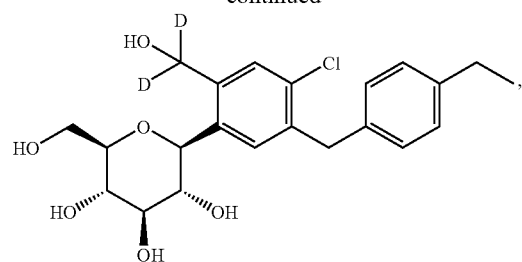
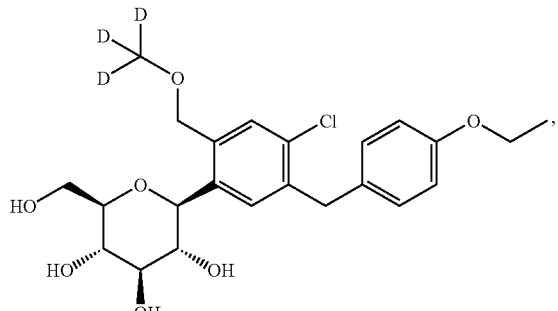
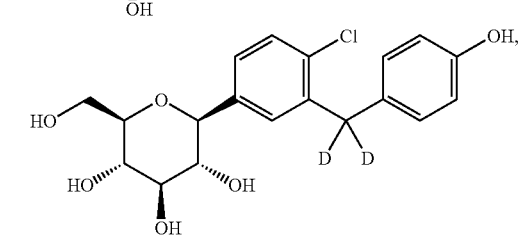
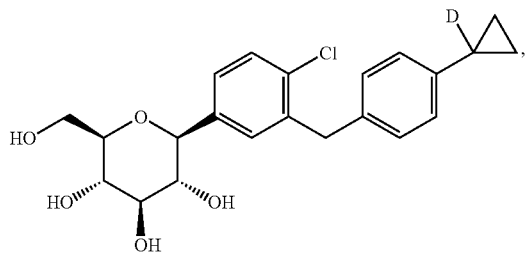
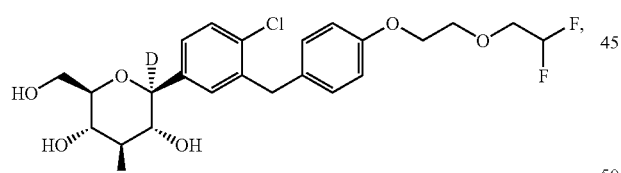
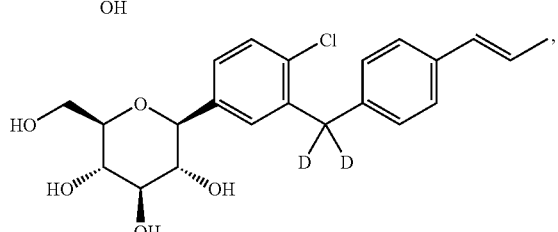
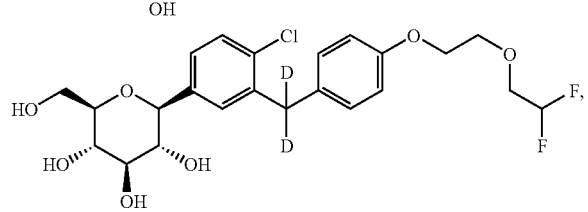
214
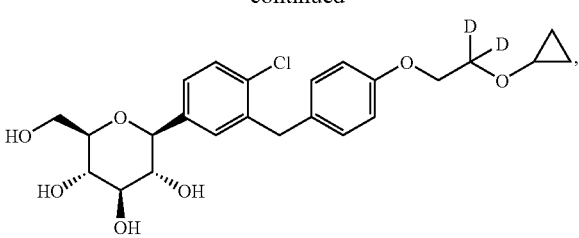
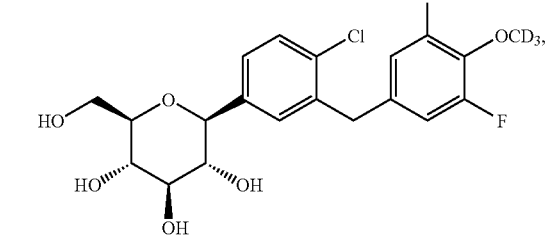
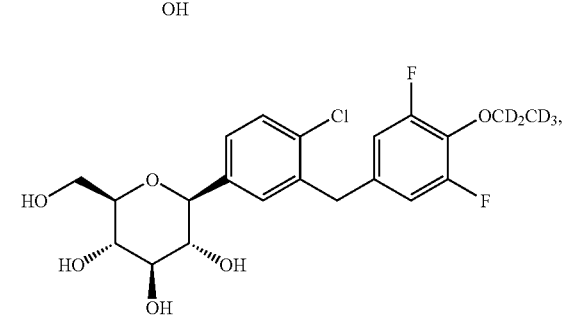
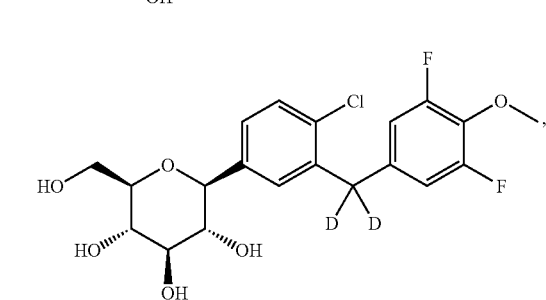
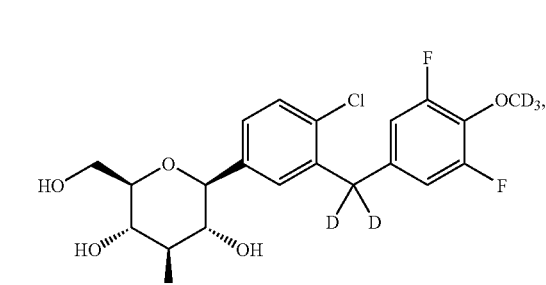
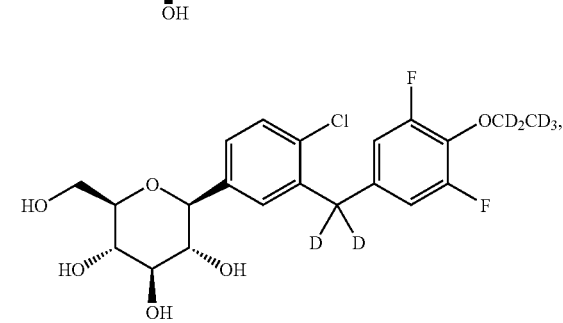

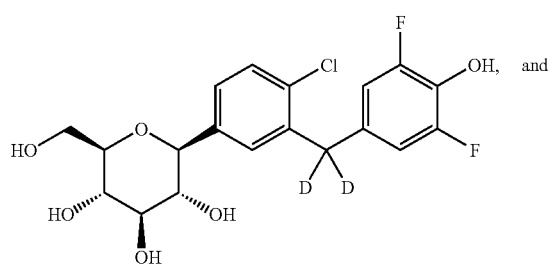

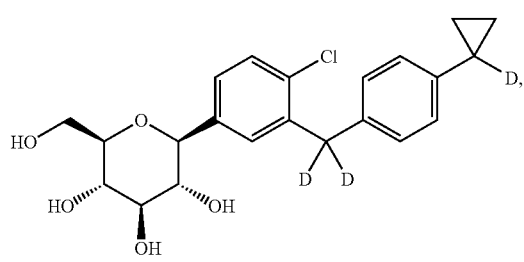

or any stereoisomer or tautomer thereof, or any pharmaceutically acceptable salt thereof;

wherein said composition has an isotopic enrichment factor for deuterium of at least 5 for said compound.

17. The composition of claim 16, wherein said compound is selected from:

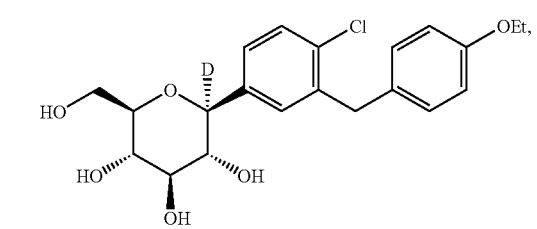

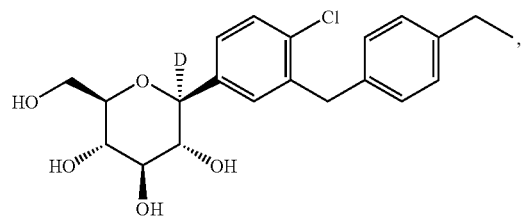

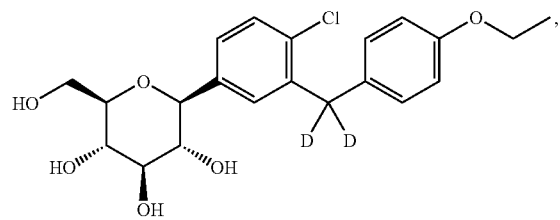

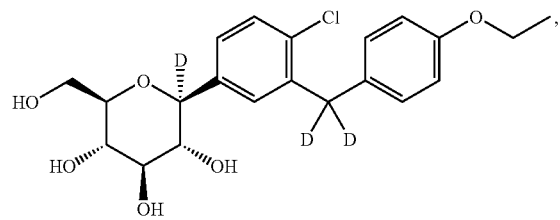

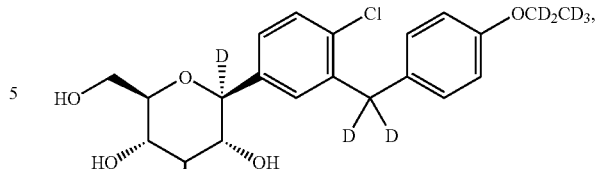

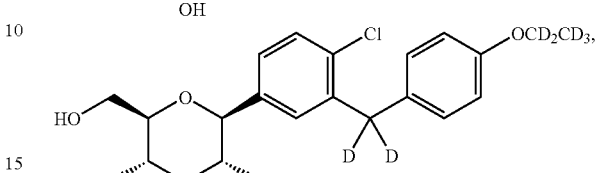

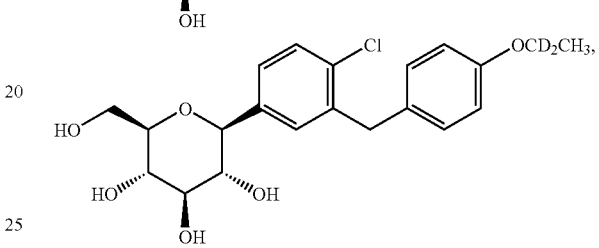

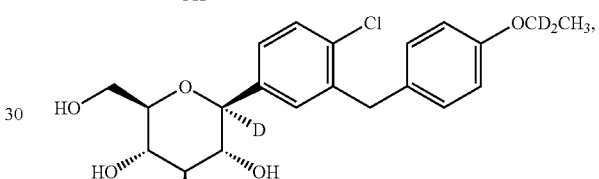

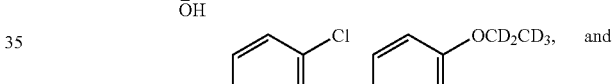

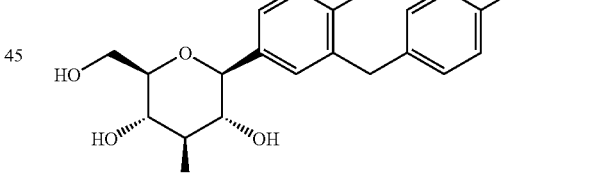

or any stereoisomer or tautomer thereof, or any pharmaceutically acceptable salt thereof.

18. The composition of claim 16, wherein said compound is selected from:

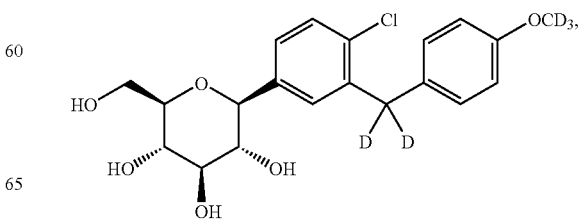

-continued

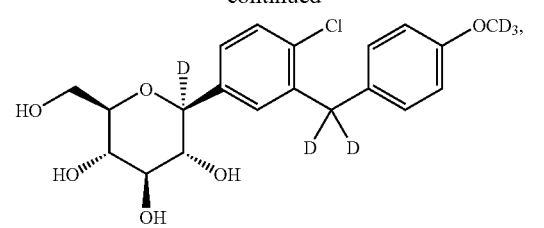

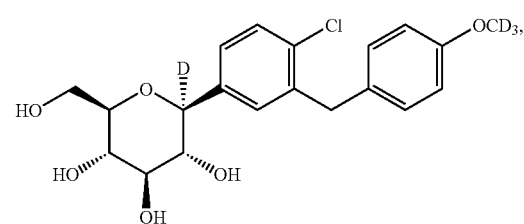

or any stereoisomer or tautomer thereof, or any pharmaceutically acceptable salt thereof.

19. The composition of claim 16, wherein said compound is selected from:

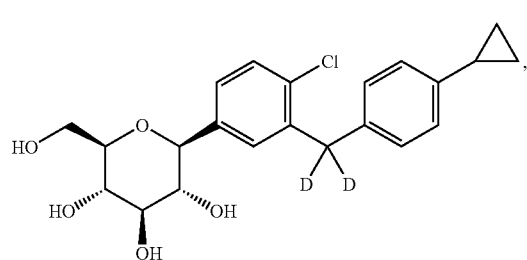

-continued

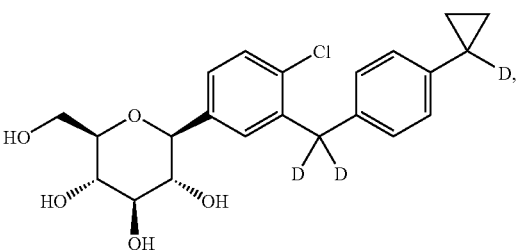

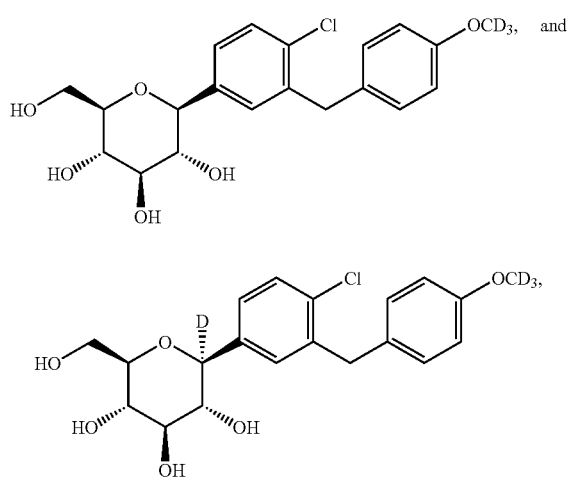

or any stereoisomer or tautomer thereof, or any pharmaceutically acceptable salt thereof.

20. The composition of claim 16, wherein said compound is selected from:

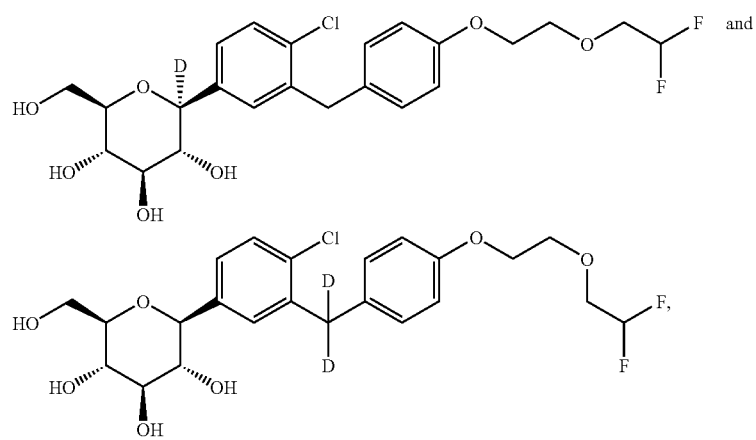

or any stereoisomer or tautomer thereof, or any pharmaceutically acceptable salt thereof.

21. The composition of claim 16, wherein said compound is

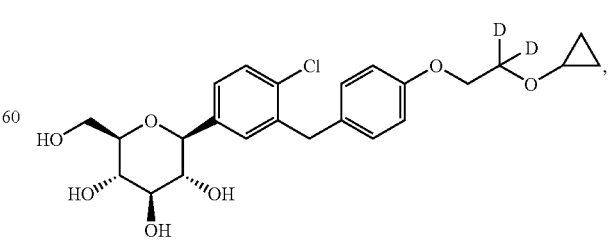

or any stereoisomer or tautomer thereof, or any pharmaceutically acceptable salt thereof.

22. The composition of claim 1, wherein said isotopic enrichment factor for deuterium is at least 500, 1000, or 3000 for said compound.

23. The composition of claim 1, wherein said composition further comprises a pharmaceutically acceptable carrier, and wherein said compound of Formula (I) is present in an effective amount.

24. The composition of claim 8, wherein $R^{14}$, $R^{15}$, and $R^{16}$ are H; and wherein $R^{19}$ is hydroxy.

25. The composition of claim 24, wherein $R^{11}$ and $R^{12}$ are both -D.

26. The composition of claim 24, wherein $R^{13}$ is -D.

27. The composition of claim 24, wherein $R^1$ is a deuterated substituent.

28. The composition of claim 24, wherein $R^8$ is a deuterated substituent.

29. A method of treating a disease affected by inhibition of the sodium-dependent glucose transporter (SGLT), comprising administering the composition of claim 1.

30. The method of claim 29, wherein said disease affected by inhibition of the SGLT is: type 1 diabetes mellitus, type 2 diabetes mellitus, hyperglycemia, diabetic complications, insulin resistance, metabolic syndrome (Syndrome X), hyperinsulinemia, hypertension, hyperuricemia, obesity, edema, dyslipidemia, chronic heart failure, or atherosclerosis.

31. The method of claim 29, wherein said method further comprises administering a second therapeutic agent.

32. The method of claim 31, wherein said therapeutic agent is: an antidiabetic agent, a lipid-lowering/lipid-modulating agent, an agent for treating diabetic complications, an anti-obesity agent, an antihypertensive agent, an antihyperuricemic agent, an agent for treating chronic heart failure, or an agent for treating atherosclerosis.

33. The method of claim 29, wherein said disease is type 1 diabetes mellitus or type 2 diabetes mellitus.

* * * * *